(12) United States Patent
Mascola et al.

(10) Patent No.: US 10,273,291 B2
(45) Date of Patent: Apr. 30, 2019

(54) FOCUSED EVOLUTION OF HIV-1 NEUTRALIZING ANTIBODIES REVEALED BY CRYSTAL STRUCTURES AND DEEP SEQUENCING

(75) Inventors: John R. Mascola, Bethesda, MD (US); Gary Nabel, Bethesda, MD (US); Barton F. Haynes, Durham, NC (US); Xueling Wu, Bethesda, MD (US); Thomas B. Kepler, Boston, MA (US); Peter Kwong, Bethesda, MD (US)

(73) Assignees: Duke University, Durham, NC (US); THE UNITED STATES OF AMERICA, AS REPRESENTED BY THE SECRETARY, DEPARTMENT OF HEALTH AND HUMAN SERVICES OFFICE OF TECHNOLOGY TRANSFER, NATIONAL INSTITUTES OF HEALTH, Washington, DC (US)

( * ) Notice: Subject to any disclaimer, the term of this patent is extended or adjusted under 35 U.S.C. 154(b) by 0 days.

(21) Appl. No.: 14/116,710

(22) PCT Filed: Mar. 23, 2012

(86) PCT No.: PCT/US2012/030436
§ 371 (c)(1),
(2), (4) Date: Nov. 8, 2013

(87) PCT Pub. No.: WO2012/154311
PCT Pub. Date: Nov. 15, 2012

(65) Prior Publication Data
US 2014/0205607 A1    Jul. 24, 2014

Related U.S. Application Data

(60) Provisional application No. 61/484,184, filed on May 9, 2011.

(51) Int. Cl.
| | | |
|---|---|---|
| *C07K 16/10* | (2006.01) | |
| *A61K 39/42* | (2006.01) | |
| *G01N 33/569* | (2006.01) | |

(52) U.S. Cl.
CPC .......... *C07K 16/1063* (2013.01); *A61K 39/42* (2013.01); *G01N 33/56988* (2013.01); *C07K 2317/21* (2013.01); *C07K 2317/565* (2013.01); *C07K 2317/76* (2013.01)

(58) Field of Classification Search
CPC ............ C07K 16/1063; C07K 2317/76; C07K 2317/565; A61K 39/42
See application file for complete search history.

(56) References Cited

U.S. PATENT DOCUMENTS

| | | |
|---|---|---|
| 4,946,778 A | 8/1990 | Ladner et al. |
| 6,241,986 B1 | 6/2001 | Zolla et al. |
| 6,309,880 B1 | 10/2001 | Chang et al. |

FOREIGN PATENT DOCUMENTS

| | | |
|---|---|---|
| EP | 0404097 A2 | 12/1990 |
| WO | WO-1993011161 A1 | 6/1993 |
| WO | WO 2011/038290 A2 | 3/2011 |
| WO | WO 2011/046623 A2 | 4/2011 |
| WO | WO 2012/040562 A2 | 3/2012 |
| WO | WO 2013/090644 A2 | 6/2013 |

OTHER PUBLICATIONS

Xiang, J., et al., 1991, Modification in framework region I results in a decreased affinity of chimeric anti-TAG72 antibody, Mol. Immunol. 28:141-148.*
Li, Y., et al., 1996, The I binding specificity of human VH4-34 (VH4-21) encoded antibodies is determined by both VH framework region 1 and complementarity determining region 3, J. Mol. Biol. 256:577-589.*
Winkler, K., 2000, Changing the antigen binding specificity by single point mutations of an anti-p24 (HIV-1) antibody, J. Immunol. 165:4505-4514.*
International Search Report for PCT/US2012/036783, dated Nov. 23, 2012.
Bonsignori, M et al., "Two District Broadly Neutralizing Antibody Specifications of Different Clonal Lineages in a Single HIV-1-Infected Donor: Implications for Vaccine Design", Journal of Virology, vol. 86, No. 8 (Feb. 1, 2012), pp. 4688-4692.
Wu, X et al., Focused Evolution of HIV-1 Neutralizing Antibodies Revealed by Structures and Deep Sequencing, Science, vol. 333, pp. 1593-1602, (Sep. 16, 2011), (Author Manuscript).
Wu, X et al., "Rational Design of Envelope Identifies Broadly Neutralizing Human Monoclonal Antibodies to HIV-1", Science, vol. 329, (Aug. 13, 2010), pp. 856-861, (Author Manuscript).

(Continued)

*Primary Examiner* — Jeffrey S Parkin
(74) *Attorney, Agent, or Firm* — Wilmer Cutler Pickering Hale and Dorr LLP

(57) ABSTRACT

Antibody VRC01 represents a human immunoglobulin that neutralizes—~90% of diverse HIV-1 isolates. To understand how such broadly neutralizing HIV-1 antibodies develop and recognize the viral envelope, we used X-ray crystallography and 454 pyrosequencing to characterize additional antibodies from HIV-1-infected individuals. Crystal structures revealed a convergent mode of binding of different antibodies to the same CD4-binding-site epitope. Antibody recognition was achieved through the evolution of complementary contact domains that were generated in diverse ways. Phylogenetic analysis of expressed heavy and light chains determined by deep sequencing revealed a common pathway of antibody heavy chain maturation confined to IGHV1-2*02 lineage that could pair with different light chains. The maturation pathway inferred by antibodyomics reveals that diverse antibodies evolve to a highly affinity-matured state to recognize an invariant viral structure, providing insight into the development and evolution of broadly neutralizing HIV-1 immunity.

40 Claims, 146 Drawing Sheets

Specification includes a Sequence Listing.

(56) References Cited

OTHER PUBLICATIONS

McElrath et al, "Induction of Immunity to Human Immunodeficiency Virus Type-1 by Vaccination", Immunity 2010; 33(4):542-554.
Supplementary European Search Report dated Nov. 28, 2014, issued in connection with European Application No. 12782672.5.
Adams et al., "PHENIX: Building New Software for Automated Crystallographic Structure Determination", Acta Crystallographica, Section D58, pp. 1948-1954 (2002).
Altschul et al., "Gapped BLAST and PSI-BLAST: a new generation of protein database search programs", Nucleic Acids Research, vol. 25, No. 17, pp. 3389-3402 (1997).
Baker et al., "Electrostatics of Nanosystems: Application to Microtubules and the Ribosome", Proc Natl Acad Sci USA, vol. 98, No. 18, pp. 10037-10041 (Aug. 28, 2001).
Barouch et al., "Adenovirus Vector-Based Vaccines for Human Immunodeficiency Virus Type 1", Human Gene Therapy, vol. 16, pp. 149-156 (Feb. 2005).
Bonsignori et al., "Immunoregulation of HIV-1 Broadly Neutralizing Antibody Responses: Deciphering Maturation Paths for Antibody Induction", Aids Research and Human Retroviruses, vol. 26, No. 10, Abstract P04.52LB, p. A153 (2010).
Brochet et al., "IMGT/V-QUEST: The Highly Customized and Integrated System for IG and TR Standardized V-J and V-D-J Sequence Analysis", Nucleic Acids Research, vol. 36, Web Server Issue pp. W503-W508 (2008).
Brockman et al., "Quality scores and SNP detection in sequencing-by-synthesis systems", Genome Research, vol. 18, pp. 763-770 (2008).
Burton et al., "Efficient Neutralization of Primary Isolates of HIV-1 by a Recombinant Human Monoclonal Antibody", Science, vol. 266, No. 5187, pp. 1024-1027, 6 pages total, (Nov. 11, 1994).
Burton, et al., "HIV Vaccine Design and the Neutralizing Antibody Problem", Nature Immunology, vol. 5, No. 3, pp. 233-236 (Mar. 2004).
By Collaborative Computational Project No. 4, "The CCP4 Suite: Programs for Protein Crystallography", Acta Crystallographica, Section D50, pp. 760-763 (1994).
Chen et al., "Structural Basis of Immune Evasion at the Site of CD4 Attachment on HIV-1 gp120", Science, vol. 326, No. 5956, pp. 1123-1127 (Author Manuscript, consisting of 11 pages total) (Nov. 20, 2009).
Crooks et al., "WebLogo: A Sequence Logo Generator", Genome Research, vol. 14, pp. 1188-1190 (2004).
D. E. McRee, "XtalView/Xfit—A versatile program for manipulating atomic coordinates and electron density", J Struct Biol 125, 156-165 (1999).
Davis et al., "MolProbity: All-Atom Contacts and Structure Validation for Proteins and Nucleic Acids", Nucleic Acids Research, vol. 35, Web Server Issue pp. W375-W383 (2007).
Emsley et al., "Coot: Model-Building Tools for Molecular Graphics", Acta Crystallographica, Section D60, pp. 2126-2132 (2004).
Gorny et al., "Preferential Use of the VH5-51 Gene Segment by the Human Immune Response to Code for Antibodies against the V3 Domain of HIV-I", Mol Immunol, vol. 46, No. 5, pp. 917-926 (Author Manuscript, consisting of 24 pages total) (Feb. 2009).
Huson et al., "Dendroscope: An Interactive Viewer for Large Phylogenetic Trees", BioMed Central—Bioinformatics, vol. 8, No. 460, consisting of 6 pages total (2007).
Johnson et al., "Vector-mediated Gene Transfer Engenders Long-Lived Neutralizing Activity and Protection against SIV Infection in Monkeys", Nature Medicine vol. 15, No. 8, pp. 901-906 (Author Manuscript, consisting of 18 pages total) (Aug. 2009).
Kozbor, et al., "The Production of Monoclonal Antibodies from Human Lymphocytes", Immunology Today, vol. 4, No. 3, pp. 72-79 (1983).
Krissinel et al., "Inference of Macromolecular Assemblies from Crystalline State", Journal of Molecular Biology, vol. 372, pp. 774-797 (2007).

Kwong et al., "HIV-1 Evades Antibody-Mediated Neutralization through Conformational Masking of Receptor-Binding Sites", Nature, vol. 420, pp. 678-682 (2002).
Köhler, et al., "Continuous Culture of Fused Cells Secreting Antibody of Predefined Specificity", Nature, vol. 256, pp. 495-497 (Aug. 7, 1975).
Li et al., "Analysis of Neutralization Specificities in Polyclonal Sera Derived from Human Immunodeficiency Virus Type 1-Infected Individuals", J Virol, vol. 83, No. 2, pp. 1045-1059 (Jan. 2009).
Li et al., "Broad HIV-1 Neutralization Mediated by CD4-binding Site Antibodies", Nat Med, vol. 13, No. 9, pp. 1032-1034 (Author Manuscript, consisting of 7 pages total) (Sep. 2007).
Li et al., "Human Immunodeficiency Virus Type 1 env Clones from Acute and Early Subtype B Infections for Standardized Assessments of Vaccine-Elicited Neutralizing Antibodies", Journal of Virology, vol. 79, No. 16, pp. 10108-10125 (Aug. 2005).
Liao et al., "High-throughput Isolation of Immunoglobulin Genes from Single Human B Cells and Expression as Monoclonal Antibodies", J. Virol. Methods, vol. 158, Nos. 1-2, pp. 171-179 (Author Manuscript, consisting of 22 pages total) (Jun. 2009).
Lutteke et al., "pdb-care (PDB carbohydrate REsidue check): a program to support annotation of complex carbohydrate structures in PDB files", BioMed Central—Bioinformatics, vol. 5, consisting of 6 pages total (2004).
Malcolm et al., "Localization of Human Immunoglobulin K Light Chain Variable Region Genes to the Short Arm of Chromosome 2 by In Situ Hybridization", Proc. Natl. Acad. Sci. USA, vol. 79, 4957-4961 (Aug. 1982).
McCoy et al., "Phaser Crystallographic Software", Journal of Applied Crystallography, vol. 40, pp. 658-674 (2007).
Munshaw et al., SoDA2: a Hidden Markov Model approach for identification of immunoglobulin rearrangements, Bioinformatics, vol. 26, No. 7, pp. 867-872 (2010).
Neuberger, et al., "Recombinant Antibodies Possessing Novel Effector Functions", Nature, vol. 312, pp. 604-608 (Dec. 1984).
Nicholls et al., "Protein Folding and Association: Insights from the Interfacial and Thermodynamic Properties of Hydrocarbons", Proteins: Structure, Function and Genetics, vol. 11, pp. 281-296 (1991).
Otwinowski et al., "Processing of X-Ray Diffraction Data Collected in Oscillation Mode", Methods in Enzymology, vol. 276, pp. 307-326 (1997).
Pantophlet, et al., "GP120: Target for Neutralizing HIV-1 Antibodies", Annu. Rev. Immunol., vol. 24, pp. 739-769, consisting of 33 pages in total (2006).
Petrey et al., "Using Multiple Structure Alignments, Fast Model Building, and Energetic Analysis in Fold Recognition and Homology Modeling", Proteins: Structure, Function and Genetics, vol. 53, pp. 430-435 (2003).
R. A Lerner, "Rare Antibodies from Combinatorial Libraries Suggests an S.O.S. Component of the Human Immunological Repertoire", Mol. Biosyst., vol. 7, pp. 1004-1012 (2011).
R. C. Edgar, MUSCLE: A Multiple Sequence Alignment Method with Reduced Time and Space Complexity, BioMed Central—Bioinformatics, vol. 5, No. 113, consisting of 19 pages total (2004).
R. C. Edgar, MUSCLE: Multiple Sequence Alignment with High Accuracy and High Throughput, Nucleic Acids Research, vol. 32, No. 5, pp. 1792-1797 (2004).
Scheid et al., "Broad Diversity of Neutralizing Antibodies Isolated from Memory B Cells in HIV-Infected Individuals", Nature, vol. 458, pp. 636-640 (Apr. 2, 2009).
Seaman et al., "Tiered Categorization of a Diverse Panel of HIV-1 Env Pseudoviruses for Assessment of Neutralizing Antibodies", Journal of Virology, vol. 84, No. 3, pp. 1439-1452 (Feb. 2010).
Smith et al., "Rapid Generation of Fully Human Monoclonal Antibodies Specific to a Vaccinating Antigen", Nature Protocols, vol. 4, No. 3, pp. 372-384 (Author Manuscript, consisting of 25 pages total) (2009).
Souto-Carneiro et al., "Characterization of the Human Ig Heavy Chain Antigen Binding Complementarity Determining Region 3 using a Newly Developed Software Algorithm, JOINSOLVER", The Journal Immunology, vol. 172, pp. 6790-6802, consisting of 14 pages in total (2004).

(56) References Cited

OTHER PUBLICATIONS

Stamatatos, et al., "Neutralizing Antibodies Generated during Natural HIV-I Infection: Good News for an HIV-I Vaccine?", Nature Medicine, vol. 15, No. 8, pp. 866-870 (Aug. 2009).
Strohl, et al., "Therapeutic Antibody Engineering: Current and Future Advances Driving the Strongest Growth Area in the Pharmaceutical Industry", Woodhead Publishing Series in Biomedicine: No. 11, Chapter 6: "Variable Chain Engineering Humanization and Optimization Approaches", pp. 111-129, consisting of 30 pages total (2012).
Takeda, et al., "Construction of Chimaeric Processed Immunoglobulin Genes containing Mouse Variable and Human Constant Region Sequences", Nature, vol. 314, pp. 452-454 (Apr. 4, 1985).
Tiller et al., "Efficient Generation of Monoclonal Antibodies from Single Human B Cells by Single Cell RT-PCR and Expression Vector Cloning", J Immunol Methods, vol. 329, Nos. 1-2, pp. 112-124 (Jan. 1, 2008), consisting of 11 pages total.
U.S. Appl. No. 61/542,469, filed Oct. 3, 2011 consisting of 42 pages total.
Walker et al., "A Limited Number of Antibody Specificities Mediate Broad and Potent Serum Neutralization in Selected HIV-1 Infected Individuals", PLoS Pathogens, vol. 6, No. 8, e10001028, pp. 1-14 (Aug. 2010).
Walker et al., "Broad and Potent Neutralizing Antibodies from an African Donor Reveal a New HIV-I Vaccine Target", Science, vol. 326, No. 5950, pp. 285-289 (Author Manuscript, consisting of 10 pages total) (Oct. 9, 2009).
Walker et al., "High Through-Put Functional Screening of Activated B Cells from 4 African Elite Neutralizers Yields a Panel of Novel Broadly Neutralizing Antibodies", Aids Research and Human Retroviruses, vol. 26, No. 10, Abstract OA10.06LB, p. A149-A150 (2010).
Wu et al., "Mechanism of Human Immunodeficiency Virus Type 1 Resistance to Monoclonal Antibody b12 that Effectively Targets the Site of CD4 Attachment", Journal of Virology, vol. 83, No. 21, pp. 10892-10907 (2009).
Xiao et al., "Germline-like Predecessors of Broadly Neutralizing Antibodies Lack Measurable Binding to HIV-1 Envelope Glycoproteins: Implications for Evasion of Immune Responses and Design of Vaccine Immunogens", Biochem Biophys Res Commun., vol. 390, No. 3, pp. 404-409 (Author Manuscript, consisting of 14 pages total) (Dec. 18, 2009).
Zapata et al, "Engineering Linear F(ab$_2$) Fragments for Efficient Production in *Escherichia coli* and Enhanced Antiproliferative Activity", Protein Engineering, vol. 8, No. 10, pp. 1057-1062, 1995.
Zhou et al., "Structural Basis for Broad and Potent Neutralization of HIV-1 by Antibody VRC01", Science, vol. 329, pp. 811-817 (Author Manuscript, consisting of 19 pages total) (Aug. 13, 2010).
Zhou et al., "Structural Definition of a Conserved Neutralization Epitope on HIV-1 gp120", Nature, vol. 445, No. 7129, pp. 732-737 (Author Manuscript, consisting of 15 pages total) (Feb. 15, 2007).
Zhu et al., "Refining Homology Models by Combining Replica-Exchange Molecular Dynamics and Statistical Potentials", Proteins, vol. 72, No. 4, pp. 1171-1188 (Author Manuscript, consisting of 33 pages in total) (Sep. 2008).
Cote et al., "Generation of Human Monoclonal Antibodies Reactive with Cellular Antigens", PNAS, vol. 80, pp. 2026-2030 (Apr. 1983).
Morrison et al., "Chimeric Human Antibody Molecules: Mouse Antigen-binding Domains with Human Costant Region Domains", PNAS, vol. 81, pp. 6851-6855 (Nov. 1984).
Carayannopoulos et al., "Recombinant Human IgA Expressed in Insect Cells", Proc. Natl. Sci. USA, vol. 91, pp. 8348-8352 (Aug. 1994).
Sather et al., "Factors Associated with the Development of Cross-Reactive Neutralizing Antibodies during Human Immunodeficiency Virus Type I Infection", Journal of Virology, vol. 83, No. 2, pp. 757-769 (Jan. 2009).
Simek et al., "Human Immunodeficiency Virus Type I Elite Neutralizers: Individuals with Broad and Potent Neutralizing Activity Identified by Using a High-Throughput Neutralization Assay together with an Analytical Selection Algorithm", Journal of Virology, vol. 83, No. 14, pp. 7337-7348 (Jul. 2009).
Doria-Rose et al., "Breadth of Human Immunodeficiency Virus-Specific Neutralizing Activity in Sera: Clustering Analysis and Association with Clinical Variables", Journal of Virology, vol. 84, No. 3, pp. 1631-1636 (Feb. 2010).
Gnanakaran et al., "Genetic Signatures in the Envelope Glycoproteins of HIV-I that Associate with Broadly Neutralizing Antibodies", PLoS Computational Biology, vol. 6, No. 10, 1000955, pp. 1-26 (Oct. 2010).
Gray et al., "Antibody Specificities Associated with Neutralization Breadth in Plasma from Human Immunodeficiency Virus Type I Subtype C-Infected Blood Donors", Journal of Virology, vol. 83, No. 17, pp. 8925-8937 (Sep. 2009).
Muster et al., "A Conserved Neutralizing Epitope on gp41 of Human Immunodeficiency Virus Type 1", Journal of Virology, vol. 67, No. 11, pp. 6642-6647 (Nov. 1993).
Zwick et al., "Broadly Neutralizing Antibodies Targeted to the Membrane-Proximal External Region of Human Immunodeficiency Virus Type I Glycoprotein gp41", Journal of Virology, vol. 75, No. 22, pp. 10892-10905 (Nov. 2001).
Trkola et al., "Human Monoclonal Antibody 2G12 Defines a Distinctive Neutralization Epitope on the gp120 Glycoprotein of Human Immunodeficiency Virus Type 1", Journal of Virology, vol. 70, No. 2, pp. 1100-1108 (Feb. 1996).
Corti et al., "Analysis of Memory B cell Responses and Isolation of Novel Monoclonal Antibodies with Neutralizing Breadth from HIV-1-Infected Individuals", PLoS One, vol. 5, No. 1, e8805, pp. 1-15 (Jan. 2010).
Wrammert et al., "Broadly Cross-Reactive Antibodies Dominate the Human B Cell Response against 2009 Pandemic H1N1 Influenza Virus Infection", J Exp Med, vol. 208, No. 1, pp. 181-193 (Jan. 17, 2011).
Huber et al., "Very Few Substitutions in a Germ Line Antibody are Required to Initiate Significant Domain Exchange", Journal of Virology, vol. 84, No. 20, pp. 10700-10707 (Oct. 2010).
Huang et al., "Structural Basis of Tyrosine Sulfation and VH-gene Usage in Antibodies that Recognize the HIV Type 1 Coreceptor-Binding Site on gp120", Proc Natl Acad Sci USA, vol. 101, No. 9, pp. 2706-2711 (Mar. 2, 2004).
Sabin et al., "Crystal Structure and Size-Dependent Neutralization Properties of HK20, a Human Monoclonal Antibody Binding to the Highly Conserved Heptad Repeat 1 of gp41", PLoS Pathogens, vol. 6, No. 11, e1001195, pp. 1-11 (Nov. 2010).
Breden et al., "Comparison of Antibody Repertoires Produced by HIV-I Infection, Other Chronic and Acute Infections, and Systemic Autoimmune Disease", PLoS One, vol. 6, No. 3, e16857, pp. 1-11 (Mar. 2011).
Nemazee et al., "Revising B Cell Receptors", J Exp Med, vol. 191, No. 11, pp. 1813-1817 (Jun. 5, 2000).
Edry et al., "Receptor Editing in Positive and Negative Selection of B Lymphopoiesis", J Immunol, No. 173, pp. 4265-4271 (2004).
Glanville et al., "Precise Determination of the Diversity of a Combinatorial Antibody Library Gives Insight into the Human Immunoglobulin Repertoire", Proceedings of the National Academy of Sciences of the United States of America, vol. 106, No. 48, pp. 20216-20221 (Dec. 1, 2009).
Zhou et al., "Distance-scaled, Finite Ideal-gas Reference State Improves Structure-derived Potentials of Mean Force for Structure Selection and Stability Prediction", Protein Sci, vol. 11, pp. 2714-2726 (2002).
International Search Report for PCT/US2012/030436 dated Oct. 29, 2012 consisting of 4 pages total.
Written Opinion for PCT/US2012/030436 dated Oct. 29, 2012 consisting of 5 pages total.

\* cited by examiner

>Vf4 Light Chain (VRC-CH30)
GACATCCAGATGACCCAGTCTCCATCGTCCTTGTCTGCATCACTCGGAGACA
GAGTCACCATCACTTGTCAGGCGAGTCGGGGCATTGGTAAAGATTTAAATTG
GTACCAGCAGAAACCGGGAAAGGCCCCTAAGTTACTGGTCTCTGATGCATCC
ATTTTGGAAGGGGGGGTCCCATCAAGGTTCAGTGGGAGTGGATTTCACCAA
AATTTTAGTCTGACCATCAGCAGCCTGCAGCCTGAGGATGTTGCGACATACT
TCTGTCAGCAGTACGAGACTTTTGGCCAGGGGACCAAAGTGGACATCAAA
>Vf4 Heavy Chain (VRC-CH30)
CAGGTGCAGCTGGTGCAGTCAGGGGCTGCCGTGAGGAAGCCTGGGGCCTC
AGTGACTGTCTCCTGCAAATTCGCTGAAGACGACGACTACTCTCCACACTGG
GTGAATCCGGCCCCTGAACACTATATTCACTTTCTACGACAGGCCCCTGGAC
AGCAACTGGAGTGGTTGGCATGGATGAACCCTACGAATGGCGCCGTCAATT
ATGCATGGCAGCTTCATGGCAGGCTCACGGCGACCAGAGACGGGTCCATGA
CTACAGCCTTTTTGGAAGTGAGGAGTCTAAGATCTGACGACACGGCCGTCTA
TTATTGTGCGAGGGCCCAGAAAAGGGGGCGGAGTGAATGGGCCTACGCCC
ACTGGGGCCAGGGAACCCCGGTCGCCGTCTCCTCA
>VRC-CH31 (vf5) Light Chain
GACATCCAGATGACCCAGTCTCCATCGTCCCTGTCTGCATCACTCGGGGACA
GAGTCACCATCACTTGCCAGGCGAGTCGGGGCATTGGCAAAGATTTAAATT
GGTACCAGCAGAAAGCGGGAAAAGCCCCTAAGTTACTGGTCTCTGATGCAT
CCACTTTGGAAGGGGGGGTCCCATCAAGGTTCAGTGGGAGTGGATTTCACC
AAAATTTTAGTCTGACTATCAGCAGCCTGCAGGCTGAGGATGTTGCAACATA
CTTCTGTCAACAATACGAGACTTTTGGCCAGGGGACCAAGGTGGACATCAAA

Figure 1G continued

>VRC-CH31 (vf5) Heavy Chain
CAGGTGCAGCTGGTGCAGTCAGGGGCTGCCGTGAGGAAGCCTGGGGCCTC
AGTGACTGTCTCCTGTAAATTCGCTGAAGACGACGACTACTCTCCATACTGG
GTGAATCCGGCCCCTGAACATTTTATTCACTTTTTGCGACAGGCCCCTGGACA
ACAACTAGAGTGGCTGGCATGGATGAACCCAACGAATGGCGCCGTTAATTA
TGCATGGTACCTTAATGGCAGGGTCACGGCGACCAGGGACAGGTCCATGAC
TACAGCCTTTTTGGAAGTGAAGAGTCTAAGATCTGACGACACGGCCGTCTAC
TATTGTGCGAGGGCCCAGAAAAGGGGGCGGAGTGAGTGGGCCTACGCCCA
CTGGGGTCAGGGCACTCCGGTCGTCGTCTCGTCA >Vf6 Light Chain (VRC-CH32)
GACATCCAGATGACCCAGTCTCCATCGTCCCTGTCTGCATCACTCGGAGACA
GAGTCACCATCACTTGCCAGGCGAGTCGGGGCATTGGCAAAGATTTAAATT
GGTACCAACAGAAACCGGGAAGAGCCCCTAAGTTACTAGTCTCTGATGCATC
CATTTTGGAAGGGGGGGTCCCAACGAGATTCAGTGGGAGTGGATTTCACCA
AAACTTTAGCCTGACCATCAGCAGCCTGCAGGCTGAGGATGTTGCAACATAT
TTCTGTCAGCAATACGAAACTTTTGGCCAGGGGACCAAGGTGGACATCAAA >Vf6 Heavy Chain (VRC-CH32)
CAGGTGCAGCTGGTGCAGTCAGGGGCTGCCGTGAGGAAGCCTGGGGCCTC
AGTGACTGTCTCCTGCAAGTTCGCTGAAGACGACGACTTCTCTCCACACTGG
GTGAATCCGGCCCCTGAACACTATATTCATTTTCTGCGACAGGCACCTGGAC
AACAACTAGAGTGGTTGGCATGGATGAAGCCTACGAATGGTGCCGTCAATT
ATGCATGGCAACTTCAGGGCAGGGTCACGGTGACCAGGGACAGGTCCCAGA
CTACAGCCTTTTTGGAAGTTAAGAATCTGAGATCTGACGACACGGCCGTCTA
TTATTGTGCGAGGGCCCAGAAAAGGGGGCGCAGCGAGTGGGCCTATGCCC
ACTGGGGCCAGGGAACCCCGGTCGTCATCTCCGCA

Figure 3C

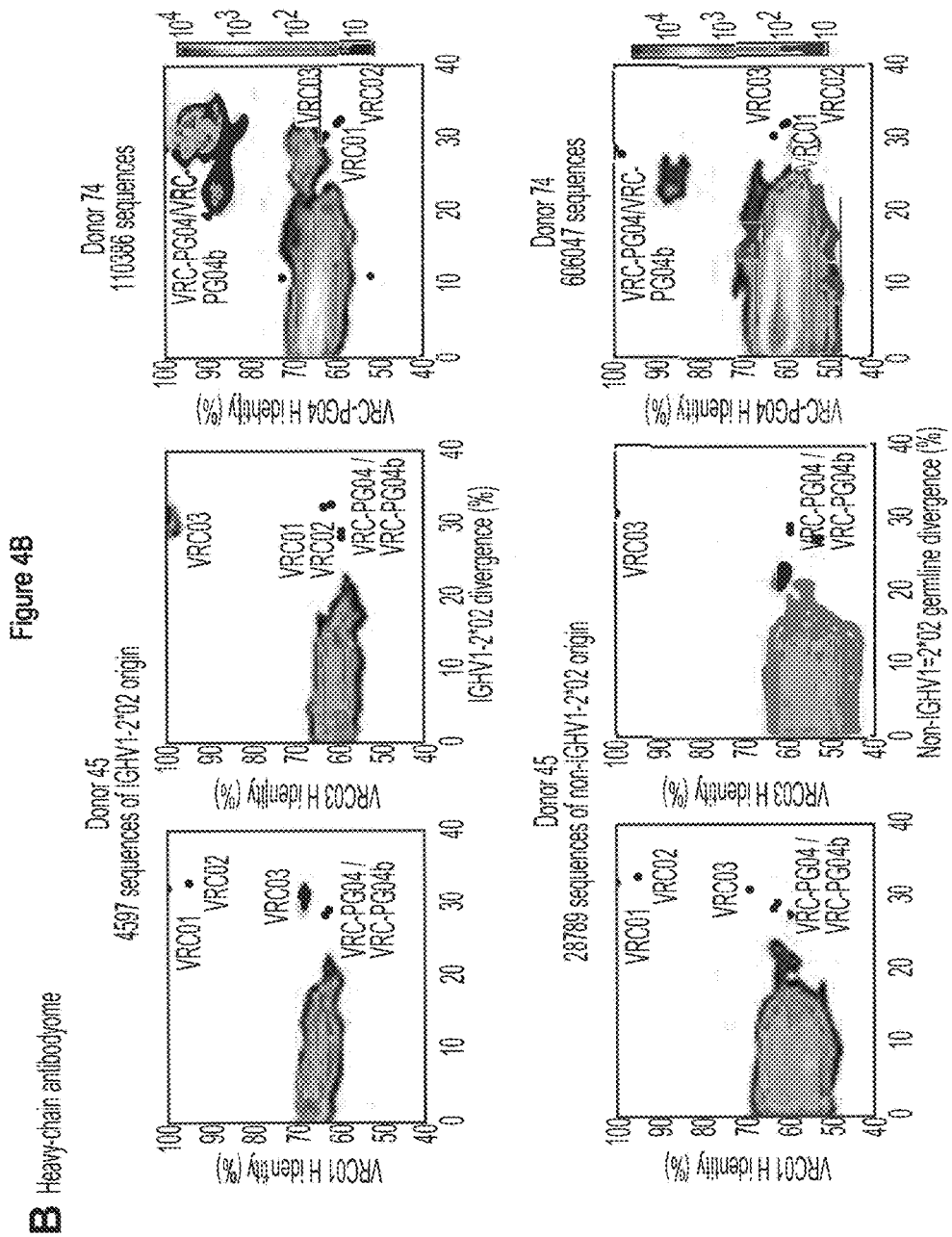

C Light-chain antibodyome

D Light-chain neutralization

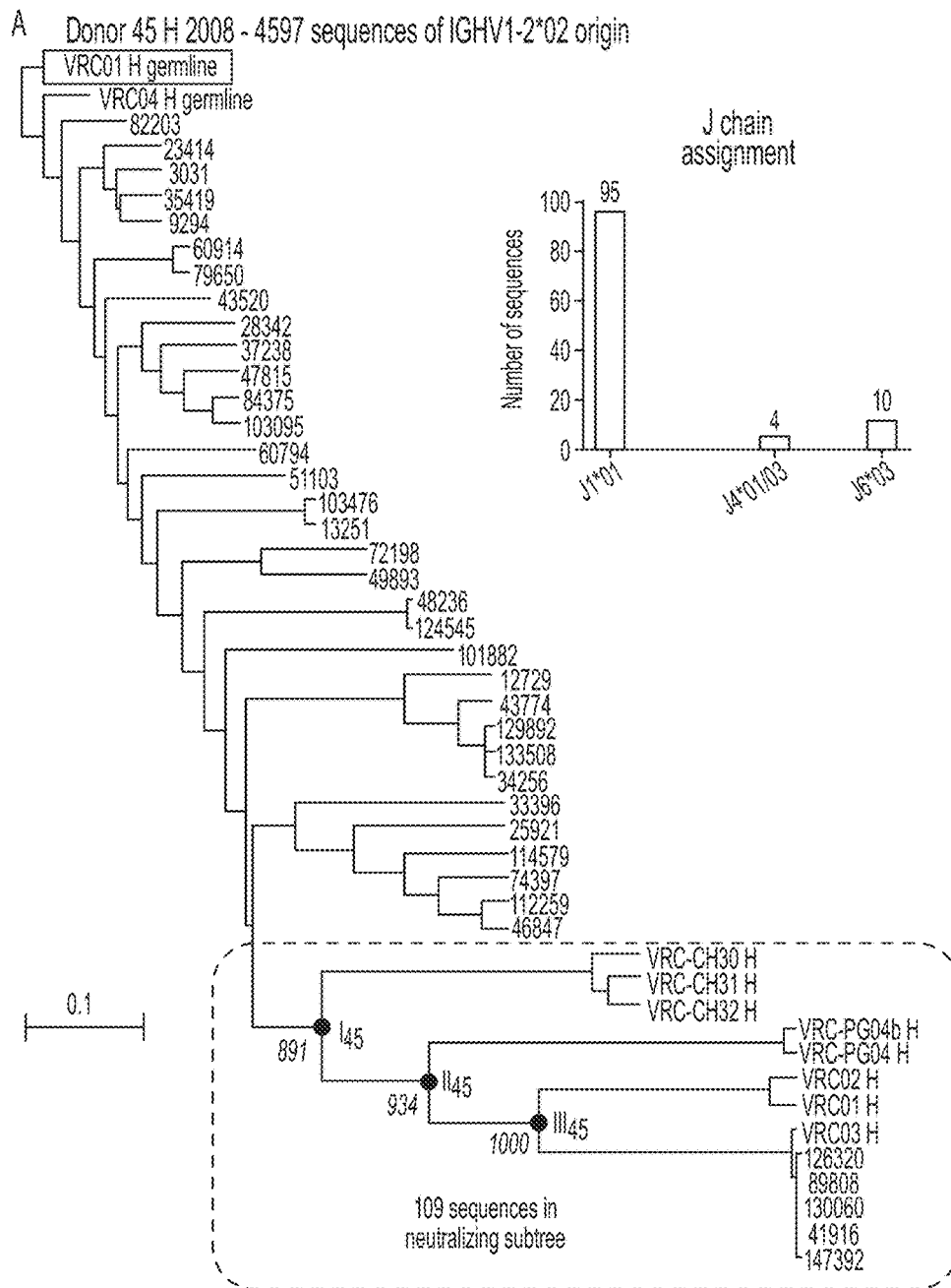

A   IGHV1-2*02 heavy chain antibodyome with grid neutralization assessment

C   Expression of grid-selected chimeric antibodies

D   Phylogeny-predicted neutralization
P-value = 0.0085

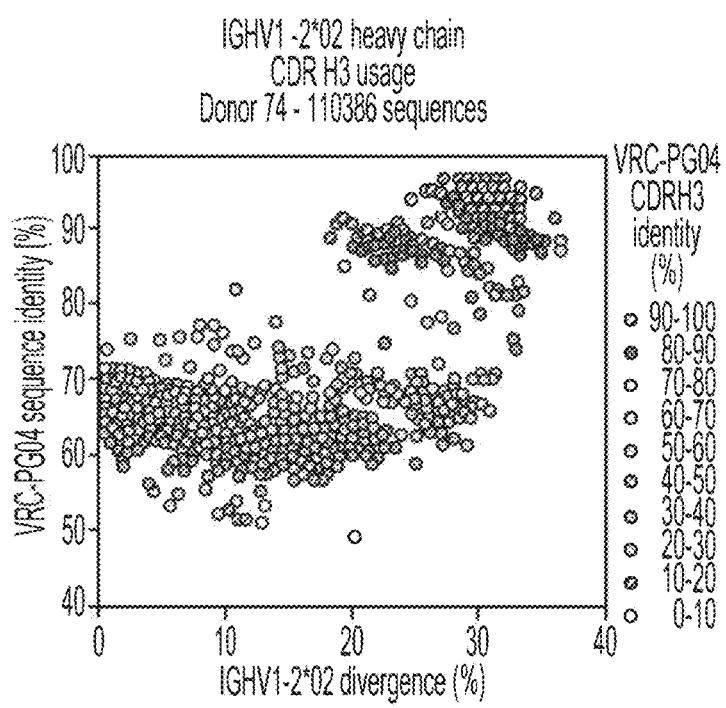

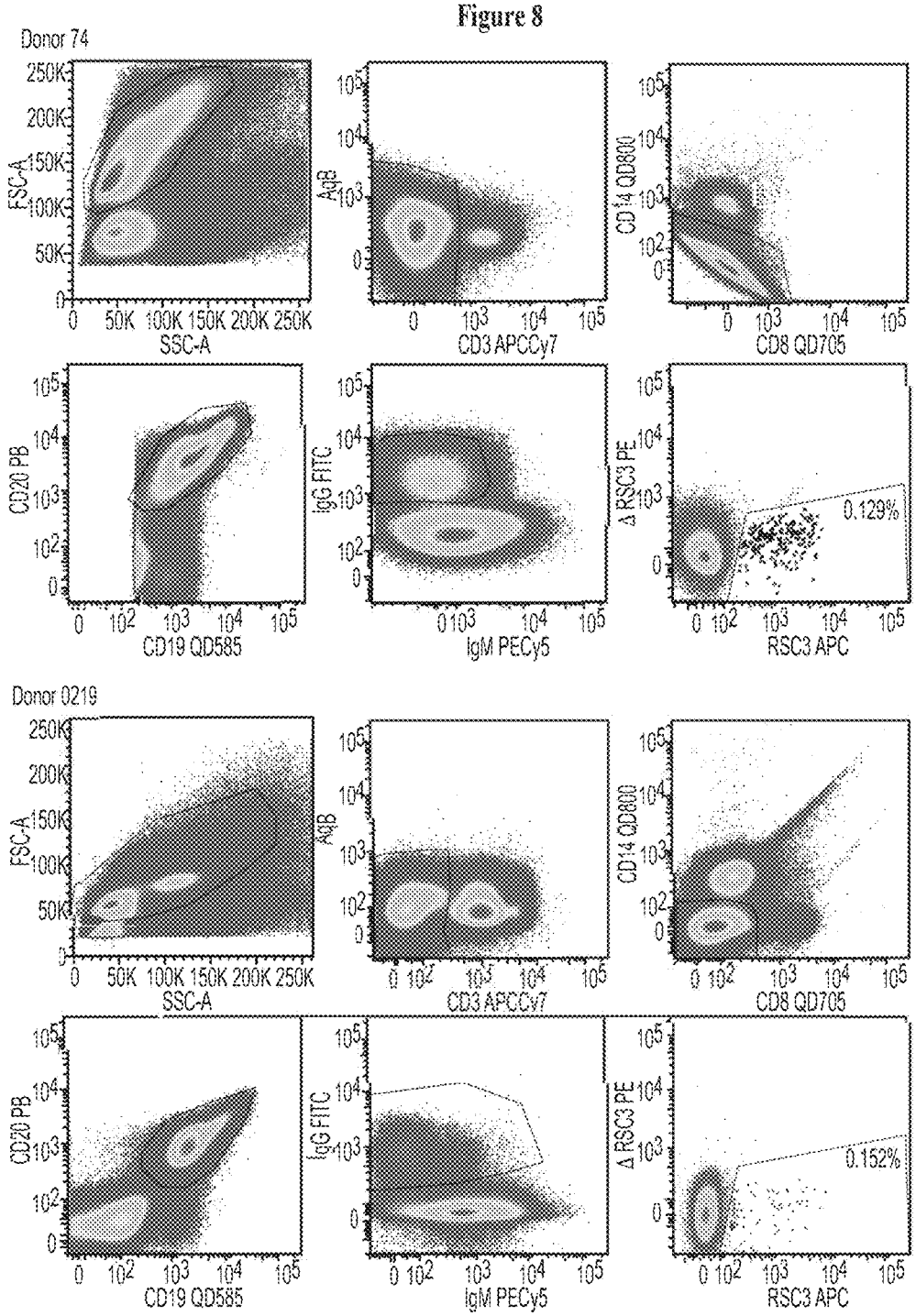

Figure 8 Continued

LSR and Aria Detector Configuration

| Laser (nm / mW) | Detector Name | Fluorochrome Detected | Dichroic LP Filter | BP Filter |
|---|---|---|---|---|
| Blue 488 / 50 | FSC | Forward Scatter | | |
| Blue 488 / 50 | B710 | Cy55PerCP*, PerCP** | 685LP | 710/50 |
| Blue 488 / 50 | B515 | FITC, CFSE, GFP, Alexa 488, GrViD, Cy2 | 505LP | 515/20 |
| Blue 488 / 50 | SSC | Side Scatter | 488LP | |
| Green 532 / 150 | G780 | Cy7PE, Alexa 750PE | 740LP | 780/40 |
| Green 532 / 150 | G710 | Cy55PE, Alexa 700PE | 690LP | 710/50 |
| Green 532 / 150 | G660 | Cy5PE, Alexa 647PE, 7AAD | 640LP | 660/40 |
| Green 532 / 150 | G610 | TRPE, TR, OrViD, RFP, Alexa 594, PI, EMA | 600LP | 610/20 |
| Green 532 / 150 | G560 | PE, Cy3, Alexa 532 | empty | 575/25 |
| Green 532 / 150 | Empty | na | | |
| Green 532 / 150 | Empty | na | | |
| Green 532 / 150 | Empty | na | | |
| Red 628 / 200 | R780 | Cy7APC, Alexa 750APC | 740LP | 780/60 |
| Red 628 / 200 | R710 | Cy55APC, Alexa 660, 680, 700 | 685LP | 710/50 |
| Red 628 / 200 | R660 | APC, Alexa 647 | empty | 660/20 |
| Violet 408 / 100 | V800 | QD800 | 740LP | 780/60 |
| Violet 408 / 100 | V705 | QD705 | 670LP | 705/70 |
| Violet 408 / 100 | V655 | QD655 | 630LP | 660/40 |
| Violet 408 / 100 | V605 | QD605 | 595LP | 605/30 |
| Violet 408 / 100 | V585 | QD585 | 570LP | 585/42 |
| Violet 408 / 100 | V565 | QD565 | 557LP | 560/40 |
| Violet 408 / 100 | V545 | QD545, Pacific Orange, Aqua Blue*** | 535LP | 560/40 |
| Violet 408 / 100 | V450 | CBlue, ViViD, PacBlue | empty | 450/50 |

\*    Conjugate is incompatible with QD705
\*\*   Required filter change: 640LP + 660/50 and is incompatible with QD705
\*\*\*  Required filter change: 505LP + 515/20
Complete reference list: http://www3.nimd.nih.gov/labs/aboutlabs/VRC/PDF/table1commonfluorochromes1.pdf Figure 15
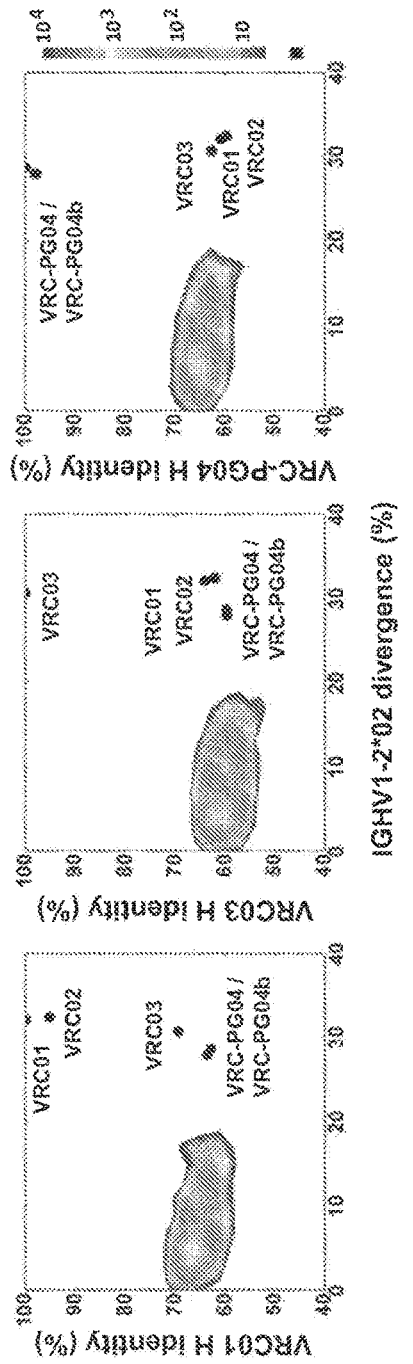
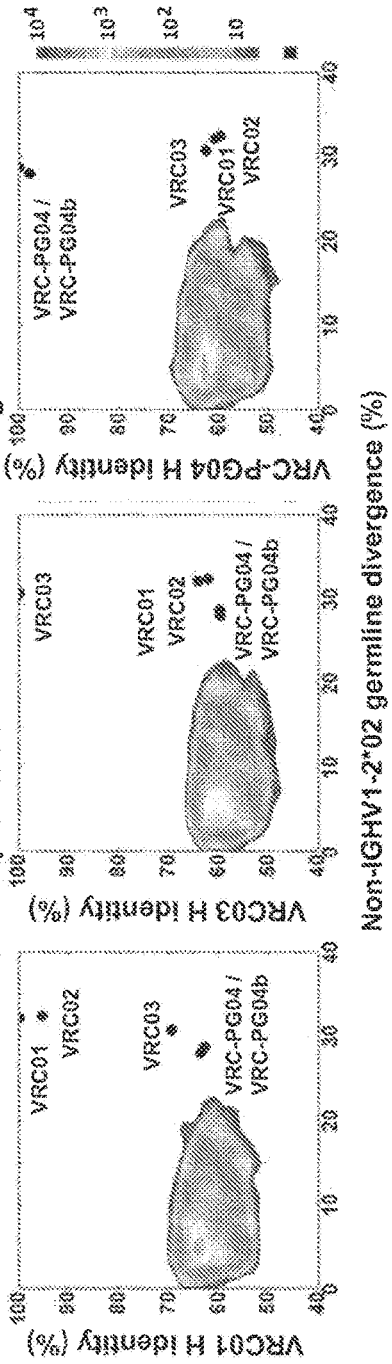

Figure 19

```
Heavy chain  ----------FR1------------------    CDR1    -------FR2----         CDR
IGHV1-2*02   QVQLVQSGAEVKKPGASVKVSCKASGYTFTG......YYMHWVRQAPGQGLEWMGWINPNSGGTN CDRH3-1 (J4*02)
143251_3     QVQLVQAGGGVKKPGASVTLSCKTADEDVFD.....AAYMHWVRQAPGQTFEWLGWMKPVTGAVS CDRH3-2 (J6*02)
121325_4     QVQLVAGRGGVKKPGASVTLSCKTADEDVFD.....AAYMHWVRQAPGQTFEWLGWMKPVTGAVN CDRH3-3 (J2*01)
13826_2      QVQLVQSEAEVKKPGASMVSCETADEDIFU.....AAYMHWVRQAPGQTFEWLGWMKPVTGAVN
179400_4     QVQLVQSGAEVKKPGASVTLSCKTADEDVFD.....AAYMHWVRQAPGQTFEWLGWMKPVTGAVS
167612_4     QVQLVQAGGGVKKPGASVTLSCKTADEDVFD.....AAYMHWVRQAPGQTFEWLGWMKPVTGAVN
164922_3     QVQLVQSGAVKKPGSSVKVSCKASGYIFTG......YYIHWIRQAPGQGLEWMGWINPSTGDTK
166726_3     QVQLVQSGAEVKKPGASVKVSCKASGYTFTG......YYMHWVRQAPGQTFEWLGWMKPVTGAVN
179500_4     QVQLVQSGSAMKKPGASVRVSCWTSEDIFDT.....TELIYWVRQAPGQGLEWIGWKIVSGTVN CDRH3-4 (J2*01)
95589_2      QVQLVQSGGGVKKPGASASFSCRTSEDPFDN.PFFDSEFMHWVRLTPGQRPEWMGWINPRSGGVN CDRH3-5 (J2*01)
24972_2      QVQLVQSGGGVKKPGTSASFSCRTSDDIYDN.EFFDSAFMHWVRLIPGQRPEWMGWINPRSGAVN CDRH3-6 (J2*01)
10731_1      QVQLVQSGSGVKKPGASVRVSCRASEDLFGDEIIYDDEVIHWLRQVPGQRPEWMGWIRPKTGARN
```

Figure 19 Continued

```
2              --------FR3-------------        CDR3        -----FR4----
Y.AQKFQGRVTMTRDTSISTAYMELSRLRSDDTAVYYCAR

Y.ARKFQGRVSFYRTRELGIAYMDLRNLRFDDTAVYYCARVGGAADD..SGYFEPPS..DYWGQGTLVTVSS

Y.ARKFQGRVSFYRTRELGIAYMDLRNLRFDDTAVYYCARAGVWFGELLPHWSGVGGGMDVWGQGTTVTVSS

Y.ARKFQGRISFYRTRELATAYMDLRDLRFDDTAVYFCARKTAGDVSGD....NRGYPFDLWGRGSRVIVSS
Y.ARKFQGRVSFYLTRELGIAYMDLRNLRFDDTAVYFCARKTAGDVSGD....NRGYPFDLWGRGSRVIVSS
Y.ARKFQGRVSFYRTRELGIAYMDLRNLRFDDTAVYFCARKTAGDVSGD....KRGFPFDLWGRGSRVIVSS
Q.ARQFQGRVSFYRTRELGIAYMDLRDLKFDDTAVYFCARKTKGDVSGD....DRGFPFDLWGRGTRVIVSS
Y.ARQFQGRVSFYRTRELGIAYMDLRDLKFDDTAVYFCARKTKADVSGD....DRGFFFDLWGRGTRVIVSS
Q.ARQFQGRVSFYRTRELGIAYMDLRDLKFDDTAVYFCARKTKGDVSGD....DRGFPFDLWGRGTRVIVSS

Y.AGQFRPRMSMWRDRELSTAYMELRDLTPADTGLYFCARRKEDD........YDWYYDLWGRGAHIIVSA

YA.RQLQPRVSMYRDRDLSTAYMEFKSLTSADTGTYFCARKKRGDG.......FNLYFDLWGRGSQVIVSS

QA.RQFQPRISLTRDRALSTAYLDLNSLTSADSGTYFCARQTFKPDFYF...AQGWSFNLWGRGAHFIVSS
```

Figure 19 Continued

CDRH3-7 (J2*01)

| ID | Sequence 1 | Sequence 2 |
|---|---|---|
| 149768_4 | QVQLVQSGAEVKKPGSSVKVSCKASGGTFRH | ....SPISWVRQAPGQGLEWIGWVKAVSGAVNY |
| 120119_4 | QVQLVQSGAEVKKPGSSVKVSCKVSGGFTS | ....YAVYWVRQAPGQGLEWIGWVKAVSGAVNY |
| 186275_2 | QVQLVQSGAEVKKPGASVKVSCKASGYTFTG | ....YYMHWVRQAPGQGLEWIGWVKTVSGAVNY |
| 86984_2 | QVQLVQSGAEVKKPGASVQVSCKASGYPFTK | ....YYMHWVRQAPGQGLEWIGWVKAVSGAVNY |
| 196147_4 | QVQLVQSGAEVKKPGASVKVSCKASGYTFTS | ....YMHWVRQAPGQGLEWIGWVKPVTGAVNY |
| 195462_4 | QVQLVQVRDEVKKPGSMKVSCTASRGTFSS | ....YAISWVRQAPGQGLEWIGWVKTVTGAVNY |
| 43567_2 | QVQLVQSGAEVKKPGASVKVSCKASGYTFTS | ....YDINWVRQAPGQGLEWIGWVKTVTGAVNY |
| 31458_3 | QVQLVQSGAEVKKPGASVKVSCKASGYTFTT | ....YGISWVRQAPGQGLEWIGWVKTVTGAVNY |
| 127586_4 | QVQLVQSGAEVKKPGASVKVSCKASGYTFTT | ....YGISWVRQAPGQGLEWIGWVKTVTGAVNY |
| 149590_4 | QVQLVQSGSGVKKVGASVRVSCNTSEDIFER | ....TELIHWVRQAPGQGLEWIGWVKAVSGAVNY |
| 53821_1 | QVQLVQSGSAMKKPGASVRVSCNTSEDIFDT | ....TELIHWVRQAPGQGLEWIGWVKAVSGAVNY |
| 86277_2 | QVQLVQSGSGVKKLGASVPVSCNTSEDIFER | ....TELIHWVRQAPGQGLEWIGWVKAVSGAVNY |
| 165478_2 | QVQLVQSGSGVKKPGASVRVSCNTSEDIFEG | ....SELIHWVRQAPGQGLEWIGWVKTVTGAVNY |
| 71632_2 | QVQLVQSGAEVKRPGASVKVSCNTSEDIFER | ....TELIHWVRQAPGQGLEWIGWVKTVSGAVNY |
| 7BC-PG04 | QVQLVQSGSGVKKPGASVRVSCNTSEDIFER | ....TELIHWVRQAPGQGLEWIGWVKTVTGAVNY |
| 61048_1 | QVQLVQSGAEVKKPGASVRVSCNTSEDIFEK | ....SELIHWVRQAPGQGLEWIGWVKTVTGAVNY |
| 69713_1 | QVQLVQSGSGVKKPGASVRVSCNTSEGIFEK | ....SELIHWVRQAPGQGLEWIGWVKTVTGAVNY |
| 9815_2 | QVQLVQSGSAMKKPGASVRVSCNTSEDIFDT | ....TELIYWVRQAPGQGLEWIGWVKIVSGTVNY |

CDRH3-8 (J2*01)

| ID | Sequence 1 | Sequence 2 |
|---|---|---|
| 186640_2 | QVQLVQSGAEVKKPGSSVRVSCNTSEDIFER | ....TELIHWVRQAPGQGLEWIGWVKTVTGAVNY |
| 135083_3 | QVQLVQSGSGVKKLGASVRVSCNTSEDIFER | ....TELIHWVRQAPGQGLEWIGWVKAVTGTVNY |
| 151901_4 | QVQLVPSGSGVKKPGASVRVSCNTSEDIFER | ....TELIHWVRQAPGQGLEWIGWVKTVTGAVNY |
| 164202_3 | QVQLVQSASGVRPGASVRVSCNTSEDIFER | ....SELIYWVRQAPGRGLEWIGWIKIVSGAVNY |
| 96298_1 | QVQLVQSGLEVKKPGASVRVSCNTSEDIFDT | ....TELIYWVRQAPGQGLEWIGWVKIVSGTVNY |
| 57729_2 | QVQLVQSGAEIKKPGSSVRVSCKTSGGSFNN | ....YAIHWVRQAPGQGLEWIGWVKTVSGTVNY |
| 18278_1 | QVQLVQSGSAMKKPGASVRVSCNTSEDIFER | ....TELIYWVRQAPGRGLEWIGWVKTVSGTVNY |
| 17720_4 | QVQLVQSGAEVKKPGASVRVSCNTSEDIFDT | ....TELIYWVRQAPGQGLEWIGWVKIVSGTVNY |

CDRH3-9 (J4*01)

| ID | Sequence 1 | Sequence 2 |
|---|---|---|
| 47890_1 | QVQLVQSGSAMKKPGASVRVSCNTSEDIFDT | ....TELIYWVRQAPGQGLEWIGWVKTVSGTVNY |

Figure 19 Continued

```
GSLDFRHRVSLTRDRDLSTAHMDIRGLTQDDTATYFCARQKFAR......GDQGWFFDLWGRGTLIVVSS
GSLDFRHRVSLTRDRDLFTAHMDIRGLTQDDTAIYFCARQKFAR......GDQGWFFDLWGRGTLIVVSS
GSLNFRHRVSLTRDRDLFTAHMDIRGLTQGDTATYFCARQKFAR......GDQGWFFDLWGRGTLIVVSS
GSLDFRHRVSLTRDRDLSTAHMDIRGLTQDDTATYFCARQKFAR......GDQGWFFDLWGRGTLIVVSS
GSPNFRHRVSLTRDRDLFTAHMDIRGLTQGDTATYFCARQKYA......GGQGWYFDLWGRGTLIVVSS
GSAYFRHRVSLTRDRDLFTAHMDIRGLTQGDTATYFCARQKFYK......GGQGWYFDLWGRGTLIVVSS
GSSDFRQRVSLTRDRDLFTAHMDIRGLTQGDTATYFCARQKFYA......GGQGWYFDLWGRGTLIVVSS
GSSDFRQRVSLTRDEDLFTAHMDIRGLTQGDTATYFCARQKFYA......GGQGWYFDLWGRGTLIVVSS
G.HQISDRVSLTRDRDLFTAHMDIRGLTQGDTATYFCARQKFYA......GGQGWYFDLWGRGTLIVVSS

GSLDFRHRVSLTRDRDLSTAHMDIRGLTQDDTATYFCARQKFAR......GDQGWFFDLWGRGTLIVVSS
GSLDFRHRVSLTRDRDLSTAHMDIRGLTQDDTATYFCARQKFAR......GDQGWFFDLWGRGTLIVVSS
GSAYFRHRVSLTRDRDLFTAHMDIRGLTQGDTATYFCARQKFMS......GGQGWYFDLWGRGTVIVVSS
GSPNFRHRVSLTRDRDLFTAHMDIRGLTQGDTATYFCARQKFER......GGQGWYFDLWGRGTLIVVSS
GSPDFRQRVSLTRDRDLFTAHMDIRGLTQGDTATYFCARQKFYT......GGQGWYFDLWGRGTLIVVSS
GSSDFRQRVSLTRDRDLFTAHMDIRGLTQGDTATYFCARQKFER......GGQGWYFDLWGRGTLIVVSS
G.HQISDRVSLTRDRDLFTAHMDIRGLTQGDTATYFCARQKFER......GGQGWIFDLWGRGTLIAVSS
ASLDFRNRISLSRDRDLFTAHMDIRGLTQGDTATYFCARQKFYA......GGQGWYFDLWGRGTLIVVSS

GSPNFRHRVSLTRDRDLFTAHMDIRGLTQGDTATYFCARQKFESRYS....GDQGSYFDLWGRGTLIIVSS
GSLNFRQRVSLTRDRDLFTAHMDIRGLTQGDTATYFCARQKFE.KYT....GGQGWYFDLWGRGTLIVVSS
GSLDFRHRISLTRDRDLFTAHMDIRGLTQGDTATYFCARQKFESRIT....GGQGWYFDLWGRGTHIVVSS
GSVDFRDRVSLTRDRDLFTAHMDIRGLTQDDTATYFCARQKFASRYS....GDQGSYFDLWGRGTLIIVSS
ASLDFRNRISLSRDRDLSTAHMDIRGLTQDDTATYFCARQKFASRYS....GDQGSYFDLWGRGTLIIVSS
ASLDFRNRISLSRDRDPSTAYMDIRGLTQDDTATYFCARQKFASRYS....GDQGSYFDLWGRGTLIVVSS
GSSDFRNRISLTRDRDLSTAHMDIRGLTQDDTATYFCARQKFESLYS....DDQGSYFDLWGRGTLIIVSS
ASLDFRNRISLSRDRDLSTAHMDIRGLTQDDTATYFCARQKFESRYT....GGQGWYFDLWGRGTHIVVSS

ASLDFRNRISLSRDRDLSTAHMDIRGLTLDDTGIYYCARGPMGG...........SHVYWGQGSLVTVSS
```

Figure 20

Blue: junctions
Red: mutations

CDRH3 class 1

```
              HV1-2*02                   HD3-22*01                                    HJ*02
              TGTGCGAGAGA     GTATTACTATGATAGTAGTGGTTATTACTAC AGTACTTGACTACTGGGGCCAGGGAACCCTGGTCACCGTCTCCTCA
              C A R           Y Y Y D S S G Y Y Y   S T L T T G A R E P W S P S P S
143251_3 (27%) TGTGCGAGAGATTCGGGTTATACCCCGCCGAGCGACTACTGGGGCCAGGGCACCCTGGTCACCGTCTCCTCA
              C A R D S G Y T P P S D Y W G Q G T L V T V S S
```

CDRH3 class 2

```
              HV1-2*02                                                HD3-10*01                                                        JH6*02
              TGTGCGAGAGA     GTATTACTATGATTCGGGGAGTTATTATAAC          ATTACTACTACTACGGTATGGACGTCTGGGGCCAAGGGACCACGGTCACCGTCTCCTCA
              C A R           V L L H F G E L L   T                    Y Y Y Y Y G M D V W G Q G T T V T V S S
121325_4 (27%) TGTGCGAGAGCTGGGGTCAATTTTGGGGAGTTATTAATTGGTCGGCTACTACTACGGTATGGACGTCTGGGGCCAAGGGACCACGGTCACCGTCTCCTCA
              C A R A G V N F G E L L I N W S A T T T V W T S G P R D H G H R S P S
```

CDRH3 class 4

HV1-2*02
TGTGCGAGAGA
 C  A  R

HD4-17*01
TGACTACGGTGACTAC
 D  Y  G  D  Y
HD4-23*01
TGACTACGGTGGTAACTCC
 D  Y  G  G  N  S

HJ2*01
GTACTGGTACTTCGATCTCTGGGGCCGTGGCACCCTGGTCACTGTCTCCTCA
 Y  W  Y  F  D  L  W  G  R  G  T  L  V  T  V  S  S

V74-08-95589_2 (318) TGCGCGAGAAGAAAAGAGGAGGACTACGATTACGATTACGATTACGACTACGGTGGGCCGTGGCCATATCATTGTCTCCGCA
                     C  A  R  R  K  E  D  D  Y  D  Y  D  Y  D  Y  D  W  Y  Y  D  L  W  G  R  G  A  I  I  I  V  S  A

Figure 20 Continued

Blue: junctions
Red: mutations

CDRH3 class 5

```
      HV1-2*02                                   HD5-24*01
      TGTGCGAGAGA                               GTAGAGATGGCTACAATTAC
      C  A  R                                    R  D  G  Y  N  Y
                                                                                    HJ2*01
                                                                    CTACTGGTACTTCGATCTCTGGGGCCGTGGCACCCTGGTCACTGTCTCCTCA
                                                                     Y  W  Y  F  D  L  W  G  R  G  T  L  V  T  V  S  S
V74-08-24972_2 (29%) TGTGCGAGAAAGAAAAGGTGGAGAGGCTTCAATCTCTATTTCGATCTCTGGGGCCGTGGCACCCAAGTCATCGTCTCCTCA
                     C  A  R  K  K  R  W  R  G  F  N  L  Y  F  D  L  W  G  R  G  Q  V  I  V  S  S
```

CDRH3 class 6

```
      HV1-2*02                                   HD2-21*01
      TGTGCGAGACA                               AGCATAATGTGTGGTGATTGCTATGCC
      C  A  R                                    A  Y  C  G  D  C  Y  A
                                                                                                HJ2*01
                                                                            CTACTGGTACTTCGATCTCTGGGGCCGTGGCACCCTGGTCACCGTCTCCTCA
                                                                             Y  W  Y  F  D  L  W  G  R  G  T  L  V  T  V  S  S
V74-08-10731_1 (27%) TGCGCGCGGCAGACAGAGAAGTTTGATTTCAGACTTTGAGTTTCAGTTTCAGATCTGGGGCCAGGGCACCGCGGCGCCACTTAATCGTCTCCTCA
                     C  A  R  Q  T  E  K  F  D  F  F  A  D  Q  G  W  S  F  N  L  W  G  R  G  A  H  F  I  V  S  S
```

Blue: junctions
Red: mutators
.: gaps

CDRH3 class 9

```
HV1-2*02
TGTGCGAGA
 C  A  R               HD3-16*01
GTATTATGATTATGTTTGGGGGAGTTATAGTTATACC
 Y  Y  D  Y  V  W  G  S  Y  S  Y  T
                                       HJ4*01
                   ACTACTTTGACTACTGGGGCCAAGGAACCCTGGTCACCGTCTCCTCA
                    T  T  L  T  T  G  Q  G  T  L  V  T  V  S  S
                    Y  F  D  Y  W  G  Q  G  T  L  V  T  V  S  S
```

```
47890_1(33%)
TGTGCGAGAGGACTGATGGGGTGCAGTAGTGGCTCACATGTATACTACTACTACGGTATGGACGTCTGGGGCCAAGGGACCACGGTCACCGTCTCCTCA
 C  A  R  G  L  M  G  C  S  H  V  Y  Y  Y  Y  G  M  D  V  W  G  Q  G  T  T  V  T  V  S  S
```

Figure 22

CDRH3 - class 3 lineage
153567_4 (5.4%)   QVQLVQSGAEVKKPGASVKVSCKASGYT.FTGYYIHWVRQAPGQGLEWMGWINP
37118_2 (10.1%)   QVQLVQSGAELKKPGASVKVSCEASGYS.FTDHMIHWVRQAPGQGLEWLGWMNP
130162_2 (12.8%)  QVQLVQSGAEVKKPGASVKVSCKASGYT.FTGYYIHWMRQAPGQGLEWMGWINP
61143_3 (18.2%)   QVQLVQSGAEVKKPGASVKVSCKASGYN.FTGYYLHWVRQAPGQTFEWLGWMKP
13826_2 (25.7%)   QVQLVQSEAEVKKPGASMTVSCETADEDIFDAAYMIHWVRQAPGQTFEWLGWMKP CDRH3 - class 6 lineage
48760_3 (10.8%)   QVQLVQSGAEVKKPGASVKVSCKASG......YTFTDYYLHWVRQAPGQGLDWVG
6019_2 (15.9%)    QVQLVQSGAEVRKPGASVRVSCKASG......YTFTAYYIHWVRQAPGQGLEWMG
170172_3 (19.9%)  QVQLVQSGAEVKKPGASVKVSCKASG......YTFTDYYIHWLRQVQGRDLSGVG
10731_1 (26.7%)   QVQLVQSGSGVKKPGASVRVSCRASEDLFGDEIIYDDEVIHWLRQVPGQRPEWMG CDRH3 - class 7 lineage
92019_2 (0.7%)    QVQLVQSGAEVKKPGASVKVSCKASGCTFTG.YYMHWVRQAPGQGLEWMGWINP
99963_4 (6.4%)    QVQLVHSGAEVKKPGASMKVSCKTSGYSFTG.YYMHWVRQAPGQGLEWMGWINP
91421_3 (16.6%)   QVQLVQSGTELRKPGASVKVSCKASGYTFSG.SYIHWVRQAPGQGLEWVGWINP
86984_2 (22.0%)   QVQLVQSGAEVKKPGASVQVSCKASGYPFTK.YYMHWVRQAPGQGLEWIGWVKA
149590_4 (30.1%)  QVQLVQSGSGVKKVGASVRVSCWTSEDIFERTELIHWVRQAPGQGLEWIGWVKA CDRH3 - class 8 lineage
15020_3 (4.7%)    QVQLVQSGAEVKKPGASVKVSCKASGYTFTA.YYMHWLRQAPGQGLEWMGWIN
161449_2 (10.8%)  QVQLVQSGAEVKKPGASVKVSCKGSGFPFN..YYIHWLRQAPGQSLEWMGWIN
3086_2 (13.9%)    QVQLVQSGTEVQKPGASVKVSCKAFGYSFTD.YYVYWVRQAPGQGLEYVAWIN
157359_4 (15.5%)  QVQLVQSGAEMKKPGASVKLSCMTSGYVFTD.FYIHWVRQAPGQGLEWMGWIN
151901_4 (31.4%)  QVQLVPSGSGVKKPGASVRVSCWTSEDIFERTELIHWVRQAPGQGLEWIGWVK

Figure 22 Continued

```
NSGATNYAQKFQGRLTIARDTSISTAYMDLRNLRFDDTAVYFCARKTAGDVSGDNRGYFFDLGRGSRVIVSS
NRGDTAYAQTFLGRVTMTRDTSINTAYMELSRLTSDDTAVYFCARKTAGDVSGDKRGFFFDLGRGSRVIVSS
NSGAVSYARKFQGRVSFLHDQGIRMAYMDLRNLRFDDTAVYFCARKTAGDVSGDNRGYFFDLGRGSRVIVSS
VTGAVSYARKFQGRVSFYMTRELGMAYMDLRNLRFDDTAVYFCARKTAGDVSGDNRGYFFDLGRGSRVIVSS
VTGAVNYARKFQGRISFYRTRELAIAYMDLRDLRFDDTAVYFCARKTAGDVSGDNRGYFFDLGRGSRVIVSS

WINPNSGGTNYAQKFQGRVAMTRDTSLSSVYLDMSLTSADSGTYFCARTFKPDFYFADQGWSFNLGRGAHFIVSS
WIRPKNGGRNQARQFQPRISLTRDRALNTAYLDMSLTSADSGTYFCARTFKPDFYFADQGWSFNLGRGAPVIVSS
WIRPRTGARNQARQFQPRISLTRDRALSTAYLDMSLTSADSGTYFCARTFKPDFYFADQGWSFNLGRGAHFIVSS
WIRPKTGARNQARQFQPRISLTRDRALSTAYLDMSLTSADSGTYFCARTFKPDFYFADQGWSFNLGRGAHFIVSS

NSGGTNY.AQKFQGRVTMTRDTSISTAYMELSRLRSDDTAVYYCARKFARGDQGWFFDLGRGTLIVVSS
SSNDTNY.AQKFQGRVTMTRDTSINTAYMELSRLRSGDTAIYFCARKFYAGGQGRYFDLGRGTLIVVSS
SSGATQC.AKKFQDKVTMTRDTTNNTVIMEVNRLISDDTATYFCARKFARGDQGWFFDLGRGTLIVVSS
VSGAVNYGSLDFRHRVSLTRDRDLSTAHMDIRGLTQDDTATYFCARKFARGDQGWFFDLGRGTLIVVSS
VSGAVNYGSLDFRHRVSLTRDRDLFTAHMDIRGLTQDDTATYFCARKFYAGGQGWYFDLGRGTLIVVSS

PHSGGTNF.AQKFQGRVTMTRDTSITTAYMELSRLRSDDTATYFCARKFASRYSGDQGSYFDLGRGTLIVVSS
PDTGGSNS.AQKFLGRVTLTRDTSITTAYMEMTRLTYDDTAIYYCASRNLRVAIVATKAHTSIGRGTLIVVSP
PSNGYFKY.AQKFQDWVTLTRDSSINTAYLQLAKVTSDDTAIYYCARKFASRYSGDQGSYFDLGRGTLIVVSS
PGTGGTIS.APRFLGRVTLTRDTSISAAYIEINRVTIDDTATYFCARKFASRYSGDQGSYFDLGRGTLIVVSS
TVTGAVNFGSLDFRHRISLTRDRDLFTAHMDIRGLTQGDTATYFCARKFESRYTGGQGWYFDLGRGTHIVVSS
```

Figure 24 Continued

```
VRC01   QVQLVQSGGQMKKPGESMRISCRASGYEF.IDCTINWIRLAPGKRPEWMGWLKPRGGAVNY.A
        EPLQGRVTMTRD......VYSDTAFLEIRSLTVDDTAVYECTRGKNCDYNW
        DFEHWGRGTPVTVSS

VRC02   QVQLVQSGGQMKKPGESMRISCQASGYEF.IDCTINWVRLAPGRRPEWMGWLKPRGGAVNY.A
        EPLQGRVTMTRD......VYSDTAFLEIRSITADDTAVYYCTRGKNCDYNW
        DFEHWGRGTPVTVSS

VRC03   QVQLVQSGAVIKTPGSVKISCRASGYNF.RDYSIHWVRLIPDKGFEWIGWIKPIWGAVSY.A
        EQLQGRVSMTRQLSQDPDDMGVAYMEFSGLTPADTAEYFCVRRGSCDYCGDFPWQ
        WGQGTMVTVSS

57203   QVQLVQSGTEVKKPGASV MVTCKASGYSF NDYYVNWVRQAPGQGLEWMGWINPKTGDTNY
        ARKFQGRVSMTRD TEITTAYLELNSLITSDDTAVYYCVRGARGMPKGAF
        DIWGQGTLVIVSS

VRC01   QVQLVQSGGQMKKPGESMRISCRASGYEF.IDCTINWIRLAPGKRPEWMGWLKPRGGAVNY.A
        EPLQGRVTMTRD......VYSDTAFLEIRSLTVDDTAVYECTRGKNCDYNW
        DFEHWGRGTPVTVSS
```

7.454 sequencing with genomic/structural motif to identify neutralizing antibodies directly from B cells in blood

Figure 24 Continued

VRC02
```
QVQLVQSGGQMKKPGESMRISCQASGYEF.IDCTLNWVRLAPGRPEWMGWLKPRGAVNY.A
RPLQGRVTMTRD.......VYSDTAFLELRSLTADDTAVYYCTRGKNCDYNW
DFEHWGRGTPVTVSS
```

VRC03
```
QVQLVQSGAVKTPGSSVKISCRASGYNF.RDYSIHWVRLIPDKGEWIGWIKPIWGAVSY.A
RQLQGRVSMTROISQDPDDWGVAYMEFSGLTPADTAEYFCVRRGSCDYCGDFPWQ
YWGQGTVVVSS
```

57203
```
QVQLVQSGTFVKKPGASVMVCKASGYSFNDYYVNWVRQAPGQGLEWMGWINPKTGDTNY
ARKFQGRVSMTRD                  TEITTAYLELNSLTSDDTAVYYCVRGARGMPKGAF
DIWGQGTLVIVSS
```

7,454 sequencing with genomic/structural motif to identify neutralizing antibodies directly from B cells in blood

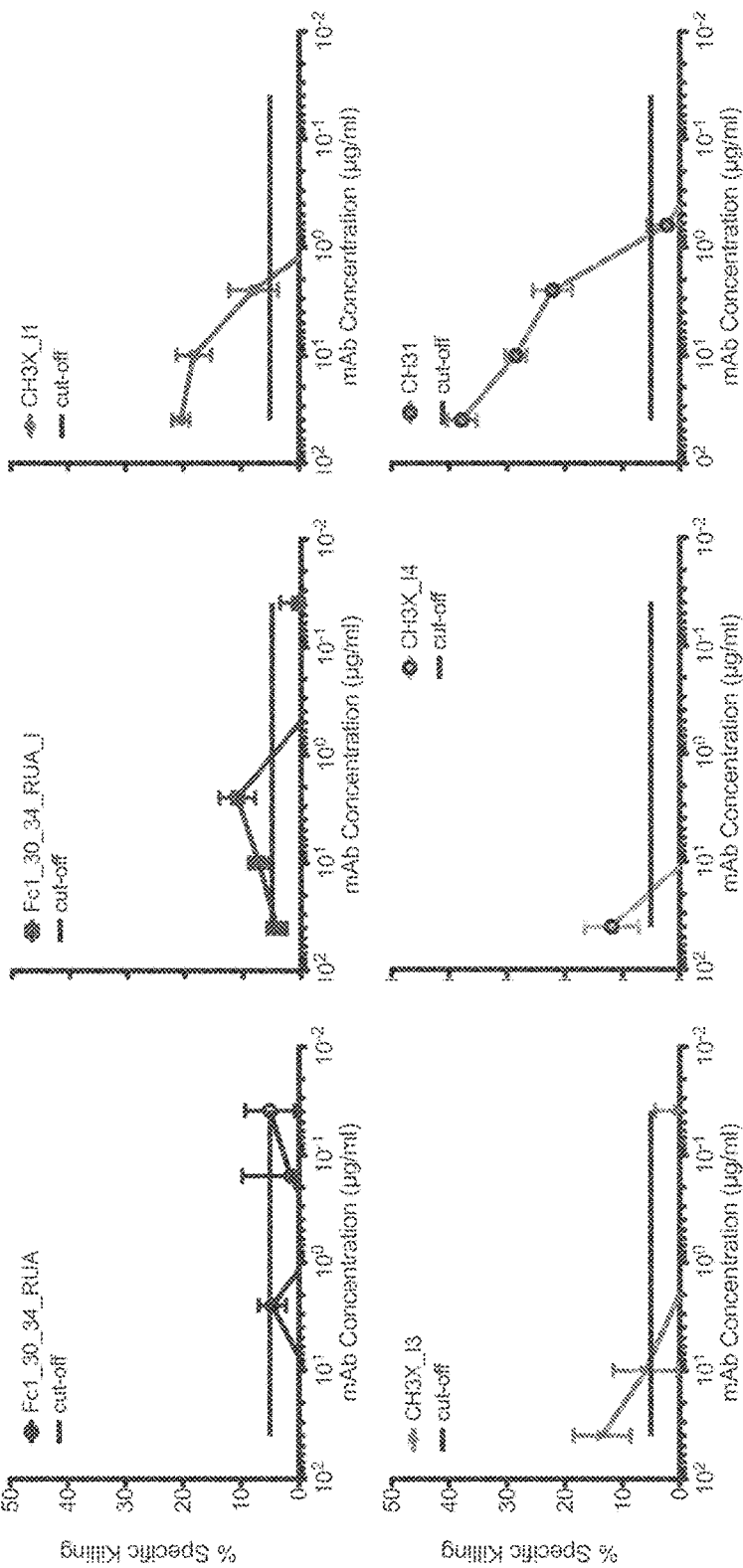
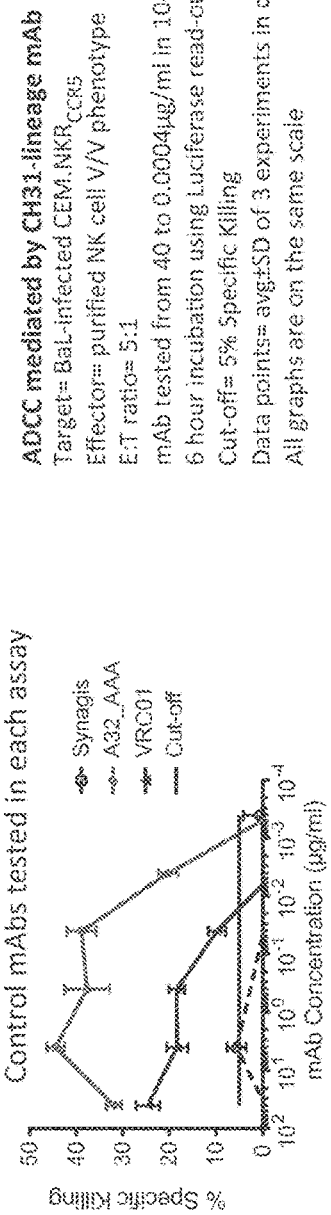
Figure 76

Figure 81

Table S1. ELISA binding profiles of VRC-PG04, VRC-PG04b, VRC-CH30, VRC-CH31 and VRC-CH32 compared to a panel of known CD4bs mAbs.

| | YU2 gp120 based proteins* | | | | | | HXB2 gp120 based proteins | | Antigenically resurfaced proteins | | |
|---|---|---|---|---|---|---|---|---|---|---|---|
| | gp120 WT | gp120 D368R | gp120 I420R | gp120 K121D | gp120 D368R/ I420R | gp120 M475S/ R476A | gp120 WT | stabilized core | RSC3 | ΔRSC3 (Δ371I) | ΔRSC3** (P363N Δ371I) |
| VRC-PG04  | ++++[b] | ++++ | ++++ | ++++ | ++ | ++++ | ++++ | ++++ | ++++ | ++ | ++ |
| VRC-PG04b | ++++ | -  | ++++ | ++++ | +  | +++ | ++++ | ++++ | ++++ | ++ | -  |
| VRC-CH30  | +++  | -  | +++  | +++  | +  | ++  | ++   | ++++ | +++  | -  | -  |
| VRC-CH31  | ++++ | ++ | +++  | +++  | ++ | +++ | +++  | ++++ | ++++ | -  | -  |
| VRC-CH32  | +++  | -  | +++  | +++  | +  | +++ | +++  | ++++ | +++  | -  | -  |
| CD4-Ig    | ++++ | -  | ++++ | ++++ | -  | -   | -    | ++++ | -    | -  | -  |
| VRC01     | ++++ | +++ | ++++ | ++++ | +++ | +++ | ++++ | ++++ | ++++ | ++ | +  |
| VRC02     | ++++ | +++ | ++++ | ++++ | +++ | +++ | ++++ | ++++ | ++++ | ++ | +  |
| VRC03     | +++  | -  | ++   | +++  | -  | -   | +++  | ++++ | ++++ | -  | -  |
| b12       | ++++ | -  | ++++ | ++++ | -  | ++  | ++++ | ++++ | ++++ | -  | -  |

*Mutant residue numbers are based on the HXB2 sequence.
** This is a double mutant of the Δ371I deletion together with the P363N mutation, which adds an N-linked glycan on the β15 strand near the CD4 binding loop.
[b]Binding was categorized based on the OD450 values at the highest concentration of antibody tested (5 μg/ml) for mAbs and CD4-Ig and the 50% effective concentration (EC50) values as shown below:

++++    $OD_{450} \geq 3.0$ and $EC_{50} \leq 0.1$
+++     $OD_{450} \geq 3.0$ and $EC_{50} > 0.1$
++      $1.0 \leq OD_{450} < 3.0$
+       $0.2 \leq OD_{450} < 1.0$
-        $OD_{450} < 0.2$

Figure 82

Table S2. Gene family analysis of mAbs VRC-PG04, VRC-PG04b, VRC-CH30, VRC-CH31 and VRC-CH32.

Heavy chain

|  | IGHV | IGHD | IGHJ | CDR3 length | VH mutation frequency |
|---|---|---|---|---|---|
| VRC01 | 1-2*02 | 3-16*01 | 1*01 | 14 | 91/288 (32%) |
| VRC03 | 1-2*02 | HD3 family | 1*01 | 16 | 86/288 (30%) |
| VRC-PG04 | 1-2*02 | 5-12*01[a] | 2*01 | 16 | 86/288 (30%) |
| VRC-PG04b | 1-2*02 | 5-12*01[a] | 2*01 | 16 | 85/288 (30%) |
| VRC-CH30 | 1-2*02 | 3-16*01 | 4*02 | 15 | 66/288 (23%) |
| VRC-CH31 | 1-2*02 | 3-16*01 | 4*02 | 15 | 68/288 (24%) |
| VRC-CH32 | 1-2*02 | 3-16*01 | 4*02 | 15 | 65/288 (23%) |

Light chain

|  | IGKV | IGKJ | CDR3 length | VK mutation frequency |
|---|---|---|---|---|
| VRC01 | 3-11*01 | 2*01 | 5 | 45/264 (17%) |
| VRC03 | 3-20*01 | 2*01 | 5 | 53/267 (20%) |
| VRC-PG04 | 3-20*01 | 5*01 | 5 | 51/267 (19%) |
| VRC-PG04b | 3-20*01 | 5*01 | 5 | 50/267 (19%) |
| VRC-CH30 | 1-33*01 | 2*01 | 5 | 41/264 (16%) |
| VRC-CH31 | 1-33*01 | 2*01 | 5 | 40/264 (15%) |
| VRC-CH32 | 1-33*01 | 2*01 | 5 | 44/264 (17%) |

[a] See detailed CDRH3 analysis in fig. S13b.

Figure 83

Table S3a: Summary of the breadth and potency of antibody neutralization against 180 HIV-1 Env-pseudoviruses

*(Table content not legibly transcribable)*

Figure 84

Table S3b: Antibody neutralization data against 28 HIV-1 clade A Env-pseudoviruses

Table S3d: Antibody neutralization data against 54 HIV-1 clade C Env-pseudoviruses

Table S3d: Antibody neutralization data against 54 HIV-1 clade C Env-pseudoviruses (continued)

Figure 87

Table S3e: Antibody neutralization data against 9 HIV-1 clade D Env-pseudoviruses

*Table image too

Figure 88

Table S3f: Antibody neutralization data against 16 HIV-1 CRF01_AE Env-pseudoviruses

| Virus ID | Clade | Origin | Neutralization $IC_{50}$ (µg/ml) VRC-PG04 | VRC-PG04b | VRC-CH30 | VRC-CH31 | VRC01 | VRC03 | CD4-Ig |
|---|---|---|---|---|---|---|---|---|---|
| 620345.c1 | AE | Thailand | >50 | >50 | | | >50 | >50 | >50 |
| C1080.c3 | AE | Thailand | 2.3 | 17.2 | 2.0 | 2.9 | 3.4 | >50 | 4.3 |
| C2101.c1 | AE | Thailand | 0.044 | 0.631 | 0.033 | 0.047 | 0.360 | >50 | 8.3 |
| C3347.c11 | AE | Thailand | >50 | >50 | 0.031 | 0.030 | 0.172 | 2.4 | >50 |
| C4118.09 | AE | Thailand | 0.082 | 0.028 | 0.043 | 0.039 | 0.110 | | |
| CNE3 | AE | China | >50 | >50 | | | 17.7 | >50 | 33.1 |
| CNE5 | AE | China | 0.494 | 3.3 | | | 0.370 | 6.0 | 12.3 |
| CNE55 | AE | China | 0.272 | 0.150 | | | 0.360 | 0.080 | 17.1 |
| CNE56 | AE | China | 0.478 | 1.885 | | | 0.420 | >50 | 14.1 |
| CNE59 | AE | China | 0.345 | 0.263 | | | 0.340 | >50 | 0.560 |
| M02138 | AE | Thailand | 0.277 | 0.211 | 1.1 | 0.500 | 0.340 | >50 | 0.267 |
| R1166.c1 | AE | Thailand | 0.762 | 0.401 | 0.146 | 0.114 | 1.7 | >50 | 30.4 |
| R2184.c4 | AE | Thailand | 0.011 | 0.098 | 0.006 | 0.007 | 0.060 | 0.050 | 7.4 |
| R3265.c6 | AE | Thailand | 1.7 | | | | 0.450 | >50 | 8.1 |
| TH966.8 | AE | Thailand | 0.164 | 0.063 | 0.049 | 0.037 | 0.324 | >50 | 0.387 |
| TH976.17 | AE | Thailand | 0.016 | 0.013 | 0.014 | 0.010 | 0.067 | >50 | 0.095 |
| Breadth | N=16 | Titer < 50 | 81% | 80% | 100% | 100% | 93% | 27% | 87% |
| | | Titer < 1 | 69% | 67% | 78% | 89% | 75% | 13% | 27% |
| Geometric mean[#] | | | 0.215 | 0.334 | 0.067 | 0.058 | 0.469 | 0.919 | 4.7 |

| Virus ID | Neutralization $IC_{80}$ (µg/ml) VRC-PG04 | VRC-PG04b | VRC-CH30 | VRC-CH31 | VRC01 | VRC03 | CD4-Ig |
|---|---|---|---|---|---|---|---|
| 620345.c1 | >50 | >50 | | | >50 | >50 | >50 |
| C1080.c3 | 27.7 | >50 | 10.5 | 10.9 | 14.4 | >50 | 18.7 |
| C2101.c1 | 1.3 | >50 | 0.337 | 0.405 | 1.2 | >50 | 28.2 |
| C3347.c11 | >50 | >50 | 0.065 | 0.450 | 0.560 | 29.1 | >50 |
| C4118.09 | 0.066 | 0.286 | 0.071 | 0.713 | 0.934 | | |
| CNE3 | >50 | >50 | | | >50 | >50 | >50 |
| CNE5 | 2.1 | 25.3 | | | 1.1 | 38.6 | 34.1 |
| CNE55 | 0.920 | 0.631 | | | 1.4 | 6.5 | >50 |
| CNE56 | 1.5 | 2.8 | | | 1.6 | >50 | >50 |
| CNE59 | 0.564 | 0.764 | | | 1.8 | >50 | 4.8 |
| M02138 | 1.3 | 1.2 | 8.4 | 2.6 | 1.6 | >50 | 2.8 |
| R1166.c1 | 3.5 | 2.5 | 0.847 | 0.828 | 4.6 | >50 | >50 |
| R2184.c4 | 0.074 | 0.048 | 0.052 | 0.094 | 0.320 | 0.148 | 25.3 |
| R3265.c6 | >50 | | | | 1.9 | >50 | 25.1 |
| TH966.8 | 0.047 | 1.0 | 0.738 | 0.360 | 1.4 | >50 | 3.2 |
| TH976.17 | 0.125 | 0.075 | 0.067 | 0.104 | 0.466 | >50 | 40.8 |
| Breadth Titer < 50 | 75% | 67% | 100% | 100% | 88% | 27% | 60% |
| Titer < 1 | 38% | 33% | 78% | 78% | 25% | 7% | 0% |
| Geometric mean[#] | 1.1 | 0.834 | 0.511 | 0.485 | 1.4 | 5.7 | 13.4 |

*Values < 1 µg/ml are highlighted in red, and values 1 – 50 µg/ml are in green. Blanks indicate not tested.

[#]Geometric means were calculated for neutralization sensitive viruses with an $IC_{50}$ (or $IC_{80}$) value < 50 µg/ml.

Figure 89

Table S3g: Antibody neutralization against 16 CRF02_AG Env-pseudoviruses

Table S4: X-ray crystallographic data and refinement statistics for VRC-PG04:gp120 and VRC03:gp120 complexes.

| Crystal | VRC-PG04:gp120 | VRC03:gp120 |
|---|---|---|
| Data collection | | |
| Space group | P2₁2₁2₁ | P2₁2₁2₁ |
| Wavelength, Å | 1.0088 | 1.0088 |
| Unit cell dimensions | | |
| a (Å) | 61.8 | 62.0 |
| b (Å) | 66.5 | 79.2 |
| c (Å) | 237.3 | 216.5 |
| α, β, γ (°) | 90.0, 90.0, 90.0 | 90.0, 90.0, 90.0 |
| Complexes per ASU | 1 | 1 |
| Resolution, Å | 2.0 | 1.9 |
| Completeness, %* | 88.3 (64.1) | 90.3 (54.8) |
| Redundancy | 3.6 (3.2) | 3.2 (2.4) |
| No. of total reflections | 510637 | 213952 |
| No. of unique reflections | 59364 | 69237 |
| I/σ* | 23.4 (1.9) | 6.3 (1.7) |
| $R_{sym}$[†] | 0.097 | 0.143 |
| | | |
| Refinement statistics (|F|>0 σ) | | |
| Resolution, Å | 2.0 | 1.9 |
| $R_{cryst}/R_{free}$, %[‡] | 19.85/23.84 | 18.79/22.84 |
| RMSD bond length, Å | 0.007 | 0.008 |
| RMSD bond angles, ° | 1.04 | 1.11 |
| Average B-factor, Å² | 47.3 | 31.0 |
| | | |
| Ramachandran analysis | | |
| Favored, % | 96.7 | 96.9 |
| Allowed, % | 100.0 | 99.5 |
| PDB ID | To be deposited | To be deposited |

*Values in parentheses are for the highest resolution shell.

[†] $R_{sym}=\Sigma|<I>-I|/\Sigma<I>$, where I is the observed intensity, and <I> is the average intensity of multiple observations of symmetry related reflections.

[‡] $R=\Sigma_{hkl}||F_{obs}|-|F_{calc}||/\Sigma_{hkl}|F_{obs}|$

[§] $R_{free}$ calculated from 5% of the reflections excluded from refinement.

Figure 92

Table S5a. List of VRC-PG04 heavy chain residues that interact with HIV-1 gp120 (table discloses the residues at positions 528-61 and 98-100A as SEQ ID NOS 10-11, respectively)

VRC-PG04 Heavy chain interaction with HIV-1 gp120

| Chain:Residue | Bond* | ASA* | BSA* | ΔiG* |
|---|---|---|---|---|
| H:GLU 33 |  | 53.36 | 3.67 | -0.06 |
| H:LEU 34 |  | 21.93 | 12.73 | 0.2 |
| H:TRP 47 |  | 70.88 | 15.95 | 0.26 |
| H:TRP 50 |  | 30.54 | 28.68 | 0.29 |
| H:LYS 52 | H | 72.66 | 34.11 | -0.9 |
| H:VAL 52B |  | 67.37 | 18.54 | 0.03 |
| H:THR 53 | H | 96 | 68.09 | 0.46 |
| H:GLY 54 |  | 21.99 | 17.94 | -0.07 |
| H:ALA 55 |  | 43.91 | 25.01 | 0.4 |
| H:VAL 56 |  | 56.95 | 39.54 | 0.46 |
| H:ASN 57 | H | 55.11 | 54.19 | -0.57 |
| H:PHE 58 |  | 21.93 | 15.66 | -0.11 |
| H:GLY 59 |  | 39.34 | 20.78 | -0.08 |
| H:SER 60 |  | 36.11 | 7.23 | 0.1 |
| H:PRO 61 |  | 113.23 | 13.72 | 0.22 |
| H:ARG 64 | HS | 133 | 87.93 | 0.14 |
| H:ARG 71 | HS | 68.07 | 25.63 | -0.66 |
| H:ARG 73 | H | 127.33 | 35.89 | -0.84 |
| H:ASP 74 |  | 121.27 | 35.10 | -0.25 |
| H:TYR 98 |  | 197.37 | 22.99 | 0.06 |
| H:THR 99 |  | 25.49 | 12.73 | -0.16 |
| H:GLY 100 |  | 70.66 | 65.09 | 0.39 |
| H:GLY 100A |  | 88.7 | 34.21 | 0.15 |
| H:GLY 100C |  | 37.99 | 8.06 | 0.06 |
| H:TRP 100D |  | 145.06 | 53.21 | 0.13 |

VRC-PG04 Heavy chain interaction with glycan on HIV-1 gp120

| Chain:Residue | Bond* | ASA* | BSA* | ΔiG* |
|---|---|---|---|---|
| H:GLY 100A | H | 88.7 | 41.21 | -0.06 |
| H:GLN 100B |  | 126.62 | 1.74 | 0.03 |
| H:GLY 100C |  | 37.99 | 14.38 | 0.22 |

* Bond type: H: Hydrogen, D: Disulphide bond, S: Salt bridge, C: Covalent link
ASA: Accessible Surface Area, Å²
BSA: Buried Surface Area, Å²
ΔiG: Solvation energy effect, kcal/mol
▓ Buried area percentage, one bar per 10%
Detailed gp120-VRC-PG04 interface data was calculated on the EBI PISA server (http://www.ebi.ac.uk/msd-srv/prot_int/pi.cgi?bin/piserver)

Figure 93

Table 5b. List of VRC-PG04 light chain residues that interact with HIV-1 gp120

VRC-PG04 light chain interaction with HIV-1 gp120

| Chain:Residue | Bond* | ASA* | BSA* | ΔiG* |
|---|---|---|---|---|
| L:GLU 1 | H | 203.92 | 70.35 | -0.4 |
| L:VAL 3 |  | 53.78 | 17.01 | 0.27 |
| L:SER 27 |  | 67.84 | 4.02 | 0.06 |
| L:TYR 30 |  | 137.09 | 0.12 | 0 |
| L:LEU 91 |  | 143.97 | 63.81 | 1.02 |
| L:GLU 96 | H | 121.88 | 37.92 | -0.18 |
| L:PHE 97 |  | 96.7 | 30.09 | 0.46 |

VRC-PG04 light chain interaction with glycan on HIV-1 gp120

| Chain:Residue | Bond* | ASA* | BSA* | ΔiG* |
|---|---|---|---|---|
| L:TYR 30 |  | 137.09 | 8.92 | -0.03 |
| L:GLY 31 |  | 25.42 | 23.81 | 0.34 |
| L:HIS 32 |  | 132.41 | 46.34 | -0.02 |
| L:GLN 90 |  | 16.81 | 0.31 | 0.01 |
| L:LEU 91 |  | 143.97 | 27.15 | 0.43 |

* Bond type: H: Hydrogen, D: Disulphide bond, S: Salt bridge C: Covalent link
ASA: Accessible Surface Area, Å²
BSA: Buried Surface Area, Å²
ΔiG: Solvation energy effect, kcal/mol
⦀ Buried area percentage, one bar per 10%
Detailed gp120:VRC-PG04 interface data was calculated on the EBI PISA server (http://www.ebi.ac.uk/msd-srv/prot_int/cgi-bin/piserver)

Figure 94

Table S5c. List of HIV-1 gp120 residues that interact with VRC-PG04 heavy chain (table discloses the residues at positions 279-283, 365-368, and 455-459, as SEQ ID NOS 12-14, respectively)

| Chain:Residue | Bond* | ASA* | BSA* | ΔiG* |
|---|---|---|---|---|
| G:LYS 97 |  | 152.48 | 23.86 | 0.03 |
| G:GLU 102 |  | 58.18 | 1.11 | -0.02 |
| G:LEU 122 |  | 65.89 | 4.36 | 0.07 |
| G:GLY 124 |  | 85.12 | 29.55 | -0.18 |
| G:GLU 275 |  | 53.04 | 20.76 | -0.06 |
| G:ASN 276 |  | 81.38 | 17.75 | -0.27 |
| G:ASN 279 |  | 61.51 | 31.36 | -0.32 |
| G:ASN 280 | H | 72.13 | 43.77 | -0.48 |
| G:ALA 281 | H | 90.09 | 76.09 | 0.73 |
| G:LYS 282 |  | 72.43 | 31.85 | -0.53 |
| G:THR 283 |  | 30.9 | 9.48 | -0.11 |
| G:SER 365 | H | 96.21 | 46.24 | 0.48 |
| G:GLY 366 |  | 48.7 | 23.28 | 0.13 |
| G:GLY 367 |  | 56.22 | 23.64 | 0.27 |
| G:ASP 368 | HS | 79.6 | 50.26 | -0.48 |
| G:ILE 371 |  | 56.28 | 45.39 | 0.73 |
| G:MET 426 |  | 16.29 | 0.12 | 0 |
| G:TRP 427 |  | 31.25 | 1.23 | -0.01 |
| G:GLY 429 | H | 68.44 | 47.60 | 0.15 |
| G:GLY 431 |  | 27.77 | 6.35 | 0.07 |
| G:THR 455 |  | 58.29 | 31.36 | 0.29 |
| G:ARG 456 | H | 31.19 | 1.84 | -0.02 |
| G:ASP 457 | S | 40.84 | 25.79 | 0.06 |
| G:GLY 458 | H | 47.21 | 36.29 | 0.01 |
| G:GLY 459 |  | 88.91 | 47.28 | 0.22 |
| G:ARG 469 |  | 49.96 | 18.57 | -0.24 |
| G:GLY 472 |  | 22.43 | 4.52 | -0.05 |
| G:GLY 473 |  | 29.7 | 17.90 | 0.2 |
| G:ASP 474 |  | 73.97 | 4.42 | -0.07 |
| G:LYS 476 |  | 59.28 | 21.78 | -0.61 |
| G:NAG 778 | H | 360.8 | 64.91 | -1.95 |

* Bond type: H: Hydrogen, D: Disulphide bond, S : Salt bridge C: Covalent link
ASA: Accessible Surface Area, Å²
BSA: Buried Surface Area, Å²
ΔiG: Solvation energy effect, kcal/mol
|||: Buried area percentage, one bar per 10%
Detailed gp120-VRC-PG04 interface data was calculated on the EBI PISA server (http://www.ebi.ac.uk/msd-srv/prot_int/cgi-bin/piserver)

Figure 95

Table S5d. List of HIV-1 gp120 residues that interact with VRC-PG04 light chain

| Chain:Residue | Bond* | ASA^ | BSA^ | ΔiG° |
|---|---|---|---|---|
| G:ASN 276 | | 81.38 | 0.36 | 0.01 |
| G:THR 278 | | 121.98 | 34.02 | -0.11 |
| G:ASN 279 | | 81.51 | 21.74 | 0.07 |
| G:ASN 280 | H | 72.13 | 21.42 | -0.24 |
| G:GLY 458 | | 47.21 | 4.53 | 0.07 |
| G:GLY 459 | | 88.91 | 9.98 | -0.06 |
| G:ASN 461 | H | 138.25 | 82.82 | -0.45 |
| G:ASN 462 | H | 162.6 | 42.36 | -0.4 |
| G:NAG 776 | | 360.8 | 125.19 | -2.59 |

* Bond type: H: Hydrogen, D: Disulfide bond, S : Salt bridge C: Covalent link
ASA: Accessible Surface Area, Å²
BSA: Buried Surface Area, Å²
ΔiG: Solvation energy effect, kcal/mol
▓: Buried area percentage, one bar per 10%
Detailed gp120-VRC-PG04 interface data was calculated on the EBI PISA server (http://www.ebi.ac.uk/msd-srv/prot_int/pistart.html)

Figure 96

Table S6a. List of VRC03 heavy chain residues that interact with HIV-1gp120 (table discloses the residues at positions 52-62 and 73-76A as SEQ ID NOS 15-16, respectively)

| Chain:Residue | Bond* | ASA^ | BSA^ | ΔiG* |
|---|---|---|---|---|
| H:ARG 30 |  | 101.57 | 57.04 | -0.36 |
| H:HIS 35 |  | 4.62 | 1.18 | -0.03 |
| H:GLU 46 |  | 38.16 | 0.31 | 0.01 |
| H:TRP 47 |  | 68.77 | 28.74 | 0.46 |
| H:TRP 50 |  | 96.82 | 51.92 | 0.36 |
| H:LYS 52 | H | 96.54 | 42.97 | -0.86 |
| H:LEU 53 |  | 95.76 | 53.26 | 0.76 |
| H:TRP 54 | H | 205.01 | 199.06 | 2.01 |
| H:GLY 55 |  | 16.03 | 13.27 | -0.1 |
| H:ALA 56 |  | 46.42 | 34.02 | 0.54 |
| H:VAL 57 |  | 55.82 | 42.38 | 0.35 |
| H:SER 58 |  | 38.46 | 32.58 | -0.13 |
| H:TYR 59 |  | 60.99 | 30.31 | 0.21 |
| H:ALA 60 |  | 5.02 | 5.02 | 0.08 |
| H:ARG 61 | H | 213.64 | 156.18 | -1.08 |
| H:GLN 62 | H | 114.87 | 59.94 | 0.09 |
| H:GLN 64 | H | 107.9 | 46.05 | -0.52 |
| H:ARG 71 | HS | 72.06 | 24.95 | -0.67 |
| H:LEU 73 |  | 30.12 | 0.67 | 0.01 |
| H:SER 74 |  | 10.73 | 7.86 | -0.09 |
| H:GLN 75 |  | 144.61 | 33.96 | -0.25 |
| H:ASP 76 |  | 62.88 | 1.68 | 0.01 |
| H:PRO 76A |  | 125.61 | 45.26 | 0.72 |
| H:PRO 76D |  | 85.16 | 19.85 | 0.27 |
| H:ASP 99 |  | 143.04 | 17.15 | -0.16 |
| H:TYR 100 |  | 212.68 | 16.56 | 0.26 |
| H:GLY 100B |  | 33.36 | 2.37 | 0.04 |
| H:ASP 100C | HS | 87.28 | 62.64 | -0.31 |
| H:PHE 100D |  | 111.1 | 33.72 | 0.54 |

* Bond type: H: Hydrogen, D: Disulphide bond, S: Salt bridge C: Covalent link
ASA: Accessible Surface Area, Å²
BSA: Buried Surface Area, Å²
ΔiG: Solvation energy effect, kcal/mol
▓ Buried area percentage, one bar per 10%
Detailed gp120/VRC03 interface data was calculated on the EBI PISA server (http://www.ebi.ac.uk/msd-srv/prot_int/cgi-bin/piserver)

Figure 97

Table S6b. List of VRC03 light chain residues that interact with HIV-1 gp120

VRC03 light chain interaction with HIV-1 gp120

| Chain:Residue | Bond* | ASA^ | BSA^ | ΔiG^ |
|---|---|---|---|---|
| L:GLU 1 |  | 153.88 | 74.77 | -0.2 |
| L:ILE 2 |  | 15.71 | 8.21 | 0.13 |
| L:GLN 27 |  | 83.2 | 6.51 | -0.11 |
| L:ASN 31 |  | 40.33 | 12.91 | -0.2 |
| L:PHE 91 |  | 131.73 | 54.69 | 0.88 |
| L:GLU 96 | H | 122.84 | 62.03 | -0.31 |
| L:PHE 97 |  | 48.56 | 25.17 | 0.4 |

VRC03 light chain interaction with glycan on HIV-1 gp120

| Chain:Residue | Bond* | ASA^ | BSA^ | ΔiG^ |
|---|---|---|---|---|
| L:ASN 31 |  | 40.33 | 9.18 | -0.02 |
| L:ALA 32 |  | 47.78 | 32.39 | 0.21 |
| L:ASP 50 |  | 69.43 | 12.21 | -0.16 |
| L:GLN 90 |  | 3.66 | 0.84 | 0.01 |
| L:PHE 91 |  | 131.73 | 23.55 | 0.37 |

* Bond type: H: Hydrogen, D: Disulphide bond, S : Salt bridge C: Covalent link
ASA: Accessible Surface Area, Å$^2$
BSA: Buried Surface Area, Å$^2$
ΔiG: Solvation energy effect, kcal/mol
: Buried area percentage, one bar per 10%
Detailed gp120:VRC-03 interface data was calculated on the EBI PISA server
(http://www.ebi.ac.uk/msdsrv/prot_int/cgi-bin/piserver)

Figure 98

Table S6c. List of HIV-1 gp120 residues that interact with VRC03 heavy chain (table discloses the residues at positions 279-283, 365-368, 455-461, and 472-475, as SEQ ID NOS 12-13 and 17-18, respectively)

| Chain:Residue | Bond* | ASA* | BSA* | ΔiG* |
|---|---|---|---|---|
| G:LYS 97 |  | 158.83 | 40.59 | -0.92 |
| G:THR 123 |  | 48.84 | 5.77 | 0.09 |
| G:GLY 124 |  | 87.08 | 80.77 | 0.31 |
| G:GLY 198 |  | 91.23 | 50.65 | 0.33 |
| G:SER 199 |  | 54.24 | 15.88 | 0.25 |
| G:THR 257 |  | 8.68 | 7.17 | 0.11 |
| G:ASN 279 | H | 60.35 | 20.99 | -0.17 |
| G:ASN 280 |  | 77.1 | 54.49 | -0.56 |
| G:ALA 281 | H | 84.01 | 70.75 | 0.64 |
| G:LYS 282 | S | 75.7 | 17.37 | 0.03 |
| G:THR 283 |  | 22.48 | 7.61 | -0.09 |
| G:SER 365 |  | 95.12 | 58.00 | 0.45 |
| G:GLY 366 |  | 46.67 | 22.26 | 0.09 |
| G:GLY 367 |  | 62.05 | 26.17 | 0.34 |
| G:ASP 368 | HS | 81.49 | 54.28 | -0.38 |
| G:GLU 370 |  | 19.22 | 17.10 | 0.27 |
| G:ILE 371 |  | 38.73 | 35.22 | 0.56 |
| G:HIS 375 |  | 14.16 | 2.73 | 0.01 |
| G:ASN 425 |  | 49.86 | 11.65 | 0.11 |
| G:MET 426 |  | 23.72 | 7.83 | -0.08 |
| G:TRP 427 |  | 50.55 | 34.07 | 0.21 |
| G:GLY 429 |  | 69.61 | 49.16 | 0.19 |
| G:THR 430 |  | 54.07 | 1.87 | 0.03 |
| G:GLY 431 |  | 30.64 | 14.86 | 0.18 |
| G:THR 455 |  | 43.78 | 23.07 | 0.32 |
| G:ARG 456 |  | 32.9 | 3.51 | -0.03 |
| G:ASP 457 | H | 53.35 | 46.31 | 0.2 |
| G:GLY 458 | H | 44.89 | 37.44 | -0.26 |
| G:GLY 459 |  | 77.9 | 37.58 | 0.45 |
| G:ALA 460 | H | 111.5 | 29.52 | -0.11 |
| G:ASN 461 |  | 119.23 | 35.73 | 0.17 |
| G:THR 463 |  | 77.05 | 26.95 | 0.04 |
| G:ASN 465 | H | 42.83 | 11.56 | -0.17 |
| G:GLU 466 |  | 28.03 | 3.34 | -0.01 |
| G:THR 467 |  | 24.58 | 15.75 | -0.09 |
| G:ARG 469 | H | 50.3 | 22.19 | -0.59 |
| G:GLY 472 |  | 31.48 | 22.96 | -0.21 |
| G:GLY 473 |  | 32.75 | 28.94 | -0.08 |
| G:ASP 474 |  | 71.26 | 2.68 | 0.04 |
| G:ILE 475 |  | 8.14 | 0.67 | 0.01 |

* Bond type: H: Hydrogen, D Disulphide bond, S:Salt bridge C: Covalent link
ASA: Accessible Surface Area, Å²
BSA: Buried Surface Area, Å²
||||: Buried area percentage, one bar per 10%
Detailed gp120:VRC-PG04 interface data was calculated on the EBI PISA server
(http://www.ebi.ac.uk/msdsrv/prot_int/cgi-bin/piserver)

Figure 99

Table S6d. List of HIV-1 gp120 residues that interact with VRC03 light chain (table discloses the residues at positions 458-462 as SEQ ID NO: 19)

| Chain:Residue | Bond* | ASA* | BSA* | ΔiG* |
|---|---|---|---|---|
| G:ASN 276 |   | 75.77 | 12.98 | -0.15 |
| G:THR 278 |   | 127.43 | 74.78 | 0.69 |
| G:ASN 279 |   | 60.35 | 14.54 | 0.06 |
| G:ASN 280 | H | 77.1 | 22.61 | -0.26 |
| G:ARG 456 |   | 32.9 | 2.42 | -0.06 |
| G:GLY 458 |   | 44.89 | 3.36 | 0.05 |
| G:GLY 459 | H | 77.9 | 35.49 | -0.11 |
| G:ALA 460 |   | 111.5 | 32.16 | 0.51 |
| G:ASN 461 |   | 119.23 | 2.58 | -0.01 |
| G:ASN 462 |   | 149.19 | 39.53 | 0.08 |
| G:NAG 776 |   | 351.09 | 107.06 | -1.06 |

* Bond type: H: Hydrogen, D: Disulphide bond, S : Salt bridge C: Covalent link
ASA: Accessible Surface Area, Å²
BSA: Buried Surface Area, Å²
ΔiG: Solvation energy effect, kcal/mol
Buried area percentage, one bar per 10%
Detailed gp120:VRC-03 interface data was calculated on the EBI PISA server
(http://www.ebi.ac.uk/msd-srv/prot_int/cgi-bin/piserver)

Figure 100

Table S7. Comparison of gp120 recognition by CD4-induced antibodies derived from a common IGVH1-69 allele.

Heavy chain

| RMSD(Å) /Angle(°) | 17b | 412d | X5 |
|---|---|---|---|
| 17b |  | 8.9/37.7 | 21.4/85.5 |
| 412d |  |  | 24.6/109.2 |
| X5 |  |  |  |

Light chain

| RMSD(Å) /Angle(°) | 17b | 412d | X5 |
|---|---|---|---|
| 17b |  |  |  |
| 412d | 24.2/40.9 |  |  |
| X5 | 38.1/87.1 | 48.0/87.6 |  |

Figure 101

Table S8. Orientations of RSC3-reactive CD4-binding site antibodies in gp120:antibody complexes.

Heavy chain

| RMSD(Å) /Angle(°) | VRC01 | VRC03 | VRC-PG04 | b12 | b13 |
|---|---|---|---|---|---|
| VRC01 |  |  |  | 24.0/125.6 | 25.5/120.5 |
| VRC03 |  |  |  | 24.0/120.9 | 25.7/118.7 |
| VRC-PG04 |  |  |  | 24.0/123.9 | 25.6/116.8 |
| b12 |  |  |  |  |  |
| b13 |  |  |  |  |  |

Light chain

| RMSD(Å) /Angle(°) | VRC01 | VRC03 | VRC-PG04 | b12 | b13 |
|---|---|---|---|---|---|
| VRC01 |  |  |  |  |  |
| VRC03 |  |  |  |  |  |
| VRC-PG04 |  |  |  |  |  |
| b12 | 48.6/68.2 | 50.1/73.9 | 49.5/70.2 |  |  |
| b13 | 53.4/60.5 | 54.7/67.5 | 54.1/63.0 |  |  |

Figure 102

Table S9. Heavy/Light-chain complementation of VRC01-like antibody

| Heavy chain | Light chain | Antibody yield (mg/L culture supernatant) |
|---|---|---|
| VRC01 | VRC03 | 77.08 |
| VRC01 | VRC04 | 73.60 |
| VRC03 | VRC01 | 70.52 |
| VRC03 | VRC-PG04 | 73.80 |
| VRC-PG04 | VRC01 | 67.24 |
| VRC-PG04 | VRC03 | 60.68 |
| VRC-CH31 | VRC01 | 25.32 |
| VRC-CH31 | VRC03 | 28.44 |
| VRC-CH31 | VRC04 | 15.00 |
| VRC01 | VRC-CH31 | 10.32 |
| VRC03 | VRC-CH31 | 5.76 |
| VRC04 | VRC-CH31 | 22.32 |

FIGURE 103

Table S10. Neutralization IC$_{50}$ titers* (μg/ml) of chimeric antibodies derived from known VRC01-like antibodies against 20 HIV-1 clade A, B and C Env-pseudoviruses

| mAb designation | Clade A (n=6) | | | | | | Clade B (n=8) | | | | | | | | Clade C (n=6) | | | | | | IC$_{50}$ < 50 μg/ml | IC$_{50}$ < 1 μg/ml | geometric mean# (μg/ml) |
|---|---|---|---|---|---|---|---|---|---|---|---|---|---|---|---|---|---|---|---|---|---|---|---|
| | Q23.17 | Q842.d12 | UG037.8 | Q168.12 | KER2008.12 | KER2018.11 | YU2 | JR-FL | JR-CSF | 7165.18 | BG1168.1 | CAAN.A2 | PVO.4 | TRO.11 | Du156.12 | ZM109.4 | ZM106.9 | TV1.29 | ZM176.66 | SO18.18 | | | |
| VRC01 | 0.0085 | 0.0030 | 0.0079 | 0.115 | 0.1370 | 0.652 | 0.126 | 0.0031 | 0.0093 | >50 | 0.276 | 0.824 | >50 | >50 | 0.089 | >50 | 0.499 | >50 | 0.0055 | 0.069 | 90% | 90% | 0.140 |
| VRC01H/VRC03L | >50 | >50 | >50 | >50 | >50 | >50 | 6.66 | >50 | >50 | >50 | >50 | 8.57 | >50 | >50 | >50 | >50 | >50 | >50 | 4.10 | >50 | 10% | 0% | 7.6 |
| VRC01H/VRC-PG04L | 0.307 | 0.031 | 0.045 | 0.115 | 2.523 | >50 | 0.117 | 0.099 | >50 | >50 | 26.1 | 0.986 | >50 | 2.99 | 0.123 | 0.30 | >50 | >50 | >50 | 0.060 | 90% | 65% | 0.482 |
| VRC01H/VRC-CH31L | >50 | 12.7 | 2.07 | >50 | >50 | 0.402 | 3.92 | 1.15 | 0.145 | >50 | >50 | >50 | >50 | >50 | >50 | 0.326 | >50 | >50 | >50 | 0.115 | 35% | 0% | 3.97 |
| VRC03 | 0.065 | >50 | >50 | 3.34 | 0.403 | 0.388 | 0.037 | 0.009 | 0.093 | >50 | >50 | 8.3 | 0.328 | 0.055 | <0.023 | 0.150 | 0.150 | >50 | 0.033 | 0.083 | 70% | 55% | 0.224 |
| VRC03H/VRC01L | 0.018 | 0.013 | 0.019 | 0.058 | 0.489 | 0.260 | 0.024 | 0.008 | 0.016 | >50 | 0.24 | 2.15 | 0.213 | 0.059 | 0.16 | 0.060 | 0.060 | >50 | >50 | 0.176 | 85% | 65% | 0.132 |
| VRC03H/VRC-PG04L | 0.017 | 0.011 | 0.021 | 0.049 | 0.0724 | 0.349 | 0.028 | 0.010 | 0.032 | >50 | 0.477 | 1.16 | 0.107 | 0.044 | 0.166 | 0.393 | 0.393 | >50 | 0.64 | 0.035 | 85% | 70% | 0.119 |
| VRC03H/VRC-CH31L | 0.012 | 0.007 | 0.004 | 0.224 | 0.213 | 3.10 | 0.055 | 0.008 | 0.117 | >50 | 0.818 | 2.7 | 0.552 | 0.168 | <0.023 | >50 | >50 | >50 | 0.053 | 0.182 | 80% | 60% | 0.199 |
| VRC-PG04 | 0.048 | 0.012 | 0.0048 | 0.050 | 0.0524 | 0.711 | 0.019 | 0.010 | 0.138 | >50 | 0.792 | 2.7 | 0.234 | 0.291 | 0.040 | >50 | >50 | >50 | 0.070 | 0.042 | 90% | 85% | 0.102 |
| VRC-P04H/VRC01L | 0.051 | 0.043 | >50 | 0.051 | 0.0524 | 3.49 | 0.096 | 0.104 | 0.043 | >50 | 0.65 | 6.9 | 0.431 | >50 | 0.079 | 1.95 | 1.95 | >50 | >50 | 0.776 | 70% | 50% | 0.196 |
| VRC-P04H/VRC03L | >50 | >50 | >50 | >50 | >50 | >50 | >50 | >50 | >50 | >50 | 55.8 | >50 | >50 | >50 | 3.57 | >50 | >50 | >50 | >50 | >50 | 0% | 0% | >50 |
| VRC-P04H/VRC-CH31L | 0.159 | 0.088 | 0.416 | >50 | 0.107 | 2.99 | 0.743 | 0.230 | >50 | >50 | 0.0653 | >50 | 0.194 | 0.199 | 0.499 | 0.069 | 0.069 | >50 | 0.008 | 0.425 | 45% | 35% | 0.499 |
| VRC-CH31 | 0.014 | 0.003 | 0.004 | 0.025 | >50 | 0.385 | <0.016 | 0.074 | >50 | >50 | >50 | 1.6 | 1.27 | 2.50 | >50 | >50 | >50 | >50 | >50 | 0.066 | 85% | 75% | 0.085 |
| VRC-CH31H/VRC01L | 0.085 | 0.029 | 0.177 | 0.423 | 0.770 | >50 | 0.648 | 0.104 | >50 | >50 | >50 | >50 | 1.27 | 2.5 | >50 | >50 | >50 | >50 | >50 | 2.55 | 60% | 30% | 0.660 |
| VRC-CH31H/VRC03L | 1.47 | >50 | >50 | >50 | 0.0621 | 2.47 | >50 | >50 | >50 | >50 | >50 | >50 | >50 | >50 | >50 | >50 | >50 | >50 | 0.008 | >50 | 5% | 0% | 1.74 |
| VRC-CH31H/VRC-PG04L | 0.031 | 0.013 | 0.067 | 0.295 | 0.0621 | 2.14 | 0.142 | >50 | 0.043 | >50 | >50 | >50 | 0.904 | 3.25 | 0.163 | >50 | >50 | >50 | >50 | 2.31 | 55% | 35% | 0.350 |

*Values < 1 μg/ml are highlighted in red, and values 1 – 50 μg/ml are in green.
Geometric means were calculated for neutralization sensitive viruses with an IC$_{50}$ value < 50 μg/ml.

Figure 104

Table S11. Sequences selected from the IGHV1-2*02 family of donor 45 heavy-chain 2008 antibodyome with high predicted structural compatibility with known VRC01-like antibody-gp120 complexes.[a]

| Seq. index | IGHV1-2*02 divergence (%) | VRC01 threading score | VRC03 threading score | VRC-PG04 threading score | VRC01 SeqID (%) | VRC03 SeqID (%) | VRC-PG04 SeqID (%) |
|---|---|---|---|---|---|---|---|
| VRC01 | 32.09 | 0.093 | 0.122 | 0.156 | 100.00 | 64.62 | 60.80 |
| VRC03 | 30.74 | 0.310 | 0.031 | 0.206 | 68.87 | 100.00 | 62.13 |
| VRC-PG04 | 28.72 | 0.185 | 0.219 | 0.092 | 62.81 | 60.26 | 100.00 |
| 65030 | 1.01 | 0.110 | 0.087 | 0.127 | 67.22 | 64.10 | 66.40 |
| 61272 | 4.39 | 0.128 | 0.090 | 0.136 | 69.97 | 62.82 | 64.80 |
| 103787 | 8.45 | 0.171 | 0.084 | 0.125 | 65.84 | 64.62 | 66.13 |
| 70542 | 9.46 | 0.160 | 0.089 | 0.122 | 65.01 | 63.59 | 65.33 |
| 87722 | 13.85 | 0.092 | 0.132 | 0.104 | 65.01 | 63.08 | 63.73 |
| 80585 | 15.88 | 0.093 | 0.133 | 0.108 | 63.36 | 62.31 | 62.13 |
| 22425 | 17.69 | 0.147 | 0.094 | 0.137 | 64.19 | 58.97 | 64.00 |
| 18761 | 23.31 | 0.155 | 0.107 | 0.145 | 60.06 | 53.59 | 60.80 |
| 49433 | 30.95 | 0.309 | 0.041 | 0.199 | 68.32 | 99.23 | 61.87 |

Figure 105

Table S12. Sequences selected from the non-IGHV1-2*02 families of donor 45 heavy-chain 2008 antibodyome with high germline divergence and large family size.[a]

| Seq. Index | V-gene family | Germline divergence (%) | VRC01 SeqID (%) | VRC03 SeqID (%) | VRC-PG04 SeqID (%) | Family size |
|---|---|---|---|---|---|---|
| 96362 | IGHV1-18*01 | 20.61 | 60.06 | 59.49 | 64.00 | 4 |
| 61822 | IGHV1-24*01 | 8.45 | 61.73 | 59.49 | 60.53 | 5 |
| 7863 | IGHV1-3*02 | 11.82 | 61.43 | 62.05 | 61.07 | 1 |
| 28241 | IGHV1-45*02 | 20.07 | 59.78 | 57.69 | 59.20 | 3 |
| 19891 | IGHV1-46*02 | 17.23 | 61.98 | 58.72 | 63.47 | 4 |
| 70083 | IGHV1-58*02 | 12.16 | 62.53 | 60.77 | 60.53 | 6 |
| 153849 | IGHV1-69*01 | 20.27 | 60.06 | 57.95 | 62.67 | 2 |
| 146940 | IGHV1-8*01 | 27.70 | 60.06 | 54.36 | 60.80 | 10 |
| 5827 | IGHV1-e*01 | 13.95 | 63.09 | 58.97 | 61.07 | 3 |

Figure 106

Table S13. Expression of antibodies with selected heavy chains derived from donor 45, 2008 (SEQ ID NOS 20-36, respectively, in order of appearance)

| Sequence ID | Paired with | Yield* (mg/L culture sup) | Neutralization* (Y/N) | Amino acid sequence of heavy chain V domain |
|---|---|---|---|---|
| 65030 | VRC01L | 12.24 | N | |
| 61272 | VRC01L | 15.00 | N | |
| 103767 | VRC01L | 16.80 | N | |
| 70542 | VRC01L | 28.32 | N | |
| 87722 | VRC01L | no expression | n/a | |
| 80585 | VRC01L | 11.52 | N | |
| 22425 | VRC01L | 15.84 | N | |
| 18761 | VRC01L | no expression | n/a | |
| 19891 | VRC01L | 0.93 | N | |
| 148940 | VRC01L | no expression | n/a | |
| 96362 | VRC01L | 4.05 | N | |
| 7863 | VRC01L | no expression | n/a | |
| 153849 | VRC01L | 5.28 | N | |
| 28241 | VRC01L | no expression | n/a | |
| 70085 | VRC01L | 3.78 | N | |
| 61822 | VRC01L | 3.63 | N | |
| 5827 | VRC01L | no expression | n/a | |

*no expression, yield was less than 0.60 mg/L; Y, yes; N, no; n/a, not available.

Figure 107

Table S14. Expression of antibodies with selected heavy chains from donor V74, 2008, paired with VRC-PG04 light chain (SEQ ID NOS 37-106, respectively, in order of appearance)

| Sequence ID | Yield* (mg/L culture sup) | Neutralization* (Y/N) | Amino acid sequence of heavy chain V domain |
|---|---|---|---|
| 10731_1 | 1.56 | Y | [sequence] |
| 124918_2 | 12.24 | N | [sequence] |
| 132797_4 | no expression | n/a | [sequence] |
| 143251_3 | 12.96 | N | [sequence] |
| 164202_3 | 18.12 | Y | [sequence] |
| 166726_3 | 8.28 | N | [sequence] |
| 168509_2 | no expression | n/a | [sequence] |
| 179400_4 | 11.40 | Y | [sequence] |
| 179500_4 | 6.84 | N | [sequence] |
| 179888_3 | 21.12 | N | [sequence] |
| 184939_4 | no expression | n/a | [sequence] |
| 185961_4 | 14.28 | N | [sequence] |
| 186275_2 | 1.80 | Y | [sequence] |
| 193526_4 | no expression | n/a | [sequence] |
| 193596_4 | no expression | n/a | [sequence] |
| 196147_4 | 11.04 | Y | [sequence] |
| 28936_1 | no expression | n/a | [sequence] |
| 30263_2 | 21.12 | N | [sequence] |
| 43243_3 | no expression | n/a | [sequence] |
| 43359_2 | 6.12 | N | [sequence] |
| 46260_1 | no expression | n/a | [sequence] |
| 47890_1 | 7.32 | Y | [sequence] |
| 69713_1 | 11.52 | N | [sequence] |
| 70679_1 | 14.88 | N | [sequence] |
| 71632_2 | 22.96 | Y | [sequence] |
| 74400_3 | 12.12 | N | [sequence] |

Figure 107 (continued)

Table S14. Expression of antibodies with selected heavy chains derived from donor V74, 2008, paired with VRC-PG04 light chain (continued)

| Sequence ID | Yield* (mg/L culture sup) | Neutralization* (Y/N) | Amino acid sequence of heavy chain V domain |
|---|---|---|---|
| 86984_2 | 1.92 | Y | (sequence) |
| 94565_1 | no expression | n/a | (sequence) |
| 96298_1 | 13.32 | Y | (sequence) |
| 9815_2 | 22.32 | Y | (sequence) |
| 104625_2 | 23.52 | N | (sequence) |
| 43555_1 | no expression | n/a | (sequence) |
| 76927_2 | no expression | n/a | (sequence) |
| 99473_3 | no expression | n/a | (sequence) |
| 121325_4 | 2.88 | N | (sequence) |
| 13826_2 | 10.68 | Y | (sequence) |
| 151901_4 | 10.68 | Y | (sequence) |
| 165478_2 | 24.72 | Y | (sequence) |
| 17720_4 | 20.28 | Y | (sequence) |
| 164922_3 | 21.48 | N | (sequence) |
| 166640_2 | 14.64 | Y | (sequence) |
| 61048_1 | 22.44 | Y | (sequence) |
| 105239_4 | no expression | n/a | (sequence) |
| 120119_4 | 9.12 | N | (sequence) |
| 127586_4 | 19.84 | N | (sequence) |
| 156858_3 | no expression | n/a | (sequence) |
| 178037_3 | no expression | n/a | (sequence) |
| 180066_4 | no expression | n/a | (sequence) |
| 89680_4 | no expression | n/a | (sequence) |
| 149768_4 | 6.24 | N | (sequence) |
| 169094_4 | no expression | n/a | (sequence) |

Figure 107 (continued)

Table S14. Expression of antibodies with selected heavy chains derived from donor V74, 2008, paired with VRC-PG04 light chain (continued)

| Sequence ID | Yield* (mg/L culture sup) | Neutralization* (Y/N) | Amino acid sequence of heavy chain V domain |
|---|---|---|---|
| 190244_4 | no expression | n/a | *illegible sequence* |
| 196283_4 | no expression | n/a | *illegible sequence* |
| 24972_4 | 19.94 | Y | *illegible sequence* |
| 74511_1 | no expression | n/a | *illegible sequence* |
| 95569_2 | 24.12 | Y | *illegible sequence* |
| 43567_2 | 12.12 | N | *illegible sequence* |
| 57729_2 | 18.24 | N | *illegible sequence* |
| 8460_4 | no expression | n/a | *illegible sequence* |
| 31456_3 | 13.40 | N | *illegible sequence* |
| 12467_3 | no expression | n/a | *illegible sequence* |
| 195462_4 | 2.16 | N | *illegible sequence* |
| 86343_1 | no expression | n/a | *illegible sequence* |
| 149590_4 | 21.48 | Y | *illegible sequence* |
| 86277_2 | no expression | n/a | *illegible sequence* |
| 18278_1 | 7.68 | Y | *illegible sequence* |
| 167612_4 | 20.52 | Y | *illegible sequence* |
| 99989_1 | no expression | n/a | *illegible sequence* |
| 135083_3 | no expression | n/a | *illegible sequence* |
| 53821_1 | 24.60 | Y | *illegible sequence* |

*no expression, yield was less than 0.60 mg/L; Y, yes; N, no; n/a, not available.

Table S16. Expression of antibodies with phylogenetic-segregation selected light chains

| Donor | Year | Sequence ID | Heavy(H) /Light(L) chain | Paired with | Antibody yield (mg/L culture supernatant) |
|---|---|---|---|---|---|
| 45 | 2001 | 223454 | L | VRC01H | 14.16 |
| 45 | 2001 | 223454 | L | VRC03H | 17.52 |
| 45 | 2001 | 223454 | L | VRC-PG04H | 19.84 |
| 45 | 2001 | 181371 | L | VRC01H | 29.16 |
| 45 | 2001 | 181371 | L | VRC03H | 18.96 |
| 45 | 2001 | 181371 | L | VRC-PG04H | 25.08 |

US 10,273,291 B2

SEQUENCE LISTING

```
<160> NUMBER OF SEQ ID NOS: 297

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(18)
<223> OTHER INFORMATION: This sequence may encompass 12-18 nucleotides

<400> SEQUENCE: 1
tttttttttt tttttttt                                                 18

<210> SEQ ID NO 2
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acaggtgccc actcccaggt gcag                                            24

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcagccacag gtgcccactc c                                               21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagcagctac aggcacccac gc                                              22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggcagcagct acaggtgtcc agtcc                                           25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggggaagac cgatgggccc ttggtgg                                         27

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggaattctc acaggagacg a                                               21

<210> SEQ ID NO 8
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctcttcctcc tgctactctg gctcccag                                          28

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgctgtcct tgctgtcctg ct                                                22

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Thr Gly Ala Val Asn Phe Gly Ser Pro
1               5                   10

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Thr Gly Gly
1

<210> SEQ ID NO 12
<211> LENGTH: 5
<212> TYPE: PRT
<213> ORGANISM: Human immunodeficiency virus

<400> SEQUENCE: 12

Asn Asn Ala Lys Thr
1               5

<210> SEQ ID NO 13
<211> LENGTH: 4
<212> TYPE: PRT
<213> ORGANISM: Human immunodeficiency virus

<400> SEQUENCE: 13

Ser Gly Gly Asp
1

<210> SEQ ID NO 14
<211> LENGTH: 5
<212> TYPE: PRT
<213> ORGANISM: Human immunodeficiency virus
```

```
<400> SEQUENCE: 14

Thr Arg Asp Gly Gly
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Leu Trp Gly Ala Val Ser Tyr Ala Arg Gln
1               5                   10

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Ser Gln Asp Pro
1               5

<210> SEQ ID NO 17
<211> LENGTH: 7
<212> TYPE: PRT
<213> ORGANISM: Human immunodeficiency virus

<400> SEQUENCE: 17

Thr Arg Asp Gly Gly Ala Asn
1               5

<210> SEQ ID NO 18
<211> LENGTH: 4
<212> TYPE: PRT
<213> ORGANISM: Human immunodeficiency virus

<400> SEQUENCE: 18

Gly Gly Asp Ile
1

<210> SEQ ID NO 19
<211> LENGTH: 5
<212> TYPE: PRT
<213> ORGANISM: Human immunodeficiency virus

<400> SEQUENCE: 19

Gly Gly Ala Asn Asn
1               5

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Arg Arg Asp Ser Ser Gly Phe Tyr Tyr Phe Asp Tyr Trp
            100                 105                 110

Gly Gln Gly Thr Leu Val Thr Val Ser Ser
            115                 120

<210> SEQ ID NO 21
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Thr Val Thr Val Thr Arg Asp Thr Ser Ile Gly Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Asp Thr Asn Ser Gly Ser Arg Phe Asp Pro
            100                 105                 110

Trp Gly Gln Gly Leu Trp Ser Pro Ser Pro Gln
            115                 120

<210> SEQ ID NO 22
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Tyr Asn Thr Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Arg Phe
50                  55                  60

```
Gln Thr Arg Val Asp Met Thr Arg Asp Thr Ser Ile Asn Thr Val Tyr
65                  70                  75                  80

Met Glu Leu Ser Gly Leu Ser Asp Asp Thr Ala Val Tyr Tyr Cys
            85                  90                  95

Val Thr Asp Phe Asn Gly Gly Ser Phe Pro Phe Thr Leu Thr
            100                 105                 110

Thr Trp Gly Gln Gly Thr Leu Val Thr Val Ser Ser
        115                 120
```

<210> SEQ ID NO 23
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Val Pro Gly Gln Gly Leu Glu Trp Ile
        35                  40                  45

Gly Trp Ile His Pro Asn Ser Gly Arg Ala Thr His Thr Gln Lys Phe
    50                  55                  60

Gln Gly Arg Val Thr Met Thr Ser Gly Thr Ser Ile Ser Thr Val Tyr
65                  70                  75                  80

Met Glu Leu Thr Gly Leu Thr Pro Asp Thr Ala Val Tyr Tyr Cys
            85                  90                  95

Ala Arg Asp Asn Tyr Arg Asn Asn Val Trp Val Leu Tyr Thr Phe Asp
            100                 105                 110

Tyr Trp Gly Gln Gly Thr Leu Val Thr Val Ser Ser
        115                 120
```

<210> SEQ ID NO 24
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Gln Val Gln Leu Val Pro Ser Gly Ala Glu Val Lys Lys Pro Gly Ala
1               5                   10                  15

Ser Met Arg Val Ser Cys Gln Thr Ser Gly Tyr Thr Phe Asn Ser Tyr
            20                  25                  30

Tyr Ile His Trp Met Arg Gln Val Pro Gly Gln Gly Leu Glu Trp Met
        35                  40                  45

Gly Trp Ile Asn Pro Asn Ser Gly Tyr Thr Asn Tyr Thr Gln Lys Phe
    50                  55                  60

Gln Asp Arg Val Thr Met Thr Arg Asp Thr Ser Ile Asn Thr Ala Tyr
65                  70                  75                  80

Leu Glu Leu Ser Ala Leu Arg Ser Asp Glu Thr Ala Val Tyr Tyr Cys
            85                  90                  95

Ala Arg Asp Phe Ser Asp Gly Trp Pro Tyr Ser Phe Asp Phe Trp Gly
            100                 105                 110
```

```
Gln Gly Thr Leu Val Thr Val Ser Ser
        115                 120
```

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Val Gln Leu Val Gln Ser Gly Ala Glu Val Lys Lys Pro Gly Ala
1               5                   10                  15

Ser Met Arg Val Ser Cys Gln Thr Ser Gly Tyr Thr Phe Asn Ser Tyr
                20                  25                  30

Tyr Ile His Trp Met Arg Gln Val Pro Gly Gln Gly Leu Glu Trp Met
            35                  40                  45

Gly Trp Ile Asn Pro Asn Ser Gly Tyr Thr Asn Tyr Thr Gln Lys Phe
    50                  55                  60

Gln Gly Arg Val Thr Met Thr Arg Asp Thr Ser Ile Asn Thr Ala Tyr
65                  70                  75                  80

Leu Glu Leu Ser Ala Leu Arg Ser Asp Glu Thr Ala Val Tyr Tyr Cys
                85                  90                  95

Ala Arg Asp Phe Ser Asp Gly Trp Pro Tyr Ser Phe Asp Phe Trp Gly
                100                 105                 110

Gln Gly Thr Leu Val Thr Val Ser Ser
        115                 120
```

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Thr Asp Gln
                20                  25                  30

His Leu Asn Trp Ile Arg Gln Ala Pro Gly Gln Gly Phe Glu Trp Leu
            35                  40                  45

Gly Arg Phe Asn Pro Ala Asn Gly Gly Thr Asp Leu Ala Gln Lys Phe
    50                  55                  60

Gln Gly Arg Val Ser Met Thr Arg Asn Met Ser Ile Thr Thr Ala Tyr
65                  70                  75                  80

Leu Glu Leu Ser Arg Leu Thr Ser Asp Asp Thr Ala Thr Tyr Tyr Cys
                85                  90                  95

Leu Asn Ser Gly Trp Thr Asn Glu Tyr His Tyr Asp His Trp Gly Gln
                100                 105                 110

Gly Thr Pro Val Thr Val Ser Ser
        115                 120
```

<210> SEQ ID NO 27
<211> LENGTH: 120
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 27

Gln Val Gln Leu Val Glu Ser Gly Arg Glu Val Lys Lys Pro Gly Pro
1               5                   10                  15

Ser Val Lys Val Ser Cys Gln Ala Ser Gly Tyr Arg Phe Thr Asp Gln
            20                  25                  30

His Leu Asn Trp Ile Arg Gln Ala Pro Gly Gln Gly Phe Glu Trp Leu
        35                  40                  45

Gly Arg Phe Asn Pro Ala Asn Gly Gly Thr Asp Leu Ala Gln Lys Phe
    50                  55                  60

Gln Val Arg Val Ser Met Thr Arg Asn Met Ser Ile Thr Thr Ala Tyr
65                  70                  75                  80

Leu Glu Leu Ser Arg Leu Thr Ser Asp Asp Thr Ala Thr Tyr Tyr Cys
                85                  90                  95

Leu Asn Ser Gly Trp Thr Asn Glu Tyr His Tyr Asp His Trp Gly Gln
            100                 105                 110

Gly Thr Pro Val Thr Val Ser Ser
        115                 120

<210> SEQ ID NO 28
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Gln Ser Gly Ala Glu Val Lys Lys Pro Gly Ala
1               5                   10                  15

Ser Leu Lys Leu Ser Cys Lys Thr Ser Gly Lys Thr Phe Asn Thr Tyr
            20                  25                  30

Tyr Trp Gln Trp Val Arg Gln Ala Pro Gly Gln Arg Leu Glu Trp Leu
        35                  40                  45

Gly Val Phe Ser Pro Arg Asp Ala Val Thr Lys Tyr Ala Arg Ala Phe
    50                  55                  60

Gln Gly Arg Leu Thr Val Thr Arg Asp Thr Ser Thr Gly Thr Thr Tyr
65                  70                  75                  80

Met Glu Leu Ser Ser Leu Arg Val Asp Asp Thr Ala Met Tyr Tyr Cys
                85                  90                  95

Ala Thr Ser Leu Glu Val Ala Ala Pro Asp Arg Ile Leu Leu Thr Ile
            100                 105                 110

Trp Gly Gln Gly Thr Met Val Ile Val Ser Ser Ala
        115                 120

<210> SEQ ID NO 29
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Gln Ser Gly Ala Glu Leu Lys Arg Pro Gly Ala
1               5                   10                  15
```

```
Ser Val Arg Val Ser Cys Gln Thr Ser Gly Asn Thr Phe Asn Asn His
            20                  25                  30

Asp Val Asn Trp Ile Arg Gln Ala Pro Gly Gly Leu Glu Trp Met
        35                  40                  45

Gly Trp Met Asn Val Lys Phe Gly Ser Gly His Ile His Lys Phe
 50                  55                  60

Asp His Arg His Thr Phe Asn Arg Asp Thr Thr Ile Asn Ala Ala Tyr
 65                  70                  75                  80

Leu Asp Leu Lys Asn Leu Lys Val Asp Thr Ala Phe Tyr Tyr Cys
                85                  90                  95

Val Val Ala Thr Gly Ser Ala Tyr Asp Ile Trp Gly His Gly Thr Leu
                100                 105                 110

Val Ser Val Ser Ser Ala
            115

<210> SEQ ID NO 30
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Val Gln Ser Gly Pro Glu Ala Gly Arg Pro Gly Ala
 1               5                  10                  15

Ser Val Lys Val Ser Cys Lys Ala Ser Gly Tyr Ile Phe Thr Ser Tyr
            20                  25                  30

Pro Ile Gly Trp Val Arg Gln Ala Pro Gly Gln Arg Leu Glu Trp Met
        35                  40                  45

Gly Trp Met Asn Pro Phe Asn Gly Tyr Val Lys Ser Ala Gln Glu Phe
 50                  55                  60

Gln Asp Arg Leu Thr Leu Ser Thr Asn Asn Ser Ala His Thr Ala Tyr
 65                  70                  75                  80

Met Glu Leu Arg Ser Leu Thr Ser Asp Thr Ala Ile Tyr Phe Cys
                85                  90                  95

Ala Arg Val Gln Phe Asp Ser Lys Tyr Tyr Thr Phe Phe Asp Leu Trp
                100                 105                 110

Gly Gln Gly Thr Leu Val Thr Val Ser Ser Ala
            115                 120

<210> SEQ ID NO 31
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Gln Ser Gly Ala Glu Met Lys Lys Pro Gly Ala
 1               5                  10                  15

Ser Val Lys Val Ser Cys Lys Ser Ser Gly Tyr Thr Phe Thr Tyr Tyr
            20                  25                  30

Ser Ile His Trp Val Arg Gln Ala Pro Gly Gln Gly Leu Glu Trp Met
        35                  40                  45

Gly Arg Ser Asn Thr Ala Ser Asp Asn Thr Lys Tyr Ser Gln Glu Phe
 50                  55                  60
```

```
Gln Val Arg Val Ala Ile Thr Arg Asp Thr Ser Ala Asn Thr Thr Tyr
 65                  70                  75                  80

Val Glu Leu Ser Ser Leu Arg Ser Asp Ala Val Asp Tyr Tyr Cys
                 85                  90                  95

Gly Arg Val Ser Trp His Arg Phe Cys Arg Gly Ile Gly Tyr Trp Gly
                100                 105                 110

Gln Gly Thr Leu Val Thr Val Ser Ser
            115                 120
```

<210> SEQ ID NO 32
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gln Val Gln Leu Val Gln Ser Gly Ala Glu Val Lys Lys Val Gly Ser
  1               5                  10                  15

Ser Val Thr Leu Ser Cys Lys Ile Ser Gly Gly Thr Phe Tyr Asp Phe
                 20                  25                  30

Ala Val Asn Trp Val Arg Gln Ala Pro Gly Gln Gly Leu Glu Trp Val
             35                  40                  45

Gly Ala Val Ile Pro Met Phe Gly Thr Pro Ile Tyr Pro Pro Lys Phe
 50                  55                  60

Arg His Arg Val Thr Val Ser Ser Tyr Gly Ser Met Thr Thr Val Tyr
 65                  70                  75                  80

Met Glu Leu Arg Asn Leu Thr Phe Glu Asp Thr Ala Ile Tyr Tyr Cys
                 85                  90                  95

Ala Arg Asp Gly Arg Glu Gly Val Asn Pro Ala Cys Gln Trp Leu Asp
                100                 105                 110

Pro Trp Gly Gln Gly Thr Leu Val Thr Val Ser Ser Thr
            115                 120                 125
```

<210> SEQ ID NO 33
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Val Gln Leu Val Gln Pro Gly Ala Glu Val Lys Lys Pro Ala Ser
  1               5                  10                  15

Ser Val Lys Val Ser Cys Gln Ala Ser Arg Tyr Thr Phe Thr Lys His
                 20                  25                  30

Phe Thr Gln Trp Val Arg Arg Gly Pro Gly Gln Gly His Glu Trp Leu
             35                  40                  45

Ala Cys Phe Lys Pro Tyr Asn Asn His Thr His Tyr Ala Gln Asn Phe
 50                  55                  60

Trp Gly Arg Leu Thr Thr Ser Thr Asp Arg Ser Val His Thr Ala Tyr
 65                  70                  75                  80

Met Asp Leu Ser Ser Val Arg Ser Glu Asp Met Val Arg Val Phe Leu
                 85                  90                  95

Cys Ala Ile Pro Glu Val Glu Arg Leu Lys Thr Leu Ile Leu Val Val
                100                 105                 110
```

```
Ile Ile Arg Trp Gly Gln Gly Thr Leu Val Thr Val Ala Ser Gly
        115                 120                 125
```

<210> SEQ ID NO 34
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Val Gln Leu Val Gln Ser Gly Pro Val Ile Lys Lys Pro Gly Thr
1               5                   10                  15

Ser Val Gln Val Ser Cys Lys Ala Ser Gly Phe Thr Phe Ser Ser Tyr
            20                  25                  30

Val Ile Gln Trp Val Arg Gln Thr Arg Gly Gln Arg Leu Glu Trp Ile
        35                  40                  45

Gly Trp Ile Val Val Gly Ser Gly Ile Thr Asn Cys Ala Gln Asn Phe
    50                  55                  60

Gln Glu Arg Val Thr Leu Ile Arg Asp Met Ser Thr Asp Thr Ala Tyr
65                  70                  75                  80

Met Glu Leu Asn Ser Leu Gly Ser Glu Asp Thr Ala Leu Tyr Tyr Cys
                85                  90                  95

Ala Ala Glu Pro Leu Arg Phe Pro Arg Val Gly Trp Ser Ile Pro Trp
            100                 105                 110

Gly Gln Gly Thr Leu Val Thr Val Ser Ser Ala
        115                 120
```

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Gln Val Gln Leu Val Gln Ser Gly Val Glu Val Lys Lys Pro Gly Ala
1               5                   10                  15

Ser Val Lys Val Ser Cys Lys Val Ser Gly Tyr Phe Leu Ser Lys Ile
            20                  25                  30

Ser Ile His Trp Val Arg Gln Ala Pro Glu Lys Gly Leu Glu Trp Met
        35                  40                  45

Gly Gly Phe Asp Ala Glu Gly Glu Thr Val Tyr Ala Gln Lys Phe
    50                  55                  60

Gln Gly Arg Val Thr Val Thr Glu Asp Thr Ser Thr Asp Thr Ala Tyr
65                  70                  75                  80

Met Asp Val Ser Ser Leu Arg Ser Glu Asp Thr Ala Val Tyr Tyr Cys
                85                  90                  95

Ala Thr Gly Ile Arg Gly Arg Pro Leu Ile Ser Trp Gly Gln Gly Thr
            100                 105                 110

Val Val Thr Val Ser Ser Ala
        115
```

<210> SEQ ID NO 36
<211> LENGTH: 132
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 36

Gln Val Gln Leu Val Ala Gly Leu Gly Arg Glu Val Arg Lys Val Trp
1               5                   10                  15

Gly Ser Val Lys Val Ser Cys Ser Phe Ser Gly Phe Thr Ile Thr Ser
            20                  25                  30

Tyr Gly Ile His Trp Val Gln Gln Ser Pro Gln Gly Leu Glu Trp
        35                  40                  45

Met Gly Trp Ile Asn Pro Gly Asn Gly Ser Pro Ser Tyr Ala Lys Lys
    50                  55                  60

Phe Gln Gly Arg Phe Thr Met Thr Arg Asp Met Ser Thr Thr Thr Ala
65                  70                  75                  80

Tyr Thr Asp Leu Ser Ser Leu Thr Ser Glu Asp Met Ala Val Tyr Tyr
                85                  90                  95

Tyr Ala Tyr Pro Gly Phe Pro Ser Tyr Tyr Tyr Asp Ser Ser Gly Tyr
            100                 105                 110

Tyr Tyr Glu Pro Leu Leu Trp Tyr Trp Gly Gln Gly Thr Leu Val Thr
        115                 120                 125

Val Ser Ser Gly
    130

<210> SEQ ID NO 37
<211> LENGTH: 131
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 37

Gln Ser Gly Ser Gly Val Lys Lys Pro Gly Ala Ser Val Arg Val Ser
1               5                   10                  15

Cys Arg Ala Ser Glu Asp Leu Phe Gly Asp Glu Ile Ile Tyr Asp Asp
            20                  25                  30

Glu Val Ile His Trp Leu Arg Gln Val Pro Gly Gln Arg Pro Glu Trp
        35                  40                  45

Met Gly Trp Ile Arg Pro Lys Thr Gly Ala Arg Asn Gln Ala Arg Gln
    50                  55                  60

Phe Gln Pro Arg Ile Ser Leu Thr Arg Asp Arg Ala Leu Ser Thr Ala
65                  70                  75                  80

Tyr Leu Asp Leu Asn Ser Leu Thr Ser Ala Asp Ser Gly Thr Tyr Phe
                85                  90                  95

Cys Ala Arg Gln Thr Phe Lys Pro Asp Phe Tyr Phe Ala Asp Gln Gly
            100                 105                 110

Trp Ser Phe Asn Leu Trp Gly Arg Gly Ala His Phe Ile Val Ser Ser
        115                 120                 125

Ala Ser Thr
    130

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Gln Ser Gly Pro Glu Val Arg Lys Pro Gly Ala Ser Val Thr Val Ser
1               5                   10                  15

Cys Lys Thr Ser Gly Tyr Thr Phe Thr Asp Asn Tyr Phe His Trp Leu
            20                  25                  30

Arg Gln Ala Pro Gly Met Gly Leu Glu Trp Met Gly Trp Ile Asn Pro
        35                  40                  45

His Asn Gly Gly Ile Lys Ser Ala Lys Lys Phe Gln Gly Arg Ile Thr
    50                  55                  60

Met Thr Arg Asp Thr Thr Ile Asp Thr Ala Tyr Met Glu Leu Ser Gly
65                  70                  75                  80

Leu Thr Ser Asp Asp Thr Ala Phe Tyr Phe Cys Ala Arg Glu Gly Gly
                85                  90                  95

His Ser Ser Gly Phe Asp Tyr Trp Gly Gln Gly Ala Leu Val Thr Val
            100                 105                 110

Thr Ser Ala Ser Thr
        115

<210> SEQ ID NO 39
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Arg Gly Ala Glu Val Lys Lys Pro Gly Ala Ser Val Lys Val Ser
1               5                   10                  15

Cys Lys Ala Ser Gly Tyr Thr Phe Thr Gly Tyr Tyr Ile His Trp Val
            20                  25                  30

Arg Gln Ala Pro Gly Gln Gly Leu Glu Trp Ile Gly Trp Val Lys Ile
        35                  40                  45

Val Ser Gly Thr Val Asn Phe Ala Ser Leu Asp Phe Arg Asn Arg Ile
    50                  55                  60

Ser Leu Ser Arg Asp Arg Asp Leu Ser Thr Ala Tyr Met Asp Ile Arg
65                  70                  75                  80

Gly Leu Thr Gln Asp Asp Thr Ala Thr Tyr Phe Cys Ala Arg Gln Lys
                85                  90                  95

Phe Ala Ser Arg Tyr Ser Gly Asp Gln Gly Ser Tyr Phe Asp Leu Trp
            100                 105                 110

Gly Arg Gly Thr Leu Ile Val Val Ser Ser Ala Ser Thr
        115                 120                 125

<210> SEQ ID NO 40
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ala Gly Gly Gly Val Lys Lys Pro Gly Ala Ser Val Thr Leu Ser
1               5                   10                  15

Cys Lys Thr Ala Asp Glu Asp Val Phe Asp Ala Ala Tyr Met His Trp
            20                  25                  30

Val Arg Gln Ala Pro Gly Gln Thr Phe Glu Trp Leu Gly Trp Met Lys 35                  40                  45
Pro Val Thr Gly Ala Val Ser Tyr Ala Arg Lys Phe Gln Gly Arg Val
        50                  55                  60
Ser Phe Tyr Met Thr Arg Glu Leu Gly Met Ala Tyr Met Asp Leu Arg
 65                  70                  75                  80
Asn Leu Arg Phe Asp Asp Thr Ala Val Tyr Tyr Cys Ala Arg Val Gly
                85                  90                  95
Gly Ala Ala Asp Asp Ser Gly Tyr Thr Glu Pro Pro Ser Asp Tyr Trp
            100                 105                 110
Gly Gln Gly Thr Leu Val Thr Val Ser Ser Ala Ser Thr
        115                 120                 125

<210> SEQ ID NO 41
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Ser Ala Ser Gly Val Arg Arg Pro Gly Ala Ser Val Arg Val Ser
 1               5                  10                  15
Cys Trp Thr Ser Glu Asp Ile Phe Glu Arg Ser Glu Leu Ile Tyr Trp
                20                  25                  30
Val Arg Gln Ala Pro Gly Arg Gly Leu Glu Trp Ile Gly Trp Ile Lys
            35                  40                  45
Leu Val Ser Gly Ala Val Asn Phe Gly Ser Val Asp Phe Arg Asp Arg
        50                  55                  60
Val Ser Leu Thr Arg Asp Arg Asp Leu Phe Thr Ala His Met Asp Ile
 65                  70                  75                  80
Arg Gly Leu Thr Gln Asp Asp Thr Ala Thr Tyr Phe Cys Ala Arg Gln
                85                  90                  95
Lys Phe Ala Ser Arg Tyr Ser Gly Asp Gln Gly Ser Tyr Phe Asp Leu
            100                 105                 110
Trp Gly Arg Gly Thr Leu Ile Ile Val Ser Ser Ala Ser Thr
        115                 120                 125

<210> SEQ ID NO 42
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Ser Gly Ala Glu Val Lys Lys Pro Gly Ala Ser Val Lys Val Ser
 1               5                  10                  15
Cys Lys Ala Ser Gly Tyr Thr Phe Thr Gly Tyr Tyr Met His Trp Val
                20                  25                  30
Arg Gln Ala Pro Gly Gln Thr Phe Glu Trp Leu Gly Trp Met Lys Pro
            35                  40                  45
Val Thr Gly Ala Val Asn Tyr Ala Arg Gln Phe Gln Gly Arg Val Ser
        50                  55                  60
Phe Tyr Arg Thr Arg Glu Leu Gly Ile Ala Tyr Met Asp Leu Arg Asp
 65                  70                  75                  80
Leu Lys Phe Asp Asp Thr Ala Val Tyr Phe Cys Ala Arg Lys Thr Lys

```
                     85                  90                  95

Ala Asp Val Ser Gly Asp Arg Gly Phe Phe Asp Leu Trp Gly
                100                 105                 110

Arg Gly Thr Arg Val Ile Val Ser Ser Ala Ser Thr
                115                 120

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Ser Gly Ser Gly Val Lys Lys Pro Gly Thr Ser Val Arg Val Ser
1               5                   10                  15

Cys Trp Thr Ser Glu Asp Ile Phe Glu Arg Thr Glu Leu Ile His Trp
                20                  25                  30

Val Arg Gln Ala Pro Gly Gln Gly Leu Glu Trp Ile Gly Trp Val Lys
            35                  40                  45

Thr Val Thr Gly Ala Val Asn Phe Gly Ser Pro Asn Phe Arg His Arg
     50                  55                  60

Val Ser Leu Thr Arg Asp Arg Asp Leu Phe Thr Ala His Met Asp Ile
65                  70                  75                  80

Arg Gly Leu Thr Gln Gly Asp Thr Ala Thr Tyr Tyr Cys Ala Arg Asp
                85                  90                  95

Trp Gly Ala Thr Val Val Val Tyr Leu Leu Asp Ser Trp Gly Gln Gly
                100                 105                 110

Thr Pro Val Thr Val Ser Ser Ala Ser Thr
            115                 120

<210> SEQ ID NO 44
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Ser Gly Ala Glu Val Lys Lys Pro Gly Ala Ser Val Thr Leu Ser
1               5                   10                  15

Cys Lys Thr Ala Asp Glu Asp Val Phe Asp Ala Ala Tyr Met His Trp
                20                  25                  30

Val Arg Gln Ala Pro Gly Gln Thr Phe Glu Trp Leu Gly Trp Met Lys
            35                  40                  45

Pro Val Thr Gly Ala Val Ser Tyr Ala Arg Lys Phe Gln Gly Arg Val
     50                  55                  60

Ser Phe Tyr Met Thr Arg Glu Leu Gly Met Ala Tyr Met Asp Leu Arg
65                  70                  75                  80

Asn Leu Arg Phe Asp Asp Thr Ala Val Tyr Phe Cys Ala Arg Lys Thr
                85                  90                  95

Ala Gly Asp Val Ser Gly Asp Asn Arg Gly Tyr Phe Phe Asp Leu Trp
                100                 105                 110

Gly Arg Gly Ser Arg Val Ile Val Ser Ser Ala Ser Thr
            115                 120                 125
```

```
<210> SEQ ID NO 45
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

Gln Ser Gly Ser Ala Met Lys Lys Pro Gly Ala Ser Val Arg Val Ser
1               5                   10                  15

Cys Trp Thr Ser Glu Asp Ile Phe Asp Thr Thr Glu Leu Ile Tyr Trp
            20                  25                  30

Val Arg Gln Ala Pro Gly Gln Gly Leu Glu Trp Ile Gly Trp Val Lys
        35                  40                  45

Ile Val Ser Gly Thr Val Asn Phe Ala Arg Gln Phe Gln Gly Arg Val
    50                  55                  60

Ser Phe Tyr Arg Thr Arg Glu Leu Gly Ile Ala Tyr Met Asp Leu Arg
65                  70                  75                  80

Asp Leu Lys Phe Asp Asp Thr Ala Val Tyr Phe Cys Ala Arg Lys Thr
                85                  90                  95

Lys Gly Asp Val Ser Gly Asp Arg Gly Phe Pro Phe Asp Leu Trp
            100                 105                 110

Gly Arg Gly Thr Arg Val Ile Val Ser Ser Ala Ser Thr
        115                 120                 125

```
<210> SEQ ID NO 46
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46
```

Glu Ser Gly Pro Glu Val Arg Lys Pro Gly Ala Ser Val Lys Ile Ser
1               5                   10                  15

Cys Lys Thr Ser Gly Tyr Ile Phe Thr Asp Asn Tyr Phe His Trp Leu
            20                  25                  30

Arg Gln Ala Pro Ala Val Gly Leu Glu Trp Met Gly Trp Ile Asn Pro
        35                  40                  45

His Asn Gly Tyr Thr Lys Ser Ala Lys Lys Phe Gln Gly Arg Ile Thr
    50                  55                  60

Met Thr Arg Asp Thr Ala Val Asp Thr Ala Tyr Met Glu Leu Ile Asp
65                  70                  75                  80

Leu Thr Ser Asp Asp Thr Ala Ile Tyr Phe Cys Ala Arg Glu Gly Gly
                85                  90                  95

His Ser Ser Gly Phe Asp Tyr Trp Gly Gln Gly Ala Leu Val Thr Val
            100                 105                 110

Thr Ser Ala Ser Thr
        115

```
<210> SEQ ID NO 47
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47
```

Gln Ser Gly Ser Ala Met Lys Pro Gly Arg Ser Val Lys Tyr Ser
1               5                   10                  15

Cys Trp Thr Ser Glu Asp Ile Phe Thr His Arg Val Asp Leu Trp Val
                20                  25                  30

Arg Gln Ala Pro Gly Gln Gly Leu Glu Trp Ile Gly Trp Val Lys Ile
            35                  40                  45

Val Ser Gly Thr Val Asn Phe Ala Ser Leu Asp Phe Arg Asn Arg Ile
50                  55                  60

Ser Leu Ser Arg Asp Arg Asp Leu Ser Thr Ala Tyr Met Asp Ile Arg
65                  70                  75                  80

Gly Leu Thr Gln Asp Asp Thr Ala Thr Tyr Phe Cys Ala Arg Gln Lys
                85                  90                  95

Phe Ala Ser Arg Tyr Ser Gly Asp Gln Gly Ser Tyr Phe Asp Leu Trp
            100                 105                 110

Gly Arg Gly Thr Leu Ile Val Val Ser Ser Ala Ser Thr
            115                 120                 125

<210> SEQ ID NO 48
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Ser Gly Ser Gly Val Lys Lys Pro Gly Ala Ser Val Arg Val Ser
1               5                   10                  15

Cys Trp Thr Ser Glu Asp Ile Phe Glu Lys Ser Glu Leu Ile His Trp
                20                  25                  30

Val Arg Gln Ala Pro Gly Gln Gly Leu Glu Trp Met Gly Trp Ile Asn
            35                  40                  45

Pro Arg Thr Gly Val Ala Asn Asn Ala Gln Lys Phe Gln Asp Arg Val
50                  55                  60

Thr Met Thr Arg Asp Thr Ser Ile Thr Thr Ala Tyr Met Glu Leu Thr
65                  70                  75                  80

Asn Leu Arg Ser Asp Asp Ser Ala Thr Tyr Tyr Cys Ala Leu Gly Asp
                85                  90                  95

Leu Ile Cys Asp Thr Arg Thr Cys Ser Tyr Asn Ser Phe Glu Pro Trp
            100                 105                 110

Gly Gln Gly Thr Leu Ile Thr Val Ser Ser Ala Ser Thr
            115                 120                 125

<210> SEQ ID NO 49
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ser Gly Ala Glu Val Lys Lys Pro Gly Ala Ser Val Lys Val Ser
1               5                   10                  15

Cys Lys Ala Ser Gly Tyr Thr Phe Thr Gly Tyr Tyr Met His Trp Val
                20                  25                  30

Arg Gln Ala Pro Gly Gln Gly Leu Glu Trp Ile Gly Trp Val Lys Thr
            35                  40                  45

Val Ser Gly Ala Val Asn Phe Gly Ser Leu Asn Phe Arg His Arg Val
 50                  55                  60

Ser Leu Thr Arg Asp Arg Asp Leu Phe Thr Ala His Met Asp Ile Arg
 65                  70                  75                  80

Gly Leu Thr Gln Gly Asp Thr Ala Thr Tyr Phe Cys Ala Arg Gln Lys
                 85                  90                  95

Phe Ala Arg Gly Asp Gln Gly Trp Phe Phe Asp Leu Trp Gly Arg Gly
            100                 105                 110

Thr Leu Ile Val Val Ser Ser Ala Ser Thr
            115                 120

<210> SEQ ID NO 50
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Ala Gly Gly Met Lys Lys Pro Gly Ala Ser Met Thr Val Ser Cys
 1               5                  10                  15

Glu Thr Ala Asp Glu Asp Ile Phe Asp Ala Ala Tyr Met His Trp Val
             20                  25                  30

Arg Gln Val Pro Gly Gln Thr Phe Glu Trp Leu Gly Trp Met Lys Pro
         35                  40                  45

Val Thr Gly Ala Val Asn Tyr Ala Arg Lys Phe Gln Gly Arg Ile Ser
 50                  55                  60

Phe Tyr Arg Thr Arg Glu Leu Ala Ile Ala Tyr Met Asp Leu Arg Asp
 65                  70                  75                  80

Leu Arg Phe Asp Asp Thr Ala Val Tyr Phe Cys Ala Arg Lys Thr Val
                 85                  90                  95

Gly Asp Val Ser Gly Asp Gly Arg Gly Phe Phe Phe Asp Leu Trp Gly
            100                 105                 110

Arg Gly Thr Arg Val Ile Ile Ser Ser Ala Ser Thr
            115                 120

<210> SEQ ID NO 51
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Ser Gly Ser Ala Met Lys Lys Pro Gly Ala Ser Val Arg Val Ser
 1               5                  10                  15

Cys Trp Thr Ser Glu Asp Ile Phe Asp Thr Thr Glu Leu Ile Tyr Trp
             20                  25                  30

Val Arg Gln Ala Pro Gly Gln Gly Leu Glu Trp Ile Gly Trp Val Lys
         35                  40                  45

Ile Val Ser Gly Thr Val Asn Phe Ala Ser Ser Asp Phe Arg Asn Arg
 50                  55                  60

Ile Ser Leu Ser Arg Asp Arg Asp Leu Ser Thr Ala His Met Asp Ile
 65                  70                  75                  80

Arg Gly Leu Thr Gln Asp Asp Thr Ala Thr Tyr Phe Cys Ala Arg Gln
                 85                  90                  95

```
Lys Phe Glu Arg Val Arg Tyr Arg Gly Asp Gln Gly Ser Tyr Phe Asp
            100                 105                 110

Leu Trp Gly Arg Gly Thr Val Ile Ile Ser Ser Ala Ser Thr
        115                 120                 125

<210> SEQ ID NO 52
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ser Gly Ala Glu Val Lys Lys Pro Gly Ala Ser Val Lys Val Ser
1               5                   10                  15

Cys Lys Ala Ser Gly Tyr Thr Phe Thr Ser Tyr Tyr Met His Trp Val
            20                  25                  30

Arg Gln Ala Pro Gly Gln Gly Leu Glu Trp Ile Gly Trp Val Lys Pro
        35                  40                  45

Val Thr Gly Ala Val Asn Phe Gly Ser Pro Asn Phe Arg His Arg Val
    50                  55                  60

Ser Leu Thr Arg Asp Arg Asp Leu Phe Thr Ala His Met Asp Ile Arg
65                  70                  75                  80

Gly Leu Thr Gln Gly Asp Thr Ala Thr Tyr Phe Cys Ala Arg Gln Lys
                85                  90                  95

Tyr Tyr Ala Gly Gly Gln Gly Trp Tyr Phe Asp Leu Trp Gly Arg Gly
            100                 105                 110

Thr Leu Ile Val Val Ser Ser Ala Ser Thr
        115                 120

<210> SEQ ID NO 53
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ser Gly Ala Glu Val Lys Lys Pro Gly Ser Ser Ile Lys Val Ser
1               5                   10                  15

Cys Lys Ala Ser Gly Asp Thr Ile Ser Arg Tyr Ala Ile Asn Trp Val
            20                  25                  30

Arg Gln Ala Pro Gly Gln Gly Leu Glu Trp Ile Gly Trp Val Lys Thr
        35                  40                  45

Val Thr Gly Ala Val Asn Phe Gly Ser Leu Asp Phe Arg His Arg Ile
    50                  55                  60

Ser Leu Thr Arg Asp Arg Asp Leu Phe Thr Ala His Met Gly Ile Arg
65                  70                  75                  80

Gly Leu Thr Gln Gly Asp Thr Ala Thr Tyr Phe Cys Ala Arg Gln Lys
                85                  90                  95

Phe Glu Ser Arg Tyr Thr Gly Gly Gln Gly Trp Tyr Phe Asp Leu Trp
            100                 105                 110

Gly Arg Gly Thr His Ile Val Val Ser Ser Ala Ser Thr
        115                 120                 125

<210> SEQ ID NO 54
```

<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ser Gly Ala Glu Val Lys Lys Pro Gly Ala Ser Ala Lys Val Ser
1               5                   10                  15

Cys Lys Ala Ser Gly Tyr Thr Phe Ser Gly Tyr His Ile His Trp Val
            20                  25                  30

Arg Gln Ala Pro Gly Gln Gly Leu Glu Trp Val Gly Trp Ile Asn Pro
        35                  40                  45

Asn Ser Gly Ala Thr Gln Cys Ala Lys Lys Phe Gln Glu Arg Val Ala
    50                  55                  60

Met Thr Arg Asp Thr Thr Asn Asn Thr Val Tyr Val Glu Leu Asn Arg
65                  70                  75                  80

Leu Thr Ser Asp Asp Thr Ala Thr Tyr Tyr Cys Ala Arg Asp Trp Gly
                85                  90                  95

Ala Thr Val Val Val Tyr Leu Leu Asp Ser Trp Gly Gln Gly Thr Pro
            100                 105                 110

Val Thr Val Ser Ser Ala Ser Thr
        115                 120

<210> SEQ ID NO 55
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Ser Gly Ala Glu Val Lys Lys Pro Gly Ala Ser Val Lys Val Ser
1               5                   10                  15

Cys Lys Ala Ser Gly Tyr Thr Tyr Thr Thr Tyr Gly Val Ser Trp Leu
            20                  25                  30

Arg Gln Val Pro Gly Gln Arg Pro Glu Trp Met Gly Trp Ile Arg Pro
        35                  40                  45

Lys Thr Gly Ala Arg Asn Gln Ala Arg Gln Phe Gln Pro Arg Ile Ser
    50                  55                  60

Leu Thr Arg Asp Arg Ala Leu Ser Thr Ala Tyr Leu Asp Leu Asn Ser
65                  70                  75                  80

Leu Thr Ser Ala Asp Ser Gly Thr Tyr Phe Cys Ala Arg Gln Thr Phe
                85                  90                  95

Lys Pro Asp Phe Tyr Phe Ala Asp Gln Gly Trp Ser Phe Asn Leu Trp
            100                 105                 110

Gly Arg Gly Ala His Phe Ile Val Ser Ser Ala Ser Thr
        115                 120                 125

<210> SEQ ID NO 56
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Gln Ser Gly Ala Glu Val Lys Arg Pro Gly Ala Ser Val Arg Val Ser
1               5                   10                  15

Cys Arg Ala Ser Gly Tyr Thr Phe Asn Asn Tyr Met Tyr Trp Val
                20                  25                  30

Arg Gln Ala Pro Gly Gln Gly Leu Glu Tyr Val Gly Trp Ile Asn Pro
            35                  40                  45

Asn Thr Gly Thr Thr Lys Tyr Ala Gln Lys Phe Gln Gly Trp Val Thr
50                  55                  60

Leu Thr Leu Asp Thr Ser Ile Thr Thr Ala Tyr Leu Glu Met Gly Arg
65                  70                  75                  80

Leu Thr Pro Asp Asp Thr Ala Leu Phe Tyr Cys Ala Thr Val Ala Gly
                85                  90                  95

Pro Ala Ala Asp Glu Ala Phe Asp Val Trp Gly Gln Gly Thr Met Val
                100                 105                 110

Thr Val Ser Ser Ala Ser Thr
            115

<210> SEQ ID NO 57
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ser Gly Ser Gly Val Lys Lys Pro Gly Ala Ser Val Arg Val Ser
1               5                   10                  15

Cys Trp Thr Ser Glu Asp Ile Phe Glu Arg Thr Glu Leu Ile His Trp
                20                  25                  30

Val Arg Gln Ala Pro Gly Gln Gly Leu Glu Trp Ile Gly Trp Val Lys
            35                  40                  45

Thr Val Thr Gly Thr Val Asn Tyr Ala Arg Lys Phe Gln Gly Arg Val
50                  55                  60

Ser Phe Tyr Arg Thr Arg Glu Leu Gly Ile Ala Tyr Met Asp Leu Arg
65                  70                  75                  80

Asn Leu Arg Phe Asp Asp Thr Ala Val Tyr Phe Cys Ala Arg Lys Thr
                85                  90                  95

Ala Gly Asp Val Ser Gly Asp Lys Arg Gly Phe Phe Phe Asp Leu Trp
                100                 105                 110

Gly Arg Gly Ser Arg Val Ile Val Ser Ser Ala Ser Thr
            115                 120                 125

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Ser Gly Ser Ala Met Lys Lys Pro Gly Ala Ser Val Arg Val Ser
1               5                   10                  15

Cys Trp Thr Ser Glu Asp Ile Phe Asp Thr Thr Glu Leu Ile Tyr Trp
                20                  25                  30

Val Arg Gln Ala Pro Gly Gln Gly Leu Glu Trp Ile Gly Trp Val Lys
            35                  40                  45
```

```
Ile Val Ser Gly Thr Val Asn Phe Ala Ser Leu Asp Phe Arg Asn Arg
 50                  55                  60

Ile Ser Leu Ser Arg Asp Arg Asp Leu Ser Thr Ala His Met Asp Ile
65                  70                  75                  80

Arg Gly Leu Thr Leu Asp Asp Thr Gly Ile Tyr Tyr Cys Ala Arg Gly
                 85                  90                  95

Pro Met Gly Gly Ser His Val Tyr Trp Gly Gln Gly Ser Leu Val Thr
            100                 105                 110

Val Ser Ser Ala Ser Thr
        115

<210> SEQ ID NO 59
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Ser Gly Ser Gly Val Lys Lys Pro Gly Ala Ser Val Arg Val Ser
1               5                   10                  15

Cys Trp Thr Ser Glu Gly Ile Phe Glu Lys Ser Glu Leu Ile His Trp
            20                  25                  30

Val Arg Gln Ala Pro Gly Gln Gly Leu Glu Trp Ile Gly Trp Val Lys
        35                  40                  45

Thr Val Thr Gly Ala Val Asn Phe Gly His Gln Ile Ser Asp Arg Val
    50                  55                  60

Ser Leu Thr Arg Asp Arg Asp Leu Phe Thr Ala His Met Asp Ile Arg
65                  70                  75                  80

Gly Leu Thr Gln Gly Asp Thr Ala Thr Tyr Phe Cys Ala Arg Gln Lys
                85                  90                  95

Phe Glu Arg Gly Gly Gln Gly Trp Ile Phe Asp Leu Trp Gly Arg Gly
            100                 105                 110

Thr Leu Ile Ala Val Ser Ser Ala Ser Thr
        115                 120

<210> SEQ ID NO 60
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Ser Gly Ala Glu Val Lys Arg Pro Gly Ala Ser Leu Asn Val Ser
1               5                   10                  15

Cys His Ala Ser Gly Tyr Leu Phe Asn Asn Tyr Tyr Ile His Trp Val
            20                  25                  30

Arg Gln Ala Pro Gly Gln Gly Leu Glu Trp Met Gly Trp Ile Asn Pro
        35                  40                  45

Thr Thr Lys Ile Thr Asn Leu Pro Leu Lys Phe Arg Gly Arg Val Thr
    50                  55                  60

Leu Thr Arg Glu Pro Ser Lys Ser Ile Leu Tyr Leu Gly Leu Asn Gly
65                  70                  75                  80

Leu Thr Pro Asp Asp Thr Ala Ile Tyr Phe Cys Ala Arg Ser Gly Glu
                85                  90                  95
```

Gln Leu Ala His Leu Asp Phe Trp Gly Gln Gly Ser Leu Ile Thr Val
                100                 105                 110

Ser Ala Ala Ser Thr
        115

<210> SEQ ID NO 61
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Ser Gly Ala Glu Val Lys Arg Pro Gly Ala Ser Val Lys Val Ser
1               5                   10                  15

Cys Trp Thr Ser Glu Asp Ile Phe Glu Arg Thr Glu Leu Ile His Trp
            20                  25                  30

Val Arg Gln Ala Pro Gly Gln Gly Leu Glu Trp Ile Gly Trp Val Lys
        35                  40                  45

Thr Val Ser Gly Ala Val Asn Phe Gly Ser Pro Asn Phe Arg His Arg
    50                  55                  60

Val Ser Leu Thr Arg Asp Arg Asp Leu Phe Thr Ala His Met Asp Ile
65                  70                  75                  80

Arg Gly Leu Thr Gln Gly Asp Thr Ala Thr Tyr Phe Cys Ala Arg Gln
                85                  90                  95

Lys Phe Glu Arg Gly Gly Gln Gly Trp Tyr Phe Asp Leu Trp Gly Arg
            100                 105                 110

Gly Thr Leu Ile Val Val Ser Ser Ala Ser Thr
        115                 120

<210> SEQ ID NO 62
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ser Gly Ala Glu Val Arg Arg Pro Gly Ala Ser Val Lys Val Ser
1               5                   10                  15

Cys Lys Ala Ser Gly Tyr Asn Phe Ile Ala Tyr His Val His Trp Val
            20                  25                  30

Arg Gln Ala Pro Gly Gln Gly Leu Thr Trp Met Gly Trp Ile Asn Pro
        35                  40                  45

Asp Ser Gly Asp Thr Val Tyr Ala Gln Asn Phe Val Asp Arg Val Met
    50                  55                  60

Met Thr Arg Asn Thr Ser Ile Gln Thr Val Tyr Leu Glu Leu Asn Val
65                  70                  75                  80

Leu Thr Leu Glu Asp Thr Ala Ile Tyr Phe Cys Ala Thr Pro Asp Lys
                85                  90                  95

Lys Ser Asp Leu Gly Trp Phe Asp Thr Trp Gly Gln Gly Ser Gln Val
            100                 105                 110

Thr Val Ser Ser Ala Ser Thr
        115

<210> SEQ ID NO 63
<211> LENGTH: 122

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Ser Gly Ala Glu Val Lys Lys Pro Gly Ala Ser Val Gln Val Ser
1               5                   10                  15

Cys Lys Ala Ser Gly Tyr Pro Phe Thr Lys Tyr Tyr Met His Trp Val
            20                  25                  30

Arg Gln Ala Pro Gly Gln Gly Leu Glu Trp Ile Gly Trp Val Lys Ala
        35                  40                  45

Val Ser Gly Ala Val Asn Tyr Gly Ser Leu Asp Phe Arg His Arg Val
    50                  55                  60

Ser Leu Thr Arg Asp Arg Asp Leu Ser Thr Ala His Met Asp Ile Arg
65                  70                  75                  80

Gly Leu Thr Gln Asp Asp Thr Ala Thr Tyr Phe Cys Ala Arg Gln Lys
                85                  90                  95

Phe Ala Arg Gly Asp Gln Gly Trp Phe Phe Asp Leu Trp Gly Arg Gly
            100                 105                 110

Thr Leu Ile Val Val Ser Ser Ala Ser Thr
        115                 120

<210> SEQ ID NO 64
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Ala Gly Gly Gly Met Lys Lys Pro Gly Ala Ser Met Thr Val Ser
1               5                   10                  15

Cys Lys Thr Ala Asp Glu Asp Ile Phe Asp Ala Ala Tyr Met His Trp
            20                  25                  30

Val Arg Gln Ala Pro Gly Gln Thr Phe Glu Trp Leu Gly Trp Met Lys
        35                  40                  45

Pro Val Thr Gly Ala Val Asn Tyr Ala Arg Gln Phe Gln Gly Arg Val
    50                  55                  60

Ser Phe Tyr Arg Thr Arg Glu Leu Gly Ile Ala Tyr Met Asp Leu Arg
65                  70                  75                  80

Asp Leu Lys Phe Asp Asp Thr Ala Val Tyr Tyr Cys Ala Arg Arg Leu
                85                  90                  95

Pro Ser Tyr Tyr Tyr Asp Ser Ser Val Met Ser Gly Asp Tyr Trp Gly
            100                 105                 110

Gln Gly Thr Leu Val Thr Val Ser Ser Ala Ser Thr
        115                 120

<210> SEQ ID NO 65
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Ser Gly Leu Glu Val Lys Lys Pro Gly Ala Ser Val Arg Val Ser

```
                1               5                   10                  15
Cys Trp Thr Ser Glu Asp Ile Phe Asp Thr Thr Glu Leu Ile Tyr Trp
                20                  25                  30

Val Arg Gln Ala Pro Gly Gln Gly Leu Glu Trp Ile Gly Trp Val Lys
                35                  40                  45

Ile Val Ser Gly Thr Val Asn Phe Ala Ser Leu Asp Phe Arg Asn Arg
                50                  55                  60

Ile Ser Leu Ser Arg Asp Arg Asp Leu Ser Thr Ala His Met Asp Ile
65                  70                  75                  80

Arg Gly Leu Thr Gln Asp Asp Thr Ala Thr Tyr Phe Cys Ala Arg Gln
                85                  90                  95

Lys Phe Ala Ser Arg Tyr Ser Gly Asp Gln Gly Ser Tyr Phe Asp Leu
                100                 105                 110

Trp Gly Arg Gly Thr Leu Ile Ile Val Ser Ser Ala Ser Thr
                115                 120                 125
```

<210> SEQ ID NO 66
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Gln Ser Gly Ser Ala Met Lys Lys Pro Gly Ala Ser Val Arg Val Ser
1               5                   10                  15

Cys Trp Thr Ser Glu Asp Ile Phe Asp Thr Thr Glu Leu Ile Tyr Trp
                20                  25                  30

Val Arg Gln Ala Pro Gly Gln Gly Leu Glu Trp Ile Gly Trp Val Lys
                35                  40                  45

Ile Val Ser Gly Thr Val Asn Phe Ala Ser Leu Asp Phe Arg Asn Arg
                50                  55                  60

Ile Ser Leu Ser Arg Asp Arg Asp Leu Phe Thr Ala His Met Asp Ile
65                  70                  75                  80

Arg Gly Leu Thr Gln Gly Asp Thr Ala Thr Tyr Phe Cys Ala Arg Gln
                85                  90                  95

Lys Phe Tyr Ala Gly Gly Gln Gly Trp Tyr Phe Asp Leu Trp Gly Arg
                100                 105                 110

Gly Thr Leu Ile Val Val Ser Ser Ala Ser Thr
                115                 120
```

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Gln Ser Gly Ala Glu Val Arg Lys Pro Gly Ala Ser Val Lys Val Ser
1               5                   10                  15

Cys Lys Ala Ser Gly Tyr Asn Phe Ile Ala Tyr Tyr Val His Trp Val
                20                  25                  30

Arg Gln Ala Pro Gly Gln Gly Leu Thr Trp Met Gly Trp Ile Asn Pro
                35                  40                  45

Asp Ser Gly Asp Thr Val Tyr Ala Gln Asn Phe Leu Asp Arg Val Thr
```

```
                    50                  55                  60
Met Thr Arg Asn Thr Ser Ile Thr Thr Val Tyr Leu Glu Leu Lys Asp
 65                  70                  75                  80

Leu Thr Leu Ala Asp Thr Ala Ile Tyr Tyr Cys Ala Thr Pro Asp Lys
                 85                  90                  95

Lys Asp Asp Leu Gly Trp Phe Asp Thr Trp Gly Gln Gly Ser Gln Val
            100                 105                 110

Thr Val Ser Ser Ala Ser Thr
            115

<210> SEQ ID NO 68
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Ser Gly Ser Ala Met Lys Lys Pro Gly Ala Ser Val Arg Val Ser
 1               5                  10                  15

Cys Trp Thr Ser Glu Asp Ile Phe Asp Thr Thr Glu Leu Ile Tyr Trp
                20                  25                  30

Met Arg Gln Ala Pro Gly Gln Gly Leu Glu Trp Ile Gly Trp Val Lys
            35                  40                  45

Ile Val Ser Gly Thr Val Asn Phe Ala Ser Leu Asp Phe Arg Asn Arg
        50                  55                  60

Ile Ser Leu Ser Arg Asp Arg Asp Leu Ser Thr Ala His Met Asp Ile
 65                  70                  75                  80

Arg Gly Leu Thr Gln Asp Asp Thr Ala Val Tyr Tyr Cys Thr Ser Asp
                 85                  90                  95

Arg Arg Gly Ser Gly Asn Ser Tyr Val Pro Asp His Tyr His Tyr Tyr
            100                 105                 110

Gly Met Asp Val Trp Gly Gln Gly Thr Thr Val Thr Val Ser Ser Ala
            115                 120                 125

Ser Thr
    130

<210> SEQ ID NO 69
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Ser Gly Ser Gly Val Lys Lys Leu Gly Ala Ser Val Arg Val Ser
 1               5                  10                  15

Cys Trp Thr Ser Glu Asp Ile Phe Glu Arg Thr Glu Leu Ile His Trp
                20                  25                  30

Val Arg Gln Ala Pro Gly Gln Gly Leu Glu Trp Met Gly Trp Ile Asn
            35                  40                  45

Pro Asn Ser Gly Gly Thr Tyr Tyr Ala Gln Lys Phe Gln Gly Arg Val
        50                  55                  60

Thr Met Thr Thr Asp Thr Ser Thr Asn Thr Ala Tyr Met Glu Leu Arg
 65                  70                  75                  80

Ser Leu Arg Ser Asp Asp Thr Ala Val Tyr Tyr Cys Ala Arg Asp Val
```

```
                85                  90                  95
Leu Arg Tyr Phe Asp Trp Phe Leu Gly Val Glu Tyr Tyr Phe Glu Tyr
            100                 105                 110

Trp Gly Gln Gly Thr Leu Val Thr Val Ser Ser Ala Ser Thr
            115                 120                 125

<210> SEQ ID NO 70
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Ser Gly Ser Gly Val Lys Lys Leu Gly Ala Ser Val Arg Val Ser
1               5                   10                  15

Cys Trp Thr Ser Glu Asp Ile Phe Glu Arg Thr Glu Leu Ile His Trp
                20                  25                  30

Val Arg Gln Ala Pro Gly Gln Gly Leu Glu Trp Ile Gly Trp Val Lys
            35                  40                  45

Ala Val Ser Gly Ala Val Asn Tyr Ala Gln Asp Phe Lys Gly Arg Val
        50                  55                  60

Ala Met Thr Arg Asp Thr Ser Ile Asn Thr Ala Tyr Met Gln Leu Ala
65                  70                  75                  80

Gly Leu Arg Ser Asp Asp Thr Ala Val Tyr Phe Cys Ala Arg Asp Gly
                85                  90                  95

Gly Thr Gly Pro Pro Arg Tyr Phe Leu Tyr Trp Gly Gln Gly Thr Leu
            100                 105                 110

Leu Thr Val Ser Ser Ala Ser Thr
        115                 120

<210> SEQ ID NO 71
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Gly Arg Gly Gly Val Lys Lys Pro Gly Ala Ser Val Thr Leu Ser
1               5                   10                  15

Cys Lys Thr Ala Asp Glu Asp Val Phe Asp Ala Ala Tyr Met His Trp
                20                  25                  30

Val Arg Gln Ala Pro Gly Gln Thr Phe Glu Trp Leu Gly Trp Met Lys
            35                  40                  45

Pro Val Thr Gly Ala Val Asn Tyr Ala Arg Lys Phe Gln Gly Arg Val
        50                  55                  60

Ser Phe Tyr Arg Thr Arg Glu Leu Gly Ile Ala Tyr Met Asp Leu Arg
65                  70                  75                  80

Asn Leu Arg Phe Asp Asp Thr Ala Val Tyr Tyr Cys Ala Arg Ala Gly
                85                  90                  95

Val Trp Phe Gly Glu Leu Leu Pro His Trp Ser Gly Val Gly Gly Gly
            100                 105                 110

Met Asp Val Trp Gly Gln Gly Thr Thr Val Thr Val Ser Ser Ala Ser
        115                 120                 125

Thr
```

<210> SEQ ID NO 72
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ser Glu Ala Glu Val Lys Lys Pro Gly Ala Ser Met Thr Val Ser
1               5                   10                  15

Cys Glu Thr Ala Asp Glu Asp Ile Phe Asp Ala Ala Tyr Met His Trp
            20                  25                  30

Val Arg Gln Ala Pro Gly Gln Thr Phe Glu Trp Leu Gly Trp Met Lys
        35                  40                  45

Pro Val Thr Gly Ala Val Asn Tyr Ala Arg Lys Phe Gln Gly Arg Ile
    50                  55                  60

Ser Phe Tyr Arg Thr Arg Glu Leu Ala Ile Ala Tyr Met Asp Leu Arg
65                  70                  75                  80

Asp Leu Arg Phe Asp Asp Thr Ala Val Tyr Phe Cys Ala Arg Lys Thr
                85                  90                  95

Ala Gly Asp Val Ser Gly Asp Asn Arg Gly Tyr Phe Phe Asp Leu Trp
            100                 105                 110

Gly Arg Gly Ser Arg Val Ile Val Ser Ser Ala Ser Thr
        115                 120                 125

<210> SEQ ID NO 73
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Pro Ser Gly Ser Gly Val Lys Lys Pro Gly Ala Ser Val Arg Val Ser
1               5                   10                  15

Cys Trp Thr Ser Glu Asp Ile Phe Glu Arg Thr Glu Leu Ile His Trp
            20                  25                  30

Val Arg Gln Ala Pro Gly Gln Gly Leu Glu Trp Ile Gly Trp Val Lys
        35                  40                  45

Thr Val Thr Gly Ala Val Asn Phe Gly Ser Leu Asp Phe Arg His Arg
    50                  55                  60

Ile Ser Leu Thr Arg Asp Arg Asp Leu Phe Thr Ala His Met Asp Ile
65                  70                  75                  80

Arg Gly Leu Thr Gln Gly Asp Thr Ala Thr Tyr Phe Cys Ala Arg Gln
                85                  90                  95

Lys Phe Glu Ser Arg Tyr Thr Gly Gly Gln Gly Trp Tyr Phe Asp Leu
            100                 105                 110

Trp Gly Arg Gly Thr His Ile Val Val Ser Ser Ala Ser Thr
        115                 120                 125

<210> SEQ ID NO 74
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Ser Gly Ser Gly Val Lys Lys Pro Gly Ala Ser Val Arg Val Ser
1               5                   10                  15

Cys Trp Thr Ser Glu Asp Ile Phe Glu Gly Ser Glu Leu Ile His Trp
            20                  25                  30

Val Arg Gln Ala Pro Gly Gln Gly Leu Glu Trp Ile Gly Trp Val Lys
        35                  40                  45

Thr Val Thr Gly Ala Val Asn Phe Gly Ser Ala Tyr Phe Arg His Arg
    50                  55                  60

Val Ser Leu Thr Arg Asp Arg Asp Leu Phe Thr Ala His Met Asp Ile
65                  70                  75                  80

Arg Gly Leu Thr Gln Gly Asp Thr Ala Thr Tyr Phe Cys Ala Arg Gln
                85                  90                  95

Lys Phe Met Ser Gly Gly Gln Gly Trp Tyr Phe Asp Leu Trp Gly Arg
            100                 105                 110

Gly Thr Val Ile Val Val Ser Ser Ala Ser Thr
        115                 120

<210> SEQ ID NO 75
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ser Gly Ala Glu Val Lys Lys Pro Gly Ala Ser Val Arg Val Ser
1               5                   10                  15

Cys Trp Thr Ser Glu Asp Ile Phe Asp Thr Thr Glu Leu Ile Tyr Trp
            20                  25                  30

Val Arg Gln Ala Pro Gly Gln Gly Leu Glu Trp Ile Gly Trp Val Lys
        35                  40                  45

Ile Val Ser Gly Thr Val Asn Phe Ala Ser Leu Asp Phe Arg Asn Arg
    50                  55                  60

Ile Ser Leu Ser Arg Asp Arg Asp Leu Ser Thr Ala His Met Asp Ile
65                  70                  75                  80

Arg Gly Leu Thr Gln Asp Asp Thr Ala Thr Tyr Phe Cys Ala Arg Gln
                85                  90                  95

Lys Phe Glu Ser Arg Tyr Thr Gly Gly Gln Gly Trp Tyr Phe Asp Leu
            100                 105                 110

Trp Gly Arg Gly Thr His Ile Val Val Ser Ser Ala Ser Thr
        115                 120                 125

<210> SEQ ID NO 76
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Ser Gly Ala Ala Val Lys Lys Pro Gly Ser Ser Val Lys Val Ser
1               5                   10                  15

Cys Lys Ala Ser Gly Tyr Ile Phe Thr Gly Tyr Tyr Ile His Trp Ile
            20                  25                  30

Arg Gln Ala Pro Gly Gln Gly Leu Glu Trp Met Gly Trp Ile Asn Pro
            35                  40                  45

Ser Thr Gly Asp Thr Lys Phe Ala Arg Gln Phe Gln Gly Arg Val Ser
 50                  55                  60

Phe Tyr Arg Thr Arg Glu Leu Gly Ile Ala Tyr Met Asp Leu Arg Asp
 65                  70                  75                  80

Leu Lys Phe Asp Asp Thr Ala Val Tyr Phe Cys Ala Arg Lys Thr Lys
                85                  90                  95

Gly Asp Val Ser Gly Asp Arg Gly Phe Phe Phe Asp Leu Trp Gly
                100                 105                 110

Arg Gly Thr Arg Val Ile Val Ser Ser Ala Ser Thr
            115                 120

<210> SEQ ID NO 77
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Ser Gly Ala Glu Val Lys Lys Pro Gly Ser Ser Val Arg Val Ser
 1               5                  10                  15

Cys Trp Thr Ser Glu Asp Ile Phe Glu Arg Thr Glu Leu Ile His Trp
                20                  25                  30

Val Arg Gln Ala Pro Gly Gln Gly Leu Glu Trp Ile Gly Trp Val Lys
            35                  40                  45

Thr Val Thr Gly Ala Val Asn Phe Gly Ser Pro Asn Phe Arg His Arg
 50                  55                  60

Val Ser Leu Thr Arg Asp Arg Asp Leu Phe Thr Ala His Met Asp Ile
 65                  70                  75                  80

Arg Gly Leu Thr Gln Gly Asp Thr Ala Thr Tyr Phe Cys Ala Arg Gln
                85                  90                  95

Lys Phe Glu Ser Arg Tyr Ser Gly Asp Gln Gly Ser Tyr Phe Asp Leu
                100                 105                 110

Trp Gly Arg Gly Thr Leu Ile Ile Val Ser Ser Ala Ser Thr
            115                 120                 125

<210> SEQ ID NO 78
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Gly Ala Glu Val Lys Lys Pro Gly Ala Ser Val Arg Val Ser
 1               5                  10                  15

Cys Trp Thr Ser Glu Asp Ile Phe Glu Lys Ser Glu Leu Ile His Trp
                20                  25                  30

Val Arg Gln Ala Pro Gly Gln Gly Leu Glu Trp Ile Gly Trp Val Lys
            35                  40                  45

Thr Val Thr Gly Ala Val Asn Phe Gly Ser Ser Asp Phe Arg Gln Arg
 50                  55                  60

Val Ser Leu Thr Arg Asp Arg Asp Leu Phe Thr Ala His Met Asp Ile
 65                  70                  75                  80

Arg Gly Leu Thr Gln Gly Asp Thr Ala Thr Tyr Phe Cys Ala Arg Gln
            85                  90                  95

Lys Phe Glu Arg Gly Gly Gln Gly Trp Tyr Phe Asp Leu Trp Gly Arg
            100                 105                 110

Gly Thr Leu Ile Val Val Ser Ser Ala Ser Thr
            115                 120

<210> SEQ ID NO 79
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Ser Gly Ala Glu Val Lys Lys Pro Gly Ala Ser Val Lys Val Ser
1               5                   10                  15

Cys Lys Ala Ser Gly Tyr Thr Phe Thr Val Tyr Tyr Met His Trp Val
            20                  25                  30

Arg Gln Ala Pro Gly Arg Gly Leu Glu Trp Ile Gly Trp Val Lys Ala
        35                  40                  45

Val Ser Gly Ala Val Asn Tyr Gly Ser Leu Asp Phe Arg His Arg Val
50                  55                  60

Ser Leu Thr Arg Asp Arg Asp Leu Phe Thr Ala His Met Asp Ile Arg
65                  70                  75                  80

Gly Leu Thr Gln Asp Asp Thr Ala Thr Tyr Phe Cys Ala Arg Gln Lys
            85                  90                  95

Phe Ala Arg Gly Asp Gln Gly Trp Phe Phe Asp Leu Trp Gly Arg Gly
            100                 105                 110

Thr Leu Ile Val Val Ser Ser Ala Ser Thr
            115                 120

<210> SEQ ID NO 80
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Ser Gly Ala Glu Val Lys Lys Pro Gly Ser Ser Val Lys Val Ser
1               5                   10                  15

Cys Lys Val Ser Gly Gly Val Phe Thr Ser Tyr Ala Val Thr Trp Val
            20                  25                  30

Arg Gln Ala Pro Gly Gln Gly Leu Glu Trp Ile Gly Trp Val Lys Ala
        35                  40                  45

Val Ser Gly Ala Val Asn Tyr Gly Ser Leu Asp Phe Arg His Arg Val
50                  55                  60

Ser Leu Thr Arg Asp Arg Asp Leu Phe Thr Ala His Met Asp Ile Arg
65                  70                  75                  80

Gly Leu Thr Gln Asp Asp Thr Ala Ile Tyr Phe Cys Ala Arg Gln Lys
            85                  90                  95

Phe Ala Arg Gly Asp Gln Gly Trp Phe Phe Asp Leu Trp Gly Arg Gly
            100                 105                 110

Thr Leu Ile Val Val Ser Ser Ala Ser Thr
            115                 120

<210> SEQ ID NO 81
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Ser Gly Ala Glu Val Lys Lys Pro Gly Ala Ser Val Lys Val Ser
1               5                   10                  15

Cys Lys Ala Ser Gly Tyr Thr Phe Thr Thr Tyr Gly Ile Ser Trp Val
            20                  25                  30

Arg Gln Ala Pro Gly Gln Gly Leu Glu Trp Ile Gly Trp Met Lys Thr
        35                  40                  45

Val Thr Gly Ala Val Asn Phe Gly His Gln Ile Ser Asp Arg Val Ser
    50                  55                  60

Leu Thr Arg Asp Arg Asp Leu Phe Thr Ala His Met Asp Ile Arg Gly
65                  70                  75                  80

Leu Thr Gln Gly Asp Thr Ala Thr Tyr Phe Cys Ala Arg Gln Lys Phe
                85                  90                  95

Tyr Ala Gly Gly Gln Gly Trp Tyr Phe Asp Leu Trp Gly Arg Gly Thr
            100                 105                 110

Leu Ile Val Val Ser Ser Ala Ser Thr
        115                 120

<210> SEQ ID NO 82
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Ser Gly Ser Ala Met Lys Lys Pro Gly Ala Ser Val Arg Val Ser
1               5                   10                  15

Cys Trp Thr Ser Glu Asp Ile Phe Asp Thr Thr Glu Leu Ile Tyr Trp
            20                  25                  30

Val Arg Gln Ala Pro Gly Gln Gly Leu Glu Trp Ile Gly Trp Val Lys
        35                  40                  45

Ile Val Ser Gly Thr Val Asn Phe Ala Ser Leu Asp Phe Arg Asn Arg
    50                  55                  60

Ile Ser Leu Ser Arg Asp Arg Asp Leu Ser Thr Ala Tyr Met Asp Ile
65                  70                  75                  80

Arg Gly Leu Thr Gln Asp Asp Thr Ala Leu Tyr Tyr Cys Ala Arg Glu
                85                  90                  95

Trp Arg Tyr Cys Thr Gly Gly Ser Pro Cys Pro Ser Glu Tyr Leu Gln
            100                 105                 110

His Trp Gly Gln Gly Thr Leu Val Lys Val Ser Leu Ala Ser Thr
        115                 120                 125

<210> SEQ ID NO 83
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Ser Gly Ser Ala Thr Glu Lys Pro Gly Ala Ser Val Arg Val Ser
1               5                   10                  15

Cys Trp Thr Ser Glu Asp Ile Phe Asp Thr Thr Glu Leu Asn Trp Val
            20                  25                  30

Arg Gln Ala Pro Gly Gln Gly Leu Glu Trp Ile Gly Trp Val Lys Ile
        35                  40                  45

Val Ser Gly Thr Val Asn Phe Gly Ser Ser Asp Phe Arg Asn Arg Ile
50                  55                  60

Ser Leu Ser Arg Asp Arg Asp Leu Ser Thr Ala His Met Asp Ile Arg
65                  70                  75                  80

Gly Leu Thr Gln Asp Asp Thr Ala Thr Tyr Phe Cys Ala Arg Gln Lys
                85                  90                  95

Phe Glu Ser Arg Tyr Arg Gly Asp Gln Gly Ser Tyr Phe Asp Leu Trp
            100                 105                 110

Gly Arg Gly Thr Leu Ile Ile Val Ser Ser Ala Ser Thr
        115                 120                 125

<210> SEQ ID NO 84
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ala Gly Gly Gly Met Lys Lys Pro Gly Ala Ser Met Thr Val Ser
1               5                   10                  15

Cys Lys Thr Ala Asp Glu Asp Ile Phe Asp Ala Ala Tyr Met His Trp
            20                  25                  30

Val Arg Gln Ala Pro Gly Gln Thr Phe Glu Trp Leu Gly Trp Met Lys
        35                  40                  45

Pro Val Thr Gly Ala Val Asn Tyr Ala Arg Arg Phe Gln Gly Arg Val
50                  55                  60

Ser Phe Tyr Arg Thr Arg Glu Leu Gly Ile Ala Tyr Met Asp Leu Arg
65                  70                  75                  80

Asp Leu Lys Phe Asp Asp Thr Ala Val Tyr Phe Cys Ala Arg Lys Thr
                85                  90                  95

Lys Gly Asp Val Ser Gly Asp Asp Arg Gly Phe Val Ser Asp Leu Trp
            100                 105                 110

Gly Arg Gly Thr Arg Val Ile Val Ser Ser Ala Ser Thr
        115                 120                 125

<210> SEQ ID NO 85
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Ser Gly Ala Glu Val Lys Lys Pro Gly Ala Ser Val Lys Val Ser
1               5                   10                  15

Cys Arg Ala Ser Gly Tyr Thr Phe Gly Asn His Ala Ile Ser Trp Val
            20                  25                  30

Arg Gln Ala Pro Gly Gln Gly Leu Glu Trp Met Gly Trp Ile Arg Pro

```
                35                  40                  45
Lys Thr Gly Ala Arg Asn Gln Ala Arg Gln Phe Gln Pro Arg Ile Ser
 50                  55                  60
Leu Thr Arg Asp Arg Ala Leu Ser Thr Ala Tyr Leu Asp Leu Asn Ser
65                  70                  75                  80
Leu Thr Ser Ala Asp Ser Gly Thr Tyr Phe Cys Ala Arg Gln Thr Phe
                85                  90                  95
Lys Pro Asp Phe Tyr Phe Ala Asp Gln Gly Trp Ser Phe Asn Leu Trp
            100                 105                 110
Gly Arg Gly Ala His Phe Ile Val Ser Ser Ala Ser Thr
        115                 120                 125

<210> SEQ ID NO 86
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Ser Gly Ala Glu Met Lys Lys Pro Gly Ser Ser Val Lys Val Ser
1               5                  10                  15
Cys Lys Ala Ser Gly Gly Thr Phe Arg His Ser Pro Ile Ser Trp Val
                20                  25                  30
Arg Gln Ala Pro Gly Gln Gly Leu Glu Trp Ile Gly Trp Val Lys Ala
            35                  40                  45
Val Ser Gly Ala Val Asn Tyr Gly Ser Leu Asp Phe Arg His Arg Val
 50                  55                  60
Ser Leu Thr Arg Asp Arg Asp Leu Ser Thr Ala His Met Asp Ile Arg
65                  70                  75                  80
Gly Leu Thr Gln Asp Asp Thr Ala Thr Tyr Phe Cys Ala Arg Gln Lys
                85                  90                  95
Phe Ala Arg Gly Asp Gln Gly Trp Phe Phe Asp Leu Trp Gly Arg Gly
            100                 105                 110
Thr Leu Ile Val Val Ser Ser Ala Ser Thr
        115                 120

<210> SEQ ID NO 87
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Ser Gly Ser Thr Gln Met Lys Lys Pro Gly Ala Ser Val Arg Val
1               5                  10                  15
Pro Cys Trp Thr Ser Glu Asp Ile Phe Asp Thr Thr Glu Leu Ile Tyr
                20                  25                  30
Trp Val Arg Gln Ala Pro Gly Gln Gly Leu Glu Trp Ile Gly Arg Val
            35                  40                  45
Lys Ile Val Ser Gly Thr Val Asn Phe Ala Ser Leu Asp Phe Arg Asn
 50                  55                  60
Arg Ile Ser Leu Ser Arg Asp Arg Asp Leu Ser Thr Ala His Met Asp
65                  70                  75                  80
Ile Arg Gly Leu Thr Gln Asp Asp Thr Ala Thr Tyr Phe Cys Ala Arg
```

```
            85                  90                  95

Gln Lys Phe Glu Ser Arg Tyr Arg Gly Asp Gln Gly Ser Tyr Phe Asp
            100                 105                 110

Leu Trp Gly Arg Gly Thr Leu Ile Ile Val Ser Ser Ala Ser Thr
            115                 120                 125

<210> SEQ ID NO 88
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asn Thr Gly Ser Ala Met Lys Lys Pro Gly Ala Ser Val Arg Val Ser
1               5                   10                  15

Cys Trp Thr Ser Glu Asp Ile Phe Asp Thr Thr Glu Leu Ile Tyr Trp
                20                  25                  30

Val Arg Gln Ala Pro Gly Gln Gly Leu Glu Trp Ile Gly Trp Val Lys
            35                  40                  45

Ile Val Ser Gly Thr Val Asn Phe Ala Ser Leu Asp Phe Arg Asn Arg
        50                  55                  60
Ile Ser Leu Ser Arg Asp Arg Asp Leu Ser Thr Ala Tyr Met Asp Ile
65                  70                  75                  80

Arg Gly Leu Thr Gln Asp Asp Thr Ala Thr Tyr Phe Cys Ala Arg Gln
                85                  90                  95

Lys Phe Ala Ser Arg Tyr Ser Gly Asp Gln Gly Ser Tyr Phe Asp Leu
            100                 105                 110

Trp Gly Arg Gly Thr Leu Ile Val Val Ser Ser Ala Ser Thr
            115                 120                 125

<210> SEQ ID NO 89
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Ser Gly Ser Gly Val Lys Lys Leu Gly Ala Ser Val Arg Val Ser
1               5                   10                  15

Cys Trp Thr Ser Glu Asp Ile Phe Glu Arg Thr Glu Leu Ile His Trp
                20                  25                  30

Val Arg Gln Ala Pro Gly Gln Gly Leu Glu Trp Ile Gly Trp Val Lys
            35                  40                  45

Ser Cys Gln Cys Ala Val Asn Tyr Gly Ser Leu Asp Phe Arg Gln Ser
        50                  55                  60

Leu Ser Leu Thr Arg Asp Arg Asp Leu Ser Thr Ala His Met Asp Ile
65                  70                  75                  80

Arg Gly Leu Thr Gln Asp Asp Thr Ala Thr Tyr Phe Cys Ala Arg Gln
                85                  90                  95

Lys Phe Cys Glu Gly His Gln Gly Trp Phe Phe Asp Leu Trp Gly Arg
            100                 105                 110

Gly Thr Leu Ile Val Val Ser Ser Ala Ser Thr
            115                 120
```

<210> SEQ ID NO 90
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Ser Gly Gly Gly Val Lys Lys Pro Gly Thr Ser Ala Ser Phe Ser
1               5                   10                  15

Cys Arg Thr Ser Asp Asp Ile Tyr Asp Asn Glu Phe Phe Asp Ser Ala
                20                  25                  30

Phe Met His Trp Val Arg Leu Ile Pro Gly Gln Arg Pro Glu Trp Met
            35                  40                  45

Gly Trp Met Asn Pro Arg Ser Gly Ala Val Asn Tyr Ala Arg Gln Leu
        50                  55                  60

Gln Pro Arg Val Ser Met Tyr Arg Asp Arg Asp Leu Ser Thr Ala Tyr
65                  70                  75                  80

Met Glu Phe Lys Ser Leu Thr Ser Ala Asp Thr Gly Thr Tyr Phe Cys
                85                  90                  95

Ala Arg Lys Lys Arg Gly Asp Gly Phe Asn Leu Tyr Phe Asp Leu Trp
                100                 105                 110

Gly Arg Gly Ser Gln Val Ile Val Ser Ser Ala Ser Thr
            115                 120                 125

<210> SEQ ID NO 91
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Ser Gly Ser Gly Val Lys Lys Pro Gly Ala Ser Val Arg Val Ser
1               5                   10                  15

Cys Trp Thr Ser Glu Asp Ile Phe Glu Arg Thr Glu Leu Ile His Trp
                20                  25                  30

Val Arg Gln Ala Pro Gly Gln Gly Leu Glu Trp Leu Gly Trp Met Lys
            35                  40                  45

Pro Val Thr Gly Ala Val Asn Tyr Ala Arg Lys Phe Gln Gly Arg Val
        50                  55                  60

Ser Phe Tyr Arg Thr Arg Glu Leu Gly Ile Ala Tyr Met Asp Leu Arg
65                  70                  75                  80

Asp Leu Lys Phe Asp Asp Thr Ala Val Tyr Phe Cys Ala Arg Lys Thr
                85                  90                  95

Lys Gly Asp Val Ser Gly Asp Gly Arg Gly Phe Phe Phe Asp Leu Trp
                100                 105                 110

Gly Arg Gly Thr Arg Val Ile Ile Ser Ser Ala Ser Thr
            115                 120                 125

<210> SEQ ID NO 92
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Gln Ser Gly Gly Gly Val Lys Pro Gly Ser Ala Ser Phe Ser
1               5                   10                  15

Cys Arg Thr Ser Glu Asp Pro Phe Asp Asn Glu Phe Phe Asp Ser Glu
            20                  25                  30

Phe Met His Trp Val Arg Leu Thr Pro Gly Gln Arg Pro Glu Trp Met
        35                  40                  45

Gly Trp Met Asn Pro Arg Ser Gly Gly Val Asn Tyr Ala Gly Gln Phe
    50                  55                  60

Arg Pro Arg Met Ser Met Trp Arg Asp Arg Glu Leu Ser Thr Ala Tyr
65                  70                  75                  80

Met Glu Leu Arg Asp Leu Thr Phe Ala Asp Thr Gly Leu Tyr Phe Cys
                85                  90                  95

Ala Arg Arg Lys Glu Asp Asp Tyr Asp Trp Tyr Tyr Asp Leu Trp Gly
            100                 105                 110

Arg Gly Ala His Ile Ile Val Ser Ala Ala Ser Thr
            115                 120
```

<210> SEQ ID NO 93
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Gln Ser Gly Ala Glu Val Lys Lys Pro Gly Ala Ser Val Lys Val Ser
1               5                   10                  15

Cys Lys Ala Ser Gly Tyr Thr Phe Thr Ser Tyr Asp Ile Asn Trp Val
            20                  25                  30

Arg Gln Ala Thr Gly Gln Gly Leu Glu Trp Ile Gly Trp Val Lys Thr
        35                  40                  45

Val Thr Gly Ala Val Asn Phe Gly Ser Ser Asp Phe Arg Gln Arg Val
    50                  55                  60

Ser Leu Thr Arg Asp Arg Asp Leu Phe Thr Ala His Met Asp Ile Arg
65                  70                  75                  80

Gly Leu Thr Gln Gly Asp Thr Ala Thr Tyr Phe Cys Ala Arg Gln Lys
                85                  90                  95

Phe Tyr Ala Gly Gly Gln Gly Trp Tyr Phe Asp Leu Trp Gly Arg Gly
            100                 105                 110

Thr Leu Ile Val Val Ser Ser Ala Ser
            115                 120
```

<210> SEQ ID NO 94
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Gln Ser Gly Ala Glu Leu Lys Lys Pro Gly Ser Ser Val Arg Val Ser
1               5                   10                  15

Cys Lys Thr Ser Gly Gly Ser Phe Asn Asn Tyr Ala Ile Asn Trp Val
            20                  25                  30

Arg Gln Ala Pro Gly Gln Gly Leu Glu Trp Ile Gly Trp Val Lys Ile
        35                  40                  45
```

Val Ser Gly Thr Val Asn Phe Ala Ser Leu Asp Phe Arg Asn Arg Ile
        50                  55                  60

Ser Leu Ser Arg Asp Arg Asp Pro Ser Thr Ala Tyr Met Asp Ile Arg
 65                  70                  75                  80

Gly Leu Thr Gln Asp Asp Thr Ala Thr Tyr Phe Cys Ala Arg Gln Lys
                85                  90                  95

Phe Ala Ser Arg Tyr Ser Gly Asp Gln Gly Ser Tyr Phe Asp Leu Trp
                100                 105                 110

Gly Arg Gly Thr Leu Ile Val Val Ser Ser Ala Ser Thr
                115                 120                 125

<210> SEQ ID NO 95
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Phe Gly Ala Glu Val Lys Lys Pro Gly Ser Ser Val Lys Val Ser
 1               5                  10                  15

Cys Lys Ala Ser Gly Gly Thr Phe Ser Asn Asn Ala Phe Ser Trp Val
                20                  25                  30

Arg Gln Ala Pro Gly Gln Gly Leu Glu Trp Ile Gly Trp Val Lys Thr
            35                  40                  45

Val Thr Gly Ala Val Asn Phe Gly Ser Leu Asp Phe Arg His Arg Ile
        50                  55                  60

Ser Leu Thr Arg Asp Arg Asp Leu Phe Thr Ala His Met Asp Ile Arg
 65                  70                  75                  80

Gly Leu Thr Gln Gly Asp Thr Ala Thr Tyr Phe Cys Ala Arg Gln Lys
                85                  90                  95

Phe Glu Ser Arg Tyr Thr Gly Gly Gln Gly Trp Tyr Phe Asp Leu Trp
                100                 105                 110

Gly Arg Gly Thr His Ile Val Val Ser Ser Ala Ser Thr
                115                 120                 125

<210> SEQ ID NO 96
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Ser Gly Ala Glu Val Lys Lys Pro Gly Ala Ser Val Lys Val Ser
 1               5                  10                  15

Cys Lys Ala Ser Gly Tyr Thr Phe Thr Thr Tyr Gly Ile Ser Trp Val
                20                  25                  30

Arg Gln Ala Pro Gly Gln Gly Leu Glu Trp Ile Gly Trp Val Lys Thr
            35                  40                  45

Val Thr Gly Ala Val Asn Phe Gly Ser Ser Asp Phe Arg Gln Arg Val
        50                  55                  60

Ser Leu Thr Arg Asp Arg Asp Leu Phe Thr Ala His Met Asp Ile Arg
 65                  70                  75                  80

Gly Leu Thr Gln Gly Asp Thr Ala Thr Tyr Phe Cys Ala Arg Gln Lys
                85                  90                  95

```
Phe Tyr Ala Gly Gly Gln Gly Trp Tyr Phe Asp Leu Trp Gly Arg Gly
            100                 105                 110

Thr Leu Ile Val Val Ser Ser Ala Ser Thr
        115                 120

<210> SEQ ID NO 97
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Ser Gly Ala Glu Val Lys Lys Pro Gly Ala Ser Val Lys Val Ser
1               5                   10                  15

Cys Lys Ala Ser Gly Tyr Thr Phe Thr Ser Tyr Gly Ile Ser Trp Val
            20                  25                  30

Arg Gln Ala Pro Gly Arg Gly Leu Glu Trp Ile Gly Trp Asn Lys Thr
        35                  40                  45

Val Ser Gly Ala Val Asn Phe Gly Ser Val Asp Phe Arg Asp Arg Val
50                  55                  60

Ser Leu Thr Arg Asp Arg Asp Leu Phe Thr Ala His Met Asp Ile Arg
65                  70                  75                  80

Gly Leu Thr Gln Gly Asp Thr Ala Thr Tyr Phe Cys Ala Arg Gln Lys
                85                  90                  95

Phe Glu Lys Leu Tyr Ser Asp Asp Gln Gly Leu Tyr Phe Asp Leu Trp
            100                 105                 110

Gly Arg Gly Thr Leu Ile Ile Val Ser Ser Ala Ser Thr
        115                 120                 125

<210> SEQ ID NO 98
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Arg Asp Glu Val Lys Lys Pro Gly Ser Ser Met Lys Val Ser
1               5                   10                  15

Cys Thr Ala Ser Arg Gly Thr Phe Ser Ser Tyr Ala Ile Ser Trp Val
            20                  25                  30

Arg Gln Ala Pro Gly Gln Gly Leu Glu Trp Ile Gly Trp Val Lys Thr
        35                  40                  45

Val Thr Gly Ala Val Asn Phe Gly Ser Ala Tyr Phe Arg His Arg Val
50                  55                  60

Ser Leu Thr Arg Asp Arg Asp Leu Phe Thr Ala His Met Asp Ile Arg
65                  70                  75                  80

Gly Leu Thr Gln Gly Asp Thr Ala Thr Tyr Phe Cys Ala Arg Gln Lys
                85                  90                  95

Phe Tyr Lys Gly Gly Gln Gly Trp Tyr Phe Asp Leu Trp Gly Arg Gly
            100                 105                 110

Thr Leu Ile Val Val Ser Ser Ala Ser Thr
        115                 120

<210> SEQ ID NO 99
```

<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

Gln Ser Gly Ala Glu Val Lys Arg Pro Gly Ala Ser Val Met Val Ser
1               5                   10                  15

Cys Lys Ala Ser Gly Tyr Thr Phe Leu Asn Tyr Ala Phe Ser Trp Val
            20                  25                  30

Arg Gln Ala Pro Gly Gln Gly Leu Glu Trp Ile Gly Trp Val Lys Thr
        35                  40                  45

Val Ser Gly Ala Val Asn Phe Gly Ser Thr Asp Phe Arg Glu Arg Val
    50                  55                  60

Ser Leu Thr Arg Asp Arg Asp Leu Phe Thr Ala His Met Asp Ile Arg
65                  70                  75                  80

Gly Leu Thr Gln Gly Asp Thr Ala Thr Tyr Phe Cys Ala Arg Gln Lys
                85                  90                  95

Phe Glu Lys Leu Tyr Thr Gly Asp Gln Gly Leu Tyr Phe Asp Leu Trp
            100                 105                 110

Gly Arg Gly Thr Leu Ile Ile Val Ser Ser Ala Ser Thr
        115                 120                 125

<210> SEQ ID NO 100
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Gln Ser Gly Ser Gly Val Lys Lys Val Gly Ala Ser Val Arg Val Ser
1               5                   10                  15

Cys Trp Thr Ser Glu Asp Ile Phe Glu Arg Thr Glu Leu Ile His Trp
            20                  25                  30

Val Arg Gln Ala Pro Gly Gln Gly Leu Glu Trp Ile Gly Trp Val Lys
        35                  40                  45

Ala Val Ser Gly Ala Val Asn Tyr Gly Ser Leu Asp Phe Arg His Arg
    50                  55                  60

Val Ser Leu Thr Arg Asp Arg Asp Leu Phe Thr Ala His Met Asp Ile
65                  70                  75                  80

Arg Gly Leu Thr Gln Asp Asp Thr Ala Ile Tyr Phe Cys Ala Arg Gln
                85                  90                  95

Lys Phe Tyr Ala Gly Gly Gln Gly Trp Tyr Phe Asp Leu Trp Gly Arg
            100                 105                 110

Gly Thr Leu Ile Val Val Ser Ser Ala Ser Thr
        115                 120

<210> SEQ ID NO 101
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

-continued

Gln Ser Gly Ser Gly Val Lys Lys Leu Gly Ala Ser Val Arg Val Ser
1               5                   10                  15

Cys Trp Thr Ser Glu Asp Ile Phe Glu Arg Thr Glu Leu Ile His Trp
            20                  25                  30

Val Arg Gln Ala Pro Gly Gln Gly Leu Glu Trp Ile Gly Trp Val Lys
        35                  40                  45

Ala Val Ser Gly Ala Val Asn Tyr Gly Ser Leu Asp Phe Arg His Arg
    50                  55                  60

Val Ser Leu Thr Arg Asp Arg Asp Leu Ser Thr Ala His Met Asp Ile
65              70                  75                  80

Arg Gly Leu Thr Gln Asp Asp Thr Ala Thr Tyr Phe Cys Ala Arg Gln
            85                  90                  95

Lys Phe Ala Arg Gly Asp Gln Gly Trp Phe Asp Leu Trp Gly Arg
                100                 105                 110

Gly Thr Leu Ile Val Val Ser Ser Ala Ser Thr
            115                 120

<210> SEQ ID NO 102
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ser Gly Ser Ala Met Lys Lys Pro Gly Ala Ser Val Arg Val Ser
1               5                   10                  15

Cys Trp Thr Ser Glu Asp Ile Phe Glu Arg Thr Glu Leu Ile Tyr Trp
            20                  25                  30

Val Arg Gln Ala Pro Gly Arg Gly Leu Glu Trp Ile Gly Trp Val Lys
        35                  40                  45

Thr Val Ser Gly Thr Val Asn Phe Gly Ser Ser Asp Phe Arg Asn Arg
    50                  55                  60

Ile Ser Leu Thr Arg Asp Arg Asp Leu Ser Thr Ala His Met Asp Ile
65              70                  75                  80

Arg Gly Leu Thr Gln Asp Asp Thr Ala Thr Tyr Phe Cys Ala Arg Gln
            85                  90                  95

Lys Phe Glu Ser Leu Tyr Ser Asp Gln Gly Ser Tyr Phe Asp Leu
                100                 105                 110

Trp Gly Arg Gly Thr Leu Ile Ile Val Ser Ser Ala Ser Thr
            115                 120                 125

<210> SEQ ID NO 103
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ala Gly Gly Gly Val Lys Lys Pro Gly Ala Ser Val Thr Leu Ser
1               5                   10                  15

Cys Lys Thr Ala Asp Glu Asp Val Phe Asp Ala Ala Tyr Met His Trp
            20                  25                  30

Val Arg Gln Ala Pro Gly Gln Thr Phe Glu Trp Leu Gly Trp Met Lys
        35                  40                  45

```
Pro Val Thr Gly Ala Val Asn Tyr Ala Arg Lys Phe Gln Gly Arg Val
            50                  55                  60

Ser Phe Tyr Arg Thr Arg Glu Leu Gly Ile Ala Tyr Met Asp Leu Arg
 65                  70                  75                  80

Asn Leu Arg Phe Asp Asp Thr Ala Val Tyr Phe Cys Ala Arg Lys Thr
                85                  90                  95

Ala Gly Asp Val Ser Gly Asp Lys Arg Gly Phe Phe Asp Leu Trp
                100                 105                 110

Gly Arg Gly Ser Arg Val Ile Val Ser Ser Ala Ser Thr
            115                 120                 125
```

<210> SEQ ID NO 104
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gln Ala Gly Gly Gly Met Lys Lys Pro Gly Ala Ser Met Thr Val Ser
 1                   5                  10                  15

Cys Lys Thr Ala Asp Glu Asp Val Phe Asp Ala Ala Tyr Met His Trp
                20                  25                  30

Val Arg Gln Ala Pro Gly Gln Thr Phe Glu Trp Leu Gly Trp Met Lys
            35                  40                  45

Pro Val Thr Gly Ala Val Asn Tyr Ala Arg Lys Phe Gln Gly Arg Val
            50                  55                  60

Ser Phe Tyr Arg Thr Arg Glu Leu Gly Ile Ala Tyr Met Asp Leu Arg
 65                  70                  75                  80

Asp Pro Lys Phe Asp Asp Thr Ala Val Tyr Phe Cys Ala Arg Lys Thr
                85                  90                  95

Lys Gly Asp Val Ser Gly Asp Gly Arg Gly Phe Phe Asp Leu Trp
                100                 105                 110

Gly Arg Gly Thr Arg Val Ile Ile Ser Ser Ala Ser Thr
            115                 120                 125
```

<210> SEQ ID NO 105
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Gln Ser Gly Ser Gly Val Lys Lys Leu Gly Ala Ser Val Arg Val Ser
 1                   5                  10                  15

Cys Trp Thr Ser Glu Asp Ile Phe Glu Arg Thr Glu Leu Ile His Trp
                20                  25                  30

Val Arg Gln Ala Pro Gly Gln Gly Leu Glu Trp Ile Gly Trp Val Lys
            35                  40                  45

Ala Val Thr Gly Thr Val Asn Phe Gly Ser Leu Asn Phe Arg Gln Arg
            50                  55                  60

Val Ser Leu Thr Arg Asp Arg Asp Leu Phe Thr Ala His Met Asp Ile
 65                  70                  75                  80

Arg Gly Leu Thr Gln Gly Asp Thr Ala Thr Tyr Phe Cys Ala Arg Gln
                85                  90                  95
```

Lys Phe Glu Lys Tyr Thr Gly Gly Gln Gly Trp Tyr Phe Asp Leu Trp
            100                 105                 110

Gly Arg Gly Thr Leu Ile Val Val Ser Ser Ala Ser Thr
        115                 120                 125

<210> SEQ ID NO 106
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Ser Gly Ser Ala Met Lys Lys Pro Gly Ala Ser Val Arg Val Ser
1               5                   10                  15

Cys Trp Thr Ser Glu Asp Ile Phe Asp Thr Thr Glu Leu Ile His Trp
            20                  25                  30

Val Arg Gln Ala Pro Gly Gln Gly Leu Glu Trp Ile Gly Trp Val Lys
        35                  40                  45

Ala Val Ser Gly Ala Val Asn Tyr Gly Ser Leu Asp Phe Arg His Arg
    50                  55                  60

Val Ser Leu Thr Arg Asp Arg Asp Leu Ser Thr Ala His Met Asp Ile
65                  70                  75                  80

Arg Gly Leu Thr Gln Asp Asp Thr Ala Thr Tyr Phe Cys Ala Arg Gln
                85                  90                  95

Lys Phe Ala Arg Gly Asp Gln Gly Trp Phe Phe Asp Leu Trp Gly Arg
            100                 105                 110

Gly Thr Leu Ile Val Val Ser Ser Ala Ser Thr
        115                 120

<210> SEQ ID NO 107
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 108
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 109
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
            20                  25                  30

Thr Leu Asn Trp Val Arg Leu Ala Pro Gly Arg Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ala Asp Asp Thr Ala Val Tyr Tyr Cys
                85                  90                  95

Thr Arg Gly Lys Asn Cys Asp Tyr Asn Trp Asp Phe Glu His Trp Gly
            100                 105                 110

Arg Gly Thr Pro Val Thr Val Ser Ser
        115                 120

<210> SEQ ID NO 110
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
            20                  25                  30

Ser Ile His Trp Val Arg Leu Ile Pro Asp Lys Gly Phe Glu Trp Ile
            35                  40                  45

Gly Trp Ile Lys Pro Leu Trp Gly Ala Val Ser Tyr Ala Arg Gln Leu
        50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Pro Ala
                85                  90                  95

Asp Thr Ala Glu Tyr Phe Cys Val Arg Arg Gly Ser Cys Asp Tyr Cys
            100                 105                 110

Gly Asp Phe Pro Trp Gln Tyr Trp Gly Gln Gly Thr Val Val Val Val
            115                 120                 125

Ser Ser
    130

<210> SEQ ID NO 111
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
    50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Tyr Thr Gly Gly Gln Gly Trp Tyr Phe
            100                 105                 110

Asp Leu Trp Gly Arg Gly Thr Leu Ile Val Val Ser Ser
            115                 120                 125

<210> SEQ ID NO 112
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
    50                  55                  60

Asn Phe Arg His Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Arg Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 113
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
                20                  25                  30

His Trp Val Asn Pro Ala Pro Glu His Tyr Ile His Phe Leu Arg Gln
            35                  40                  45

Ala Pro Gly Gln Gln Leu Glu Trp Leu Ala Trp Met Asn Pro Thr Asn
        50                  55                  60

Gly Ala Val Asn Tyr Ala Trp Gln Leu His Gly Arg Leu Thr Ala Thr
65                  70                  75                  80

Arg Asp Gly Ser Met Thr Thr Ala Phe Leu Glu Val Arg Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Ala
        115                 120                 125

Val Ser Ser
    130

<210> SEQ ID NO 114
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
                20                  25                  30

Tyr Trp Val Asn Pro Ala Pro Glu His Phe Ile His Phe Leu Arg Gln
            35                  40                  45

Ala Pro Gly Gln Gln Leu Glu Trp Leu Ala Trp Met Asn Pro Thr Asn
        50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
                100                 105                 110

Arg Ser Glu Trp Ala Tyr Ala His Trp Gly Gln Gly Thr Pro Val Val
        115                 120                 125

Val Ser Ser
    130

<210> SEQ ID NO 115
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Phe Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Lys Pro Thr Asn
    50                  55                  60

Gly Ala Val Asn Tyr Ala Trp Gln Leu Gln Gly Arg Val Thr Val Thr
65                  70                  75                  80

Arg Asp Arg Ser Gln Thr Thr Ala Phe Leu Glu Val Lys Asn Leu Arg
                85                  90                  95

Ser Asp Asp Thr Ala Val Tyr Tyr Cys Ala Arg Ala Gln Lys Arg Gly
                100                 105                 110

Arg Ser Glu Trp Ala Tyr Ala His Trp Gly Gln Gly Thr Pro Val Val
        115                 120                 125

Ile Ser Ala
    130

<210> SEQ ID NO 116
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Arg Asp Phe Thr Leu Thr Ile Ser Ser Leu Glu Pro
65                  70                  75                  80

Glu Asp Phe Ala Val Tyr Tyr Cys Gln Gln
                85                  90

<210> SEQ ID NO 117

<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys
            100

<210> SEQ ID NO 118
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Arg Asn Leu Glu Ser Gly Asp
65                  70                  75                  80

Phe Gly Leu Tyr Tyr Cys Gln Gln Tyr Glu Phe Phe Gly Gln Gly Thr
                85                  90                  95

Lys Val Gln Val Asp Ile Lys
            100

<210> SEQ ID NO 119
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

```
Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln
                 85                  90

<210> SEQ ID NO 120
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Ile Val Leu Thr Gln Ser Pro Gly Ile Leu Ser Leu Ser Pro Gly
 1               5                  10                  15

Glu Thr Ala Thr Leu Phe Cys Lys Ala Ser Gln Gly Gly Asn Ala Met
                 20                  25                  30

Thr Trp Tyr Gln Lys Arg Arg Gly Gln Val Pro Arg Leu Leu Ile Tyr
             35                  40                  45

Asp Thr Ser Arg Arg Ala Ser Gly Val Pro Asp Arg Phe Val Gly Ser
 50                  55                  60

Gly Ser Gly Thr Asp Phe Phe Leu Thr Ile Asn Lys Leu Asp Arg Glu
 65                  70                  75                  80

Asp Phe Ala Val Tyr Tyr Cys Gln Gln Phe Glu Phe Phe Gly Leu Gly
                 85                  90                  95

Ser Glu Leu Glu Val His
            100

<210> SEQ ID NO 121
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Ile Val Leu Thr Gln Ser Pro Gly Thr Leu Ser Leu Ser Pro Gly
 1               5                  10                  15

Glu Thr Ala Ser Leu Ser Cys Thr Ala Ala Ser Tyr Gly His Met Thr
                 20                  25                  30

Trp Tyr Gln Lys Lys Pro Gly Gln Pro Pro Lys Leu Leu Ile Phe Ala
             35                  40                  45

Thr Ser Lys Arg Ala Ser Gly Ile Pro Asp Arg Phe Ser Gly Ser Gln
 50                  55                  60

Phe Gly Lys Gln Tyr Thr Leu Thr Ile Thr Arg Met Glu Pro Glu Asp
 65                  70                  75                  80

Phe Ala Arg Tyr Tyr Cys Gln Gln Leu Glu Phe Phe Gly Gln Gly Thr
                 85                  90                  95

Arg Leu Glu Ile Arg
            100

<210> SEQ ID NO 122
<211> LENGTH: 101
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
50                  55                  60

Phe Gly Lys Gln Tyr Thr Leu Thr Ile Thr Arg Met Glu Pro Glu Asp
65                  70                  75                  80

Phe Ala Gly Tyr Tyr Cys Gln Gln Val Glu Phe Phe Gly Gln Gly Thr
                85                  90                  95

Arg Leu Glu Ile Arg
            100

<210> SEQ ID NO 123
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln
                85                  90

<210> SEQ ID NO 124
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Pro Gly Lys Ala Pro Lys Leu Leu Val
        35                  40                  45

Ser Asp Ala Ser Ile Leu Glu Gly Gly Val Pro Ser Arg Phe Ser Gly
```

```
                    50                  55                  60
Ser Gly Phe His Gln Asn Phe Ser Leu Thr Ile Ser Ser Leu Gln Pro
 65                  70                  75                  80

Glu Asp Val Ala Thr Tyr Phe Cys Gln Gln Tyr Glu Thr Phe Gly Gln
                 85                  90                  95

Gly Thr Lys Val Asp Ile Lys
            100

<210> SEQ ID NO 125
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Ile Gln Met Thr Gln Ser Pro Ser Ser Leu Ser Ala Ser Leu Gly
  1               5                  10                  15

Asp Arg Val Thr Ile Thr Cys Gln Ala Ser Arg Gly Ile Gly Lys Asp
                 20                  25                  30

Leu Asn Trp Tyr Gln Gln Lys Ala Gly Lys Ala Pro Lys Leu Leu Val
             35                  40                  45

Ser Asp Ala Ser Thr Leu Glu Gly Gly Val Pro Ser Arg Phe Ser Gly
         50                  55                  60

Ser Gly Phe His Gln Asn Phe Ser Leu Thr Ile Ser Ser Leu Gln Ala
 65                  70                  75                  80

Glu Asp Val Ala Thr Tyr Phe Cys Gln Gln Tyr Glu Thr Phe Gly Gln
                 85                  90                  95

Gly Thr Lys Val Asp Ile Lys
            100

<210> SEQ ID NO 126
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Gln Met Thr Gln Ser Pro Ser Ser Leu Ser Ala Ser Leu Gly
  1               5                  10                  15

Asp Arg Val Thr Ile Thr Cys Gln Ala Ser Arg Gly Ile Gly Lys Asp
                 20                  25                  30

Leu Asn Trp Tyr Gln Gln Lys Pro Gly Arg Ala Pro Lys Leu Leu Val
             35                  40                  45

Ser Asp Ala Ser Ile Leu Glu Gly Gly Val Pro Thr Arg Phe Ser Gly
         50                  55                  60

Ser Gly Phe His Gln Asn Phe Ser Leu Thr Ile Ser Ser Leu Gln Ala
 65                  70                  75                  80

Glu Asp Val Ala Thr Tyr Phe Cys Gln Gln Tyr Glu Thr Phe Gly Gln
                 85                  90                  95

Gly Thr Lys Val Asp Ile Lys
            100

<210> SEQ ID NO 127
<211> LENGTH: 309
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 127

```
gacatccaga tgacccagtc tccatcgtcc ttgtctgcat cactcggaga cagagtcacc    60
atcacttgtc aggcgagtcg gggcattggt aaagatttaa attggtacca gcagaaaccg   120
ggaaaggccc ctaagttact ggtctctgat gcatccattt tggaagggggg gtcccatca   180 aggttcagtg ggagtggatt tcaccaaaat tttagtctga ccatcagcag cctgcagcct   240
gaggatgttg cgacatactt ctgtcagcag tacgagactt ttggccaggg gaccaaagtg   300
gacatcaaa                                                           309
```

<210> SEQ ID NO 128
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
caggtgcagc tggtgcagtc aggggctgcc gtgaggaagc ctggggcctc agtgactgtc    60
tcctgcaaat tcgctgaaga cgacgactac tctccacact gggtgaatcc ggcccctgaa   120
cactatattc actttctacg acaggcccct ggacagcaac tggagtggtt ggcatggatg   180
aaccctacga atggcgccgt caattatgca tggcagcttc atggcaggct cacggcgacc   240
agagacgggt ccatgactac agccttttg gaagtgagga gtctaagatc tgacgacacg   300
gccgtctatt attgtgcgag ggcccagaaa aggggggcgga gtgaatgggc ctacgcccac   360
tggggccagg gaaccccggt cgccgtctcc tca                                 393
```

<210> SEQ ID NO 129
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
gacatccaga tgacccagtc tccatcgtcc ctgtctgcat cactcgggga cagagtcacc    60
atcacttgcc aggcgagtcg gggcattggc aaagatttaa attggtacca gcagaaagcg   120
ggaaaagccc ctaagttact ggtctctgat gcatccactt tggaaggggg gtcccatca   180 aggttcagtg ggagtggatt tcaccaaaat tttagtctga ctatcagcag cctgcaggct   240
gaggatgttg caacatactt ctgtcaacaa tacgagactt ttggccaggg gaccaaggtg   300
gacatcaaa                                                           309
```

<210> SEQ ID NO 130
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
caggtgcagc tggtgcagtc aggggctgcc gtgaggaagc ctggggcctc agtgactgtc    60
```

```
tcctgtaaat tcgctgaaga cgacgactac tctccatact gggtgaatcc ggcccctgaa    120
cattttattc acttttgcg acaggcccct ggacaacaac tagagtggct ggcatggatg    180
aacccaacga atggcgccgt taattatgca tggtaccttta atggcagggt cacggcgacc    240
agggacaggt ccatgactac agccttttg gaagtgaaga gtctaagatc tgacgacacg    300
gccgtctact attgtgcgag ggcccagaaa aggggggcgga gtgagtgggc ctacgcccac    360
tggggtcagg gcactccggt cgtcgtctcg tca                                  393

<210> SEQ ID NO 131
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
gacatccaga tgacccagtc tccatcgtcc ctgtctgcat cactcggaga cagagtcacc     60
atcacttgcc aggcgagtcg gggcattggc aaagatttaa attggtacca acagaaaccg    120
ggaagagccc ctaagttact agtctctgat gcatccattt tggaagggggg ggtcccaacg    180 agattcagtg ggagtggatt tcaccaaaac tttagcctga ccatcagcag cctgcaggct    240
gaggatgttg caacatattt ctgtcagcaa tacgaaactt ttggccaggg gaccaaggtg    300
gacatcaaa                                                             309

<210> SEQ ID NO 132
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
caggtgcagc tggtgcagtc agggggctgcc gtgaggaagc ctggggcctc agtgactgtc     60
tcctgcaagt tcgctgaaga cgacgacttc tctccacact gggtgaatcc ggcccctgaa    120
cactatattc attttctgcg acaggcacct ggacaacaac tagagtggtt ggcatggatg    180
aagcctacga atggtgccgt caattatgca tggcaacttc agggcagggt cacggtgacc    240
agggacaggt cccagactac agccttttg gaagttaaga atctgagatc tgacgacacg    300
gccgtctatt attgtgcgag ggcccagaaa aggggggcgca gcgagtgggc ctatgcccac    360
tggggccagg gaaccccggt cgtcatctcc gca                                  393

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Lys Thr Ala Gly Asp Val Ser Gly Asp Asp Arg Gly Tyr Phe Phe Asp
1               5                   10                  15
Leu

<210> SEQ ID NO 134
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Thr Phe Lys Pro Asp Phe Tyr Phe Ala Asp Gln Gly Trp Ser Phe
1               5                   10                  15

Asn Leu

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Lys Phe Tyr Arg Gly Gly Gln Gly Trp Tyr Phe Asp Leu
1               5                   10

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Lys Phe Glu Ser Arg Tyr Ser Gly Asp Gln Gly Ser Tyr Phe Asp
1               5                   10                  15

Leu

<210> SEQ ID NO 137
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Val Gln Ala Gly Gly Gly Val Lys Lys Pro Gly Ala
1               5                   10                  15

Ser Val Thr Leu Ser Cys Lys Thr Ala Asp Glu Asp Val Phe Asp Ala
                20                  25                  30

Ala Tyr Met His Trp Val Arg Gln Ala Pro Gly Gln Thr Phe Glu Trp
            35                  40                  45

Leu Gly Trp Met Lys Pro Val Thr Gly Ala Val Ser Tyr Ala Arg Lys
    50                  55                  60

Phe Gln Gly Arg Val Ser Phe Tyr Met Thr Arg Glu Leu Gly Met Ala
65                  70                  75                  80

Tyr Met Asp Leu Arg Asn Leu Arg Phe Asp Asp Thr Ala Val Tyr Tyr
                85                  90                  95

Cys Ala Arg Val Gly Gly Ala Ala Asp Asp Ser Gly Tyr Thr Glu Pro
            100                 105                 110

Pro Ser Asp Tyr Trp Gly Gln Gly Thr Leu Val Thr Val Ser Ser
        115                 120                 125
```

```
<210> SEQ ID NO 138
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Val Ala Gly Arg Gly Val Lys Lys Pro Gly Ala
1               5                   10                  15

Ser Val Thr Leu Ser Cys Lys Thr Ala Asp Glu Asp Val Phe Asp Ala
                20                  25                  30

Ala Tyr Met His Trp Val Arg Gln Ala Pro Gly Gln Thr Phe Glu Trp
            35                  40                  45

Leu Gly Trp Met Lys Pro Val Thr Gly Ala Val Asn Tyr Ala Arg Lys
    50                  55                  60

Phe Gln Gly Arg Val Ser Phe Tyr Arg Thr Arg Glu Leu Gly Ile Ala
65                  70                  75                  80

Tyr Met Asp Leu Arg Asn Leu Arg Phe Asp Asp Thr Ala Val Tyr Tyr
                85                  90                  95

Cys Ala Arg Ala Gly Val Trp Phe Gly Glu Leu Leu Pro His Trp Ser
            100                 105                 110

Gly Val Gly Gly Gly Met Asp Val Trp Gly Gln Gly Thr Thr Val Thr
        115                 120                 125

Val Ser Ser
    130

<210> SEQ ID NO 139
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Val Gln Ser Glu Ala Glu Val Lys Lys Pro Gly Ala
1               5                   10                  15

Ser Met Thr Val Ser Cys Glu Thr Ala Asp Glu Asp Ile Phe Asp Ala
                20                  25                  30

Ala Tyr Met His Trp Val Arg Gln Ala Pro Gly Gln Thr Phe Glu Trp
            35                  40                  45

Leu Gly Trp Met Lys Pro Val Thr Gly Ala Val Asn Tyr Ala Arg Lys
    50                  55                  60

Phe Gln Gly Arg Ile Ser Phe Tyr Arg Thr Arg Glu Leu Ala Ile Ala
65                  70                  75                  80

Tyr Met Asp Leu Arg Asp Leu Arg Phe Asp Asp Thr Ala Val Tyr Phe
                85                  90                  95

Cys Ala Arg Lys Thr Ala Gly Asp Val Ser Gly Asp Asn Arg Gly Tyr
            100                 105                 110

Phe Phe Asp Leu Trp Gly Arg Gly Ser Arg Val Ile Val Ser Ser
        115                 120                 125

<210> SEQ ID NO 140
<211> LENGTH: 127
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 140

Gln Val Gln Leu Val Gln Ser Gly Ala Glu Val Lys Lys Pro Gly Ala
1               5                   10                  15

Ser Val Thr Leu Ser Cys Lys Thr Ala Asp Glu Asp Val Phe Asp Ala
            20                  25                  30

Ala Tyr Met His Trp Val Arg Gln Ala Pro Gly Gln Thr Phe Glu Trp
        35                  40                  45

Leu Gly Trp Met Lys Pro Val Thr Gly Ala Val Ser Tyr Ala Arg Lys
    50                  55                  60

Phe Gln Gly Arg Val Ser Phe Tyr Met Thr Arg Glu Leu Gly Met Ala
65                  70                  75                  80

Tyr Met Asp Leu Arg Asn Leu Arg Phe Asp Thr Ala Val Tyr Phe
                85                  90                  95

Cys Ala Arg Lys Thr Ala Gly Asp Val Ser Gly Asp Asn Arg Gly Tyr
            100                 105                 110

Phe Phe Asp Leu Trp Gly Arg Gly Ser Arg Val Ile Val Ser Ser
        115                 120                 125

<210> SEQ ID NO 141
<211> LENGTH: 127
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 141

Gln Val Gln Leu Val Gln Ala Gly Gly Gly Val Lys Lys Pro Gly Ala
1               5                   10                  15

Ser Val Thr Leu Ser Cys Lys Thr Ala Asp Glu Asp Val Phe Asp Ala
            20                  25                  30

Ala Tyr Met His Trp Val Arg Gln Ala Pro Gly Gln Thr Phe Glu Trp
        35                  40                  45

Leu Gly Trp Met Lys Pro Val Thr Gly Ala Val Asn Tyr Ala Arg Lys
    50                  55                  60

Phe Gln Gly Arg Val Ser Phe Tyr Arg Thr Arg Glu Leu Gly Ile Ala
65                  70                  75                  80

Tyr Met Asp Leu Arg Asn Leu Arg Phe Asp Thr Ala Val Tyr Phe
                85                  90                  95

Cys Ala Arg Lys Thr Ala Gly Asp Val Ser Gly Asp Lys Arg Gly Phe
            100                 105                 110

Phe Phe Asp Leu Trp Gly Arg Gly Ser Arg Val Ile Val Ser Ser
        115                 120                 125

<210> SEQ ID NO 142
<211> LENGTH: 126
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 142

Gln Val Gln Leu Val Gln Ser Gly Ala Ala Val Lys Lys Pro Gly Ser
1               5                   10                  15

Ser Val Lys Val Ser Cys Lys Ala Ser Gly Tyr Ile Phe Thr Gly Tyr

```
            20                  25                  30
Tyr Ile His Trp Ile Arg Gln Ala Pro Gly Gln Gly Leu Glu Trp Met
        35                  40                  45

Gly Trp Ile Asn Pro Ser Thr Gly Asp Thr Lys Phe Ala Arg Gln Phe
    50                  55                  60

Gln Gly Arg Val Ser Phe Tyr Arg Thr Arg Glu Leu Gly Ile Ala Tyr
65                  70                  75                  80

Met Asp Leu Arg Asp Leu Lys Phe Asp Thr Ala Val Tyr Phe Cys
                85                  90                  95

Ala Arg Lys Thr Lys Gly Asp Val Ser Gly Asp Arg Gly Phe Phe
            100                 105                 110

Phe Asp Leu Trp Gly Arg Gly Thr Arg Val Ile Val Ser Ser
        115                 120                 125

<210> SEQ ID NO 143
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Thr Phe Glu Trp Leu
        35                  40                  45

Gly Trp Met Lys Pro Val Thr Gly Ala Val Asn Tyr Ala Arg Gln Phe
    50                  55                  60

Gln Gly Arg Val Ser Phe Tyr Arg Thr Arg Glu Leu Gly Ile Ala Tyr
65                  70                  75                  80

Met Asp Leu Arg Asp Leu Lys Phe Asp Thr Ala Val Tyr Phe Cys
                85                  90                  95

Ala Arg Lys Thr Lys Ala Asp Val Ser Gly Asp Arg Gly Phe Phe
            100                 105                 110

Phe Asp Leu Trp Gly Arg Gly Thr Arg Val Ile Val Ser Ser
        115                 120                 125

<210> SEQ ID NO 144
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Val Gln Ser Gly Ser Ala Met Lys Lys Pro Gly Ala
1               5                   10                  15

Ser Val Arg Val Ser Cys Trp Thr Ser Glu Asp Ile Phe Asp Thr Thr
            20                  25                  30

Glu Leu Ile Tyr Trp Val Arg Gln Ala Pro Gly Gln Gly Leu Glu Trp
        35                  40                  45

Ile Gly Trp Val Lys Ile Val Ser Gly Thr Val Asn Phe Ala Arg Gln
    50                  55                  60

Phe Gln Gly Arg Val Ser Phe Tyr Arg Thr Arg Glu Leu Gly Ile Ala
```

```
                65                  70                  75                  80
Tyr Met Asp Leu Arg Asp Leu Lys Phe Asp Asp Thr Ala Val Tyr Phe
                        85                  90                  95
Cys Ala Arg Lys Thr Lys Gly Asp Val Ser Gly Asp Asp Arg Gly Phe
                100                 105                 110
Phe Phe Asp Leu Trp Gly Arg Gly Thr Arg Val Ile Val Ser Ser
            115                 120                 125
```

<210> SEQ ID NO 145
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 145

```
Gln Val Gln Leu Val Gln Ser Gly Gly Gly Val Lys Lys Pro Gly Ala
1               5                   10                  15
Ser Ala Ser Phe Ser Cys Arg Thr Ser Glu Asp Pro Phe Asp Asn Glu
                20                  25                  30
Phe Phe Asp Ser Glu Phe Met His Trp Val Arg Leu Thr Pro Gly Gln
            35                  40                  45
Arg Pro Glu Trp Met Gly Trp Met Asn Pro Arg Ser Gly Gly Val Asn
        50                  55                  60
Tyr Ala Gly Gln Phe Arg Pro Arg Met Ser Met Trp Arg Asp Arg Glu
65                  70                  75                  80
Leu Ser Thr Ala Tyr Met Glu Leu Arg Asp Leu Thr Phe Ala Asp Thr
                85                  90                  95
Gly Leu Tyr Phe Cys Ala Arg Arg Lys Glu Asp Asp Tyr Asp Trp Tyr
                100                 105                 110
Tyr Asp Leu Trp Gly Arg Gly Ala His Ile Ile Val Ser Ala
            115                 120                 125
```

<210> SEQ ID NO 146
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Gln Val Gln Leu Val Gln Ser Gly Gly Gly Val Lys Lys Pro Gly Thr
1               5                   10                  15
Ser Ala Ser Phe Ser Cys Arg Thr Ser Asp Asp Ile Tyr Asp Asn Glu
                20                  25                  30
Phe Phe Asp Ser Ala Phe Met His Trp Val Arg Leu Ile Pro Gly Gln
            35                  40                  45
Arg Pro Glu Trp Met Gly Trp Met Asn Pro Arg Ser Gly Ala Val Asn
        50                  55                  60
Tyr Ala Arg Gln Leu Gln Pro Arg Val Ser Met Tyr Arg Asp Arg Asp
65                  70                  75                  80
Leu Ser Thr Ala Tyr Met Glu Phe Lys Ser Leu Thr Ser Ala Asp Thr
                85                  90                  95
Gly Thr Tyr Phe Cys Ala Arg Lys Lys Arg Gly Asp Gly Phe Asn Leu
                100                 105                 110
Tyr Phe Asp Leu Trp Gly Arg Gly Ser Gln Val Ile Val Ser Ser
```

-continued

```
            115                 120                 125
```

<210> SEQ ID NO 147
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Gln Val Gln Leu Val Gln Ser Gly Ser Gly Val Lys Pro Gly Ala
1               5                   10                  15

Ser Val Arg Val Ser Cys Arg Ala Ser Glu Asp Leu Phe Gly Asp Glu
            20                  25                  30

Ile Ile Tyr Asp Asp Glu Val Ile His Trp Leu Arg Gln Val Pro Gly
        35                  40                  45

Gln Arg Pro Glu Trp Met Gly Trp Ile Arg Pro Lys Thr Gly Ala Arg
    50                  55                  60

Asn Gln Ala Arg Gln Phe Gln Pro Arg Ile Ser Leu Thr Arg Asp Arg
65                  70                  75                  80

Ala Leu Ser Thr Ala Tyr Leu Asp Leu Asn Ser Leu Thr Ser Ala Asp
                85                  90                  95

Ser Gly Thr Tyr Phe Cys Ala Arg Gln Thr Phe Lys Pro Asp Phe Tyr
            100                 105                 110

Phe Ala Asp Gln Gly Trp Ser Phe Asn Leu Trp Gly Arg Gly Ala His
        115                 120                 125

Phe Ile Val Ser Ser
        130
```

<210> SEQ ID NO 148
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Gln Val Gln Leu Val Gln Ser Gly Ala Glu Met Lys Lys Pro Gly Ser
1               5                   10                  15

Ser Val Lys Val Ser Cys Lys Ala Ser Gly Gly Thr Phe Arg His Ser
            20                  25                  30

Pro Ile Ser Trp Val Arg Gln Ala Pro Gly Gln Gly Leu Glu Trp Ile
        35                  40                  45

Gly Trp Val Lys Ala Val Ser Gly Ala Val Asn Tyr Gly Ser Leu Asp
    50                  55                  60

Phe Arg His Arg Val Ser Leu Thr Arg Asp Arg Asp Leu Ser Thr Ala
65                  70                  75                  80

His Met Asp Ile Arg Gly Leu Thr Gln Asp Thr Ala Thr Tyr Phe
                85                  90                  95

Cys Ala Arg Gln Lys Phe Ala Arg Gly Asp Gln Gly Trp Phe Phe Asp
            100                 105                 110

Leu Trp Gly Arg Gly Thr Leu Ile Val Val Ser Ser
        115                 120
```

<210> SEQ ID NO 149
<211> LENGTH: 124
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Val Ser Gly Val Phe Thr Ser Tyr
            20                  25                  30

Ala Val Thr Trp Val Arg Gln Ala Pro Gly Gln Gly Leu Glu Trp Ile
        35                  40                  45

Gly Trp Val Lys Ala Val Ser Gly Ala Val Asn Tyr Gly Ser Leu Asp
    50                  55                  60

Phe Arg His Arg Val Ser Leu Thr Arg Asp Arg Asp Leu Phe Thr Ala
65                  70                  75                  80

His Met Asp Ile Arg Gly Leu Thr Gln Asp Asp Thr Ala Ile Tyr Phe
                85                  90                  95

Cys Ala Arg Gln Lys Phe Ala Arg Gly Asp Gln Gly Trp Phe Phe Asp
            100                 105                 110

Leu Trp Gly Arg Gly Thr Leu Ile Val Val Ser Ser
        115                 120

<210> SEQ ID NO 150
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Trp Val Lys Thr Val Ser Gly Ala Val Asn Phe Gly Ser Leu Asn
    50                  55                  60

Phe Arg His Arg Val Ser Leu Thr Arg Asp Arg Asp Leu Phe Thr Ala
65                  70                  75                  80

His Met Asp Ile Arg Gly Leu Thr Gln Gly Asp Thr Ala Thr Tyr Phe
                85                  90                  95

Cys Ala Arg Gln Lys Phe Ala Arg Gly Asp Gln Gly Trp Phe Phe Asp
            100                 105                 110

Leu Trp Gly Arg Gly Thr Leu Ile Val Val Ser Ser
        115                 120

<210> SEQ ID NO 151
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Gln Ser Gly Ala Glu Val Lys Lys Pro Gly Ala
1               5                   10                  15

```
Ser Val Gln Val Ser Cys Lys Ala Ser Gly Tyr Pro Phe Thr Lys Tyr
            20                  25                  30

Tyr Met His Trp Val Arg Gln Ala Pro Gly Gln Gly Leu Glu Trp Ile
        35                  40                  45

Gly Trp Val Lys Ala Val Ser Gly Ala Val Asn Tyr Gly Ser Leu Asp
 50                  55                  60

Phe Arg His Arg Val Ser Leu Thr Arg Asp Asp Leu Ser Thr Ala
 65                  70                  75                  80

His Met Asp Ile Arg Gly Leu Thr Gln Asp Asp Thr Ala Thr Tyr Phe
                85                  90                  95

Cys Ala Arg Gln Lys Phe Ala Arg Gly Asp Gln Gly Trp Phe Phe Asp
                100                 105                 110

Leu Trp Gly Arg Gly Thr Leu Ile Val Val Ser Ser
            115                 120
```

<210> SEQ ID NO 152
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Ile
        35                  40                  45

Gly Trp Val Lys Pro Val Thr Gly Ala Val Asn Phe Gly Ser Pro Asn
 50                  55                  60

Phe Arg His Arg Val Ser Leu Thr Arg Asp Arg Asp Leu Phe Thr Ala
 65                  70                  75                  80

His Met Asp Ile Arg Gly Leu Thr Gln Gly Asp Thr Ala Thr Tyr Phe
                85                  90                  95

Cys Ala Arg Gln Lys Tyr Tyr Ala Gly Gly Gln Gly Trp Tyr Phe Asp
                100                 105                 110

Leu Trp Gly Arg Gly Thr Leu Ile Val Val Ser Ser
            115                 120
```

<210> SEQ ID NO 153
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Gln Val Gln Leu Val Gln Val Arg Asp Glu Val Lys Lys Pro Gly Ser
 1               5                  10                  15

Ser Met Lys Val Ser Cys Thr Ala Ser Arg Gly Thr Phe Ser Ser Tyr
            20                  25                  30

Ala Ile Ser Trp Val Arg Gln Ala Pro Gly Gln Gly Leu Glu Trp Ile
        35                  40                  45

Gly Trp Val Lys Thr Val Thr Gly Ala Val Asn Phe Gly Ser Ala Tyr
 50                  55                  60
```

```
Phe Arg His Arg Val Ser Leu Thr Arg Asp Arg Asp Leu Phe Thr Ala
 65                  70                  75                  80

His Met Asp Ile Arg Gly Leu Thr Gln Gly Asp Thr Ala Thr Tyr Phe
                 85                  90                  95

Cys Ala Arg Gln Lys Phe Tyr Lys Gly Gly Gln Gly Trp Tyr Phe Asp
            100                 105                 110

Leu Trp Gly Arg Gly Thr Leu Ile Val Val Ser Ser
        115                 120
```

<210> SEQ ID NO 154
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Ile
            35                  40                  45

Gly Trp Val Lys Thr Val Thr Gly Ala Val Asn Phe Gly Ser Ser Asp
     50                  55                  60

Phe Arg Gln Arg Val Ser Leu Thr Arg Asp Arg Asp Leu Phe Thr Ala
 65                  70                  75                  80

His Met Asp Ile Arg Gly Leu Thr Gln Gly Asp Thr Ala Thr Tyr Phe
                 85                  90                  95

Cys Ala Arg Gln Lys Phe Tyr Ala Gly Gly Gln Gly Trp Tyr Phe Asp
            100                 105                 110

Leu Trp Gly Arg Gly Thr Leu Ile Val Val Ser Ser
        115                 120
```

<210> SEQ ID NO 155
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Thr Tyr
                 20                  25                  30

Gly Ile Ser Trp Val Arg Gln Ala Pro Gly Gln Gly Leu Glu Trp Ile
            35                  40                  45

Gly Trp Val Lys Thr Val Thr Gly Ala Val Asn Phe Gly Ser Ser Asp
     50                  55                  60

Phe Arg Gln Arg Val Ser Leu Thr Arg Asp Arg Asp Leu Phe Thr Ala
 65                  70                  75                  80

His Met Asp Ile Arg Gly Leu Thr Gln Gly Asp Thr Ala Thr Tyr Phe
                 85                  90                  95

Cys Ala Arg Gln Lys Phe Tyr Ala Gly Gly Gln Gly Trp Tyr Phe Asp
            100                 105                 110
```

```
Leu Trp Gly Arg Gly Thr Leu Ile Val Val Ser Ser
        115                 120

<210> SEQ ID NO 156
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Ile
        35                  40                  45

Gly Trp Met Lys Thr Val Thr Gly Ala Val Asn Phe Gly His Gln Ile
    50                  55                  60

Ser Asp Arg Val Ser Leu Thr Arg Asp Arg Asp Leu Phe Thr Ala His
65                  70                  75                  80

Met Asp Ile Arg Gly Leu Thr Gln Gly Asp Thr Ala Thr Tyr Phe Cys
                85                  90                  95

Ala Arg Gln Lys Phe Tyr Ala Gly Gly Gln Gly Trp Tyr Phe Asp Leu
            100                 105                 110

Trp Gly Arg Gly Thr Leu Ile Val Val Ser Ser
        115                 120

<210> SEQ ID NO 157
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Val Gln Ser Gly Ser Gly Val Lys Lys Val Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Ala Val Ser Gly Ala Val Asn Tyr Gly Ser Leu
    50                  55                  60

Asp Phe Arg His Arg Val Ser Leu Thr Arg Asp Arg Asp Leu Phe Thr
65                  70                  75                  80

Ala His Met Asp Ile Arg Gly Leu Thr Gln Asp Asp Thr Ala Ile Tyr
                85                  90                  95

Phe Cys Ala Arg Gln Lys Phe Tyr Ala Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 158
<211> LENGTH: 125
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 158

Gln Val Gln Leu Val Gln Ser Gly Ser Ala Met Lys Lys Pro Gly Ala
1               5                   10                  15

Ser Val Arg Val Ser Cys Trp Thr Ser Glu Asp Ile Phe Asp Thr Thr
            20                  25                  30

Glu Leu Ile His Trp Val Arg Gln Ala Pro Gly Gln Gly Leu Glu Trp
        35                  40                  45

Ile Gly Trp Val Lys Ala Val Ser Gly Ala Val Asn Tyr Gly Ser Leu
50                  55                  60

Asp Phe Arg His Arg Val Ser Leu Thr Arg Asp Arg Asp Leu Ser Thr
65                  70                  75                  80

Ala His Met Asp Ile Arg Gly Leu Thr Gln Asp Asp Thr Ala Thr Tyr
                85                  90                  95

Phe Cys Ala Arg Gln Lys Phe Ala Arg Gly Asp Gln Gly Trp Phe Phe
            100                 105                 110

Asp Leu Trp Gly Arg Gly Thr Leu Ile Val Val Ser Ser
        115                 120                 125

<210> SEQ ID NO 159
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Gly Ser
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Ala
50                  55                  60

Tyr Phe Arg His Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Met Ser Gly Gln Gly Trp Tyr Phe
            100                 105                 110

Asp Leu Trp Gly Arg Gly Thr Val Ile Val Val Ser Ser
        115                 120                 125

<210> SEQ ID NO 160
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Val Gln Ser Gly Ala Glu Val Lys Arg Pro Gly Ala
1               5                   10                  15
```

Ser Val Lys Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Ser Gly Ala Val Asn Phe Gly Ser Pro
    50                  55                  60

Asn Phe Arg His Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Arg Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 161
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Val Gln Ser Gly Ala Glu Val Lys Lys Pro Gly Ala
1               5                   10                  15

Ser Val Arg Val Ser Cys Trp Thr Ser Glu Asp Ile Phe Glu Lys Ser
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Ser
    50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Arg Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 162
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Val Gln Ser Gly Ser Gly Val Lys Lys Pro Gly Ala
1               5                   10                  15

Ser Val Arg Val Ser Cys Trp Thr Ser Glu Gly Ile Phe Glu Lys Ser
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly His Gln
    50                  55                  60

```
Ile Ser Asp Arg Val Ser Leu Thr Arg Asp Arg Asp Leu Phe Thr Ala
 65                  70                  75                  80

His Met Asp Ile Arg Gly Leu Thr Gln Gly Thr Ala Thr Tyr Phe
                 85                  90                  95

Cys Ala Arg Gln Lys Phe Glu Arg Gly Gly Gln Gly Trp Ile Phe Asp
                100                 105                 110

Leu Trp Gly Arg Gly Thr Leu Ile Ala Val Ser Ser
            115                 120
```

<210> SEQ ID NO 163
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Gln Val Gln Leu Val Gln Ser Gly Ser Ala Met Lys Lys Pro Gly Ala
 1               5                  10                  15

Ser Val Arg Val Ser Cys Trp Thr Ser Glu Asp Ile Phe Asp Thr Thr
                20                  25                  30

Glu Leu Ile Tyr Trp Val Arg Gln Ala Pro Gly Gln Gly Leu Glu Trp
             35                  40                  45

Ile Gly Trp Val Lys Ile Val Ser Gly Thr Val Asn Phe Ala Ser Leu
         50                  55                  60

Asp Phe Arg Asn Arg Ile Ser Leu Ser Arg Asp Arg Asp Leu Phe Thr
 65                  70                  75                  80

Ala His Met Asp Ile Arg Gly Leu Thr Gln Gly Thr Ala Thr Tyr
                 85                  90                  95

Phe Cys Ala Arg Gln Lys Phe Tyr Ala Gly Gly Gln Gly Trp Tyr Phe
                100                 105                 110

Asp Leu Trp Gly Arg Gly Thr Leu Ile Val Val Ser Ser
            115                 120                 125
```

<210> SEQ ID NO 164
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Gln Val Gln Leu Val Gln Ser Gly Ala Glu Val Lys Lys Pro Gly Ser
 1               5                  10                  15

Ser Val Arg Val Ser Cys Trp Thr Ser Glu Asp Ile Phe Glu Arg Thr
                20                  25                  30

Glu Leu Ile His Trp Val Arg Gln Ala Pro Gly Gln Gly Leu Glu Trp
             35                  40                  45

Ile Gly Trp Val Lys Thr Val Thr Gly Ala Val Asn Phe Gly Ser Pro
         50                  55                  60

Asn Phe Arg His Arg Val Ser Leu Thr Arg Asp Arg Asp Leu Phe Thr
 65                  70                  75                  80

Ala His Met Asp Ile Arg Gly Leu Thr Gln Gly Thr Ala Thr Tyr
                 85                  90                  95

Phe Cys Ala Arg Gln Lys Phe Glu Ser Arg Tyr Ser Gly Asp Gln Gly
                100                 105                 110
```

```
Ser Tyr Phe Asp Leu Trp Gly Arg Gly Thr Leu Ile Ile Val Ser Ser
        115                 120                 125
```

<210> SEQ ID NO 165
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Gln Val Gln Leu Val Pro Ser Gly Ser Gly Val Lys Lys Pro Gly Ala
1               5                   10                  15

Ser Val Arg Val Ser Cys Trp Thr Ser Glu Asp Ile Phe Glu Arg Thr
                20                  25                  30

Glu Leu Ile His Trp Val Arg Gln Ala Pro Gly Gln Gly Leu Glu Trp
            35                  40                  45

Ile Gly Trp Val Lys Thr Val Thr Gly Ala Val Asn Phe Gly Ser Leu
        50                  55                  60

Asp Phe Arg His Arg Ile Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Ser Arg Tyr Thr Gly Gly Gln Gly
            100                 105                 110

Trp Tyr Phe Asp Leu Trp Gly Arg Gly Thr His Ile Val Val Ser Ser
        115                 120                 125
```

<210> SEQ ID NO 166
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

```
Gln Val Gln Leu Val Gln Ser Ala Ser Gly Val Arg Arg Pro Gly Ala
1               5                   10                  15

Ser Val Arg Val Ser Cys Trp Thr Ser Glu Asp Ile Phe Glu Arg Ser
                20                  25                  30

Glu Leu Ile Tyr Trp Val Arg Gln Ala Pro Gly Arg Gly Leu Glu Trp
            35                  40                  45

Ile Gly Trp Ile Lys Leu Val Ser Gly Ala Val Asn Phe Gly Ser Val
        50                  55                  60

Asp Phe Arg Asp Arg Val Ser Leu Thr Arg Asp Arg Asp Leu Phe Thr
65                  70                  75                  80

Ala His Met Asp Ile Arg Gly Leu Thr Gln Asp Asp Thr Ala Thr Tyr
                85                  90                  95

Phe Cys Ala Arg Gln Lys Phe Ala Ser Arg Tyr Ser Gly Asp Gln Gly
            100                 105                 110

Ser Tyr Phe Asp Leu Trp Gly Arg Gly Thr Leu Ile Ile Val Ser Ser
        115                 120                 125
```

<210> SEQ ID NO 167
<211> LENGTH: 128
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 167

Gln Val Gln Leu Val Gln Ser Gly Leu Glu Val Lys Lys Pro Gly Ala
1               5                   10                  15

Ser Val Arg Val Ser Cys Trp Thr Ser Glu Asp Ile Phe Asp Thr Thr
            20                  25                  30

Glu Leu Ile Tyr Trp Val Arg Gln Ala Pro Gly Gln Gly Leu Glu Trp
        35                  40                  45

Ile Gly Trp Val Lys Ile Val Ser Gly Thr Val Asn Phe Ala Ser Leu
    50                  55                  60

Asp Phe Arg Asn Arg Ile Ser Leu Ser Arg Asp Arg Asp Leu Ser Thr
65                  70                  75                  80

Ala His Met Asp Ile Arg Gly Leu Thr Gln Asp Thr Ala Thr Tyr
                85                  90                  95

Phe Cys Ala Arg Gln Lys Phe Ala Ser Arg Tyr Ser Gly Asp Gln Gly
            100                 105                 110

Ser Tyr Phe Asp Leu Trp Gly Arg Gly Thr Leu Ile Ile Val Ser Ser
        115                 120                 125

<210> SEQ ID NO 168
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Leu Val Gln Ser Gly Ala Glu Leu Lys Lys Pro Gly Ser
1               5                   10                  15

Ser Val Arg Val Ser Cys Lys Thr Ser Gly Gly Ser Phe Asn Asn Tyr
            20                  25                  30

Ala Ile Asn Trp Val Arg Gln Ala Pro Gly Gln Gly Leu Glu Trp Ile
        35                  40                  45

Gly Trp Val Lys Ile Val Ser Gly Thr Val Asn Phe Ala Ser Leu Asp
    50                  55                  60

Phe Arg Asn Arg Ile Ser Leu Ser Arg Asp Arg Asp Pro Ser Thr Ala
65                  70                  75                  80

Tyr Met Asp Ile Arg Gly Leu Thr Gln Asp Asp Thr Ala Thr Tyr Phe
                85                  90                  95

Cys Ala Arg Gln Lys Phe Ala Ser Arg Tyr Ser Gly Asp Gln Gly Ser
            100                 105                 110

Tyr Phe Asp Leu Trp Gly Arg Gly Thr Leu Ile Val Val Ser Ser
        115                 120                 125

<210> SEQ ID NO 169
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Val Gln Leu Val Gln Ser Gly Ser Ala Met Lys Lys Pro Gly Ala
1               5                   10                  15

Ser Val Arg Val Ser Cys Trp Thr Ser Glu Asp Ile Phe Glu Arg Thr

```
            20                  25                  30
Glu Leu Ile Tyr Trp Val Arg Gln Ala Pro Gly Arg Gly Leu Glu Trp
            35                  40                  45

Ile Gly Trp Val Lys Thr Val Ser Gly Thr Val Asn Phe Gly Ser Ser
        50                  55                  60

Asp Phe Arg Asn Arg Ile Ser Leu Thr Arg Asp Arg Asp Leu Ser Thr
65                  70                  75                  80

Ala His Met Asp Ile Arg Gly Leu Thr Gln Asp Thr Ala Thr Tyr
                85                  90                  95

Phe Cys Ala Arg Gln Lys Phe Glu Ser Leu Tyr Ser Asp Asp Gln Gly
                100                 105                 110

Ser Tyr Phe Asp Leu Trp Gly Arg Gly Thr Leu Ile Ile Val Ser Ser
            115                 120                 125

<210> SEQ ID NO 170
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Leu Val Gln Ser Gly Ala Glu Val Lys Lys Pro Gly Ala
1               5                   10                  15

Ser Val Arg Val Ser Cys Trp Thr Ser Glu Asp Ile Phe Asp Thr Thr
            20                  25                  30

Glu Leu Ile Tyr Trp Val Arg Gln Ala Pro Gly Gln Gly Leu Glu Trp
            35                  40                  45

Ile Gly Trp Val Lys Ile Val Ser Gly Thr Val Asn Phe Ala Ser Leu
        50                  55                  60

Asp Phe Arg Asn Arg Ile Ser Leu Ser Arg Asp Arg Asp Leu Ser Thr
65                  70                  75                  80

Ala His Met Asp Ile Arg Gly Leu Thr Gln Asp Asp Thr Ala Thr Tyr
                85                  90                  95

Phe Cys Ala Arg Gln Lys Phe Glu Ser Arg Tyr Thr Gly Gly Gln Gly
                100                 105                 110

Trp Tyr Phe Asp Leu Trp Gly Arg Gly Thr His Ile Val Val Ser Ser
            115                 120                 125

<210> SEQ ID NO 171
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Val Gln Ser Gly Ser Ala Met Lys Lys Pro Gly Ala
1               5                   10                  15

Ser Val Arg Val Ser Cys Trp Thr Ser Glu Asp Ile Phe Asp Thr Thr
            20                  25                  30

Glu Leu Ile Tyr Trp Val Arg Gln Ala Pro Gly Gln Gly Leu Glu Trp
            35                  40                  45

Ile Gly Trp Val Lys Ile Val Ser Gly Thr Val Asn Phe Ala Ser Leu
        50                  55                  60

Asp Phe Arg Asn Arg Ile Ser Leu Ser Arg Asp Arg Asp Leu Ser Thr
```

```
                65                  70                  75                  80
Ala His Met Asp Ile Arg Gly Leu Thr Leu Asp Asp Thr Gly Ile Tyr
                    85                  90                  95
Tyr Cys Ala Arg Gly Pro Met Gly Gly Ser His Val Tyr Trp Gly Gln
                100                 105                 110
Gly Ser Leu Val Thr Val Ser Ser
        115                 120

<210> SEQ ID NO 172
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tgtgcgagag a                                                                 11

<210> SEQ ID NO 173
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(31)

<400> SEQUENCE: 173 g tat tac tat gat agt agt ggt tat tac tac                                    31
  Tyr Tyr Tyr Asp Ser Ser Gly Tyr Tyr Tyr
  1               5                   10

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Tyr Tyr Tyr Asp Ser Ser Gly Tyr Tyr Tyr
1               5                   10

<210> SEQ ID NO 175
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(47)

<400> SEQUENCE: 175 ac tac ttt gac tac tgg ggc cag gga acc ctg gtc acc gtc tcc tca              47
   Tyr Phe Asp Tyr Trp Gly Gln Gly Thr Leu Val Thr Val Ser Ser
   1               5                   10                  15

<210> SEQ ID NO 176
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 176

Tyr Phe Asp Tyr Trp Gly Gln Gly Thr Leu Val Thr Val Ser Ser
1               5                   10                  15

<210> SEQ ID NO 177
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 177 tgt gcg aga gtg ggt gga gcc gct gat gat agt ggt tat aca gag ccc        48
Cys Ala Arg Val Gly Gly Ala Ala Asp Asp Ser Gly Tyr Thr Glu Pro
1               5                   10                  15 cct tct gac tac tgg ggc cag gga acc ctg gtc acc gtc tcc tca            93
Pro Ser Asp Tyr Trp Gly Gln Gly Thr Leu Val Thr Val Ser Ser
                20                  25                  30

<210> SEQ ID NO 178
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Cys Ala Arg Val Gly Gly Ala Ala Asp Asp Ser Gly Tyr Thr Glu Pro
1               5                   10                  15

Pro Ser Asp Tyr Trp Gly Gln Gly Thr Leu Val Thr Val Ser Ser
                20                  25                  30

<210> SEQ ID NO 179
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(27)

<400> SEQUENCE: 179 gta tta cta tgg ttc ggg gag tta tta taac                               31
Val Leu Leu Trp Phe Gly Glu Leu Leu
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Val Leu Leu Trp Phe Gly Glu Leu Leu
1               5
```

<210> SEQ ID NO 181
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(62)

<400> SEQUENCE: 181 at tac tac tac tac tac ggt atg gac gtc tgg ggc caa ggg acc acg      47
   Tyr Tyr Tyr Tyr Tyr Gly Met Asp Val Trp Gly Gln Gly Thr Thr
   1               5                   10                  15 gtc acc gtc tcc tca                                                 62
Val Thr Val Ser Ser
            20

<210> SEQ ID NO 182
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Tyr Tyr Tyr Tyr Tyr Gly Met Asp Val Trp Gly Gln Gly Thr Thr Val
1               5                   10                  15

Thr Val Ser Ser
            20

<210> SEQ ID NO 183
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(105)

<400> SEQUENCE: 183 tgt gcg aga gca ggg gta tgg ttc ggg gag tta tta cct cat tgg tca     48
Cys Ala Arg Ala Gly Val Trp Phe Gly Glu Leu Leu Pro His Trp Ser
1               5                   10                  15 ggc gtc ggt ggg ggt atg gac gtc tgg ggc caa ggg acc acg gtc acc     96
Gly Val Gly Gly Gly Met Asp Val Trp Gly Gln Gly Thr Thr Val Thr
            20                  25                  30 gtc tcc tca                                                        105
Val Ser Ser
        35

<210> SEQ ID NO 184
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Cys Ala Arg Ala Gly Val Trp Phe Gly Glu Leu Leu Pro His Trp Ser
1               5                   10                  15

Gly Val Gly Gly Gly Met Asp Val Trp Gly Gln Gly Thr Thr Val Thr
            20                  25                  30

Val Ser Ser
        35

<210> SEQ ID NO 185
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(16)

<400> SEQUENCE: 185 t gac tac ggt gac tac                                            16
  Asp Tyr Gly Asp Tyr
  1               5

<210> SEQ ID NO 186
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Tyr Gly Asp Tyr
1               5

<210> SEQ ID NO 187
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(52)

<400> SEQUENCE: 187 c tac tgg tac ttc gat ctc tgg ggc cgt ggc acc ctg gtc act gtc tcc    49
  Tyr Trp Tyr Phe Asp Leu Trp Gly Arg Gly Thr Leu Val Thr Val Ser
  1               5                  10                  15 tca                                                                 52
Ser

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Tyr Trp Tyr Phe Asp Leu Trp Gly Arg Gly Thr Leu Val Thr Val Ser
1               5                  10                  15

Ser

<210> SEQ ID NO 189
<211> LENGTH: 93

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 189 tgt gcg aga aag aca aag ggc gat gtc agc ggt gac gac cgg ggc ttc      48
Cys Ala Arg Lys Thr Lys Gly Asp Val Ser Gly Asp Asp Arg Gly Phe
1               5                   10                  15 ttc ttc gat ctc tgg ggc cgc ggc acc cgg gtc att gtt tcg tca          93
Phe Phe Asp Leu Trp Gly Arg Gly Thr Arg Val Ile Val Ser Ser
            20                  25                  30

<210> SEQ ID NO 190
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Cys Ala Arg Lys Thr Lys Gly Asp Val Ser Gly Asp Asp Arg Gly Phe
1               5                   10                  15

Phe Phe Asp Leu Trp Gly Arg Gly Thr Arg Val Ile Val Ser Ser
            20                  25                  30

<210> SEQ ID NO 191
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 191 tgt gcg aga aag aca aag gcc gat gtc agc ggt gac gac cgg ggc ttc      48
Cys Ala Arg Lys Thr Lys Ala Asp Val Ser Gly Asp Asp Arg Gly Phe
1               5                   10                  15 ttc ttc gat ctc tgg ggc cgc ggc acc cgg gtc att gtt tcg tca          93
Phe Phe Asp Leu Trp Gly Arg Gly Thr Arg Val Ile Val Ser Ser
            20                  25                  30

<210> SEQ ID NO 192
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Cys Ala Arg Lys Thr Lys Ala Asp Val Ser Gly Asp Asp Arg Gly Phe
1               5                   10                  15

Phe Phe Asp Leu Trp Gly Arg Gly Thr Arg Val Ile Val Ser Ser
            20                  25                  30

<210> SEQ ID NO 193
<211> LENGTH: 93
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 193 tgt gcg aga aag aca aag ggc gat gtc agc ggt gac gac cgg ggc ttc        48
Cys Ala Arg Lys Thr Lys Gly Asp Val Ser Gly Asp Asp Arg Gly Phe
1               5                   10                  15 ttc ttc gat ctc tgg ggc cgc ggc acc cgg gtc att gtt tcg tca            93
Phe Phe Asp Leu Trp Gly Arg Gly Thr Arg Val Ile Val Ser Ser
            20                  25                  30

<210> SEQ ID NO 194
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Cys Ala Arg Lys Thr Lys Gly Asp Val Ser Gly Asp Asp Arg Gly Phe
1               5                   10                  15

Phe Phe Asp Leu Trp Gly Arg Gly Thr Arg Val Ile Val Ser Ser
            20                  25                  30

<210> SEQ ID NO 195
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 195 tgt gcg aga aag aca gcg ggc gac gtc agc ggt gac aac cgg ggc tac        48
Cys Ala Arg Lys Thr Ala Gly Asp Val Ser Gly Asp Asn Arg Gly Tyr
1               5                   10                  15 ttc ttc gat ctc tgg ggc cgt ggc tcc cgg gtc att gtt tcg tca            93
Phe Phe Asp Leu Trp Gly Arg Gly Ser Arg Val Ile Val Ser Ser
            20                  25                  30

<210> SEQ ID NO 196
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Cys Ala Arg Lys Thr Ala Gly Asp Val Ser Gly Asp Asn Arg Gly Tyr
1               5                   10                  15

Phe Phe Asp Leu Trp Gly Arg Gly Ser Arg Val Ile Val Ser Ser
            20                  25                  30

<210> SEQ ID NO 197
<211> LENGTH: 93
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 197 tgt gcg aga aag aca gcg ggc gac gtc agc ggt gac aac cgg ggc tac      48
Cys Ala Arg Lys Thr Ala Gly Asp Val Ser Gly Asp Asn Arg Gly Tyr
1               5                   10                  15 ttc ttc gat ctc tgg ggc cgt ggc tcc cgg gtc att gtt tcg tca          93
Phe Phe Asp Leu Trp Gly Arg Gly Ser Arg Val Ile Val Ser Ser
            20                  25                  30

<210> SEQ ID NO 198
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Cys Ala Arg Lys Thr Ala Gly Asp Val Ser Gly Asp Asn Arg Gly Tyr
1               5                   10                  15

Phe Phe Asp Leu Trp Gly Arg Gly Ser Arg Val Ile Val Ser Ser
            20                  25                  30

<210> SEQ ID NO 199
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 199 tgt gcg aga aag aca gcg ggc gac gtc agc ggt gac aag cgg ggc ttc      48
Cys Ala Arg Lys Thr Ala Gly Asp Val Ser Gly Asp Lys Arg Gly Phe
1               5                   10                  15 ttc ttc gat ctc tgg ggc cgt ggc tcc cga gtc att gtt tcg tca          93
Phe Phe Asp Leu Trp Gly Arg Gly Ser Arg Val Ile Val Ser Ser
            20                  25                  30

<210> SEQ ID NO 200
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Cys Ala Arg Lys Thr Ala Gly Asp Val Ser Gly Asp Lys Arg Gly Phe
1               5                   10                  15

Phe Phe Asp Leu Trp Gly Arg Gly Ser Arg Val Ile Val Ser Ser
            20                  25                  30

<210> SEQ ID NO 201
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: CDS
<222> LOCATION: (2)..(19)

<400> SEQUENCE: 201 t gac tac ggt ggt aac tcc                                              19
  Asp Tyr Gly Gly Asn Ser
  1               5

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asp Tyr Gly Gly Asn Ser
1               5

<210> SEQ ID NO 203
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(78)

<400> SEQUENCE: 203 tgc gcg aga aga aaa gag gac gac tac gac tgg tat tac gat ctc tgg        48
Cys Ala Arg Arg Lys Glu Asp Asp Tyr Asp Trp Tyr Tyr Asp Leu Trp
1               5                   10                  15 ggc cgt ggc gcc cat atc att gtc tcc gca                                78
Gly Arg Gly Ala His Ile Ile Val Ser Ala
            20                  25

<210> SEQ ID NO 204
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Cys Ala Arg Arg Lys Glu Asp Asp Tyr Asp Trp Tyr Tyr Asp Leu Trp
1               5                   10                  15

Gly Arg Gly Ala His Ile Ile Val Ser Ala
            20                  25

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(20)

<400> SEQUENCE: 205
```

```
                                                                                                       20
gt aga gat ggc tac aat tac
   Arg Asp Gly Tyr Asn Tyr
   1               5
```

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

```
Arg Asp Gly Tyr Asn Tyr
1               5
```

<210> SEQ ID NO 207
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(81)

<400> SEQUENCE: 207

```
tgc gcg aga aag aaa agg ggg gac ggc ttc aat ttg tat ttc gat ctc     48
Cys Ala Arg Lys Lys Arg Gly Asp Gly Phe Asn Leu Tyr Phe Asp Leu
1               5                   10                  15 tgg ggc cgt ggc tcc caa gtc ata gtc tcc tca                         81
Trp Gly Arg Gly Ser Gln Val Ile Val Ser Ser
            20                  25
```

<210> SEQ ID NO 208
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

```
Cys Ala Arg Lys Lys Arg Gly Asp Gly Phe Asn Leu Tyr Phe Asp Leu
1               5                   10                  15

Trp Gly Arg Gly Ser Gln Val Ile Val Ser Ser
            20                  25
```

<210> SEQ ID NO 209
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(28)

<400> SEQUENCE: 209

```
a gca tat tgt ggt ggt gat tgc tat tcc                               28
  Ala Tyr Cys Gly Gly Asp Cys Tyr Ser
  1               5
```

<210> SEQ ID NO 210
<211> LENGTH: 9
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 210

Ala Tyr Cys Gly Gly Asp Cys Tyr Ser
1               5

<210> SEQ ID NO 211
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(96)

<400> SEQUENCE: 211 tgc gcg cgg cag act ttc aag cct gat ttc tac ttt gcg gac cag ggc    48
Cys Ala Arg Gln Thr Phe Lys Pro Asp Phe Tyr Phe Ala Asp Gln Gly
1               5                   10                  15 tgg agt ttc aat ctc tgg ggc cgg ggc gcc cac ttt atc gtc tcc tca    96
Trp Ser Phe Asn Leu Trp Gly Arg Gly Ala His Phe Ile Val Ser Ser
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Cys Ala Arg Gln Thr Phe Lys Pro Asp Phe Tyr Phe Ala Asp Gln Gly
1               5                   10                  15

Trp Ser Phe Asn Leu Trp Gly Arg Gly Ala His Phe Ile Val Ser Ser
            20                  25                  30

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(23)

<400> SEQUENCE: 213 gt gga tat agt ggc tac gat tac                                     23
   Gly Tyr Ser Gly Tyr Asp Tyr
   1               5

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Tyr Ser Gly Tyr Asp Tyr
```

<210> SEQ ID NO 215
<211> LENGTH: 93
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(93)

<400> SEQUENCE: 215 tgc gcg aga cag aaa ttt gcg agt cgc tat agt ggc gac caa ggc tca     48
Cys Ala Arg Gln Lys Phe Ala Ser Arg Tyr Ser Gly Asp Gln Gly Ser
1               5                   10                  15 tac ttc gat ctc tgg ggc cga gga acc ctc att gtt gtc tcc tca         93
Tyr Phe Asp Leu Trp Gly Arg Gly Thr Leu Ile Val Val Ser Ser
            20                  25                  30

<210> SEQ ID NO 216
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

Cys Ala Arg Gln Lys Phe Ala Ser Arg Tyr Ser Gly Asp Gln Gly Ser
1               5                   10                  15

Tyr Phe Asp Leu Trp Gly Arg Gly Thr Leu Ile Val Val Ser Ser
            20                  25                  30

<210> SEQ ID NO 217
<211> LENGTH: 93
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(93)

<400> SEQUENCE: 217 tgc gcg aga cag aaa ttt gcg agt cgc tat agt ggc gac caa ggc tca     48
Cys Ala Arg Gln Lys Phe Ala Ser Arg Tyr Ser Gly Asp Gln Gly Ser
1               5                   10                  15 tac ttc gat ctc tgg ggc cga gga acc ctc att gtt gtc tcc tca         93
Tyr Phe Asp Leu Trp Gly Arg Gly Thr Leu Ile Val Val Ser Ser
            20                  25                  30

<210> SEQ ID NO 218
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

Cys Ala Arg Gln Lys Phe Ala Ser Arg Tyr Ser Gly Asp Gln Gly Ser
1               5                   10                  15

Tyr Phe Asp Leu Trp Gly Arg Gly Thr Leu Ile Val Val Ser Ser
            20                  25                  30

<210> SEQ ID NO 219
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(93)

<400> SEQUENCE: 219

```
tgc gcg aga cag aaa ttt gcg agt cgc tat agt ggc gac caa ggc tca    48
Cys Ala Arg Gln Lys Phe Ala Ser Arg Tyr Ser Gly Asp Gln Gly Ser
1               5                   10                  15 tac ttc gat ctt tgg ggc cga gga acc ctc att att gtc tct tca        93
Tyr Phe Asp Leu Trp Gly Arg Gly Thr Leu Ile Ile Val Ser Ser
            20                  25                  30
```

<210> SEQ ID NO 220
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 220

```
Cys Ala Arg Gln Lys Phe Ala Ser Arg Tyr Ser Gly Asp Gln Gly Ser
1               5                   10                  15

Tyr Phe Asp Leu Trp Gly Arg Gly Thr Leu Ile Ile Val Ser Ser
            20                  25                  30
```

<210> SEQ ID NO 221
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(93)

<400> SEQUENCE: 221

```
tgc gcg aga cag aaa ttt gcg agt cgc tat agt ggc gac caa ggc tca    48
Cys Ala Arg Gln Lys Phe Ala Ser Arg Tyr Ser Gly Asp Gln Gly Ser
1               5                   10                  15 tac ttc gat ctt tgg ggc cga gga acc ctc att att gtc tct tca        93
Tyr Phe Asp Leu Trp Gly Arg Gly Thr Leu Ile Ile Val Ser Ser
            20                  25                  30
```

<210> SEQ ID NO 222
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 222

```
Cys Ala Arg Gln Lys Phe Ala Ser Arg Tyr Ser Gly Asp Gln Gly Ser
1               5                   10                  15

Tyr Phe Asp Leu Trp Gly Arg Gly Thr Leu Ile Ile Val Ser Ser
            20                  25                  30
```

<210> SEQ ID NO 223
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 223

```
tgc gcg aga cag aaa ttt gag agt cgc tat agt ggc gac caa ggc tca       48
Cys Ala Arg Gln Lys Phe Glu Ser Arg Tyr Ser Gly Asp Gln Gly Ser
1               5                   10                  15 tac ttc gat ctc tgg ggc cga gga acc ctc att att gtc tcc tca           93
Tyr Phe Asp Leu Trp Gly Arg Gly Thr Leu Ile Ile Val Ser Ser
            20                  25                  30
```

<210> SEQ ID NO 224
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

```
Cys Ala Arg Gln Lys Phe Glu Ser Arg Tyr Ser Gly Asp Gln Gly Ser
1               5                   10                  15

Tyr Phe Asp Leu Trp Gly Arg Gly Thr Leu Ile Ile Val Ser Ser
            20                  25                  30
```

<210> SEQ ID NO 225
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 225

```
tgc gcg aga cag aaa ttt gag agc cgc tat acg ggc ggc caa ggc tgg       48
Cys Ala Arg Gln Lys Phe Glu Ser Arg Tyr Thr Gly Gly Gln Gly Trp
1               5                   10                  15 tac ttc gat ctc tgg ggc cgt gga acc cac att gtt gtc tcg tca           93
Tyr Phe Asp Leu Trp Gly Arg Gly Thr His Ile Val Val Ser Ser
            20                  25                  30
```

<210> SEQ ID NO 226
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

```
Cys Ala Arg Gln Lys Phe Glu Ser Arg Tyr Thr Gly Gly Gln Gly Trp
1               5                   10                  15

Tyr Phe Asp Leu Trp Gly Arg Gly Thr His Ile Val Val Ser Ser
            20                  25                  30
```

```
<210> SEQ ID NO 227
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 227 tgc gcg aga cag aaa ttt gag agc cgc tat acg ggc ggc caa ggc tgg    48
Cys Ala Arg Gln Lys Phe Glu Ser Arg Tyr Thr Gly Gly Gln Gly Trp
1               5                   10                  15 tac ttc gat ctc tgg ggc cgt gga acc cac att gtt gtc tcg tca        93
Tyr Phe Asp Leu Trp Gly Arg Gly Thr His Ile Val Val Ser Ser
            20                  25                  30

<210> SEQ ID NO 228
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Cys Ala Arg Gln Lys Phe Glu Ser Arg Tyr Thr Gly Gly Gln Gly Trp
1               5                   10                  15

Tyr Phe Asp Leu Trp Gly Arg Gly Thr His Ile Val Val Ser Ser
            20                  25                  30

<210> SEQ ID NO 229
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 229 tgc gcg aga cag aaa ttt gag agt ctc tat agt gac gac caa ggc tcg    48
Cys Ala Arg Gln Lys Phe Glu Ser Leu Tyr Ser Asp Asp Gln Gly Ser
1               5                   10                  15 tac ttc gat ctc tgg ggc cga gga acc ctc att att gtc tcc tca        93
Tyr Phe Asp Leu Trp Gly Arg Gly Thr Leu Ile Ile Val Ser Ser
            20                  25                  30

<210> SEQ ID NO 230
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Cys Ala Arg Gln Lys Phe Glu Ser Leu Tyr Ser Asp Asp Gln Gly Ser
1               5                   10                  15

Tyr Phe Asp Leu Trp Gly Arg Gly Thr Leu Ile Ile Val Ser Ser
            20                  25                  30

<210> SEQ ID NO 231
```

```
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 231 tgt gcg aga cag aaa ttt gcg agg ggc gac caa ggc tgg ttc ttc gat    48
Cys Ala Arg Gln Lys Phe Ala Arg Gly Asp Gln Gly Trp Phe Phe Asp
1               5                   10                  15 ctc tgg ggc cgt gga acc ctc att gtt gtc tcg tca                    84
Leu Trp Gly Arg Gly Thr Leu Ile Val Val Ser Ser
            20                  25

<210> SEQ ID NO 232
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Cys Ala Arg Gln Lys Phe Ala Arg Gly Asp Gln Gly Trp Phe Phe Asp
1               5                   10                  15

Leu Trp Gly Arg Gly Thr Leu Ile Val Val Ser Ser
            20                  25

<210> SEQ ID NO 233
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 233 tgc gcg aga cag aaa ttt gcg agg ggc gac caa ggc tgg ttc ttc gat    48
Cys Ala Arg Gln Lys Phe Ala Arg Gly Asp Gln Gly Trp Phe Phe Asp
1               5                   10                  15 ctc tgg ggc cgt gga acc ctc att gtt gtc tcg tca                    84
Leu Trp Gly Arg Gly Thr Leu Ile Val Val Ser Ser
            20                  25

<210> SEQ ID NO 234
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Cys Ala Arg Gln Lys Phe Ala Arg Gly Asp Gln Gly Trp Phe Phe Asp
1               5                   10                  15

Leu Trp Gly Arg Gly Thr Leu Ile Val Val Ser Ser
            20                  25

<210> SEQ ID NO 235
<211> LENGTH: 84
```

<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: CDS
<222> LOCATION: (1)..(84)

<400> SEQUENCE: 235

```
tgt gcg aga cag aaa ttt gcg agg ggc gac caa ggc tgg ttc ttc gat      48
Cys Ala Arg Gln Lys Phe Ala Arg Gly Asp Gln Gly Trp Phe Phe Asp
1               5                   10                  15 ctc tgg ggc cgt gga acc ctc att gtt gtc tcg tca                      84
Leu Trp Gly Arg Gly Thr Leu Ile Val Val Ser Ser
            20                  25
```

<210> SEQ ID NO 236
<211> LENGTH: 28
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 236

```
Cys Ala Arg Gln Lys Phe Ala Arg Gly Asp Gln Gly Trp Phe Phe Asp
1               5                   10                  15

Leu Trp Gly Arg Gly Thr Leu Ile Val Val Ser Ser
            20                  25
```

<210> SEQ ID NO 237
<211> LENGTH: 84
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: CDS
<222> LOCATION: (1)..(84)

<400> SEQUENCE: 237

```
tgt gcg aga cag aaa ttt gcg agg ggc gac caa ggc tgg ttc ttc gat      48
Cys Ala Arg Gln Lys Phe Ala Arg Gly Asp Gln Gly Trp Phe Phe Asp
1               5                   10                  15 ctc tgg ggc cgt gga acc ctc att gtt gtc tcg tca                      84
Leu Trp Gly Arg Gly Thr Leu Ile Val Val Ser Ser
            20                  25
```

<210> SEQ ID NO 238
<211> LENGTH: 28
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 238

```
Cys Ala Arg Gln Lys Phe Ala Arg Gly Asp Gln Gly Trp Phe Phe Asp
1               5                   10                  15

Leu Trp Gly Arg Gly Thr Leu Ile Val Val Ser Ser
            20                  25
```

<210> SEQ ID NO 239
<211> LENGTH: 84
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 239

```
tgc gcg aga cag aaa ttt gcg agg ggc gac caa ggc tgg ttc ttc gat      48
Cys Ala Arg Gln Lys Phe Ala Arg Gly Asp Gln Gly Trp Phe Phe Asp
1               5                   10                  15 ctc tgg ggc cgt gga acc ctc att gtt gtc tcg tca                      84
Leu Trp Gly Arg Gly Thr Leu Ile Val Val Ser Ser
            20                  25
```

<210> SEQ ID NO 240
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

```
Cys Ala Arg Gln Lys Phe Ala Arg Gly Asp Gln Gly Trp Phe Phe Asp
1               5                   10                  15

Leu Trp Gly Arg Gly Thr Leu Ile Val Val Ser Ser
            20                  25
```

<210> SEQ ID NO 241
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 241

```
tgt gcg aga cag aaa ttt gcg agg ggc gac caa ggc tgg ttc ttc gat      48
Cys Ala Arg Gln Lys Phe Ala Arg Gly Asp Gln Gly Trp Phe Phe Asp
1               5                   10                  15 ctc tgg ggc cgt gga acc ctc att gtt gtc tcg tca                      84
Leu Trp Gly Arg Gly Thr Leu Ile Val Val Ser Ser
            20                  25
```

<210> SEQ ID NO 242
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

```
Cys Ala Arg Gln Lys Phe Ala Arg Gly Asp Gln Gly Trp Phe Phe Asp
1               5                   10                  15

Leu Trp Gly Arg Gly Thr Leu Ile Val Val Ser Ser
            20                  25
```

<210> SEQ ID NO 243
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 243 tgc gcg aga cag aaa ttt gag agg ggc ggc caa ggc tgg tac ttc gat       48
Cys Ala Arg Gln Lys Phe Glu Arg Gly Gly Gln Gly Trp Tyr Phe Asp
1               5                   10                  15 ctc tgg ggc cgt gga acc ctc att gtt gtc tcg tca                       84
Leu Trp Gly Arg Gly Thr Leu Ile Val Val Ser Ser
            20                  25

<210> SEQ ID NO 244
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Cys Ala Arg Gln Lys Phe Glu Arg Gly Gly Gln Gly Trp Tyr Phe Asp
1               5                   10                  15

Leu Trp Gly Arg Gly Thr Leu Ile Val Val Ser Ser
            20                  25

<210> SEQ ID NO 245
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 245 tgc gcg aga cag aaa ttt gag agg ggc ggc caa ggc tgg tat ttc gat       48
Cys Ala Arg Gln Lys Phe Glu Arg Gly Gly Gln Gly Trp Tyr Phe Asp
1               5                   10                  15 ctc tgg ggc cgt gga acc ctc att gtt gtc tcg tca                       84
Leu Trp Gly Arg Gly Thr Leu Ile Val Val Ser Ser
            20                  25

<210> SEQ ID NO 246
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Cys Ala Arg Gln Lys Phe Glu Arg Gly Gly Gln Gly Trp Tyr Phe Asp
1               5                   10                  15

Leu Trp Gly Arg Gly Thr Leu Ile Val Val Ser Ser
            20                  25

<210> SEQ ID NO 247
<211> LENGTH: 84
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 247 tgc gcg aga cag aaa ttt gag agg ggc ggc caa ggc tgg tat ttc gat      48
Cys Ala Arg Gln Lys Phe Glu Arg Gly Gly Gln Gly Trp Tyr Phe Asp
1               5                   10                  15 ctc tgg ggc cgt gga acc ctc att gtt gtc tcg tca                      84
Leu Trp Gly Arg Gly Thr Leu Ile Val Val Ser Ser
            20                  25

<210> SEQ ID NO 248
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Cys Ala Arg Gln Lys Phe Glu Arg Gly Gly Gln Gly Trp Tyr Phe Asp
1               5                   10                  15

Leu Trp Gly Arg Gly Thr Leu Ile Val Val Ser Ser
            20                  25

<210> SEQ ID NO 249
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 249 tgc gcg aga cag aaa ttt gag agg ggc ggc caa ggc tgg atc ttc gat      48
Cys Ala Arg Gln Lys Phe Glu Arg Gly Gly Gln Gly Trp Ile Phe Asp
1               5                   10                  15 ctc tgg ggc cgc gga acc ctc att gct gtc tcg tca                      84
Leu Trp Gly Arg Gly Thr Leu Ile Ala Val Ser Ser
            20                  25

<210> SEQ ID NO 250
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Ala Arg Gln Lys Phe Glu Arg Gly Gly Gln Gly Trp Ile Phe Asp
1               5                   10                  15

Leu Trp Gly Arg Gly Thr Leu Ile Ala Val Ser Ser
            20                  25

<210> SEQ ID NO 251
<211> LENGTH: 84
<212> TYPE: DNA
<213> ORGANISM: Artificial Sequence
<220> FEATURE:
<223> OTHER INFORMATION: Description of Artificial Sequence: Synthetic
```

```
                       oligonucleotide
<220> FEATURE:
<221> NAME/KEY: CDS
<222> LOCATION: (1)..(84)

<400> SEQUENCE: 251 tgt gcg aga cag aaa ttt tat gcg ggc ggc caa ggc tgg tac ttc gat    48
Cys Ala Arg Gln Lys Phe Tyr Ala Gly Gly Gln Gly Trp Tyr Phe Asp
1               5                  10                  15 ctc tgg ggc cgt gga acc ctc att gtt gtc tcg tca                    84
Leu Trp Gly Arg Gly Thr Leu Ile Val Val Ser Ser
            20                  25

<210> SEQ ID NO 252
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Cys Ala Arg Gln Lys Phe Tyr Ala Gly Gly Gln Gly Trp Tyr Phe Asp
1               5                  10                  15

Leu Trp Gly Arg Gly Thr Leu Ile Val Val Ser Ser
            20                  25

<210> SEQ ID NO 253
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 253 tgc gcg aga cag aaa ttt tat gcg ggc ggc caa ggc tgg tac ttc gat    48
Cys Ala Arg Gln Lys Phe Tyr Ala Gly Gly Gln Gly Trp Tyr Phe Asp
1               5                  10                  15 ctc tgg ggc cgt gga acc ctc att gtt gtc tcg tca                    84
Leu Trp Gly Arg Gly Thr Leu Ile Val Val Ser Ser
            20                  25

<210> SEQ ID NO 254
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Cys Ala Arg Gln Lys Phe Tyr Ala Gly Gly Gln Gly Trp Tyr Phe Asp
1               5                  10                  15

Leu Trp Gly Arg Gly Thr Leu Ile Val Val Ser Ser
            20                  25

<210> SEQ ID NO 255
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: CDS
<222> LOCATION: (1)..(84)

<400> SEQUENCE: 255 tgc gcg aga cag aaa ttt tat gcg ggc ggc caa ggc tgg tac ttc gat     48
Cys Ala Arg Gln Lys Phe Tyr Ala Gly Gly Gln Gly Trp Tyr Phe Asp
1               5                   10                  15 ctc tgg ggc cgt gga acc ctc att gtt gtc tcg tca                     84
Leu Trp Gly Arg Gly Thr Leu Ile Val Val Ser Ser
            20                  25

<210> SEQ ID NO 256
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Cys Ala Arg Gln Lys Phe Tyr Ala Gly Gly Gln Gly Trp Tyr Phe Asp
1               5                   10                  15

Leu Trp Gly Arg Gly Thr Leu Ile Val Val Ser Ser
            20                  25

<210> SEQ ID NO 257
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 257 tgc gcg aga cag aaa ttt tat gcg ggc ggc caa ggc tgg tac ttc gat     48
Cys Ala Arg Gln Lys Phe Tyr Ala Gly Gly Gln Gly Trp Tyr Phe Asp
1               5                   10                  15 ctc tgg ggc cgt gga acc ctc att gtt gtc tcg tca                     84
Leu Trp Gly Arg Gly Thr Leu Ile Val Val Ser Ser
            20                  25

<210> SEQ ID NO 258
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Ala Arg Gln Lys Phe Tyr Ala Gly Gly Gln Gly Trp Tyr Phe Asp
1               5                   10                  15

Leu Trp Gly Arg Gly Thr Leu Ile Val Val Ser Ser
            20                  25

<210> SEQ ID NO 259
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: CDS
<222> LOCATION: (1)..(84)

<400> SEQUENCE: 259 tgc gcg aga cag aag ttc tat aag ggc ggc caa ggc tgg tac ttc gat    48
Cys Ala Arg Gln Lys Phe Tyr Lys Gly Gly Gln Gly Trp Tyr Phe Asp
1               5                   10                  15 ctc tgg ggc cgt gga acc ctc att gtt gtc tcg tca                    84
Leu Trp Gly Arg Gly Thr Leu Ile Val Val Ser Ser
            20                  25

<210> SEQ ID NO 260
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Cys Ala Arg Gln Lys Phe Tyr Lys Gly Gly Gln Gly Trp Tyr Phe Asp
1               5                   10                  15

Leu Trp Gly Arg Gly Thr Leu Ile Val Val Ser Ser
            20                  25

<210> SEQ ID NO 261
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 261 tgc gcg aga cag aaa tac tat gcg ggc ggc caa ggc tgg tat ttc gat    48
Cys Ala Arg Gln Lys Tyr Tyr Ala Gly Gly Gln Gly Trp Tyr Phe Asp
1               5                   10                  15 ctc tgg ggc cgt gga acc ctc att gtt gtc tcg tca                    84
Leu Trp Gly Arg Gly Thr Leu Ile Val Val Ser Ser
            20                  25

<210> SEQ ID NO 262
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Cys Ala Arg Gln Lys Tyr Tyr Ala Gly Gly Gln Gly Trp Tyr Phe Asp
1               5                   10                  15

Leu Trp Gly Arg Gly Thr Leu Ile Val Val Ser Ser
            20                  25

<210> SEQ ID NO 263
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
```

<222> LOCATION: (1)..(84)

<400> SEQUENCE: 263

```
tgc gcg aga cag aaa ttt tat acg ggc ggc caa ggc tgg tac ttc gat    48
Cys Ala Arg Gln Lys Phe Tyr Thr Gly Gly Gln Gly Trp Tyr Phe Asp
1               5                   10                  15 ctc tgg ggc cgt gga acc ctc att gtt gtc tcg tca                    84
Leu Trp Gly Arg Gly Thr Leu Ile Val Val Ser Ser
            20                  25
```

<210> SEQ ID NO 264
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

```
Cys Ala Arg Gln Lys Phe Tyr Thr Gly Gly Gln Gly Trp Tyr Phe Asp
1               5                   10                  15

Leu Trp Gly Arg Gly Thr Leu Ile Val Val Ser Ser
            20                  25
```

<210> SEQ ID NO 265
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(84)

<400> SEQUENCE: 265

```
tgc gcg aga cag aaa ttt tat gcg ggc ggc caa ggc tgg tac ttc gat    48
Cys Ala Arg Gln Lys Phe Tyr Ala Gly Gly Gln Gly Trp Tyr Phe Asp
1               5                   10                  15 ctc tgg ggc cgt gga acc ctc att gtt gtc tcg tca                    84
Leu Trp Gly Arg Gly Thr Leu Ile Val Val Ser Ser
            20                  25
```

<210> SEQ ID NO 266
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

```
Cys Ala Arg Gln Lys Phe Tyr Ala Gly Gly Gln Gly Trp Tyr Phe Asp
1               5                   10                  15

Leu Trp Gly Arg Gly Thr Leu Ile Val Val Ser Ser
            20                  25
```

<210> SEQ ID NO 267
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(84)

<400> SEQUENCE: 267

```
tgc gcg aga cag aaa ttt atg tcg ggc ggc caa ggc tgg tac ttc gat    48
Cys Ala Arg Gln Lys Phe Met Ser Gly Gly Gln Gly Trp Tyr Phe Asp
1               5                   10                  15 ctc tgg gga cgt gga acc gtc att gtt gtc tcg tca                    84
Leu Trp Gly Arg Gly Thr Val Ile Val Val Ser Ser
            20                  25
```

<210> SEQ ID NO 268
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

```
Cys Ala Arg Gln Lys Phe Met Ser Gly Gly Gln Gly Trp Tyr Phe Asp
1               5                   10                  15

Leu Trp Gly Arg Gly Thr Val Ile Val Val Ser Ser
            20                  25
```

<210> SEQ ID NO 269
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(84)

<400> SEQUENCE: 269

```
tgc gcg aga cag aaa ttt tat gcg ggc ggc caa ggc tgg tac ttc gat    48
Cys Ala Arg Gln Lys Phe Tyr Ala Gly Gly Gln Gly Trp Tyr Phe Asp
1               5                   10                  15 ctc tgg ggc cgt gga acc ctc att gtt gtc tcg tca                    84
Leu Trp Gly Arg Gly Thr Leu Ile Val Val Ser Ser
            20                  25
```

<210> SEQ ID NO 270
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

```
Cys Ala Arg Gln Lys Phe Tyr Ala Gly Gly Gln Gly Trp Tyr Phe Asp
1               5                   10                  15

Leu Trp Gly Arg Gly Thr Leu Ile Val Val Ser Ser
            20                  25
```

<210> SEQ ID NO 271
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (2)..(37)

```
<400> SEQUENCE: 271 g tat tat gat tac gtt tgg ggg agt tat gct tat acc                    37
  Tyr Tyr Asp Tyr Val Trp Gly Ser Tyr Ala Tyr Thr
   1               5                  10

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Tyr Tyr Asp Tyr Val Trp Gly Ser Tyr Ala Tyr Thr
 1               5                  10

<210> SEQ ID NO 273
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(47)

<400> SEQUENCE: 273 ac tac ttt gac tac tgg ggc caa gga acc ctg gtc acc gtc tcc tca       47
   Tyr Phe Asp Tyr Trp Gly Gln Gly Thr Leu Val Thr Val Ser Ser
    1               5                  10                  15

<210> SEQ ID NO 274
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Tyr Phe Asp Tyr Trp Gly Gln Gly Thr Leu Val Thr Val Ser Ser
 1               5                  10                  15

<210> SEQ ID NO 275
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(69)

<400> SEQUENCE: 275 tgt gcg cgc gga ccc atg gga ggg agt cat gtc tac tgg ggc caa gga     48
Cys Ala Arg Gly Pro Met Gly Gly Ser His Val Tyr Trp Gly Gln Gly
 1               5                  10                  15 tcc ctg gtc acc gtc tcg tca                                          69
Ser Leu Val Thr Val Ser Ser
            20

<210> SEQ ID NO 276
<211> LENGTH: 23
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 276

Cys Ala Arg Gly Pro Met Gly Gly Ser His Val Tyr Trp Gln Gly
1               5                   10                  15

Ser Leu Val Thr Val Ser Ser
            20

<210> SEQ ID NO 277
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Ala Thr Asn Tyr Ala Gln Lys Phe
    50                  55                  60

Gln Gly Arg Leu Thr Ile Ala Arg Asp Thr Ser Ile Ser Thr Ala Tyr
65                  70                  75                  80

Met Asp Leu Arg Asn Leu Arg Phe Asp Thr Ala Val Tyr Phe Cys
                85                  90                  95

Ala Arg Lys Thr Ala Gly Asp Val Ser Gly Asp Asn Arg Gly Tyr Phe
            100                 105                 110

Phe Asp Leu Trp Gly Arg Gly Ser Arg Val Ile Val Ser Ser
        115                 120                 125

<210> SEQ ID NO 278
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Gln Val Gln Leu Val Gln Ser Gly Ala Glu Leu Lys Lys Pro Gly Ala
1               5                   10                  15

Ser Val Lys Val Ser Cys Glu Ala Ser Gly Tyr Ser Phe Thr Asp His
            20                  25                  30

His Ile His Trp Val Arg Gln Ala Pro Gly Gln Gly Leu Glu Trp Leu
        35                  40                  45

Gly Trp Met Asn Pro Asn Asn Gly Asp Thr Ala Tyr Ala Gln Thr Phe
    50                  55                  60

Leu Gly Arg Val Thr Met Thr Arg Asp Thr Ser Ile Asn Thr Ala Tyr
65                  70                  75                  80

Met Glu Leu Ser Arg Leu Thr Ser Asp Thr Ala Val Tyr Phe Cys
                85                  90                  95

Ala Arg Lys Thr Ala Gly Asp Val Ser Gly Asp Lys Arg Gly Phe Phe
            100                 105                 110
```

```
Phe Asp Leu Trp Gly Arg Gly Ser Arg Val Ile Val Ser Ser
        115                 120                 125
```

<210> SEQ ID NO 279
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Met Arg Gln Ala Pro Gly Gln Gly Leu Glu Trp Met
        35                  40                  45

Gly Trp Ile Asn Pro Asn Ser Gly Ala Val Ser Tyr Ala Arg Lys Phe
    50                  55                  60

Gln Gly Arg Val Ser Phe Leu His Asp Gln Gly Ile Arg Met Ala Tyr
65                  70                  75                  80

Met Asp Leu Arg Asn Leu Arg Phe Asp Thr Ala Val Tyr Phe Cys
                85                  90                  95

Ala Arg Lys Thr Ala Gly Asp Val Ser Gly Asp Asn Arg Gly Tyr Phe
            100                 105                 110

Phe Asp Leu Trp Gly Arg Gly Ser Arg Val Ile Val Ser Ser
        115                 120                 125
```

<210> SEQ ID NO 280
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Gly Tyr
            20                  25                  30

Tyr Leu His Trp Val Arg Gln Ala Pro Gly Gln Thr Phe Glu Trp Leu
        35                  40                  45

Gly Trp Met Lys Pro Val Thr Gly Ala Val Ser Tyr Ala Arg Lys Phe
    50                  55                  60

Gln Gly Arg Val Ser Phe Tyr Met Thr Arg Glu Leu Gly Met Ala Tyr
65                  70                  75                  80

Met Asp Leu Arg Asn Leu Arg Phe Asp Thr Ala Val Tyr Phe Cys
                85                  90                  95

Ala Arg Lys Thr Ala Gly Asp Val Ser Gly Asp Asn Arg Gly Tyr Phe
            100                 105                 110

Phe Asp Leu Trp Gly Arg Gly Ser Arg Val Ile Val Ser Ser
        115                 120                 125
```

<210> SEQ ID NO 281
<211> LENGTH: 127
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 281

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Asp Trp Val
        35                  40                  45

Gly Trp Ile Asn Pro Asn Ser Gly Thr Asn Tyr Ala Gln Lys Phe
    50                  55                  60

Gln Gly Arg Val Ala Met Thr Arg Asp Thr Ser Leu Ser Val Tyr
65                  70                  75                  80

Leu Asp Leu Asn Ser Leu Thr Ser Ala Asp Ser Gly Thr Tyr Phe Cys
                85                  90                  95

Ala Arg Gln Thr Phe Lys Pro Asp Phe Tyr Phe Ala Asp Gln Gly Trp
            100                 105                 110

Ser Phe Asn Leu Trp Gly Arg Gly Ala His Phe Ile Val Ser Ser
        115                 120                 125

<210> SEQ ID NO 282
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Gln Val Gln Leu Val Gln Ser Gly Ala Glu Val Arg Lys Pro Gly Ala
1               5                   10                  15

Ser Val Arg Val Ser Cys Lys Ala Ser Gly Tyr Thr Phe Thr Ala Tyr
            20                  25                  30

Tyr Ile His Trp Val Arg Gln Ala Pro Gly Gln Gly Leu Glu Trp Met
        35                  40                  45

Gly Trp Ile Arg Pro Lys Asn Gly Gly Arg Asn Gln Ala Arg Gln Phe
    50                  55                  60

Gln Pro Arg Ile Ser Leu Thr Arg Asp Arg Ala Leu Asn Thr Ala Tyr
65                  70                  75                  80

Leu Asp Leu Asn Ser Leu Thr Ser Ala Asp Ser Gly Thr Tyr Phe Cys
                85                  90                  95

Ala Arg Gln Thr Phe Lys Pro Asp Phe Tyr Phe Ala Asp Gln Gly Trp
            100                 105                 110

Ser Phe Asn Leu Trp Gly Arg Gly Ala Arg Val Ile Val Ser Ser
        115                 120                 125

<210> SEQ ID NO 283
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr

```
                    20                  25                  30

Tyr Ile His Trp Leu Arg Gln Val Gln Gly Arg Asp Leu Ser Gly Val
            35                  40                  45

Gly Trp Ile Arg Pro Arg Thr Gly Ala Arg Asn Gln Ala Arg Gln Phe
        50                  55                  60

Gln Pro Arg Ile Ser Leu Thr Arg Asp Arg Ala Leu Ser Thr Ala Tyr
65                  70                  75                  80

Leu Asp Leu Asn Ser Leu Thr Ser Ala Asp Ser Gly Thr Tyr Phe Cys
                85                  90                  95

Ala Arg Gln Thr Phe Lys Pro Asp Phe Tyr Phe Ala Asp Gln Gly Trp
            100                 105                 110

Ser Phe Asn Leu Trp Gly Arg Gly Ala His Phe Ile Val Ser Ser
        115                 120                 125

<210> SEQ ID NO 284
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Gln Val Gln Leu Val Gln Ser Gly Ala Glu Val Lys Lys Pro Gly Ala
1               5                   10                  15

Ser Val Lys Val Ser Cys Lys Ala Ser Gly Cys Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gln Lys Phe Ala Arg Gly Asp Gln Gly Trp Phe Phe Asp Leu
            100                 105                 110

Trp Gly Arg Gly Thr Leu Ile Val Val Ser Ser
        115                 120

<210> SEQ ID NO 285
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Gln Val Gln Leu Val His Ser Gly Ala Glu Val Lys Lys Pro Gly Ala
1               5                   10                  15

Ser Met Lys Val Ser Cys Lys Thr Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Asn Asp Thr Asn Tyr Ala Gln Lys Phe
    50                  55                  60

Gln Gly Arg Val Thr Met Thr Arg Asp Thr Ser Ile Asn Thr Ala Tyr
```

```
                65                  70                  75                  80
Met Glu Leu Ser Arg Leu Arg Ser Gly Asp Thr Ala Ile Tyr Phe Cys
                    85                  90                  95

Ala Arg Gln Lys Phe Tyr Ala Gly Gly Gln Gly Trp Tyr Phe Asp Leu
                100                 105                 110

Trp Gly Arg Gly Thr Leu Ile Val Val Ser Ser
            115                 120

<210> SEQ ID NO 286
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gln Val Gln Leu Val Gln Ser Gly Thr Glu Leu Arg Lys Pro Gly Ala
1               5                   10                  15

Ser Val Lys Val Ser Cys Lys Ala Ser Gly Tyr Thr Phe Ser Gly Ser
                20                  25                  30

Tyr Ile His Trp Val Arg Gln Ala Pro Gly Gln Gly Leu Glu Trp Val
            35                  40                  45

Gly Trp Ile Asn Pro Ser Ser Gly Ala Thr Gln Cys Ala Lys Lys Phe
        50                  55                  60

Gln Asp Lys Val Thr Met Thr Arg Asp Thr Thr Asn Asn Thr Val Tyr
65                  70                  75                  80

Met Glu Val Asn Arg Leu Ile Ser Asp Asp Thr Ala Tyr Phe Cys
                    85                  90                  95

Ala Arg Gln Lys Phe Ala Arg Gly Asp Gln Gly Trp Phe Phe Asp Leu
                100                 105                 110

Trp Gly Arg Gly Thr Leu Ile Val Val Ser Ser
            115                 120

<210> SEQ ID NO 287
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Tyr Met His Trp Leu Arg Gln Ala Pro Gly Gln Gly Leu Glu Trp Met
            35                  40                  45

Gly Trp Ile Asn Pro His Ser Gly Gly Thr Asn Phe Ala Gln Lys Phe
        50                  55                  60

Gln Gly Arg Val Thr Met Thr Arg Asp Thr Ser Ile Thr Thr Ala Tyr
65                  70                  75                  80

Met Glu Leu Ser Arg Leu Arg Ser Asp Asp Thr Ala Tyr Phe Cys
                    85                  90                  95

Ala Arg Gln Lys Phe Ala Ser Arg Tyr Ser Gly Asp Gln Gly Ser Tyr
                100                 105                 110

Phe Asp Leu Trp Gly Arg Gly Thr Leu Ile Val Val Ser Ser
```

<210> SEQ ID NO 288
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Gln Val Gln Leu Val Gln Ser Gly Ala Glu Val Lys Lys Pro Gly Ala
1               5                   10                  15

Ser Val Lys Val Ser Cys Lys Gly Ser Gly Phe Pro Phe Asn Tyr Tyr
            20                  25                  30

Ile His Trp Leu Arg Gln Ala Pro Gly Gln Ser Leu Glu Trp Met Gly
        35                  40                  45

Trp Ile Asn Pro Asp Thr Gly Gly Ser Asn Ser Ala Gln Lys Phe Leu
    50                  55                  60

Gly Arg Val Thr Leu Thr Arg Asp Thr Ser Ile Thr Thr Ala Tyr Met
65                  70                  75                  80

Glu Met Thr Arg Leu Thr Tyr Asp Asp Thr Ala Ile Tyr Tyr Cys Ala
                85                  90                  95

Arg Asp Arg Asn Leu Arg Val Ala Ile Val Ala Thr Lys Ala His Thr
            100                 105                 110

Ser Ile Trp Gly Arg Gly Thr Leu Ile Val Val Ser Pro
        115                 120                 125

<210> SEQ ID NO 289
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Gln Val Gln Leu Val Gln Ser Gly Thr Glu Val Gln Lys Pro Gly Ala
1               5                   10                  15

Ser Val Lys Val Ser Cys Lys Ala Phe Gly Tyr Ser Phe Thr Asp Tyr
            20                  25                  30

Tyr Val Tyr Trp Val Arg Gln Ala Pro Gly Gln Gly Leu Glu Tyr Val
        35                  40                  45

Ala Trp Ile Asn Pro Ser Asn Gly Tyr Thr Lys Tyr Ala Gln Lys Phe
    50                  55                  60

Gln Asp Trp Val Thr Leu Thr Arg Asp Ser Ser Ile Asn Thr Ala Tyr
65                  70                  75                  80

Leu Gln Leu Ala Arg Val Thr Ser Asp Asp Thr Ala Ile Tyr Tyr Cys
                85                  90                  95

Ala Arg Gln Lys Phe Ala Ser Arg Tyr Ser Gly Asp Gln Gly Ser Tyr
            100                 105                 110

Phe Asp Leu Trp Gly Arg Gly Thr Leu Ile Val Val Ser Ser
        115                 120                 125

<210> SEQ ID NO 290
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 290

Gln Val Gln Leu Val Gln Ser Gly Ala Glu Met Lys Lys Pro Gly Ala
1               5                   10                  15

Ser Val Lys Leu Ser Cys Met Thr Ser Gly Tyr Val Phe Thr Asp Phe
            20                  25                  30

Tyr Ile His Trp Val Arg Gln Ala Pro Gly Gln Gly Leu Glu Trp Met
        35                  40                  45

Gly Trp Ile Asn Pro Gly Thr Gly Gly Thr Ile Ser Ala Pro Arg Phe
    50                  55                  60

Leu Gly Arg Val Thr Leu Thr Arg Asp Thr Ser Ile Ser Ala Ala Tyr
65                  70                  75                  80

Ile Glu Ile Asn Arg Val Thr Ile Asp Asp Thr Ala Thr Tyr Phe Cys
                85                  90                  95

Ala Arg Gln Lys Phe Ala Ser Arg Tyr Ser Gly Asp Gln Gly Ser Tyr
            100                 105                 110

Phe Asp Leu Trp Gly Arg Gly Thr Leu Ile Val Val Ser Ser
        115                 120                 125

<210> SEQ ID NO 291
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Val Gln Leu Val Gln Ser Gly Thr Glu Val Lys Lys Pro Gly Ala
1               5                   10                  15

Ser Val Met Val Thr Cys Lys Ala Ser Gly Tyr Ser Phe Asn Asp Tyr
            20                  25                  30

Tyr Val Asn Trp Val Arg Gln Ala Pro Gly Gln Gly Leu Glu Trp Met
        35                  40                  45

Gly Trp Ile Asn Pro Lys Thr Gly Asp Thr Asn Tyr Ala Arg Lys Phe
    50                  55                  60

Gln Gly Arg Val Ser Met Thr Arg Asp Thr Phe Ile Thr Thr Ala Tyr
65                  70                  75                  80

Leu Glu Leu Asn Ser Leu Thr Ser Asp Asp Thr Ala Val Tyr Tyr Cys
                85                  90                  95

Val Arg Gly Ala Arg Gly Met Pro Lys Gly Ala Phe Asp Ile Trp Gly
            100                 105                 110

Gln Gly Thr Leu Val Ile Val Ser Ser
        115                 120

<210> SEQ ID NO 292
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

His Trp Val Asn Pro Ala Pro Glu His Tyr Ile His Phe Leu Arg Gln
            35                  40                  45

Ala Pro Gly Gln Gln Leu Glu Trp Leu Ala Trp Met Asn Pro Thr Asn
        50                  55                  60

Gly Ala Val Asn Tyr Ala Trp Gln Leu Gln Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 293
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Asp Tyr Ser Pro
            20                  25                  30

His Trp Val Asn Pro Ala Pro Glu His Tyr Ile His Phe Leu Arg Gln
            35                  40                  45

Ala Pro Gly Gln Gln Leu Glu Trp Leu Ala Trp Met Asn Pro Thr Asn
        50                  55                  60

Gly Ala Val Asn Tyr Ala Trp Gln Leu His Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 294
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Asp Tyr Ser Pro
            20                  25                  30

His Trp Val Asn Pro Ala Pro Glu His Tyr Ile His Phe Leu Arg Gln
            35                  40                  45

```
Ala Pro Gly Gln Gln Leu Glu Trp Leu Ala Trp Met Asn Pro Thr Asn
        50                  55                  60

Gly Ala Val Asn Tyr Ala Trp Gln Leu His Gly Arg Leu Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 295
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
        50                  55                  60

Gly Ala Val Asn Tyr Ala Trp Gln Leu His Gly Arg Leu Thr Ala Thr
65                  70                  75                  80

Arg Asp Arg Ser Met Thr Thr Ala Phe Leu Glu Val Arg Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 296
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Pro Gly Lys Ala Pro Lys Leu Leu Val
        35                  40                  45

Ser Asp Ala Ser Ile Leu Glu Gly Gly Val Pro Ser Arg Phe Ser Gly
    50                  55                  60
```

```
Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 297
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
                20                  25                  30

Leu Asn Trp Tyr Gln Gln Lys Pro Gly Lys Ala Pro Lys Leu Leu Val
            35                  40                  45

Ser Asp Ala Ser Ile Leu Glu Gly Gly Val Pro Ser Arg Phe Ser Gly
    50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100
```

FOCUSED EVOLUTION OF HIV-1 NEUTRALIZING ANTIBODIES REVEALED BY CRYSTAL STRUCTURES AND DEEP SEQUENCING

This application is a National Phase of PCT/US2012/030436, filed on Mar. 23, 2012, which designated the U.S. and claims priority from U.S. Provisional application No. 61/484,184, filed May 9, 2011, the entire content of each of which are incorporated herein by reference.

GOVERNMENT SUPPORT

This invention was made with government support under Grant No. AI 067854 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 20, 2014, is named 1579-1928_SL.txt and is 255,827 bytes in size.

BACKGROUND

Antibody VRC01 represents a human immunoglobulin that neutralizes .about.90% of diverse HIV-1 isolates. To understand how such broadly neutralizing HIV-1 antibodies develop and recognize the viral envelope, we used X-ray crystallography and 454 pyrosequencing to characterize additional antibodies from HIV-1-infected individuals. Crystal structures revealed a convergent mode of binding of different antibodies to the same CD4-binding-site epitope. Antibody recognition was achieved through the evolution of complementary contact domains that were generated in diverse ways. Phylogenetic analysis of expressed heavy and light chains determined by deep sequencing revealed a common pathway of antibody heavy chain maturation confined to IGHV1-2*02 lineage that could pair with different light chains. The maturation pathway inferred by antibodyomics reveals that diverse antibodies evolve to a highly affinity-matured state to recognize an invariant viral structure, providing insight into the development and evolution of broadly neutralizing HIV-1 immunity.

BRIEF DESCRIPTION OF THE DRAWINGS

FIGS. 1A-G. Identification and characterization of broadly neutralizing CD4-binding-site mAbs from HIV-1-infected donors, 74 and 0219. The RSC3 probe was used to identify five broadly neutralizing mAbs, all of which were inferred to derive from the IGVH1-2*02 allele and displayed a high levels of somatic mutation. (A) RSC3 analysis of serum. Twelve sera from the IAVI Protocol G cohort (donors 17-74) and one serum from the CHAVI 001 cohort (donor 0219) were analyzed for RSC3 reduction in serum neutralization on HIV-1 strains JR-FL, PVO.4, YU2 and ZA12.29. Blue bars show the mean serum reduction in neutralization $IC_{50}$ resulting from RSC3 versus ΔRSC3 competition. Sera with greatest reduction were further analyzed on HIV-1 strains Q168.a2, RW020.2, Du156.12 and ZM109.4. Red bars show the mean reduction on eight viruses. (B) RSC3- and ΔRSC3-binding profile of IgG+13 cells from donors 74 and 0219. Gating and percentage of B rolls of interest (RSC3+ΔRSC3−) are indicated, with 40 and 26 sorted single B cells from donors 74 and 0219, respectively. Additional sorting details are shown in FIG. 8. (C) Protein sequences of heavy and light chain variable regions of mAbs VRC-PG04 and VRC-PG04b, isolated from donor 74, and mAbs VRC-CH30, VRC-CH31 and VRC-CH32, isolated from donor 0219, Sequences are aligned to putative germline ancestral genes and to previously identified broadly neutralizing antibodies VRC01 and VRC03. Framework regions (FR) and complementary-determining regions (CDRs) are based on Kabat nomenclature (41). Figure discloses SEQ ID NOS 107-126, respectively, in order of appearance. (D) Competition ELISAs. The binding to YU2 gp120 by a single concentration of biotin-labeled VRC-PG04 or VRC-CH31 was assessed against increasing concentrations of competitive ligand. CD4-Ig is a fusion protein of the N-terminal two domains of CD4 with IgG1 Fc. (E) Amino acid sequence identities between VRC-PG04 or VRC-CH31 and other antibodies reactive with the CD4-binding site on gp120 (CD4bs) or with the CD4-induced co-receptor-binding site (CD4i). (F) Neutralization dendrograms. VRC-PG04 and VRC-CH31 were tested against genetically diverse Env-pseudoviruses representing the major HIV-1 clades. Neighbor-joining dendrograms display the protein distance of gp160 sequences from 179 HIV-1 isolates tested against VRC-PG04 and a subset (52 isolates) tested against VRC-CH31. A scale bar denotes the distance corresponding to a 1% change in amino acid sequence. Dendrogram branches are colored by the neutralization potencies of VRC-PG04 and VRC-CH31 against each particular virus. (G) FIG. 1 G describes the following sequences Vf4 Light Chain (VRC-CH30) (SEQ ID NO: 127); Vf4 Heavy Chain (VRC-CH30) (SEQ ID NO: 128); VRC-CH31 (vf5) Light Chain (SEQ ID NO: 129); VRC-CH31 (vf5) Heavy Chain (SEQ ID NO: 130); Vf6 Light Chain (VRC-CH32) (SEQ ID NO: 131); and Vf6 Heavy Chain (VRC-CH32) (SEQ ID NO: 132). FIGS. 1A-G are referred to as FIGS. 1A-G throughout the specification and Examples.

FIGS. 2A-C are referred to as FIGS. 2A-C throughout the specification and Examples.

FIGS. 3A-C. Focused evolution of VRC01-like antibodies. The maturational processes that facilitate the evolution of VRC01-like antibodies from low affinity unmutated antibodies to high affinity potent neutralizers involve divergence in antibody sequence and convergence in epitope recognition. (A) Antibody convergence. The gp120 portions of liganded complexes with VRC01, VRC03 and VRC-PG04 were superimposed to determine the average antibody per-residue Cα deviation, and the per-residue hydrophobic interaction ($\Delta^{iG}$) was calculated (42). These two quantities were found to correlate (P-value=0.0427), with antibody residues containing strong hydrophobic interactions (e.g. at positions, 53, 55, 91 and 97) displaying high structural conservation. This correlation is visualized on VRC-PG04 in the left image, where the ribbon thickness is proportional to the corresponding per-residue Cα deviation and the paratope surface is colored according to hydrophobicity, from white (low) to red (high); notably, red surface patches map to thin ribbons. (B) Epitope convergence. The HIV-1 gp120 surface involved with CD4 binding contains conformationally invariant regions (e.g. associated with the outer domain) and conformationally variable regions (e.g. associated with the bridging sheet). We previously hypothesized that the conformationally invariant outer domain-contact for CD4 represents a site of vulnerability (19). We analyzed the precision of CD4-binding-site ligand recognition (vertical axis) versus the $IC_{50}$ neutralization breadth (horizontal axis) and observed significant correlation ($R^2$=0.6, P-value=0.040). (C) Divergences in sequence and convergences in recognition. The development of VRC01-like antibodies involves a heavy chain derived from the IGHV1-2*02 allele and selected light chain Vκ alleles. The far left image depicts ribbon representation model of a putative germline antibody. Somatic hypermutation during the process of affinity maturation leads to a divergence in sequence, yet results in the convergent recognition of similar epitopes. Intersection of the epitope surfaces recognized by VRC01, VRC03 and VRC-PG04 (far right image), reveals a remarkable similarity to the site of vulnerability. The primary divergence of this intersection from the hypothesized site of vulnerability occurs in the region of HIV-1 gp120 recognized by the light chain of the VRC01-like antibodies. While the separate epitopes on gp120 do show differences in recognition surface, these primarily involve the bridging sheet region, which is likely to adopt a different conformation in the functional viral spike prior to engagement of CD4. FIGS. 3A-C are referred to as FIGS. 3A-C throughout the specification and Examples.

FIGS. 4A-E. Deep sequencing of expressed heavy and light chains from donors 45 and 74. 454 pyrosequencing facilitates the determination of the repertoire of heavy and light chain sequences (the heavy and light chain antibody-omes). Heavy and light chain complementation, computational bioinformatics, and neutralization measurements on reconstituted chimeric antibodies provide functional assessment. (A) Heavy and light chain complementation. The neutralization profiles of VRC01 and VRC03 (donor 45), VRC-PG04 (donor 74), and VRC-CH31 (donor 0219) and their heavy and light chain chimeric swaps are depicted with 20-isolate neutralization dendrograms. Explicit neutralization $IC_{50}$s are provided in Table S10. (B) The repertoire of heavy chain sequences from donor 45 (2008 sample) and donor 74 (2008 sample). Heavy chain sequences are plotted as a function of sequence identity to the heavy chain of VRC01 (left), VRC03 (middle) and VRC-PG04 (right) and of sequence divergence from putative genomic VH-alleles: upper row plots show sequences of putative IGHV1-2*02 allelic origin; lower row plots show sequences from other allelic origins. Color coding indicates the number of sequences. (C) Repertoire of expressed light chain sequences from donor 45 (2001 sample). Light chain sequences are plotted as a function of sequence identify to VRC01 (left) and VRC03 (right) light chains, and of sequence divergence from putative genomic V-gene alleles. Sequences with 2-residue deletions in the CDR L1 region (which is observed in VRC01 and VRC03) are shown as black dots. Two sequences, with 92.0% identify to VRC01 (sequence ID 181371) and with 90.3% identify to VRC03 (sequence ID 223454) are highlighted with red triangles. (D) Functional assessment of light chain sequences identified by deep sequencing. The neutralization profiles of sequence 181371 reconstituted with the VRC01 heavy chain (named gVRC-L1$_{d45}$) and of sequence 223454 reconstituted with the VRC03 heavy chain (named gVRC-L2$_{d45}$) are depicted with 20-isolate neutralization dendrograms; explicit neutralization $IC_{50}$s are shown provided in Table S15. (E) Functional assessment of heavy chain sequences identified by deep sequencing. Heavy chain sequences from donors 45 and 74 were synthesized and expressed with either the light chain of VRC01 or VRC03 (for donor 45) or the light chain of VRC-PG04 (for donor 74) and evaluated for neutralization. Neutralizing antibodies are shown as red stars and are labeled. Comprehensive expression and neutralization results are presented in Tables S14 and S15 (43). gVRC-H (n) refers to the heavy chains with confirmed neutralization when reconstituted with the light chain of VRC-PG04 (Tables S14 and S15). FIGS. 4A-E are referred to as FIGS. 4A-E throughout the specification and Examples.

FIGS. 5A-B are referred to as FIGS. 5A-B throughout the specification and Examples.

FIGS. 6A-E. Analysis of the heavy chain antibodyome of donor 74 and identification of heavy chains with HIV-1 neutralizing activity. Identity/diversity-grid analysis, cross-donor phylogenetic analysis, and CDR H3 analysis when coupled to functional characterization of selected heavy chain sequences, provides a means for identification of novel heavy chains with HIV-1 neutralizing activity. (A) Identity/diversity-grid analysis. The location of the 70 synthesized heavy chains from donor 74 is shown, including neutralizing (red stars) and non-neutralizing (black stars) sequences. (B) Cross-donor phylogenetic analysis and CDR H3 lineage analysis. A maximum-likelihood phylogenetic tree of the 70 synthesized heavy chain sequences is rooted in the putative reverted unmutated ancestor of VRC-PG04. The probe-identified VRC-PG and VRC-CH antibodies are shown in red text. Grid location and CDR H3 class is specified for neutralizing and non-neutralizing sequences. Within each CDR H3 class, all sequences with identical CDR H3s are highlighted in orange in the far right grids (with the number of total sequences corresponding to each CDR H3 class shown). (C) Expression levels of selected heavy chains reconstituted with the light chain of VRC-PG04 versus breadth of neutralization. (D) Neutralization potency of reconstituted phylogenetically-predicted antibodies on seven HIV-1 isolates. (E) CDR H3 analysis of donor 74 heavy chain sequences. For each of the 110,386 sequences with derived from the IGHV1-2*02 allele, the CDR H3 was determined and its percent identity to that of the VRC-PG04 heavy chain was graphed. The sequences with high CDR H3 identity to VRC-PG04 reside in regions of high overall heavy chain sequence identity, even for sequences with a low divergence from IGHV1-2*02. FIGS. 6A-E are referred to as FIGS. 6A-E throughout the specification and Examples.

FIGS. 7A-C are referred to as FIGS. 7A-C throughout the specification and Examples.

FIG. 8. Single RSC3-specific B cell sorting. About 20 million PBMC from donors 74 and 0219 were incubated with APC and PE labeled RSC3 and RSC3, respectively. Memory B cells were selected on the basis of the presented gating strategy. The percentages of B cells that reacted with RSC3 and not RSC3 within IgG+ B cells are indicated. The actually sorted single B cells were 40 from donor 74 and 26 from donor 0219. The sorter configurations are indicated in the bottom panel. FIG. 8 is referred to as FIG. 8 or FIG. S1 throughout the specification and Examples.

FIG. 9 is referred to as FIG. 9 or FIG. S2 throughout the specification and Examples.

FIG. 10 is referred to as FIG. 10 or FIG. S3 throughout the specification and Examples.

FIGS. 11A-C are referred to as FIGS. 11A-C or FIG. S4 throughout the specification and Examples.

FIG. 12 is referred to as FIG. 12 or FIG. S5 throughout the specification and Examples.

FIG. 13 is referred to as FIG. 13 or FIG. S6 throughout the specification and Examples.

FIG. 14 is referred to as FIG. 14 or FIG. S7 throughout the specification and Examples.

FIG. 15. The sequence distribution of 454-pyrosequencing-determined donor 74 heavy-chain antibodyome (obtained from Beckman Coulter Genomics) plotted as a function of sequence identity to VRC01, VRC03 and VRC-PG04 and sequence divergence from respective germlines. Row one plots sequences of IGHV1-2*02 origin and row two plots sequences of non-IGHV1-2*02 origin. FIG. 15 is referred to as FIG. 15 or FIG. S8 throughout the specification and Examples.

FIG. 16 is referred to as FIG. 16 or FIG. S9 throughout the specification and Examples.

FIG. 17 is referred to as FIG. 17 or FIG. S10 throughout the specification and Examples.

FIG. 18 is referred to as FIG. 18 or FIG. S11 throughout the specification and Examples.

FIG. 19. CDR H3 classification of 35 expressed and experimentally tested heavy-chain sequences (SEQ ID NOS 137-171, respectively, in order of appearance) in the neutralization tree shown in FIG. 6, with the J gene of each CDR H3 class listed in parentheses. The Germline sequence, IGHV1-2*02 (SEQ ID NO: 107), is used as reference in sequence alignment and VRC-PG04 heavy-chain sequence (SEQ ID NO: 111) is included for comparison. Amino acids in the variable region that are different from IGHV1-2*02 are highlighted in red. Note that of the 35 sequences 22 showed neutralizing activity, as highlighted in red in FIG. 6. FIG. 19 is referred to as FIG. 19 or FIG. S12 throughout the specification and Examples.

Figure 20:
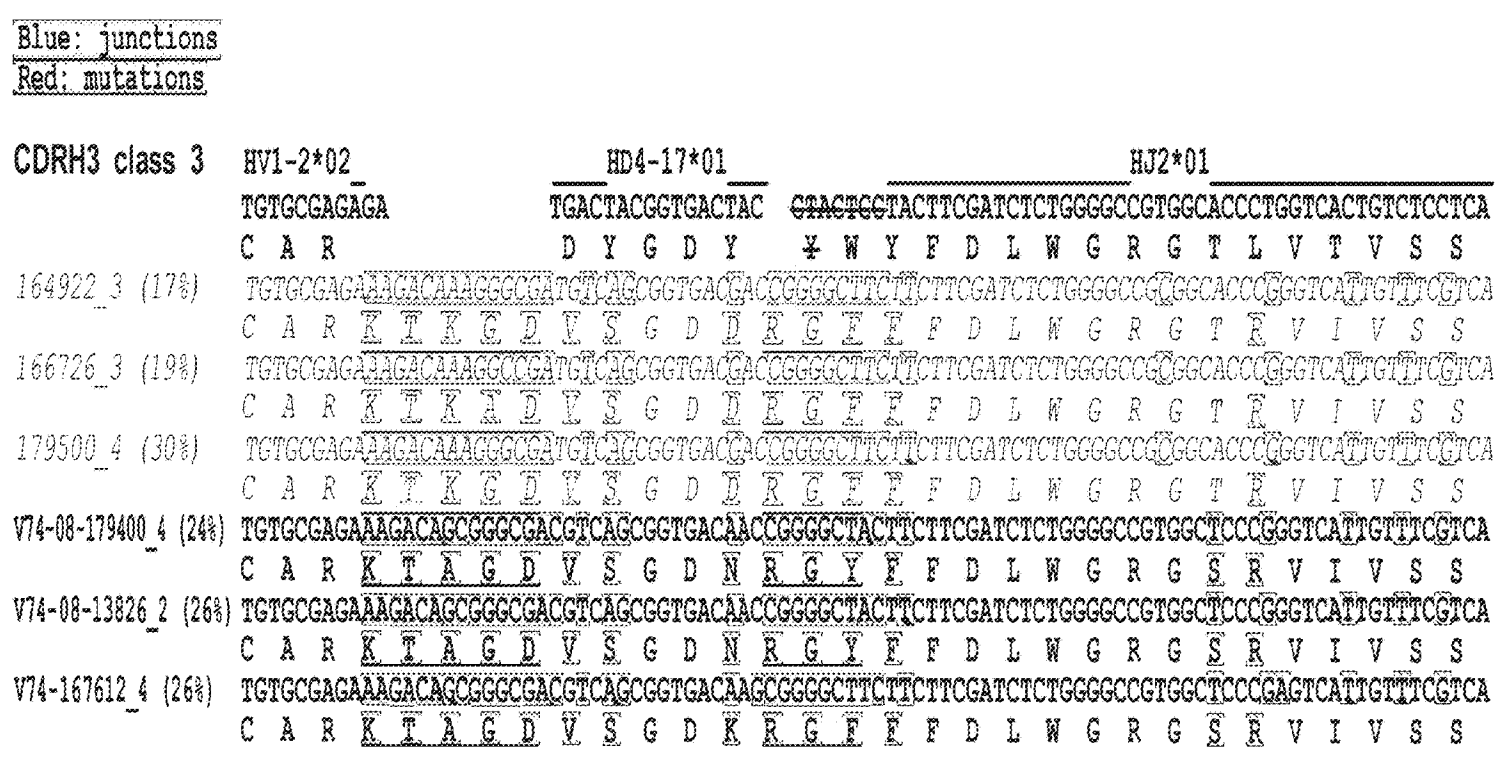

FIG. 20. CDRH3 analysis of expressed heavy chain sequences from donor 74. CDRH3 and HJ alignments of nucleotide and amino acid for CDRH3 classes 1-6 sequences, aligned to the putative V, D and J germline genes. Putative nucleotide excisions are indicated with strikethrough lines. In blue are the putative TdT N additions in V-D and D-J junctions. In red are mutations from the putative germline genes and the TdT N additions. The non-neutralizing sequences are shown in italic. Figure discloses SEQ ID NOS 172-173, 175, 174, 176-178, 172, 179, 181, 180, 182-184, 172, 185, 187, 186, 188-200, 172, 185-186, 201-202, 187-188, 203-204, 172, 205-206, 187-188, 207-208, 172, 209, 187, 210, 188, and 211-212, left to right, top to bottom, respectively, in order of appearance. FIG. 20 is referred to as FIG. 20 or FIG. S13a throughout the specification and Examples.

Figure 21:
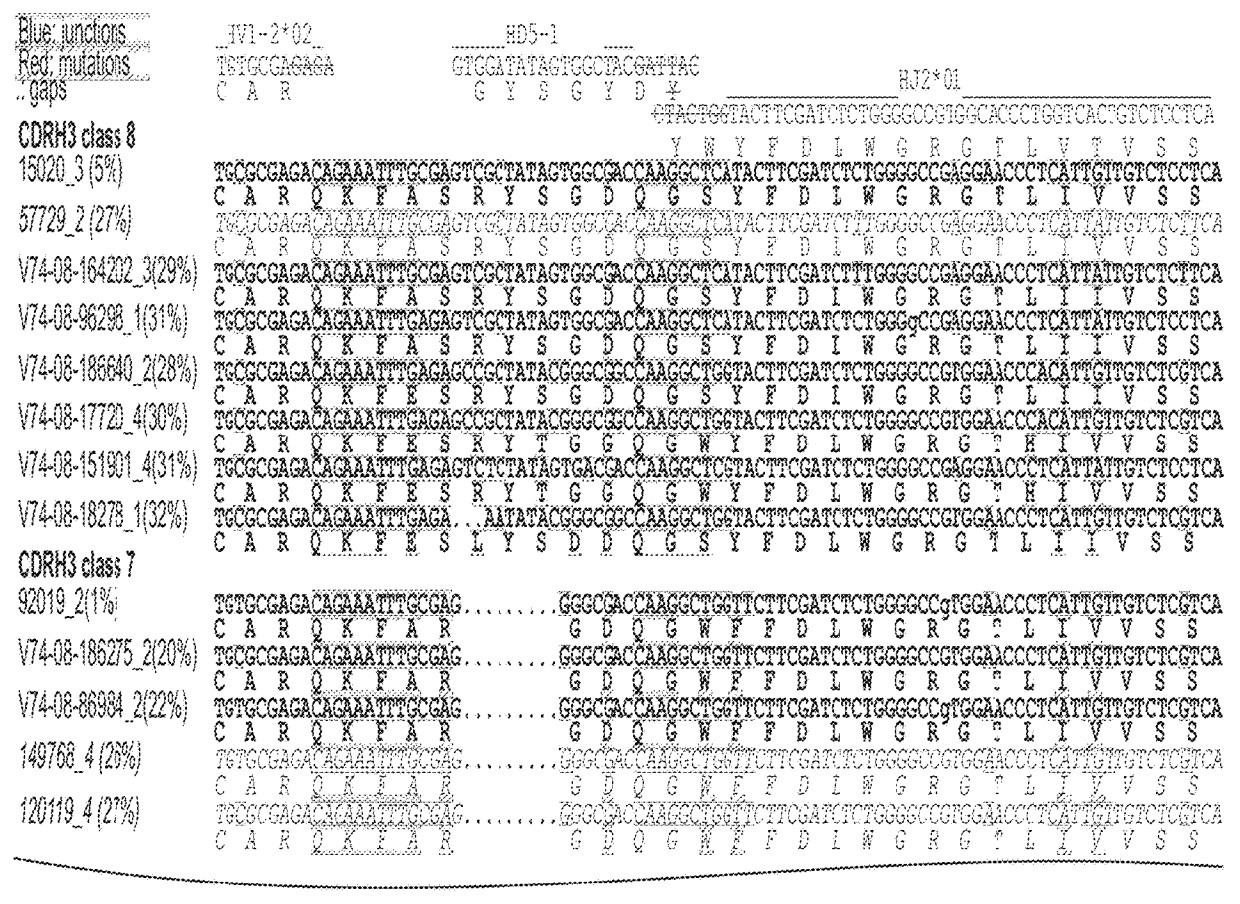
Figure 21:
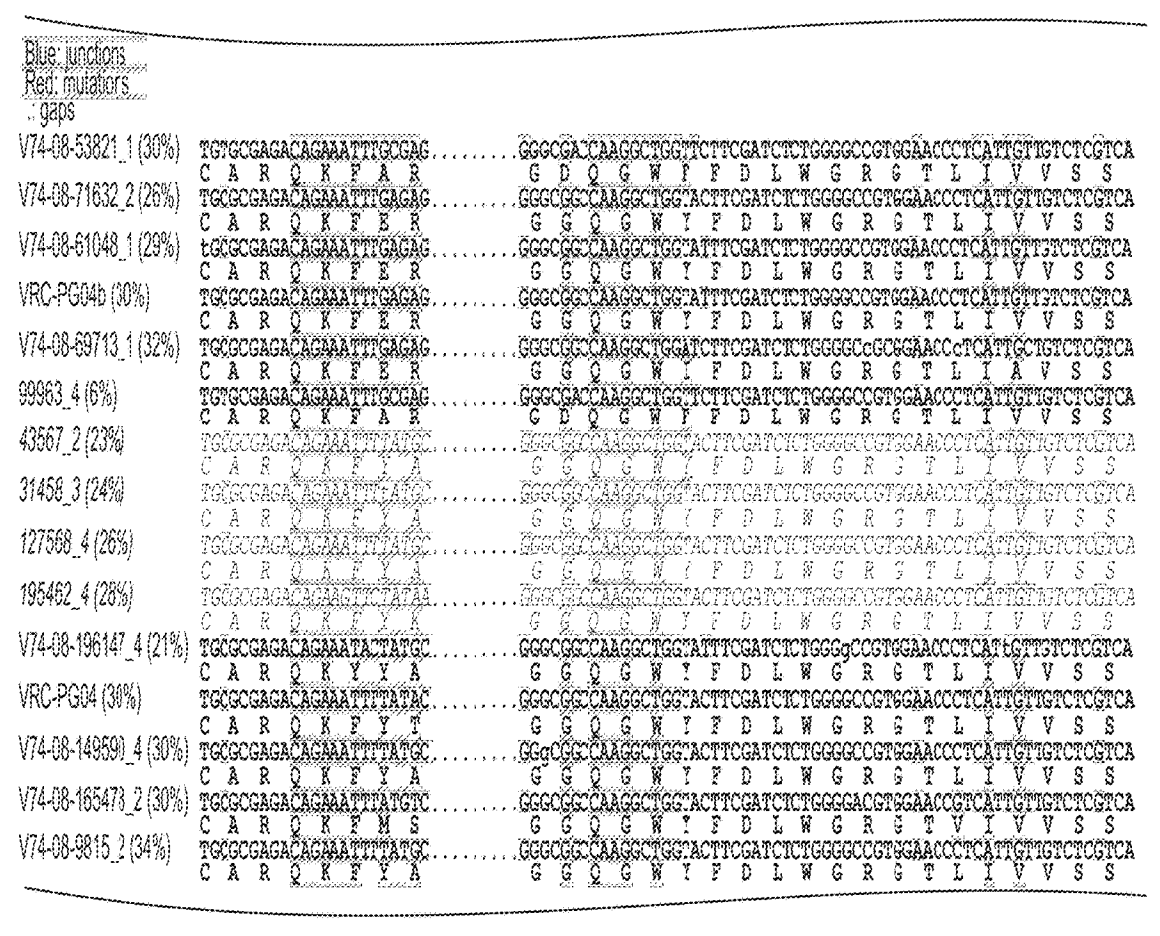

FIG. 21. CDRH3 analysis of expressed heavy chain sequences from donor 74. CDRH3 and HJ alignments of nucleotide and amino acid for VRC-PG04, 04b and their clonally related sequences, aligned to the putative V, D and J germline genes. Putative nucleotide excisions are indicated with strikethrough lines. In blue are the putative TdT N additions in V-D and D-J junctions. In red are mutations from the putative germline genes and the TdT N additions. The alignment analysis suggested that the CDRH3 classes 7 and 8 might be clonally related, as indicated by conserved V-D and D-J junctions, despite that a deletion "." occurred in the CDRH3 region. The non-neutralizing sequences are shown in italic. Figure discloses SEQ ID NOS 172, 213-214, 187-188, 215-270, 172, and 271-276, left to right, top to bottom, respectively, in order of appearance. FIG. 21 is referred to as FIG. 21 or FIG. S13b throughout the specification and Examples.

FIG. 22. Sequence alignment of maturation intermediates in CDR H3 classes 3, 6, 7 and 8 shown in FIG. 7. The neutralizing heavy-chain sequences are highlighted in red and CDR H3 region is circled by dotted line. Figure discloses SEQ ID NOS 277-280, 139, 281-283, 147, 284-286, 151, 157, 287-290, and 165, respectively, in order of appearance. FIG. 22 is referred to as FIG. 22 or FIG. S14 throughout the specification and Examples.

FIG. 23 is referred to as FIG. 23 or FIG. S15 throughout the specification and Examples.

FIG. 24 is referred to as FIG. 24 or FIG. S16 throughout the specification and Examples.

FIG. 25 is referred to as FIG. 25 or FIG. A-1 throughout the specification and Examples.

FIG. 26 is referred to as FIG. 26 or FIG. A-2 throughout the specification and Examples.

$$Coverage_{Germline} = \frac{\text{Length(aligned region)}}{\text{Length(Germline gene)}}$$

$$Coverage_{Query\,sequence\,from\,454} = \frac{\text{Length(aligned region)}}{\text{Length(Query sequence)}}$$

Figure 27:
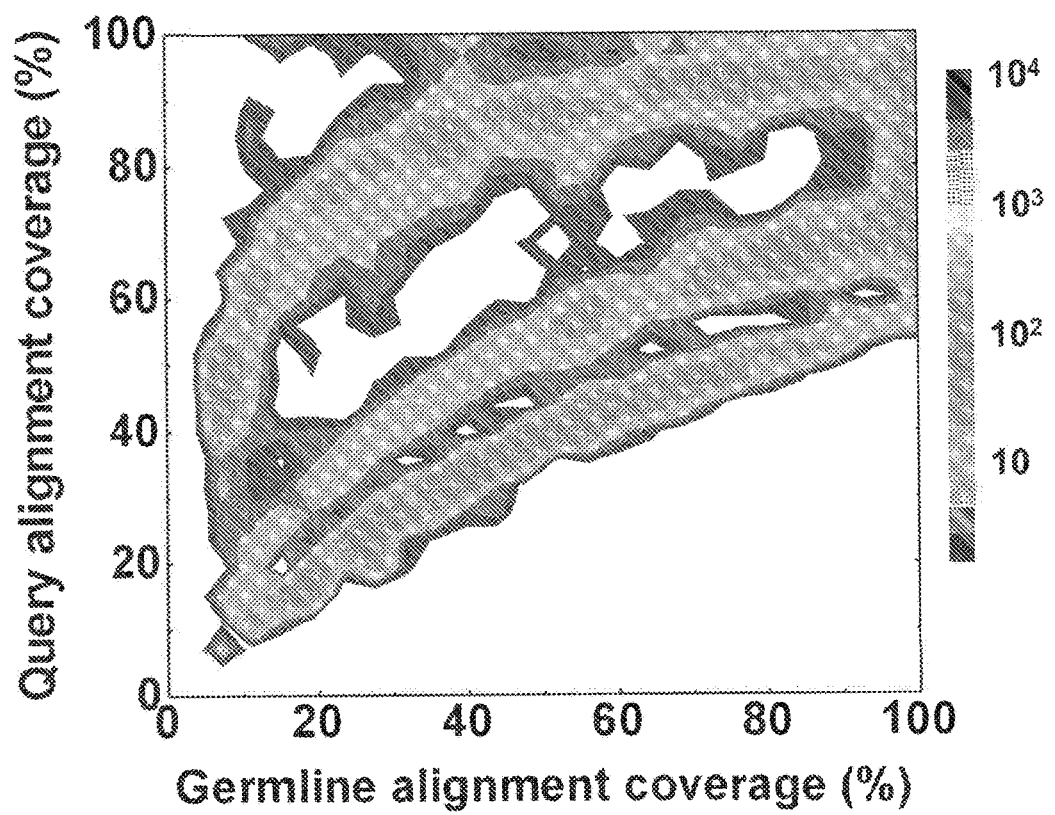
FIG. 27. We defined a metric—alignment coverage—to characterize the effect of sequence length variation on the alignment of a 454 sequence to a germline gene.

When aligned to their respective germline genes, 61471 sequences (or 38.8%) could cover 95% of the germline sequence and thus were considered to contain the "complete" variable (V) gene. FIG. 27 is referred to as FIG. 27 or FIG. A-3 throughout the specification and Examples.

Figure 28:
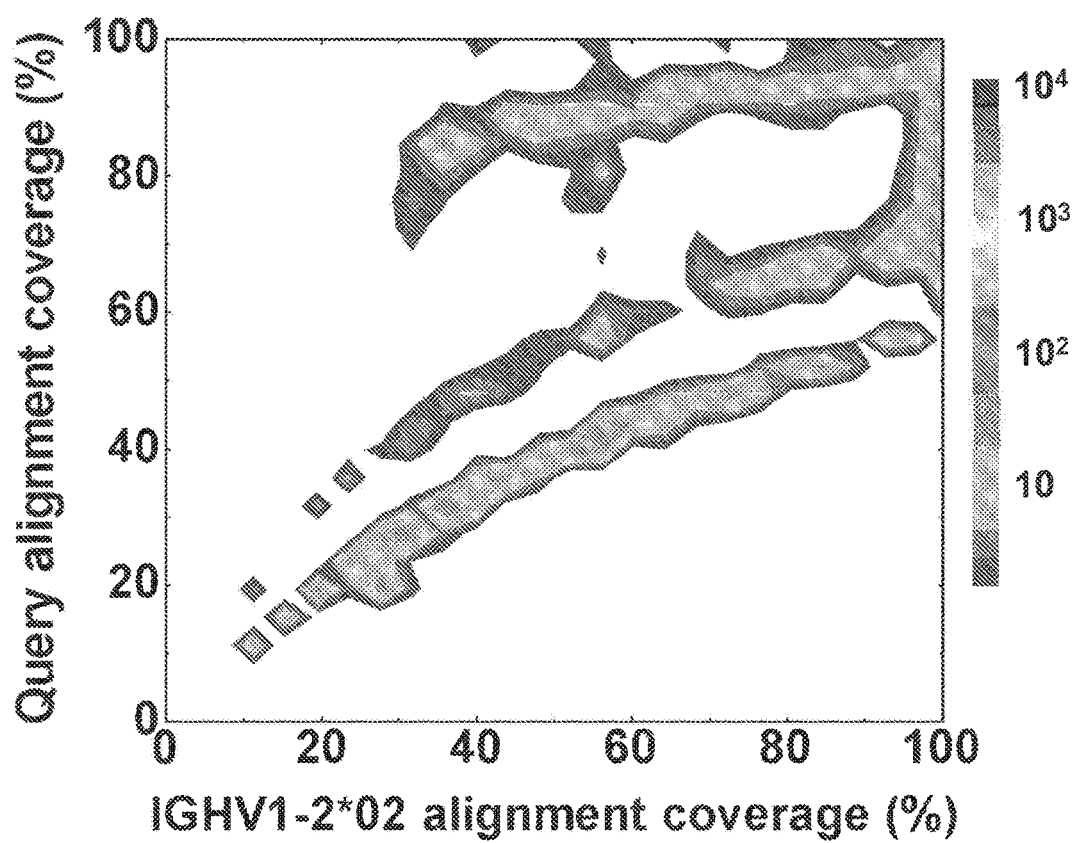

FIG. 28. Alignment coverage was also used to characterize the sequences that were assigned to IGHV1-2*02 family. Note that alleles IGVH1-2*01, IGHV1-2*03 and IGHV1-2*04 were also considered in the calculation due to their high similarities to IGHV1-2*02. When aligned to the germline genes, 9598 sequences (or 42.1%) of IGHV1-2*02 family could cover 95% of the germline sequence and thus were considered to contain the "complete" IGHV1-2*02 gene. FIG. 28 is referred to as FIG. 28 or FIG. A-4 throughout the specification and Examples.

Figure 29:
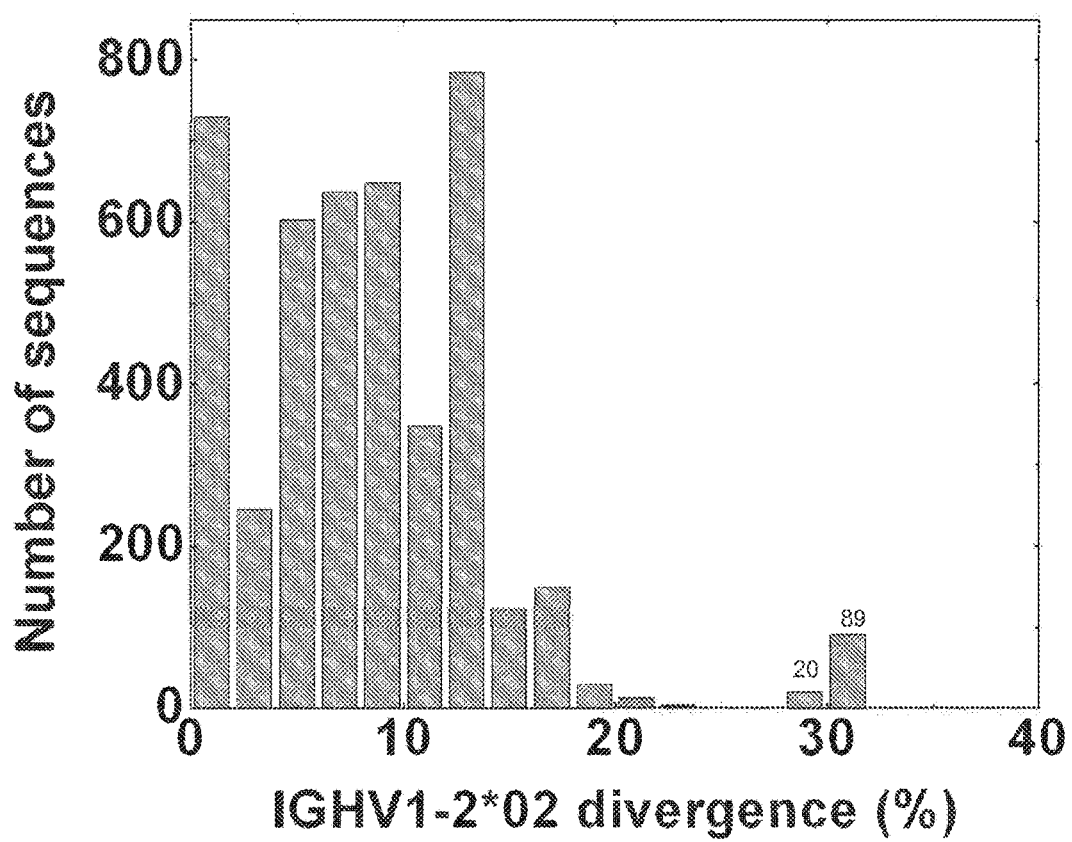

FIG. 29. The full-length sequences were extracted from the data set using VRC01 H sequence as a template, resulting in a total of 26445 sequences with 4417 sequences assigned to IGHV1-2*02 family (IGHV1-2*01, IGHV1-2*03 and IGHV1-2*04 alleles included). The divergence of full length IGHV1-2*02 sequences was calculated and plotted as a histogram. A total of 109 highly divergent sequences were found, with 20 in the 28-30% bin and 89 in the 30-32% bin. FIG. 29 is referred to as FIG. 29 or FIG. A-5 throughout the specification and Examples.

Figure 30:
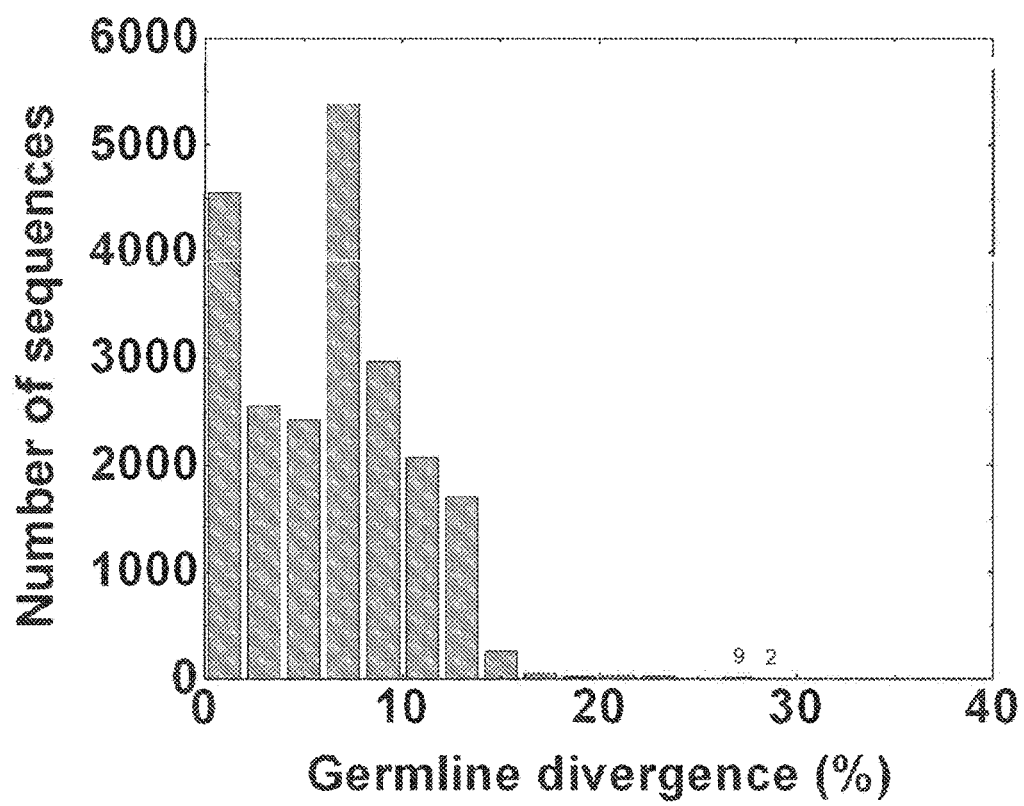

FIG. 30. The divergence of full-length sequences that were assigned to non-IGHV1-2*02 germlines was calculated and plotted as a histogram. A total of 11 highly divergent sequences were found, with 9 in the 26-28% bin and 2 in the 28-30% bin. No sequences were found to be more divergent than 30%. FIG. 30 is referred to as FIG. 30 or FIG. A-6 throughout the specification and Examples.

Figure 31:
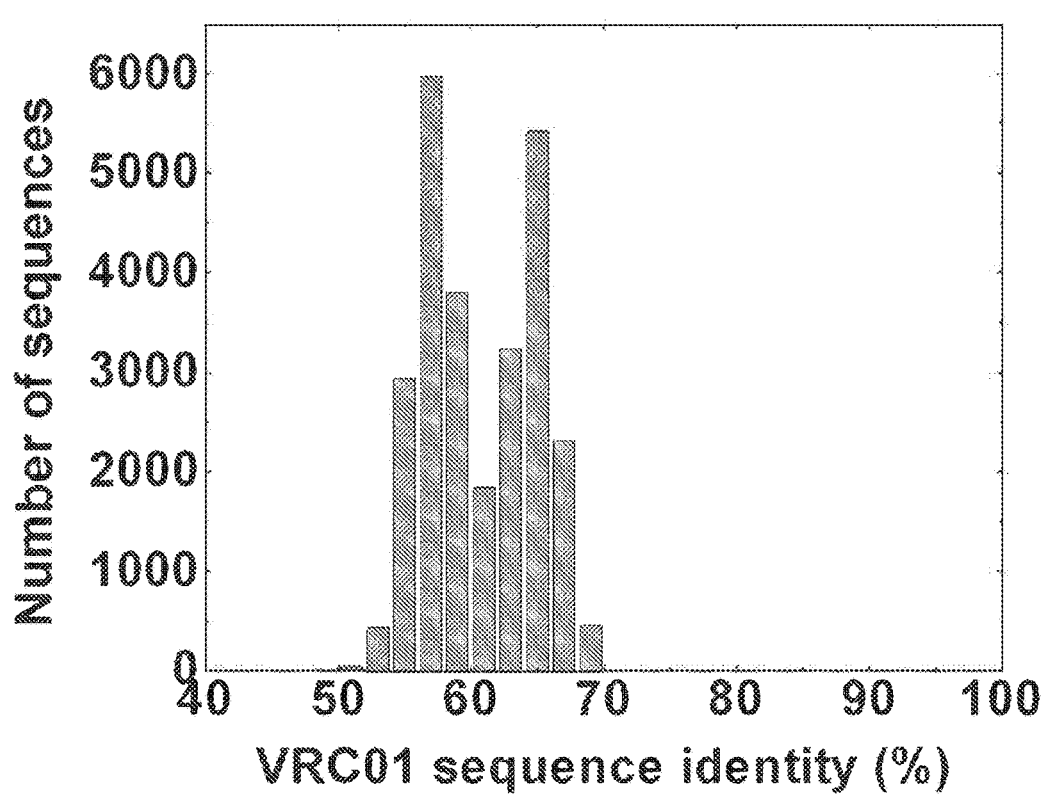

FIG. 31. The sequence identity to VRC01 H (at the nucleotide level) was calculated for all full-length sequences and plotted as a histogram. No sequences in the data set were found to be over 70% identical to the VRC01 H sequence. FIG. 31 is referred to as FIG. 31 or FIG. A-7 throughout the specification and Examples.

Figure 32:
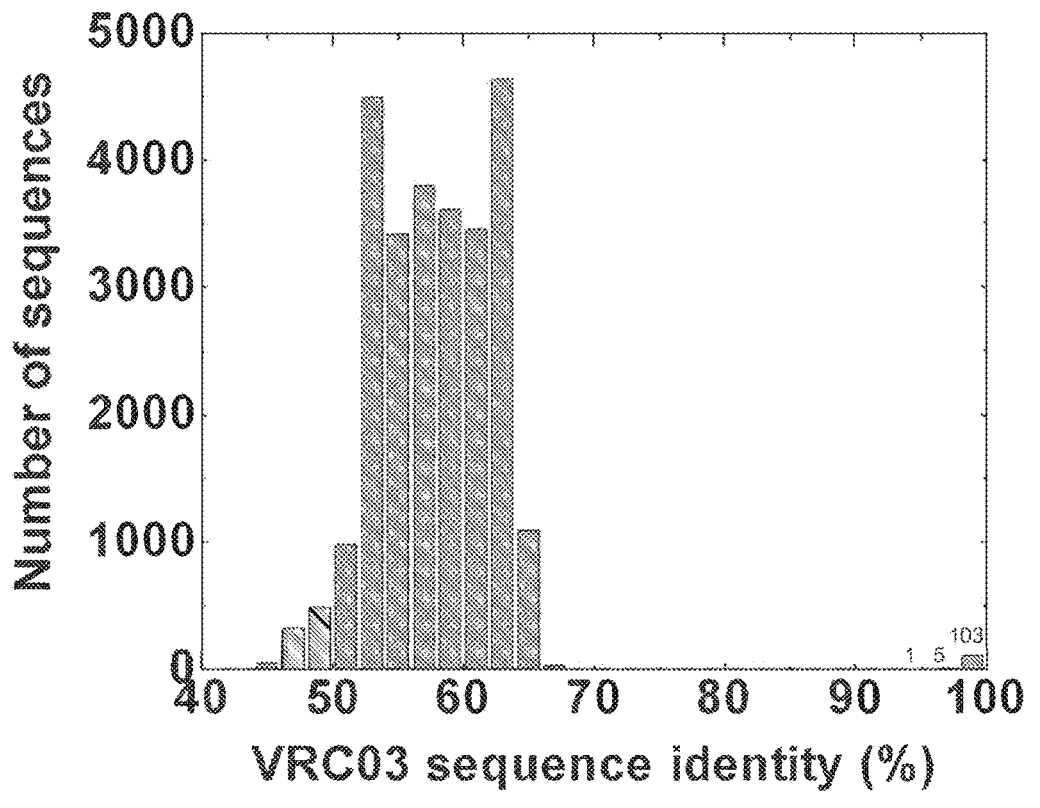

FIG. 32. The sequence identity to VRC03 H (at the nucleotide level) was calculated for all full-length sequences and plotted as a histogram. 109 sequences were found to be over 90% identical to the VRC03 H sequence, with 1 in the 92-94% bin, 5 in the 96-98% bin, and 103 in the 98-100% bin. FIG. 32 is referred to as FIG. 32 or FIG. A-8 throughout the specification and Examples.

Figure 33:
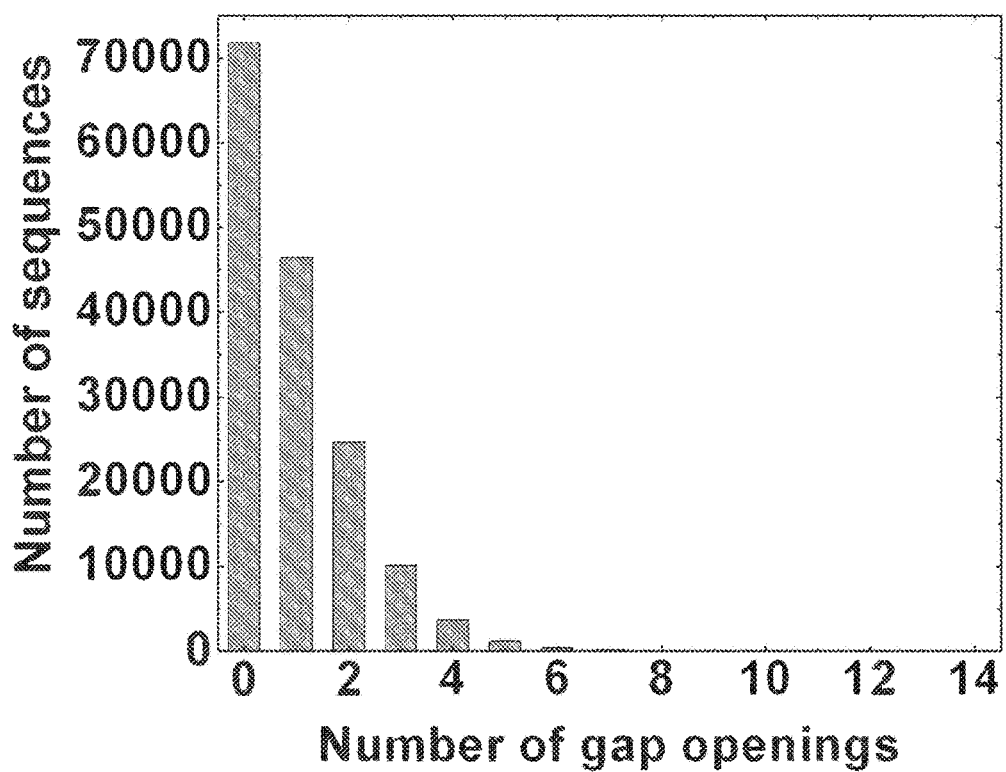

FIG. 33. After aligned to the respective germlines, the number of gap openings in the variable region was calculated and plotted as a histogram for the whole data set. 54.7% of the sequences were found to have at least one gap opening in the variable region alignment, which might be caused by 454 sequencing error or naturally occurring insertion/deletion. FIG. 33 is referred to as FIG. 33 or FIG. A-9 throughout the specification and Examples.

Figure 34:
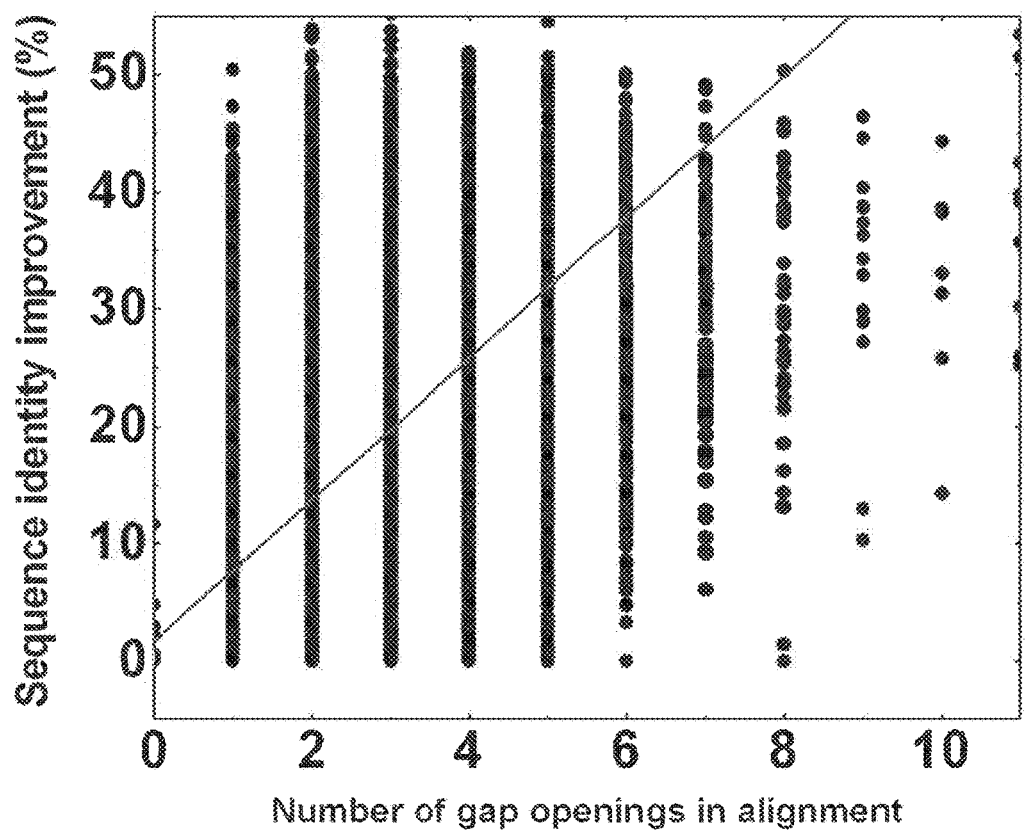

FIG. 34. The sequencing errors in the variable region were corrected based on the respective germline and the improvement of sequence identity to the germline sequence was plotted as a function of number gap openings in the variable region. The linear regression R value is 0.652 and the P-value is lower than 0.0001, suggesting that the correlation is significant. FIG. 34 is referred to as FIG. 34 or FIG. A-10 throughout the specification and Examples.

Figure 35:
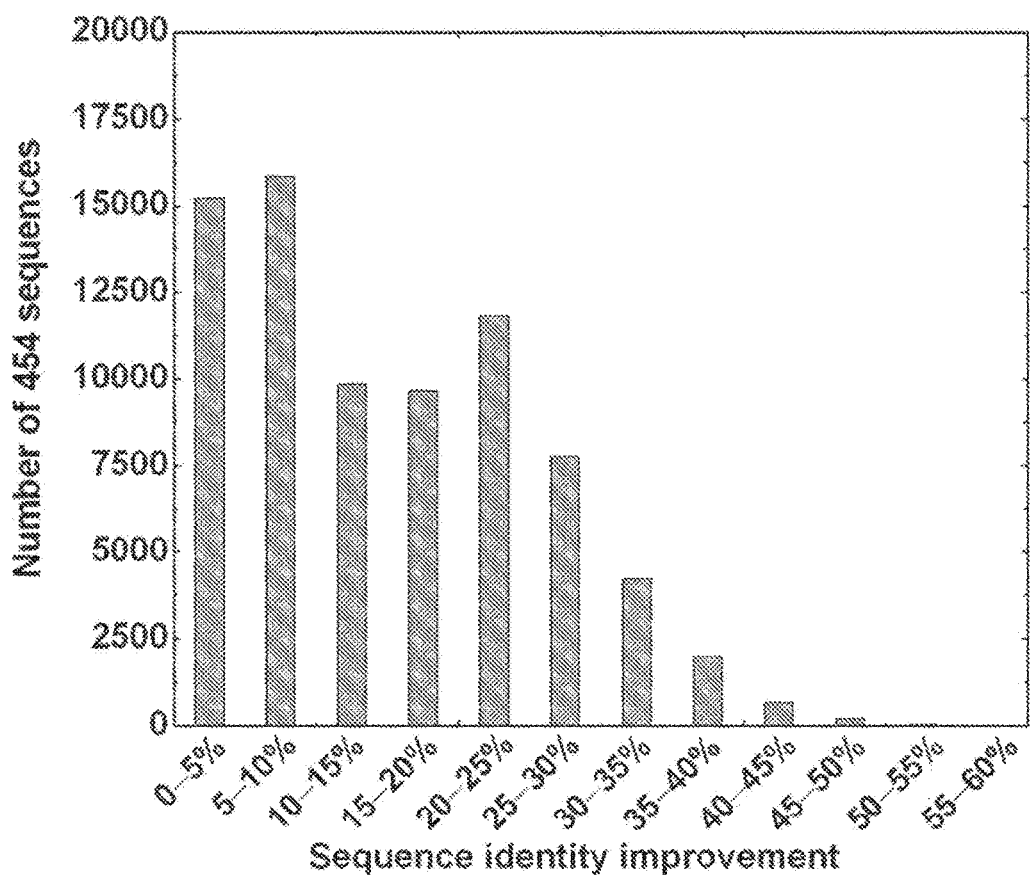

FIG. 35. The improvement of sequence identity to the respective germline was calculated for the whole data set and plotted as a histogram. The average improvement is 15.1%. FIG. 35 is referred to as FIG. 35 or FIG. A-11 throughout the specification and Examples.

Figure 36:
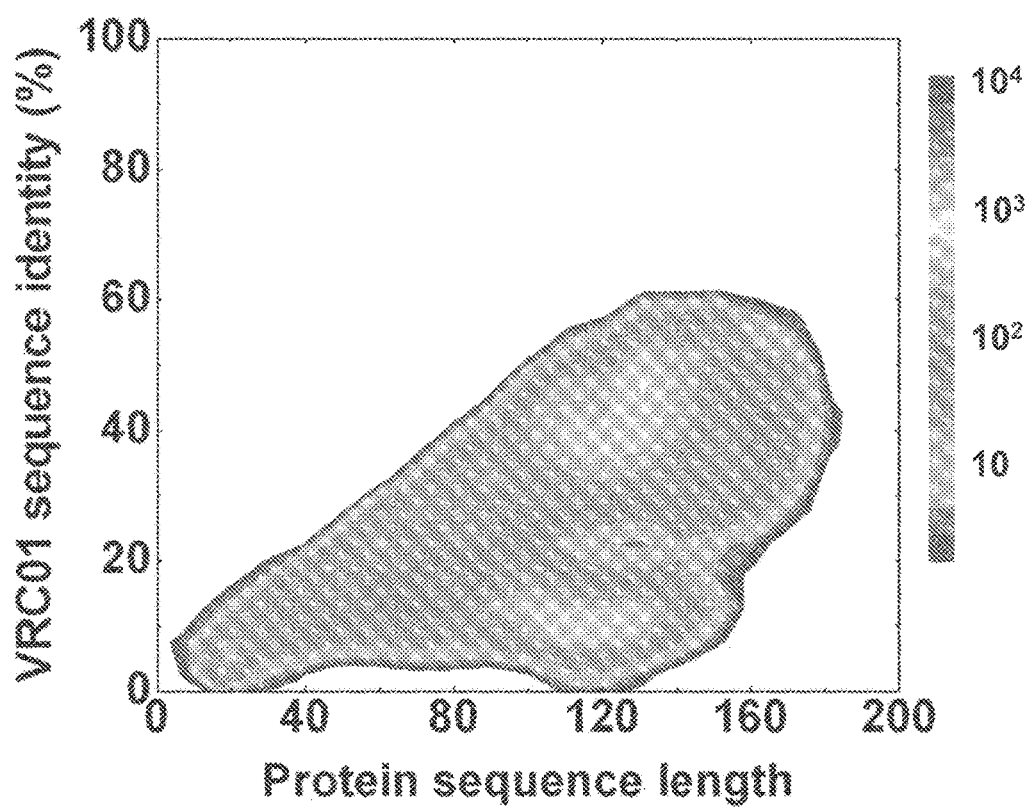

FIG. 36. The protein sequences translated from corrected nucleotide sequences were plotted as a function of sequence length and sequence identity to VRC01 H. No VRC01-like sequences were identified from this analysis. FIG. 36 is referred to as FIG. 36 or FIG. A-12 throughout the specification and Examples.

Figure 37:
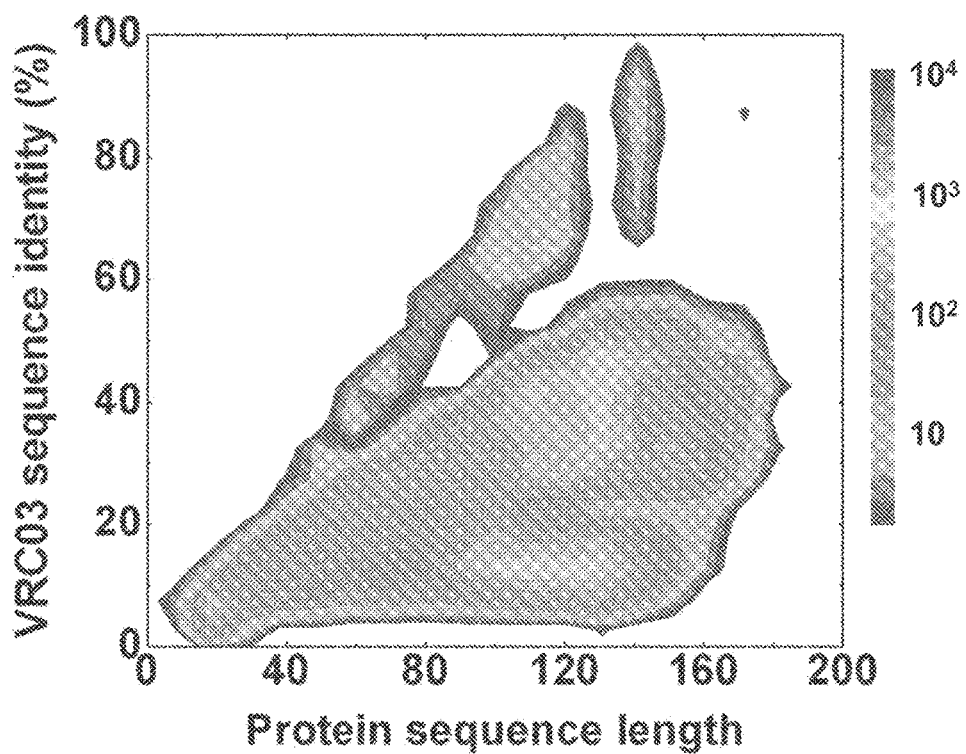

FIG. 37. The protein sequences translated from corrected nucleotide sequences were plotted as a function of sequence length and sequence identity to VRC03 H. A set of sequences that extend from the main population to the 100% identity to VRC03 H was identified from the analysis. Within this set, 109 sequences were full-length and identical to those identified by nucleotide-level divergence and sequence identity analyses. FIG. 37 is referred to as FIG. 37 or FIG. A-13 throughout the specification and Examples.

Figure 38:
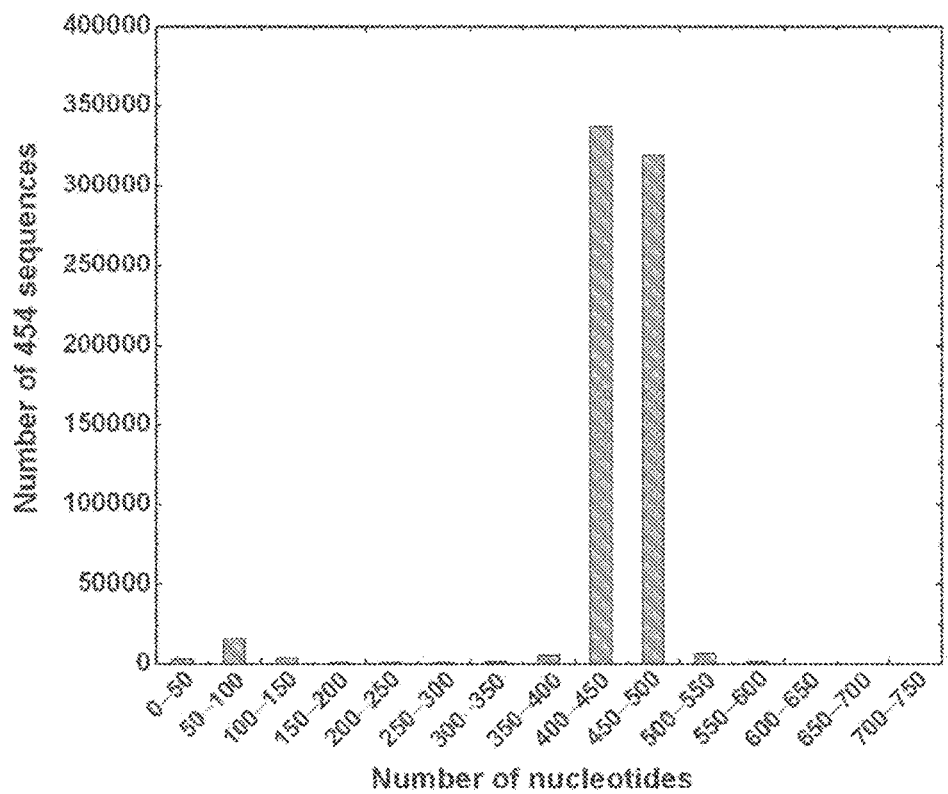

FIG. 38. There are 697079 reads in the data set. 669247 (or 96.0%) reads are longer than 350 nucleotides. The average read length is 437.5. FIG. 38 is referred to as FIG. 38 or FIG. A-14 throughout the specification and Examples.

Figure 39:
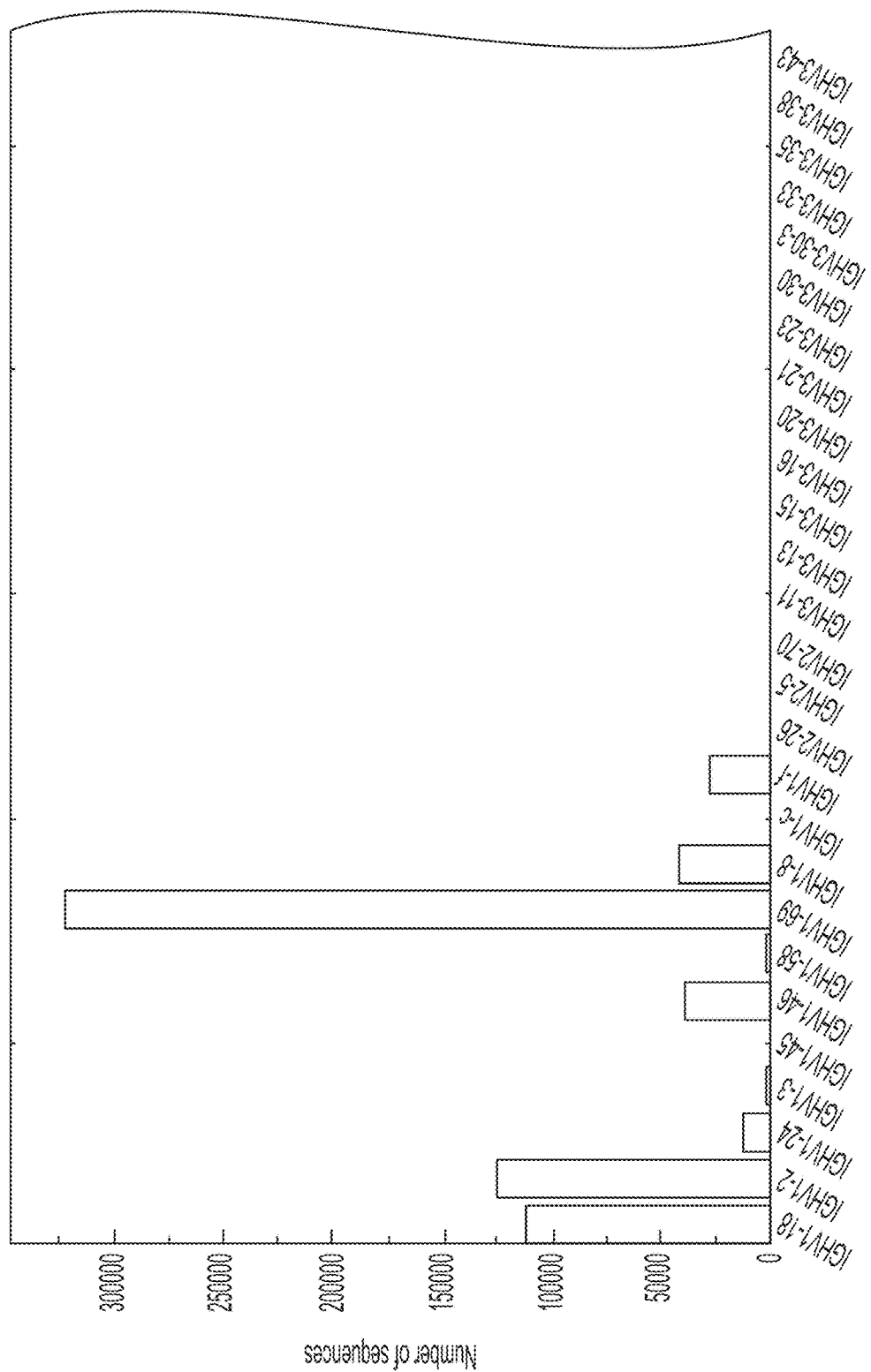
Figure 39:
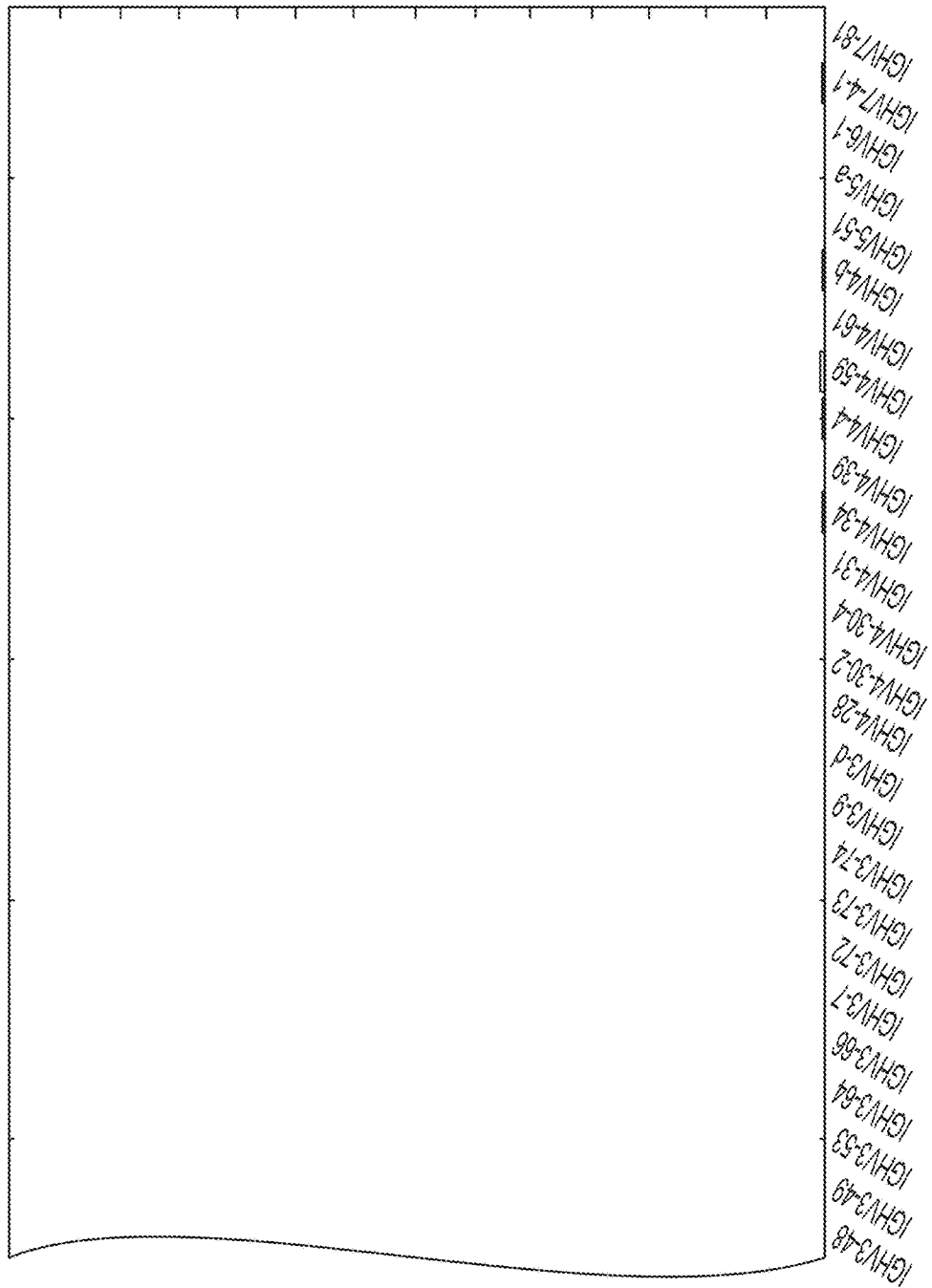

FIG. 39. E-value from IGBlast was used to determine whether the assignment is reliable. A cutoff of 1.0E-3 was used in current analysis 680047 reads remained after removing the sequences with an E-value lower than 1.0E-3. 124109 sequences were assigned to IGHV1-2 family with four possible alleles, IGHV1-2*01, IGHV1-2*02, IGHV1-2*03 and IGHV1-2*04. FIG. 39 is referred to as FIG. 39 or FIG. A-15 throughout the specification and Examples.

Figure 40:
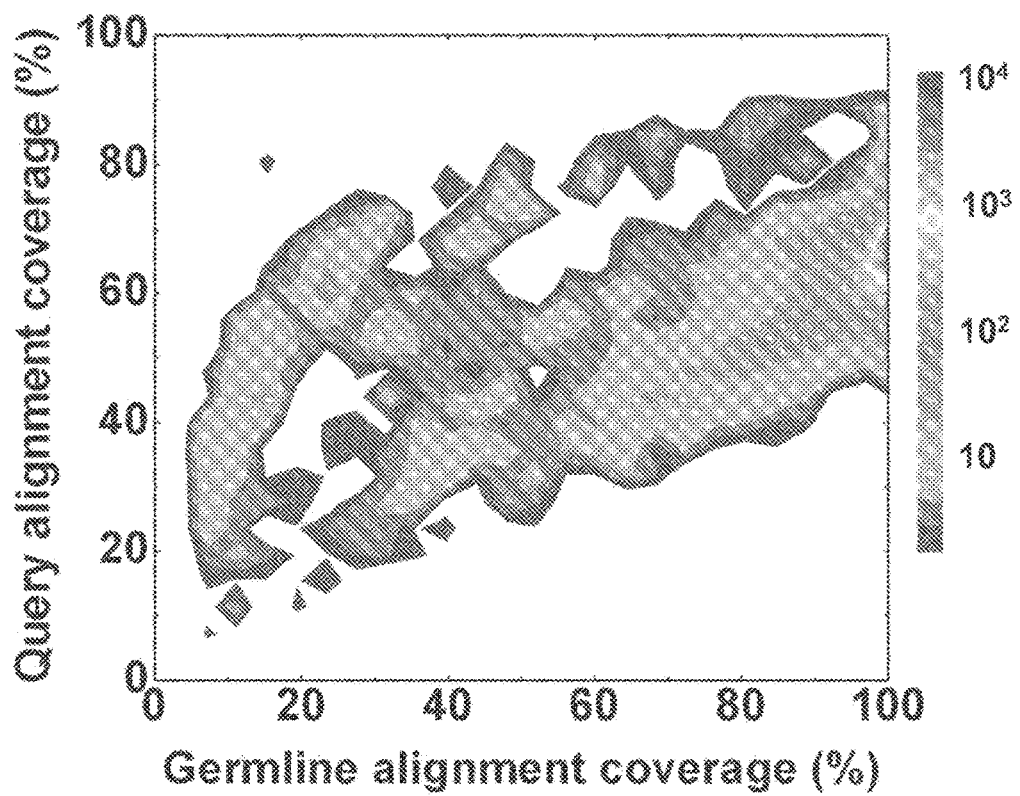

FIG. 40. A metric—alignment coverage—was defined to characterize the effect of sequence length variation on the alignment of a 454 sequence to a germline gene.

$$Coverage_{Germline} = \frac{\text{Length(aligned region)}}{\text{Length(Germline gene)}}$$

$$Coverage_{Query\,sequence\,from\,454} = \frac{\text{Length(aligned region)}}{\text{Length(Query sequence)}}$$

When aligned to their respective germline genes, 642754 sequences (or 94.5%) could cover 95% of the germline sequence and thus were considered to contain the "complete" variable (V) gene. FIG. 40 is referred to as FIG. 40 or FIG. A-16 throughout the specification and Examples.

Figure 41:
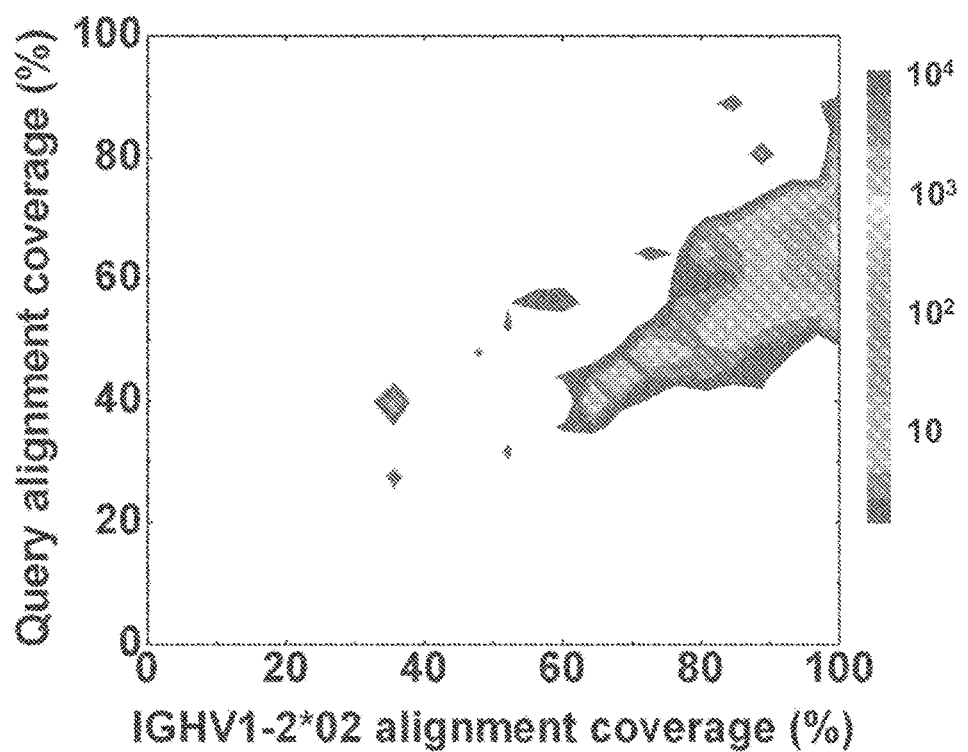

FIG. 41. Alignment coverage was also used to characterize the sequences that were assigned to IGHV1-2*02 family. Note that alleles IGHV1-2*01, IGHV1-2*03 and IGHV1-2*04 were also considered in the calculation due to their high similarities to IGHV1-2*02. When aligned to the germline genes, 116563 sequences (or 93.9%) of IGHV1-2*02 family could cover 95% of the germline sequence and thus were considered to contain the "complete" IGHV1-2*02 gene. FIG. FIG. 41 is referred to as FIG. 41 or FIG. A-17 throughout the specification and Examples.

Figure 42:
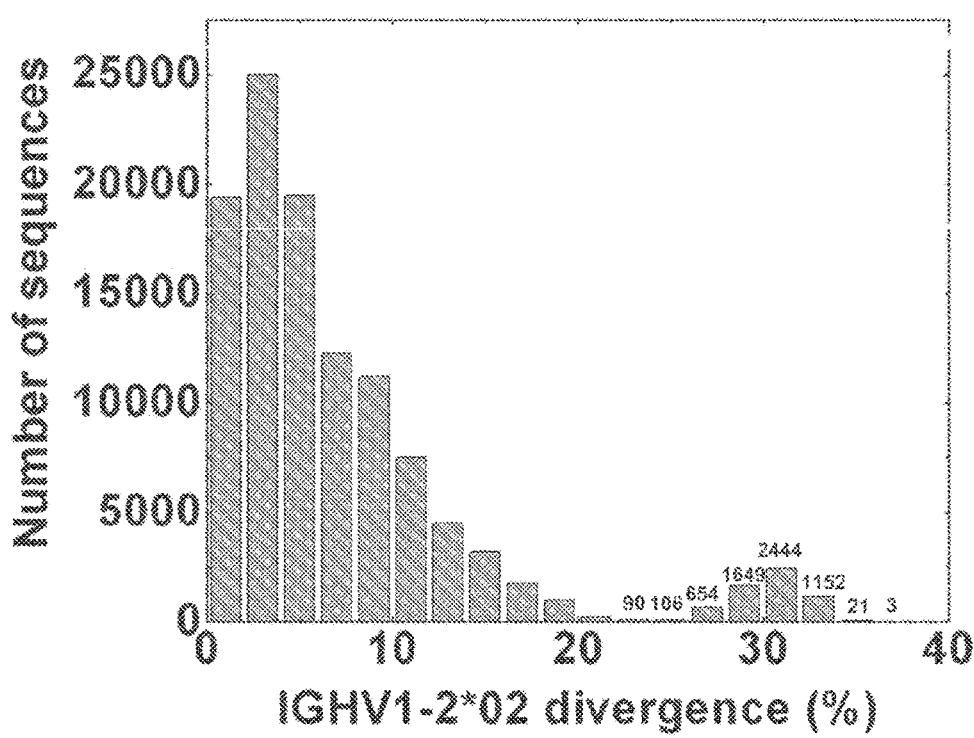

FIG. 42. The full-length sequences were extracted from the data set using VRC01 H sequence as a template, resulting in a total of 615876 sequences with 111692 sequences assigned to IGHV1-2*02 family (IGHV1-2*01, IGHV1-2*03 and IGHV1-2*04 alleles included). The divergence of full-length IGHV1-2*02 sequences was calculated and plotted as a histogram. A population of highly divergent sequences were found to be centered at a divergence value of 31%. The number of sequences in each bin is labeled on the histogram. FIG. 42 is referred to as FIG. 42 or FIG. A-18 throughout the specification and Examples.

Figure 43:
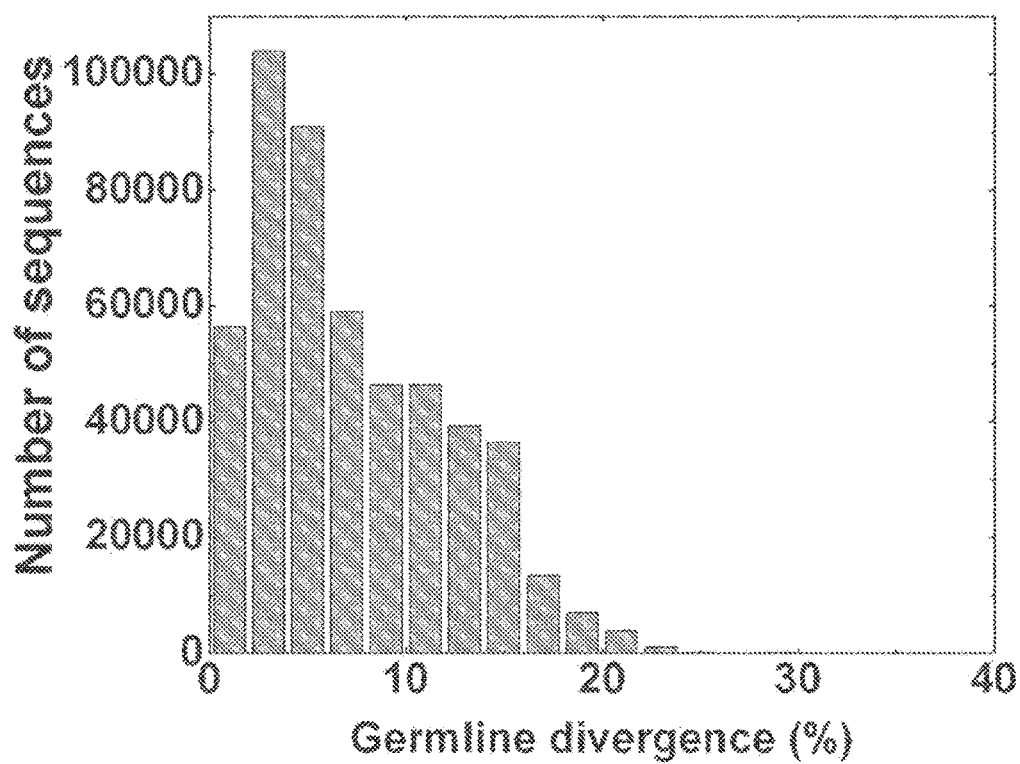

FIG. 43. The divergence of full-length sequences that were assigned to non-IGHV1-2*02 germlines was calculated and plotted as a histogram. A small group of highly divergent sequences were found to be centered at a divergence value of 29%, with 48 in the 26-28% bin, 150 in 28-30%, and rest beyond 30%. 18 sequences were found to be more divergent than 30%, with 12 in the 30-32% bin, 4 in the 32-34% bin, and 2 in the 34-36%. FIG. 43 is referred to as FIG. 43 is referred to as FIG. 43 or FIG. A-19 throughout the specification and Examples.

Figure 44:
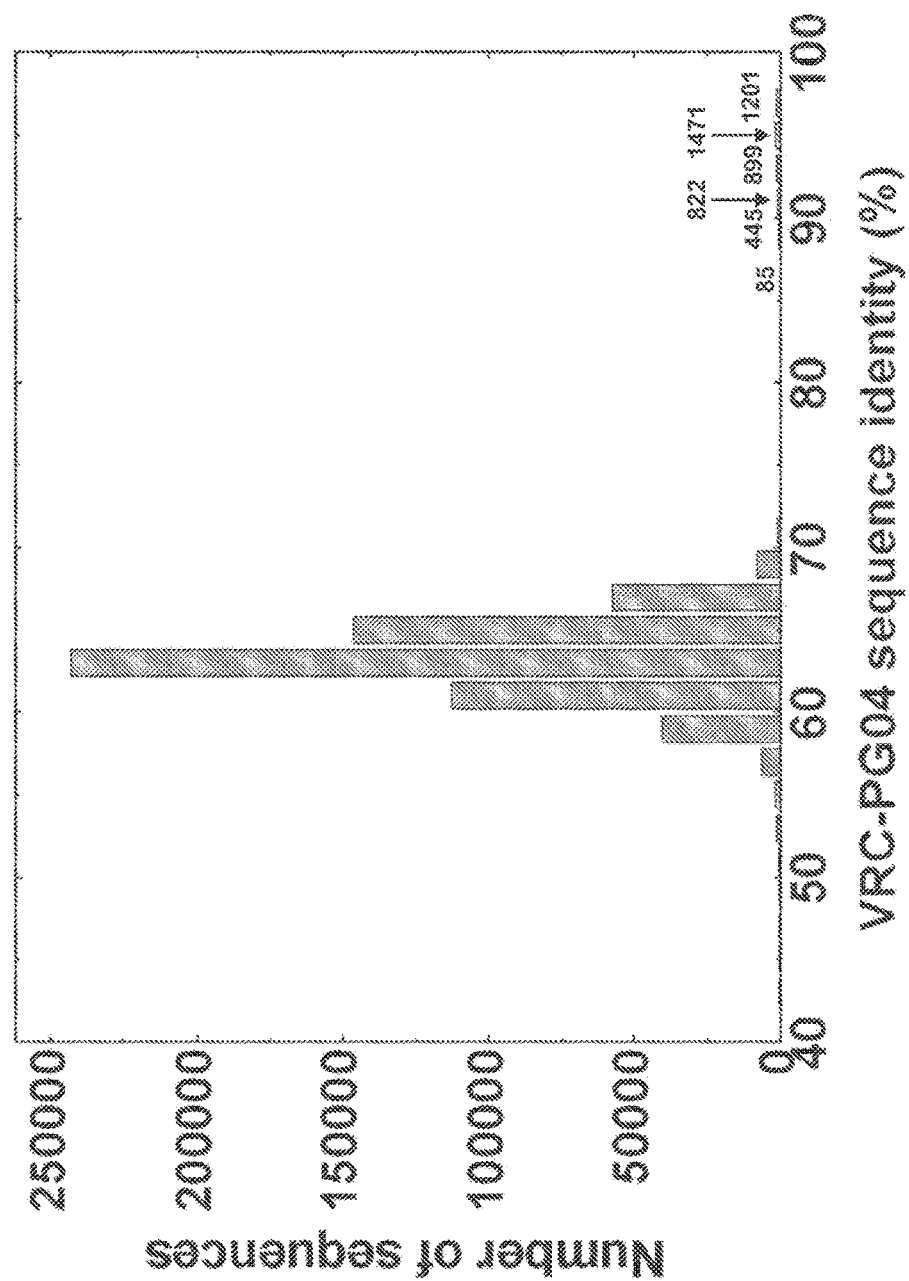

FIG. 44. The sequence identity to VRC-PG04 H (at the nucleotide level) was calculated for all full-length sequences and plotted as a histogram. A population of sequences were found to have a identity of 85 to 97% to VRC-PG04 H. The number of sequences in each bin is labeled on the histogram. FIG. 44 is referred to as FIG. 44 or FIG. A-20 throughout the specification and Examples.

Figure 45:
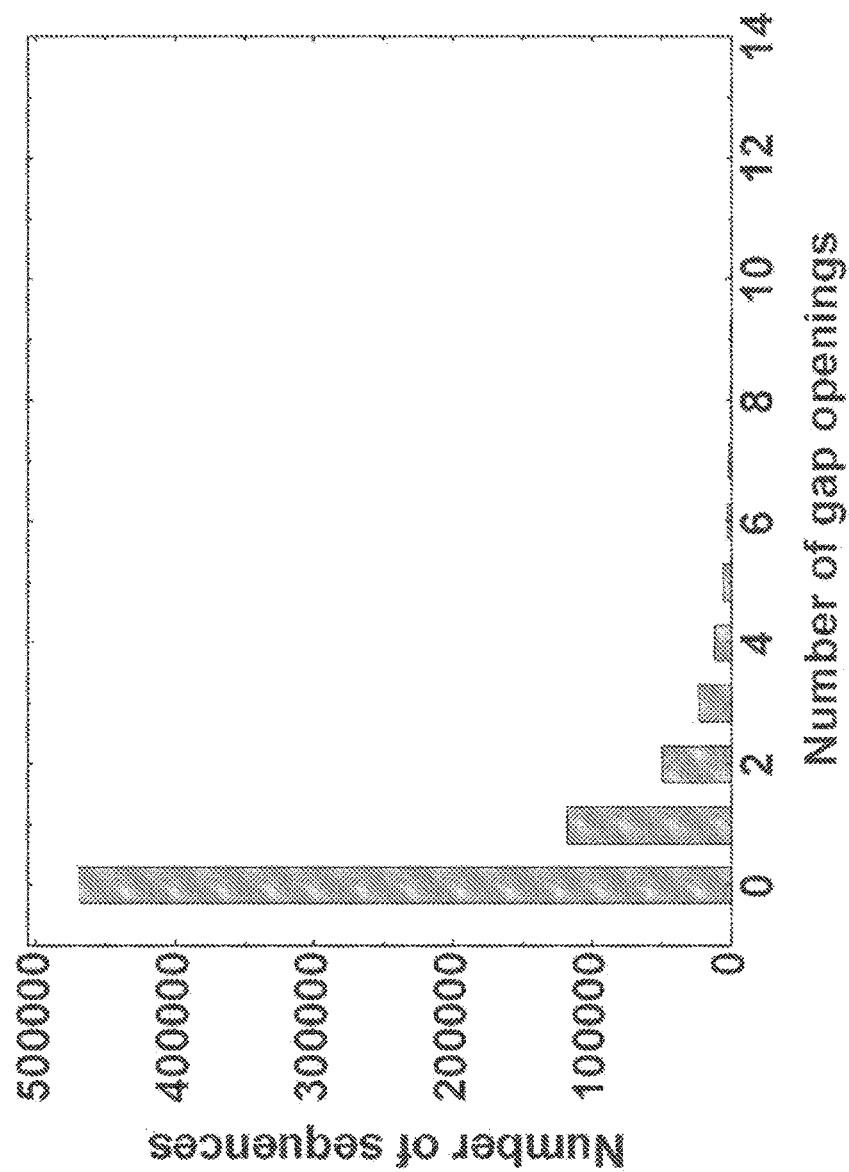

FIG. 45. After aligned to the respective germlines the number of gap openings in the variable region was calculated and plotted as a histogram for the whole data set 31.2% of the sequences were found to have at least one gap opening in the variable region alignment, which might be caused by 454 sequencing error or naturally occurring insertion/deletion. FIG. 45 is referred to as FIG. 45 or FIG. A-21 throughout the specification and Examples.

Figure 46:
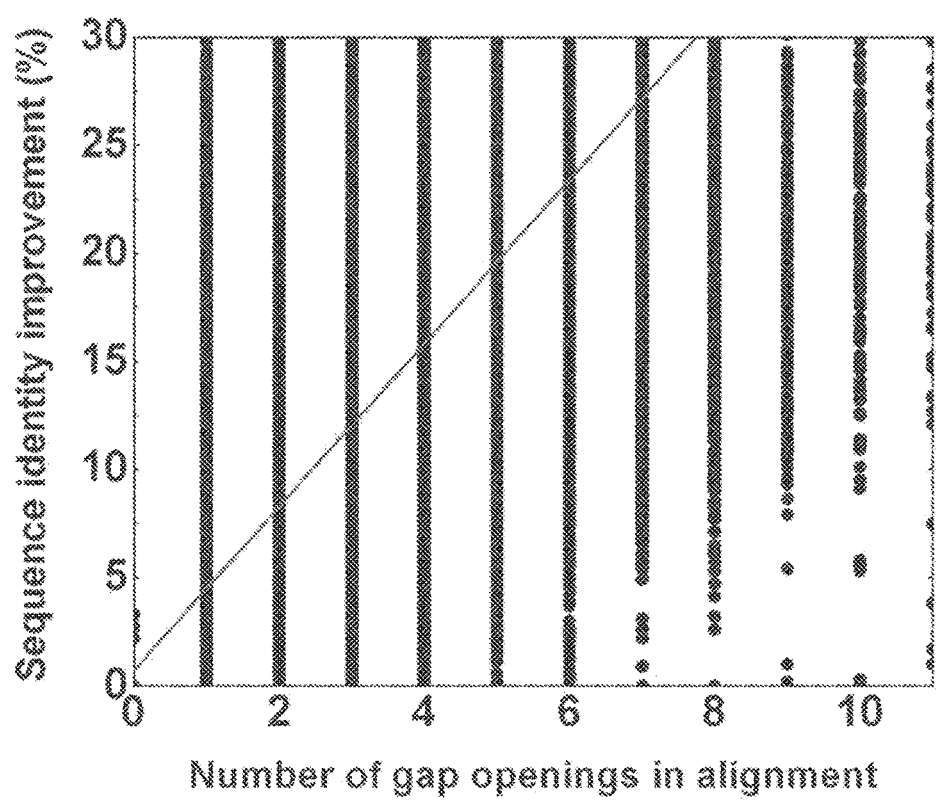

FIG. 46. The sequencing errors in the variable region were corrected based on the respective germline and the improvement of sequence identity to the germline sequence was plotted as a function of number gap openings in the variable region. The linear regression R value is 0.717 and the P-value is lower than 0.0001, suggesting that the correlation is significant. FIG. 46 is referred to as FIG. 46 or FIG. A-22 throughout the specification and Examples.

Figure 47:
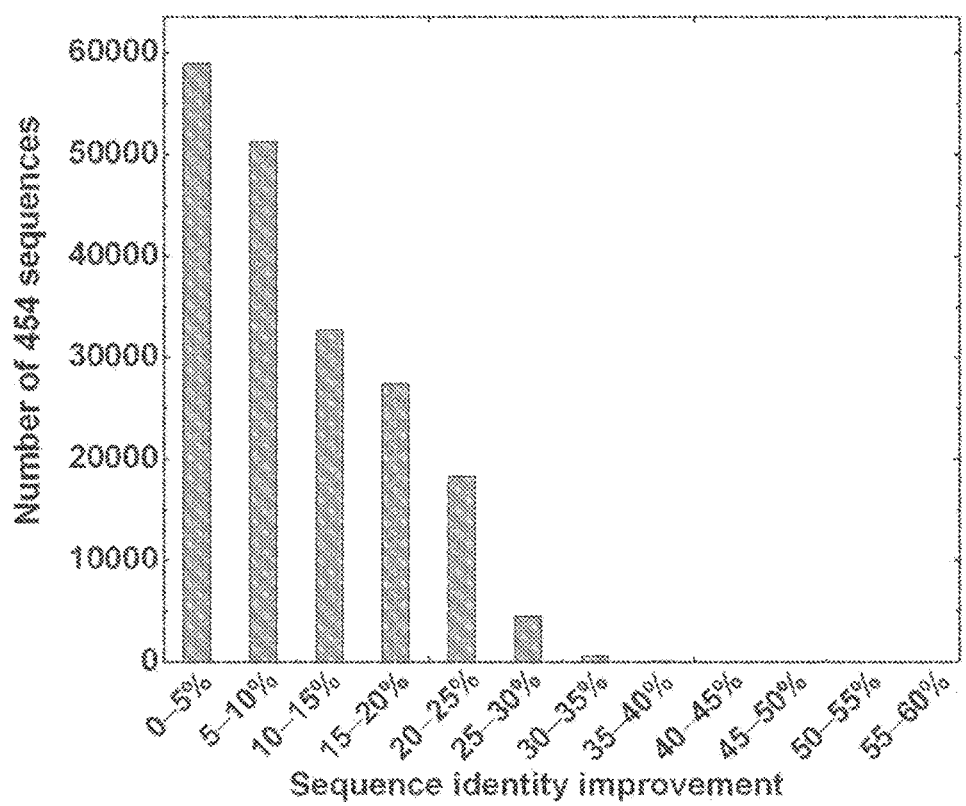

FIG. 47. The improvement of sequence identity to the respective germline was calculated for the whole data set and plotted as a histogram. The average improvement is 10.2%. FIG. 47 is referred to as FIG. 47 or FIG. A-23 throughout the specification and Examples.

Figure 48:
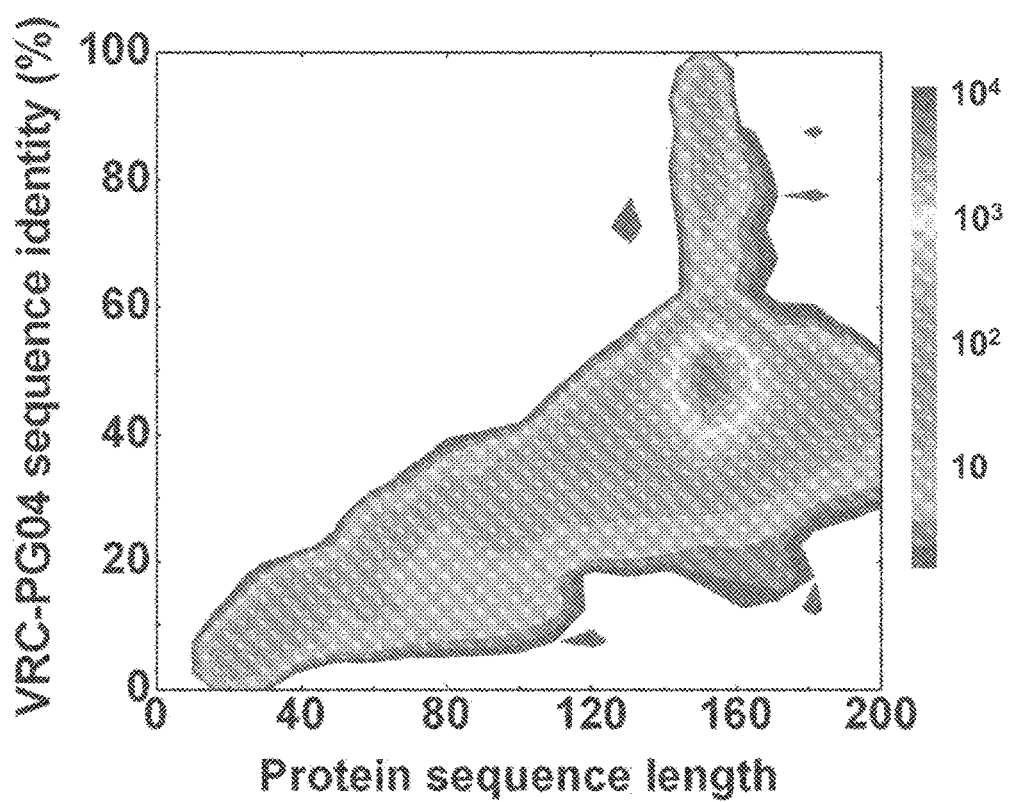

FIG. 48. The protein sequences translated from corrected nucleotide sequences were plotted as a function of sequence length and sequence identity to VRC03 H. A set of sequences that extend from the main population to the 100% identity to VRC-PG04 H was identified from the analysis. A subset of these sequences correspond to those identified by nucleotide-level divergence and sequence identity analyses. FIG. 48 is referred to as FIG. 48 or FIG. A-24 throughout the specification and Examples.

Figure 49:
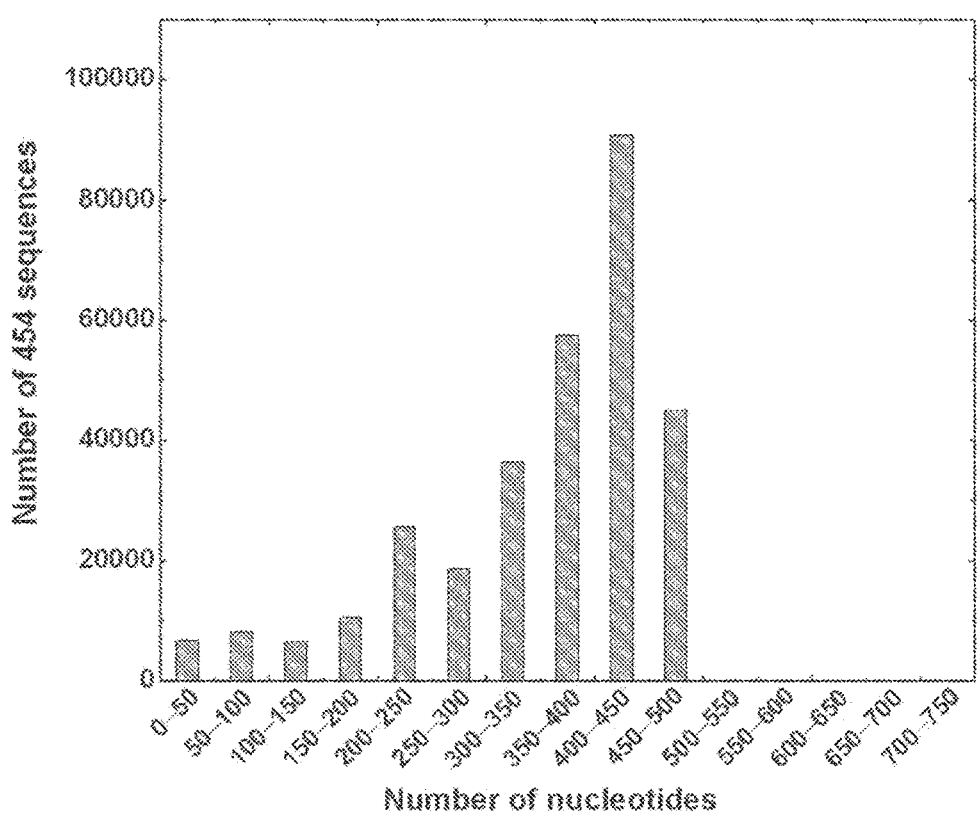

FIG. 49. There are 305475 reads in the data set. 230126 (or 75.3%) reads are longer than 300 nucleotides. The average read length is 352.0. FIG. 49 is referred to as FIG. 49 or FIG. A-25 throughout the specification and Examples.

Figure 50:
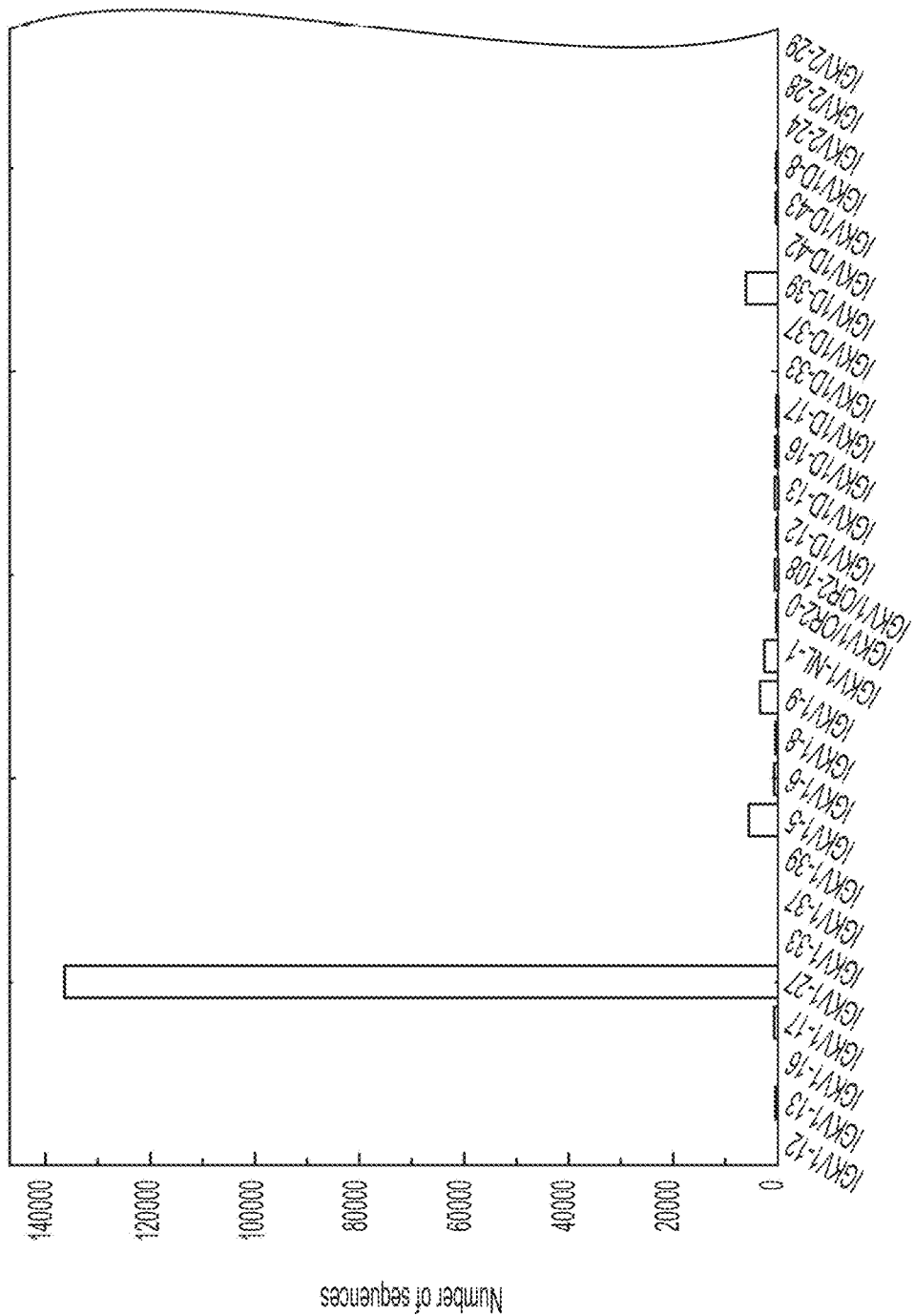
Figure 50:
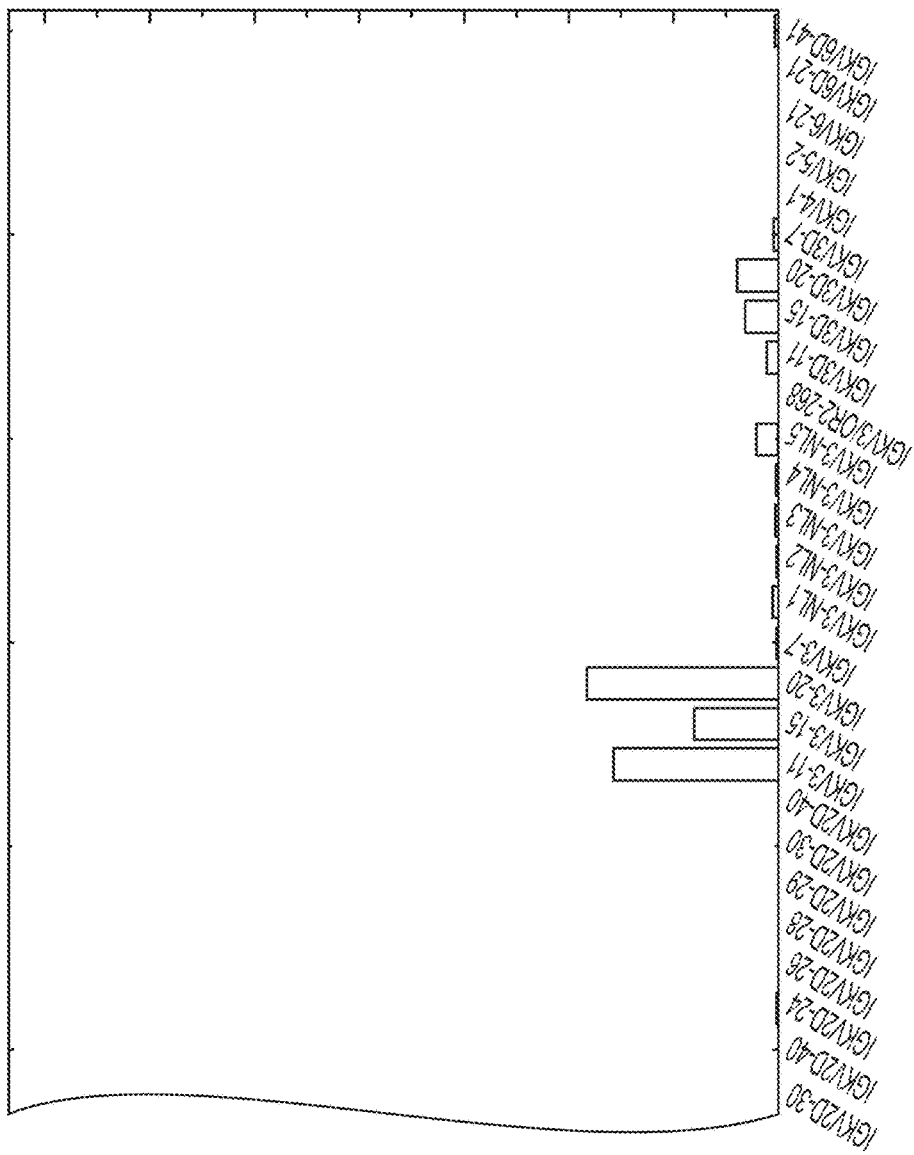

FIG. 50. E-value from IGBlast was used to determine whether the assignment is reliable. A cutoff of 1.0E-3 was used in current analysis. 260615 reads remained after removing the sequences with an E-value lower than 1.0E-3. Since VRC01 L and VRC03 L will be assigned to IGKV3-NL1*01 and IGKV3-NL5*01 by IGBlast, we included these two as possible germlines of VRC01 L and VRC03 L. 70994 sequences were assigned to IGKV3-11*01, IGKV3-20*01, IGKV3-NL1*01, and IGKV3-NL5*01. FIG. 50 is referred to as FIG. 50 or FIG. A-26 throughout the specification and Examples.

Figure 51:
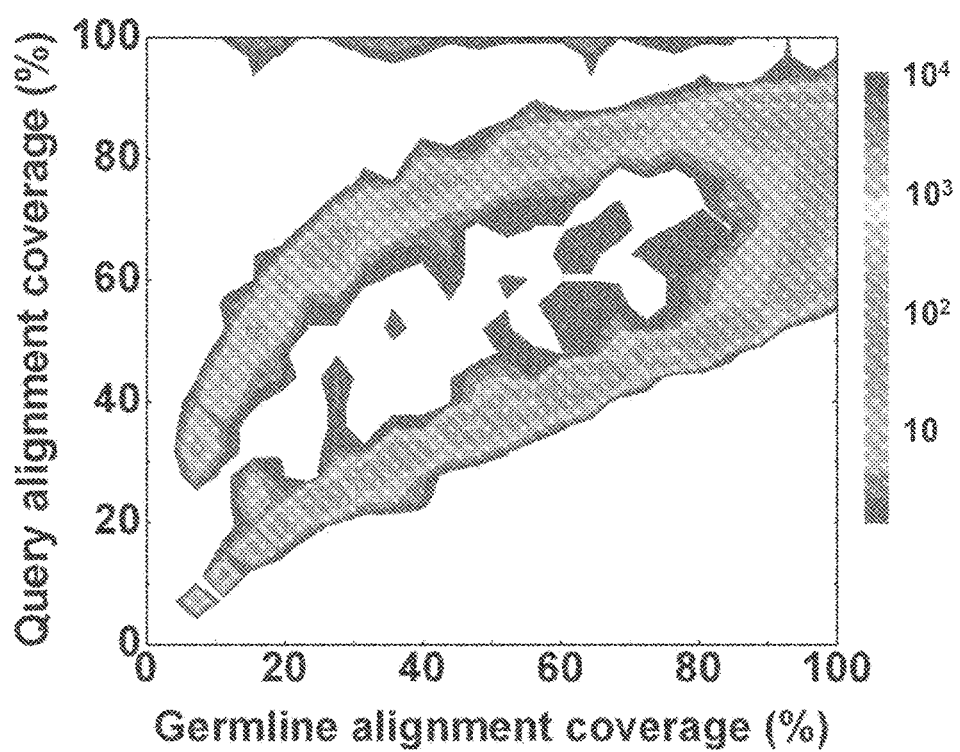

FIG. 51. A metric—alignment coverage—was defined to characterize the effect of sequence length variation on the alignment of a 454 sequence to a germline gene.

$$Coverage_{Germline} = \frac{\text{Length(aligned region)}}{\text{Length(Germline gene)}}$$

$$Coverage_{Query\,sequence\,from\,454} = \frac{\text{Length(aligned region)}}{\text{Length(Query sequence)}}$$

When aligned to their respective germline genes, 103066 sequences (or 39.5%) could cover 95% of the germline sequence and thus were considered to contain the "complete" variable (V) gene. FIG. 51 is referred to as FIG. 51 or FIG. A-27 throughout the specification and Examples.

Figure 52:
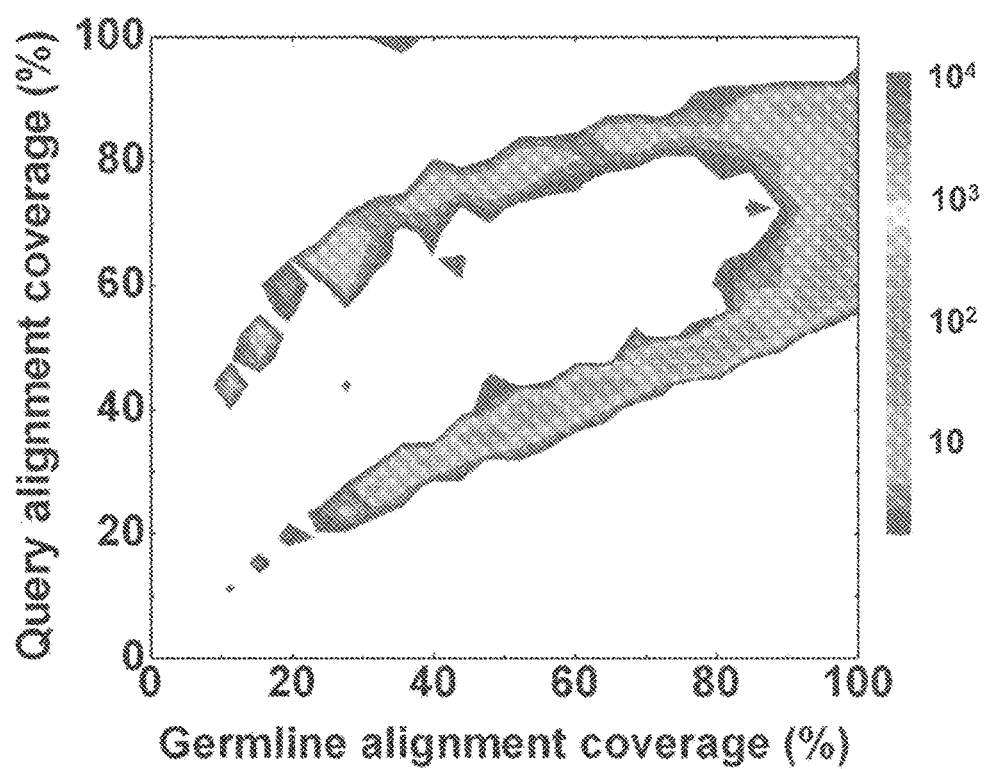

FIG. 52. Alignment coverage was also used to characterize the sequences that were assigned to the 4 possible germline families, IGKV3-11*01, IGKV3-20*01, IGKV3-NL1*01, and IGKV3-NL5*01. When aligned to the germline genes, 32878 sequences (or 46.3%) of these 4 families could cover 95% of the germline sequence and thus were considered to contain the "complete" V gene. FIG. 52 is referred to as FIG. 52 or FIG. A-28 throughout the specification and Examples.

Figure 53:
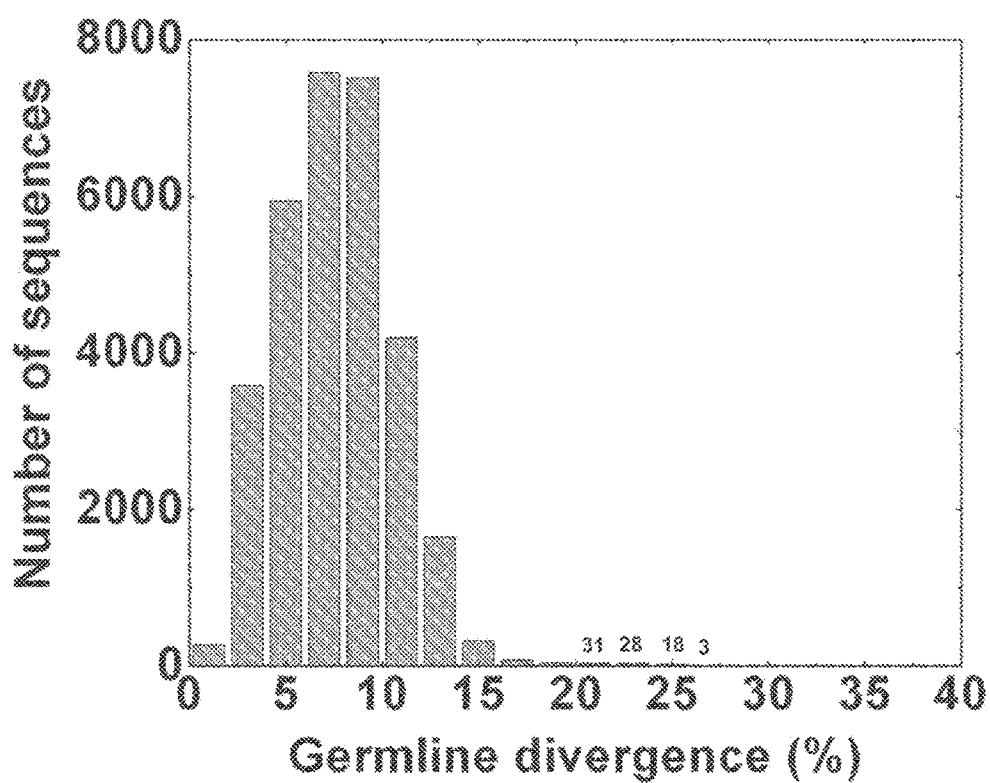

FIG. 53. The full-length sequences were extracted from the data set using VRC01 H sequence as a template, resulting in a total of 87658 sequences with 31194 sequences assigned to the 4 possible germline families, IGKV3-11*01, IGKV3-20*01, IGKV3-NL1*01 and IGKV3-NL5*01. The divergence of full-length sequences from these 4 germline families was calculated and plotted as a histogram. A total of 80 sequences were found to have a divergence of 20% or higher, with 31 in the 20-22% bin, 28 in the 22-24% bin, 18 in the 24-26% bin, and 3 in the 26-28% bin, as labeled on the histogram. FIG. 53 is referred to as FIG. 53 or FIG. A-29 throughout the specification and Examples.

Figure 54:
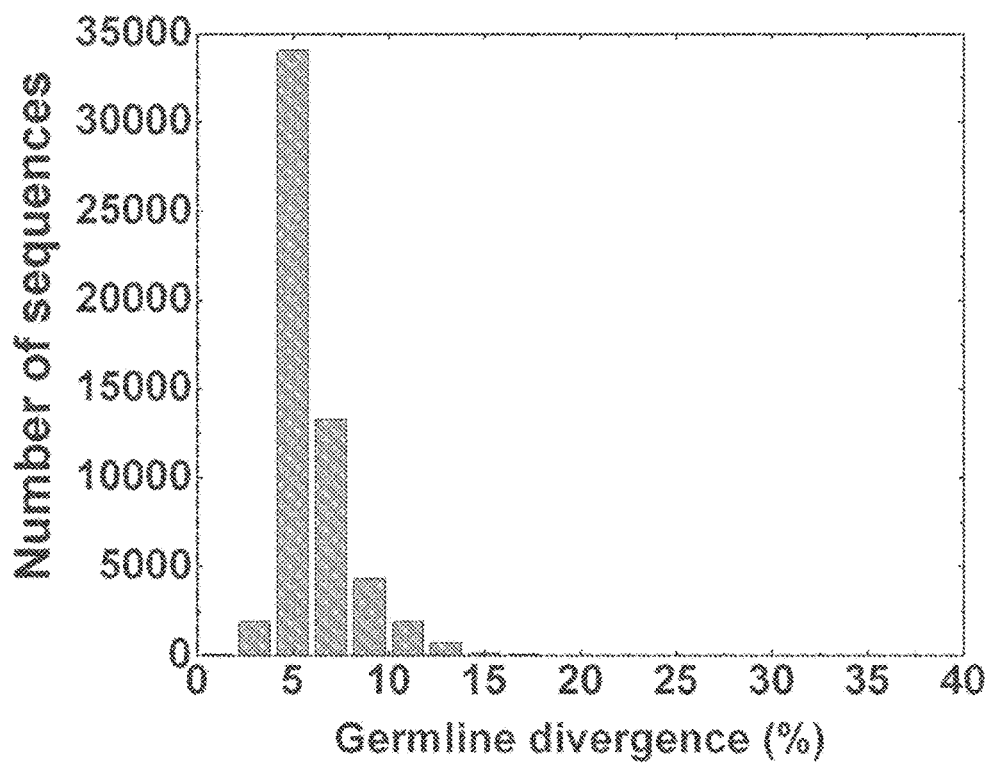

FIG. 54. The divergence of full-length sequences that were assigned to other germline families was calculated and plotted as a histogram. A total of 12 sequences were found to have a divergence of 20% or higher, with 7 in the 20-22% bin, 1 in the 22-24% bin, 2 in the 24-26% bin, and 2 in the 26-28% bin. FIG. 54 is referred to as FIG. 54 or FIG. A-30 throughout the specification and Examples.

Figure 55:
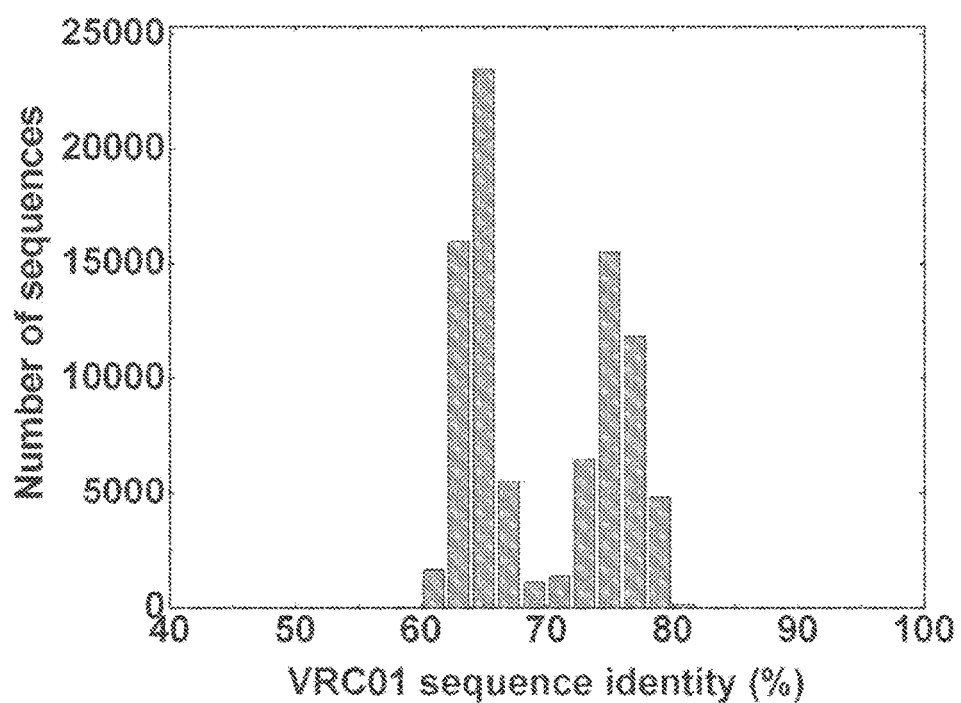

FIG. 55. The sequence identity to VRC01 L (at the nucleotide level) was calculated for all full-length sequences and plotted as a histogram. One sequence, #181371, was found to be in the 90-92% bin with a sequence identity of 92.0% to VRC01 light chain. 43 sequences were identified to have the VRC01-like deletion, including #181371. FIG. 55 is referred to as FIG. 55 or FIG. A-31 throughout the specification and Examples.

Figure 56:
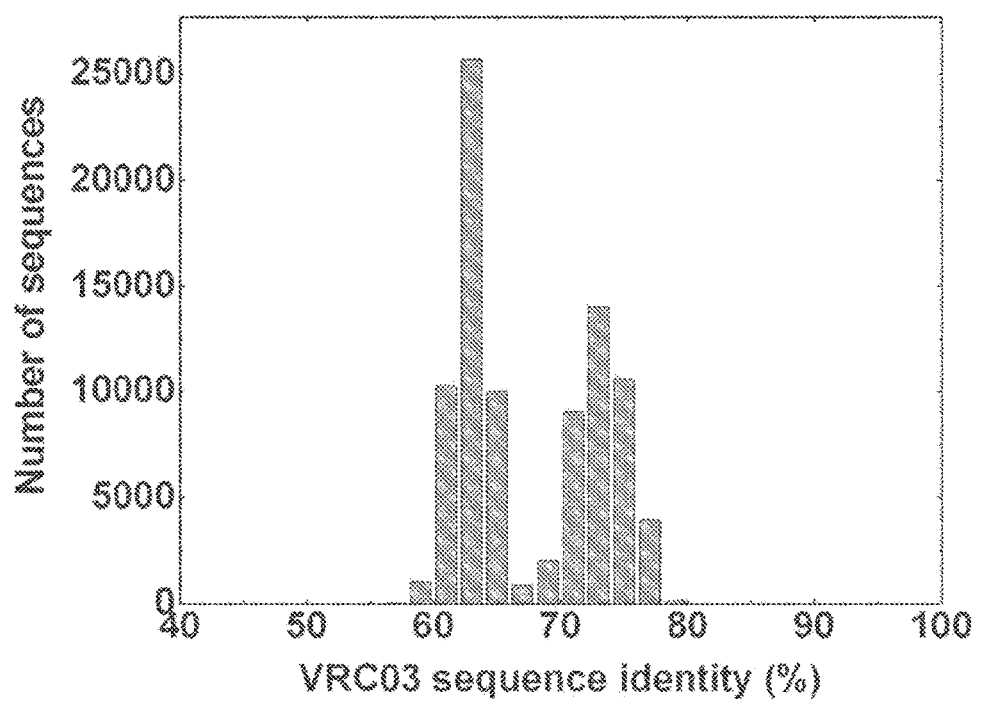

FIG. 56. The sequence identity to VRC03 L (at the nucleotide level) was calculated for all full-length sequences and plotted as a histogram. One sequence, #223454, was found to be in the 90-92% bin with a sequence identity of 90.3% to VRC03 light chain. 55 sequences were identified to have the VRC03-like deletion. FIG. 56 is referred to as FIG. 56 or FIG. A-32 throughout the specification and Examples.

Figure 57:
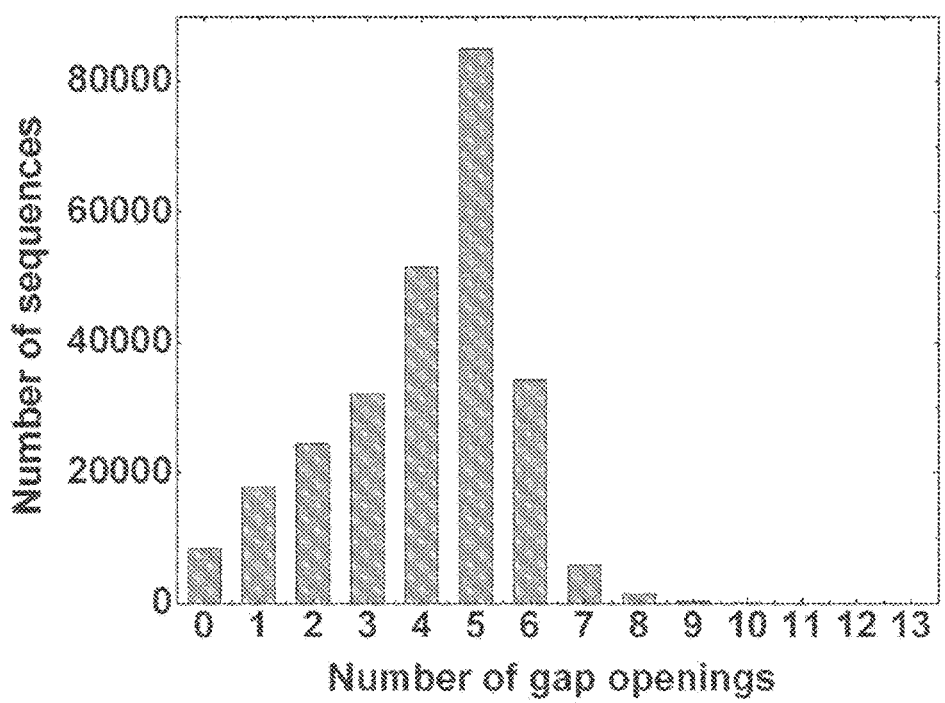

FIG. 57. After aligned to the respective germlines, the number of gap openings in the variable region was calculated and plotted as a histogram for the whole data set. 96.8% of the sequences were found to have at least one gap opening in the variable region alignment, which might be caused by 454 sequencing error or naturally occurring insertion/deletion. FIG. 57 is referred to as FIG. 57 or FIG. A-33 throughout the specification and Examples.

Figure 58:
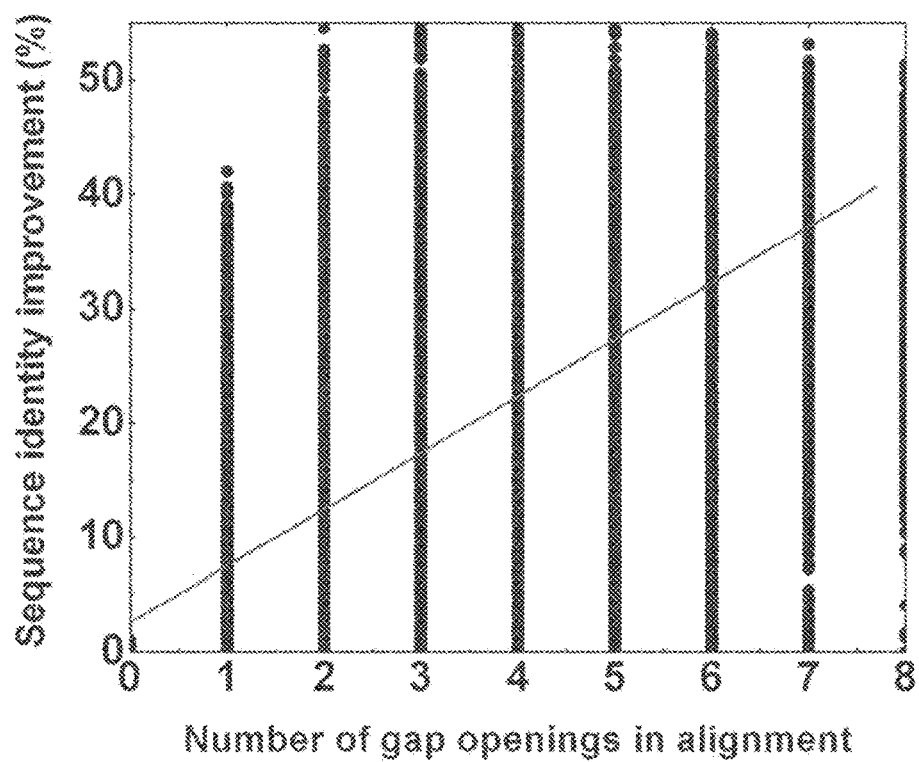

FIG. 58. The sequencing errors in the variable region were corrected based on the respective germline and the improvement of sequence identity to the germline sequence was plotted as a function of number gap openings in the variable region. The linear regression R value is 0.662 and the P-value is lower than 0.0001, suggesting that the correlation is significant. FIG. 58 is referred to as FIG. 58 or FIG. A-34 throughout the specification and Examples.

Figure 59:
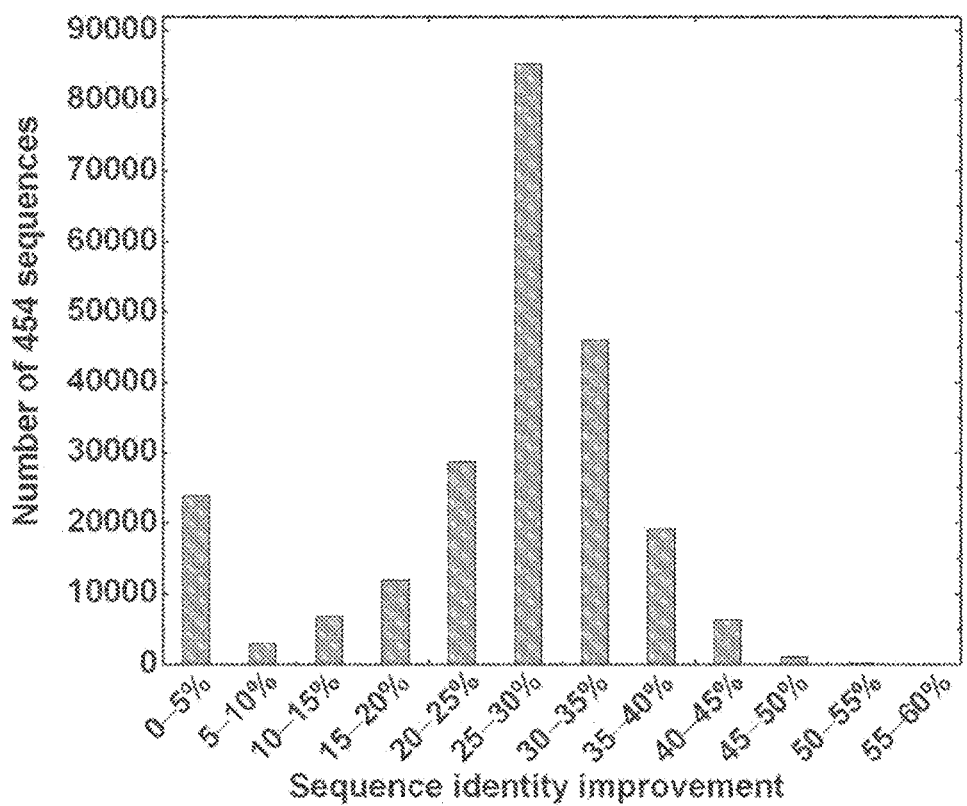

FIG. 59. The improvement of sequence identity to the respective germline was calculated for the whole data set and plotted as a histogram. The average improvement is 25.4%. FIG. 59 is referred to as FIG. 59 or FIG. A-35 throughout the specification and Examples.

Figure 60:
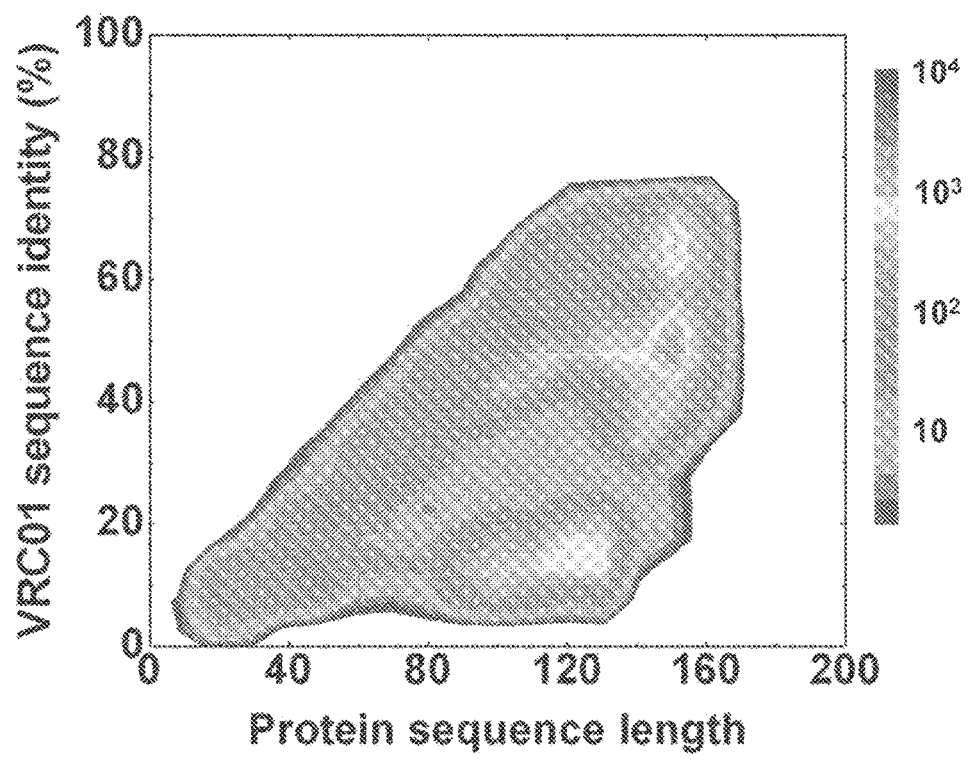

FIG. 60. The protein sequences translated from corrected nucleotide sequences were plotted as a function of sequence length and sequence identity to VRC01 L. No VRC01-like sequences were identified from this analysis except #181371. FIG. 60 is referred to as FIG. 60 or FIG. A-36 throughout the specification and Examples.

Figure 61:
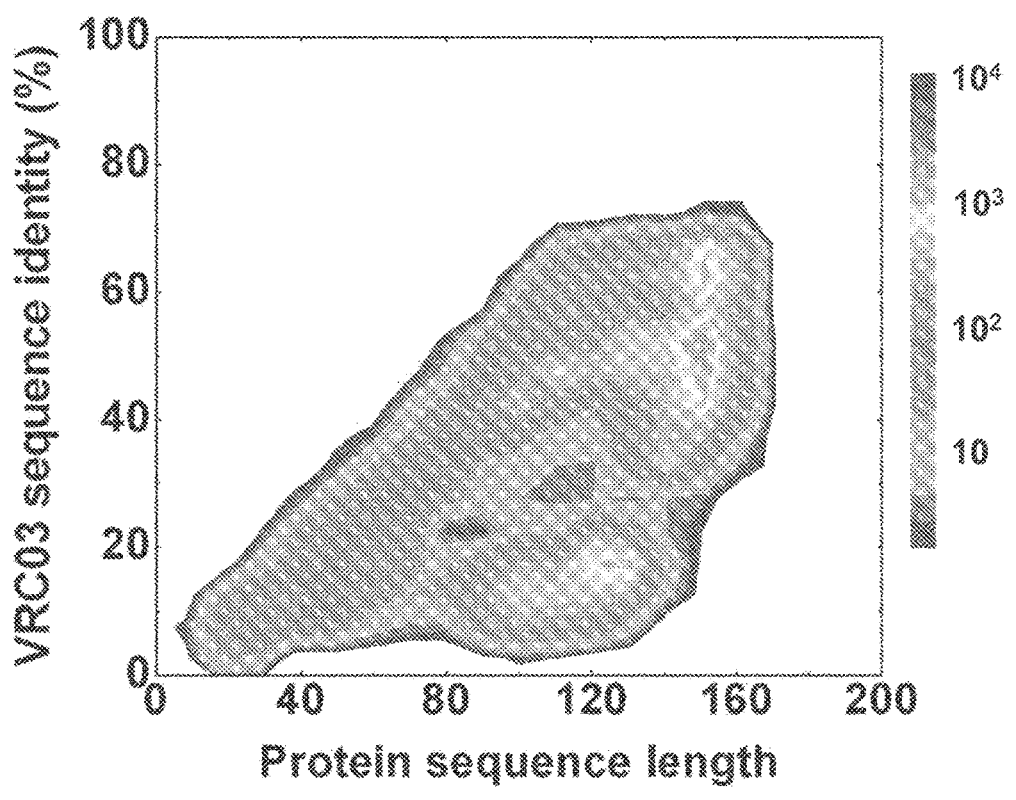

FIG. 61. The protein sequences translated from corrected nucleotide sequences were plotted as a function of sequence length and sequence identity to VRC03 L. No VRC03-like sequences were identified from this analysis except #223454. FIG. 61 is referred to as FIG. 61 or FIG. A-37 throughout the specification and Examples.

Figure 62:
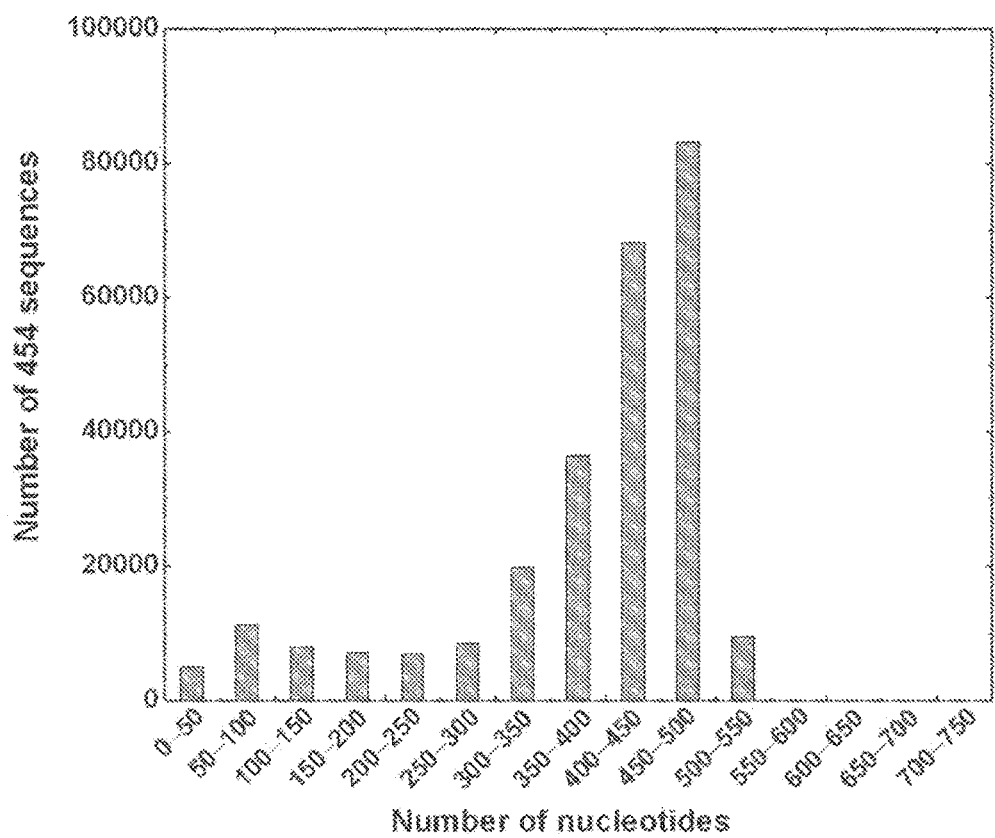

FIG. 62. There are 263764 reads in the data set. 197503 (or 74.9%) reads are longer than 350 nucleotides. The average read length is 383.1. FIG. 62 is referred to as FIG. 62 or FIG. A-38 throughout the specification and Examples.

Figure 63:
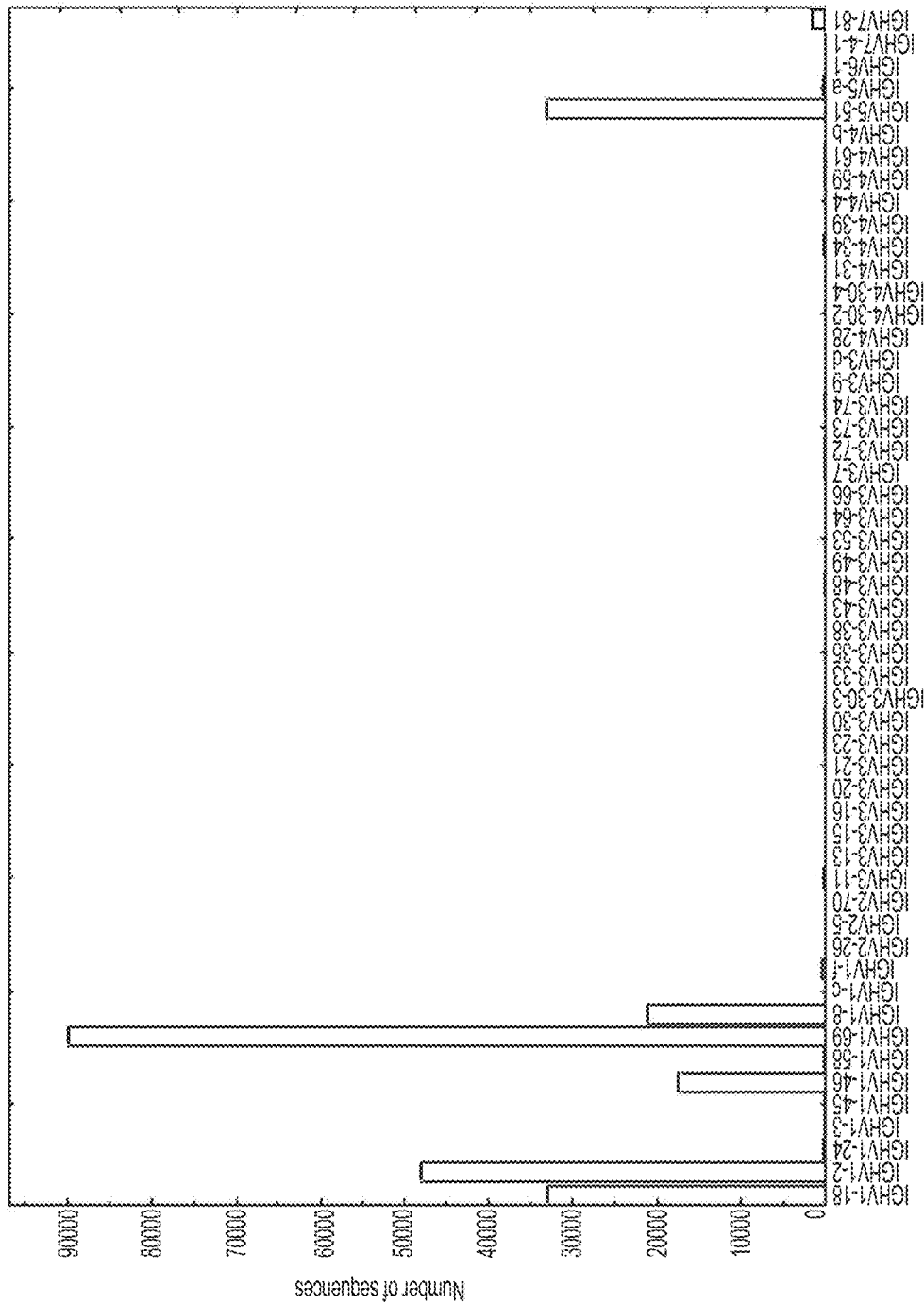

FIG. 63. E-value from IGBlast was used to determine whether the assignment is reliable. A cutoff of 1.0E-3 was used in current analysis. 246261 reads remained after removing the sequences with an E-value lower than 1.0E-3. 48061 sequences were assigned to IGHV1-2 family with four possible alleles, IGHV1-2*01, IGHV1-2*02, IGHV1-2*03 and IGHV1-2*04. FIG. 63 is referred to as FIG. 63 or FIG. A-39 throughout the specification and Examples.

Figure 64:
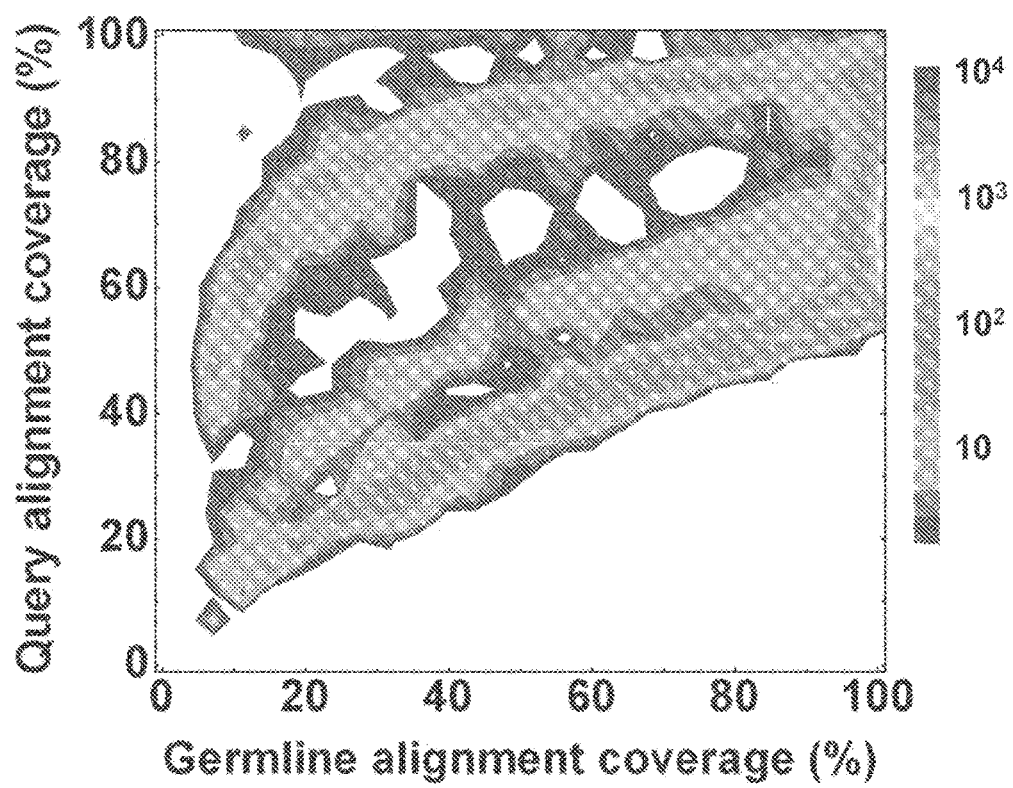

FIG. 64. A metric—alignment coverage—was defined to characterize the effect of sequence length variation on the alignment of a 454 sequence to a germline gene.

$$Coverage_{Germline} = \frac{\text{Length(aligned region)}}{\text{Length(Germline gene)}}$$

$$Coverage_{Query\ sequence\ from\ 454} = \frac{\text{Length(aligned region)}}{\text{Length(Query sequence)}}$$

When aligned to their respective germline genes, 131457 sequences (or 53.4%) could cover 95% of the germline sequence and thus were considered to contain the "complete" variable (V) gene. FIG. 64 is referred to as FIG. 64 or FIG. A-40 throughout the specification and Examples.

Figure 65:
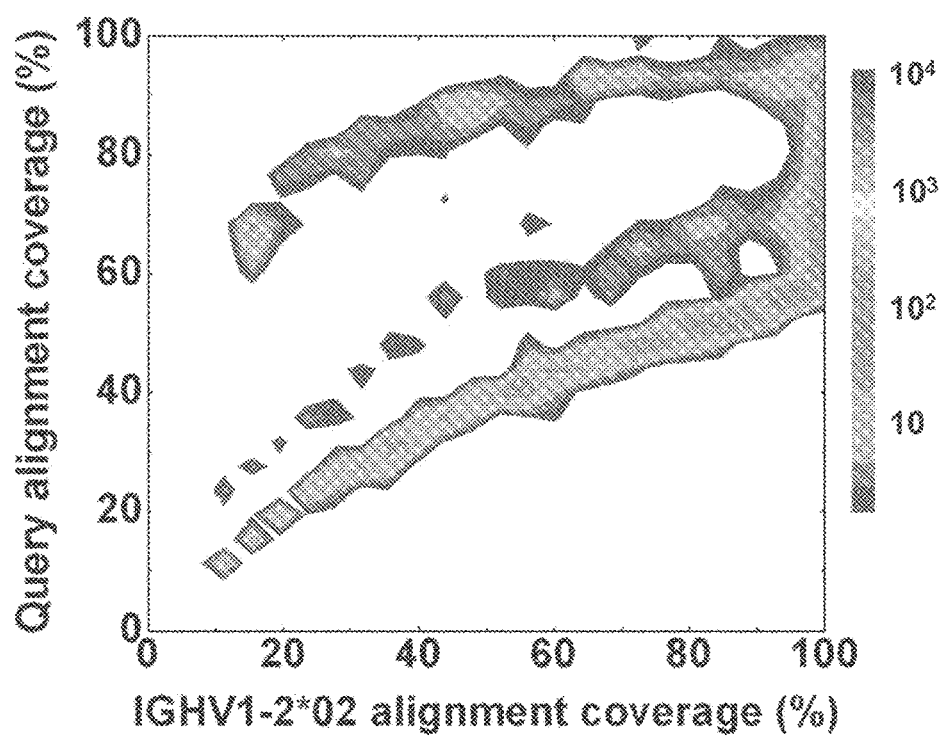

FIG. 65. Alignment coverage was also used to characterize the sequences that were assigned to IGHV1-2*02 family. Note that alleles IGVH1-2*01, IGHV1-2*03 and IGHV1-2*04 were also considered in the calculation due to their high similarities to IGHV1-2*02. When aligned to the germline genes, 27101 sequences (or 56.4%) of IGHV1-2*02 family could cover 95% of the germline sequence and thus were considered to contain the "complete" IGHV1-2*02 gene. FIG. 65 is referred to as FIG. 65 or FIG. A-41 throughout the specification and Examples.

Figure 66:
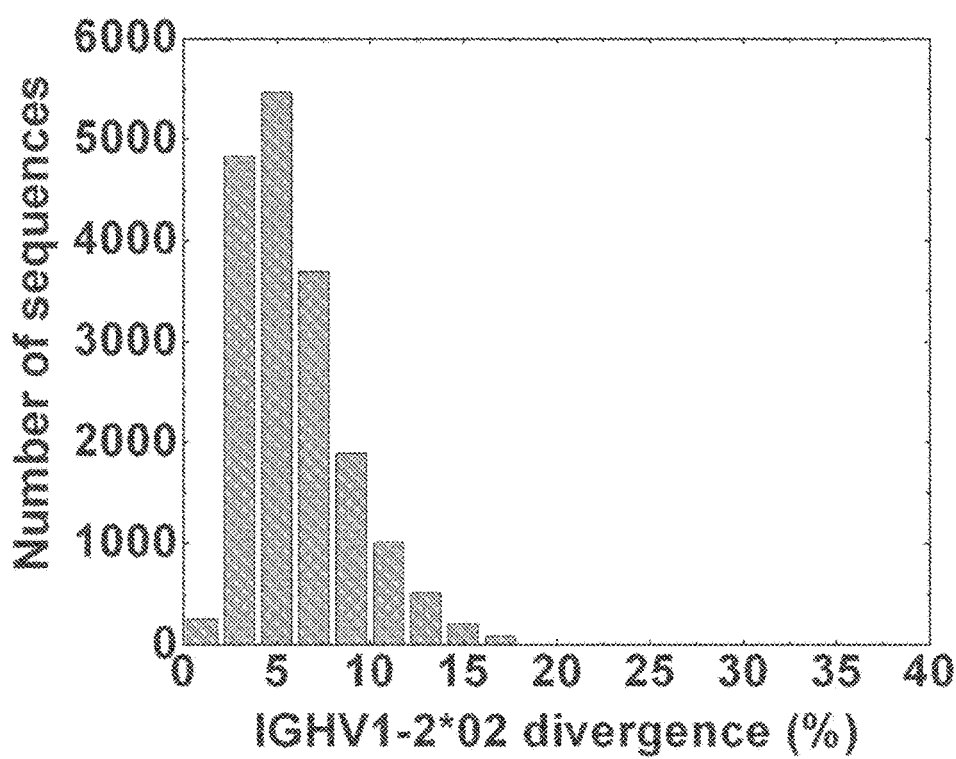

FIG. 66. The full-length sequences were extracted from the data set using VRC01 H sequence as a template, resulting in a total of 85851 sequences with 17945 sequences assigned to IGHV1-2*02 family (IGHV1-2*01, IGHV1-2*03 and IGHV1-2*04 alleles included). The divergence of full-length IGHV1-2*02 sequences was calculated and plotted as a histogram. No sequences were found to be more divergent than 24%. FIG. 66 is referred to as FIG. 66 or FIG. A-42 throughout the specification and Examples.

Figure 67:
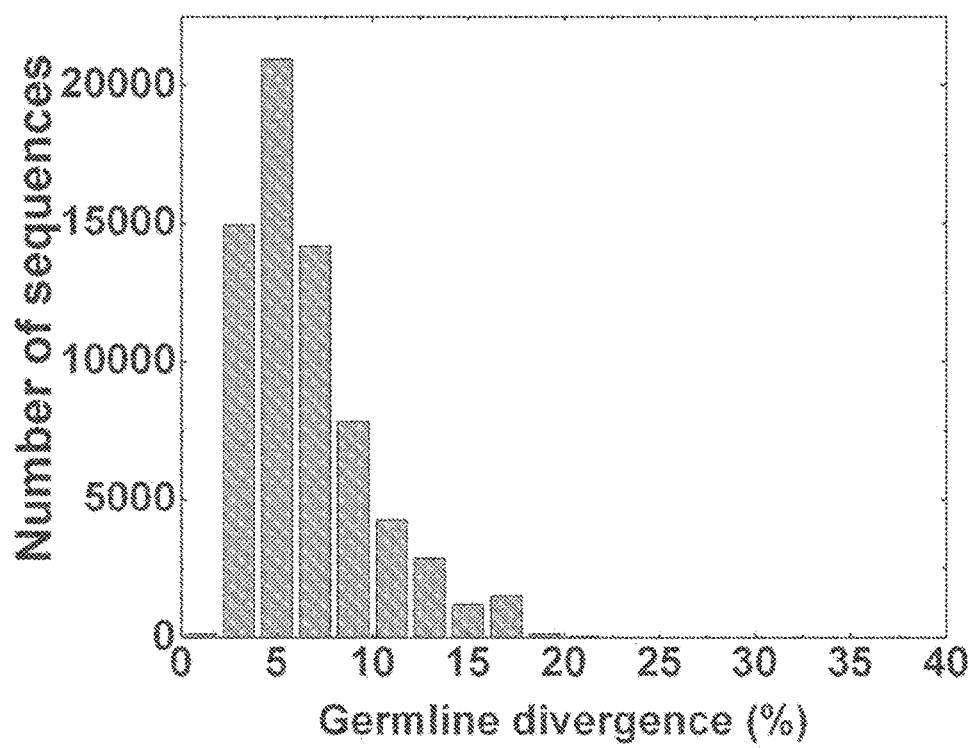

FIG. 67. The divergence of full-length sequences that were assigned to non-IGHV1-2*02 germlines was calculated and plotted as a histogram. Only three sequences were found to be more divergent than 24%. FIG. 67 is referred to as FIG. 67 or FIG. A-43 throughout the specification and Examples.

Figure 68:
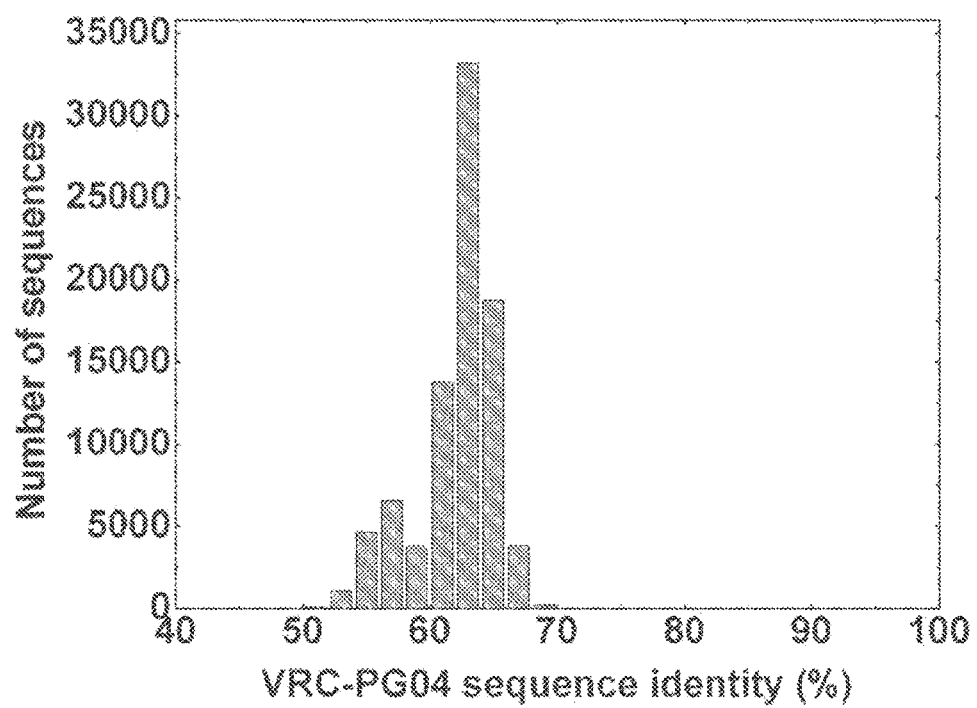

FIG. 68. The sequence identity to VRC-PG04 H (at the nucleotide level) was calculated for all full-length sequences and plotted as a histogram. 2. No sequences in the data set were found to be over 72% identical to the VRC-PG04 H sequence. FIG. 68 is referred to as FIG. 68 or FIG. A-44 throughout the specification and Examples.

Figure 69:
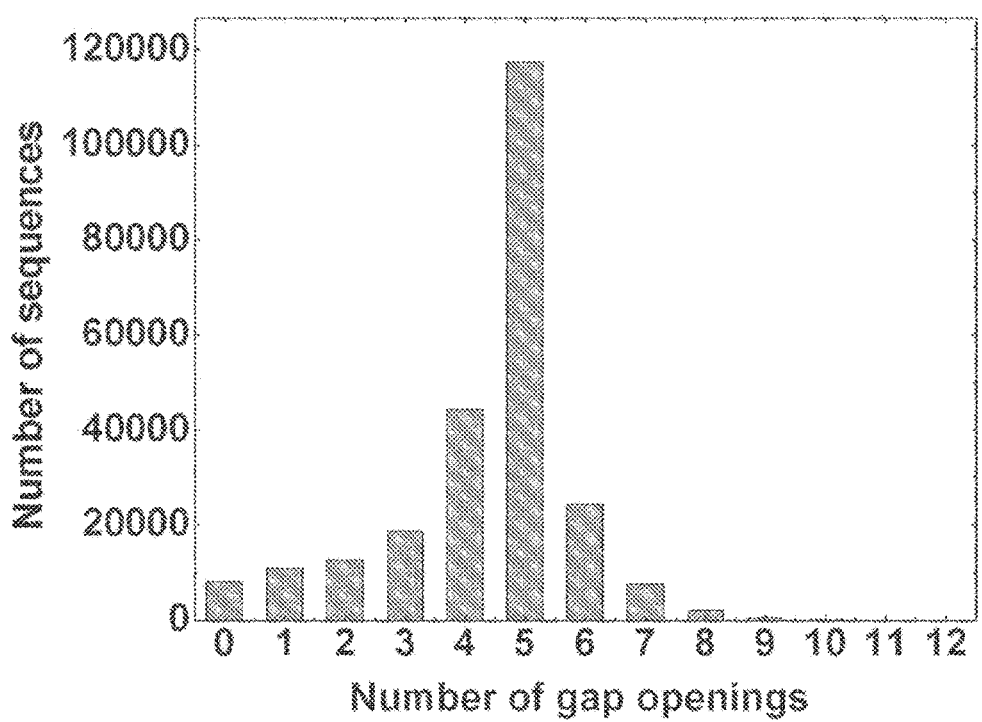

FIG. 69. After aligned to the respective germlines, the number of gap openings in the variable region was calculated and plotted as a histogram for the whole data set. 96.7% of the sequences were found to have at least one gap opening in the variable region alignment, which might be caused by 454 sequencing error or naturally occurring insertion/deletion. FIG. 69 is referred to as FIG. 69 or FIG. A-45 throughout the specification and Examples.

Figure 70:
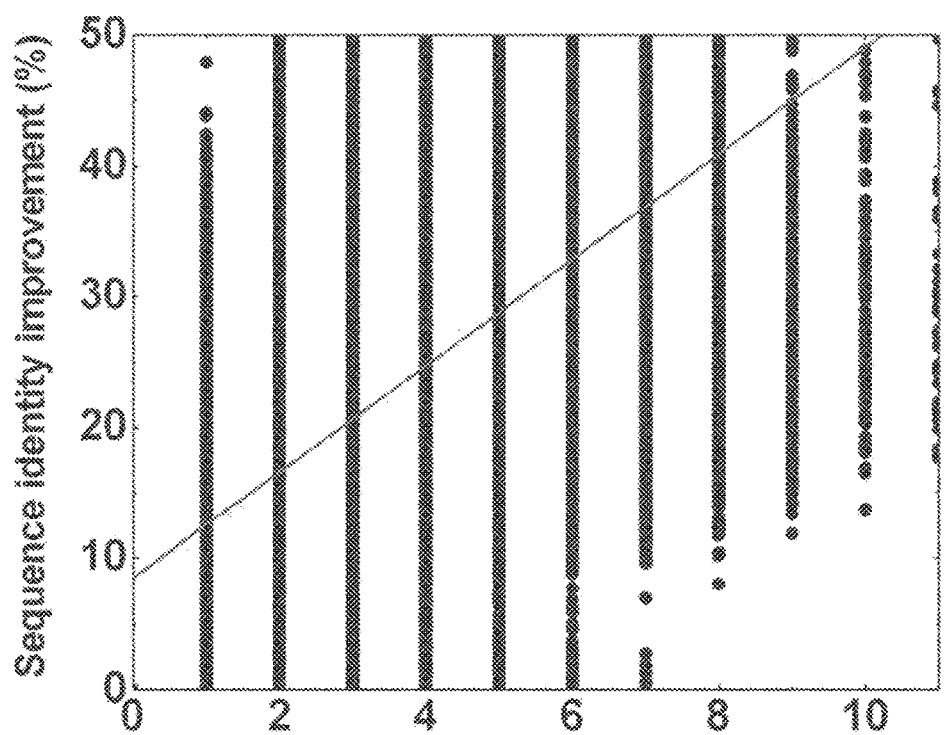

FIG. 70. The sequencing errors in the variable region were corrected based on the respective germline and the improvement of sequence identity to the germline sequence was plotted as a function of number gap openings in the variable region. The linear regression R value is 0.583 and the P-value is lower than 0.0001, suggesting that the correlation is significant. FIG. 70 is referred to as FIG. 70 or FIG. A-46 throughout the specification and Examples.

Figure 71:
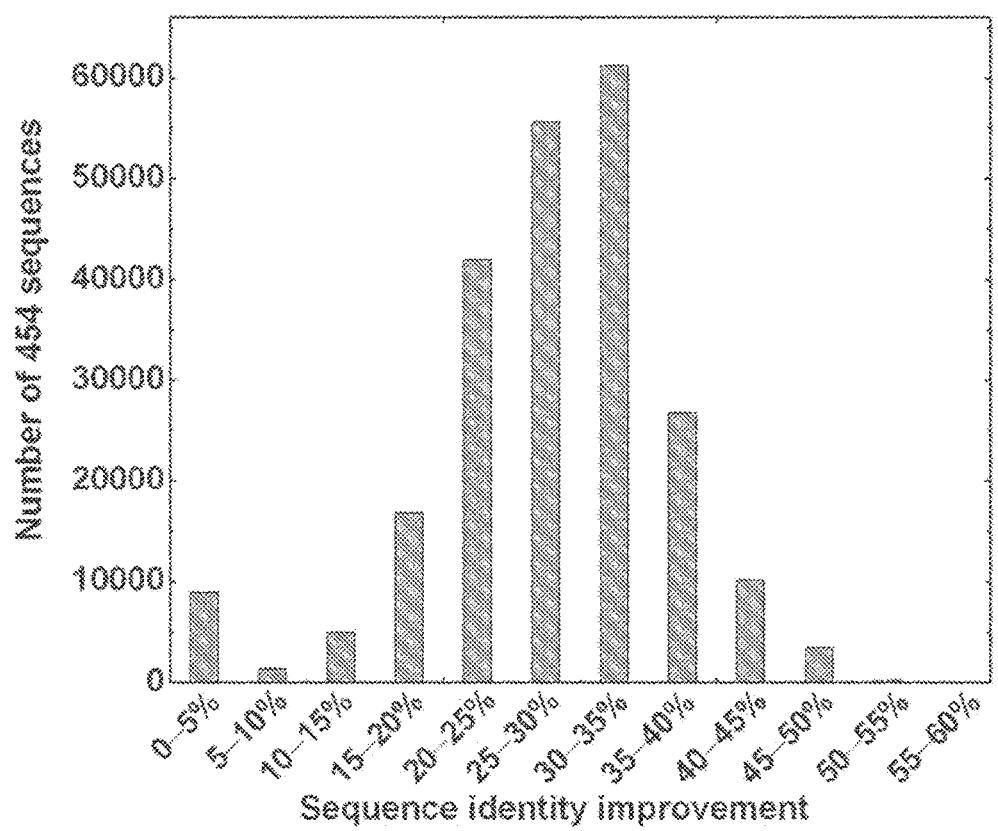

FIG. 71. The improvement of sequence identity to the respective germline was calculated for the whole data set and plotted as a histogram. The average improvement is 27.9%. FIG. 71 is referred to as FIG. 71 or FIG. A-47 throughout the specification and Examples.

Figure 72:
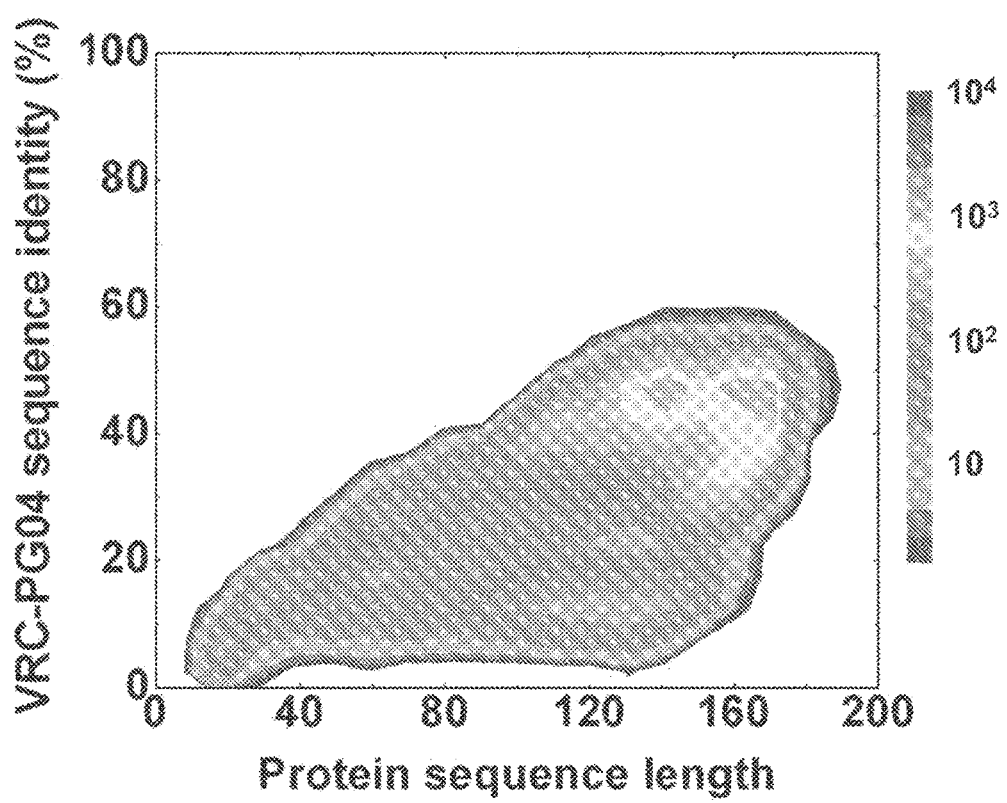

FIG. 72. The protein sequences translated from corrected nucleotide sequences were plotted as a function of sequence length and sequence identity to VRC-PG04 H. No VRC- PG04-like sequences were identified from this analysis. FIG. 72 is referred to as FIG. 72 or FIG. A48 throughout the specification and Examples.

Figure 73:
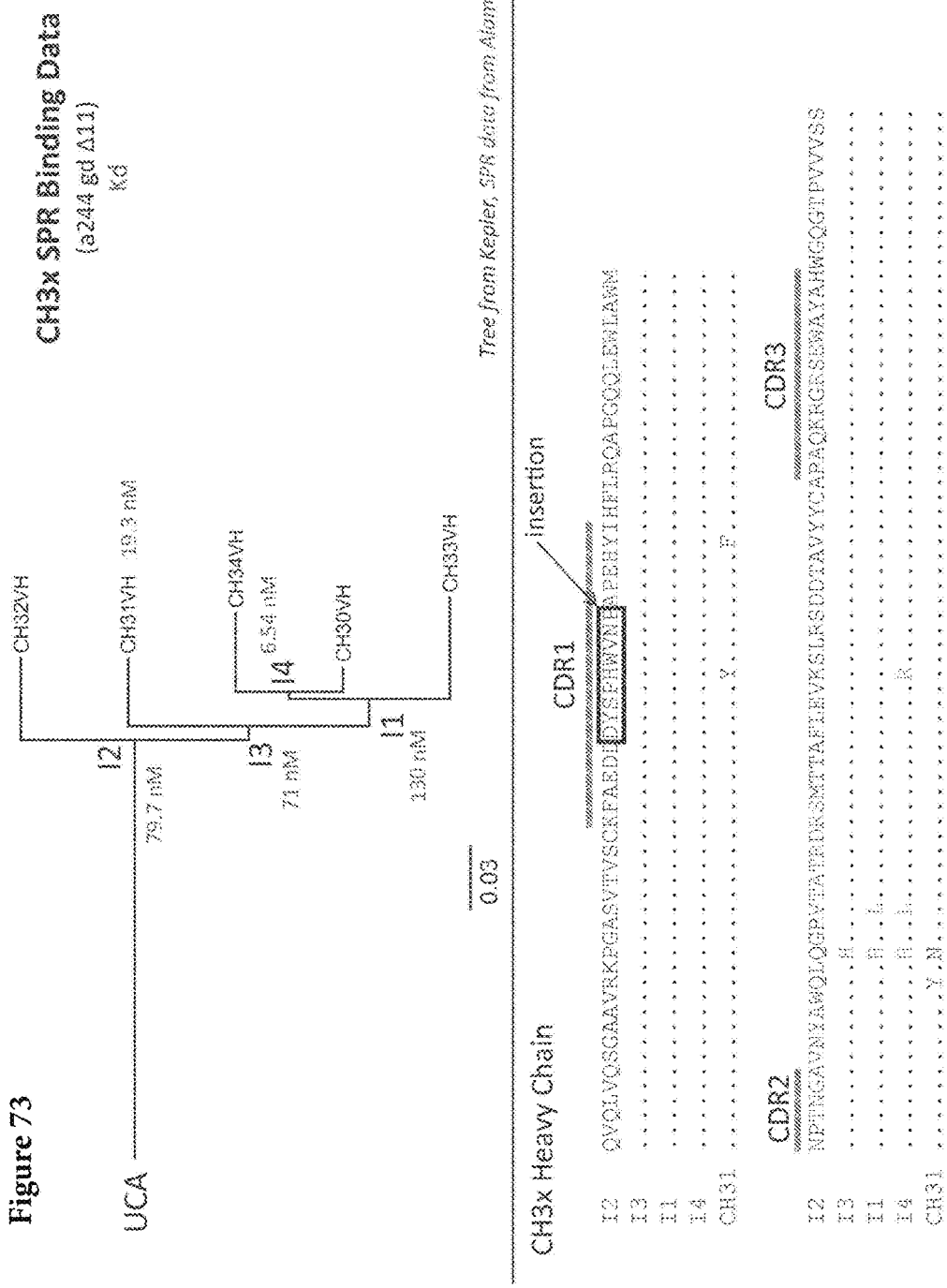

FIG. 73 shows the clonal lineage of the broadly neutralizing antibodies CH30-34 with unmutated common ancestors and intermediate antibodies (11, 12, 13, 14), as well as mature antibodies (CH30, CH31, CH32, CH33, CH34). The RUAs and IAs are inferred models of the B cell receptors of precursors of mature CH30-CH34 antibodies. The figure shows the Kds of binding of the antibodies in the clonal lineage to the E.A244 gp120 Delta 11 recombinant Env as measured in surface plasmon reasonance. The sequences shown are the sequences of the clonal lineage heavy chains (SEQ ID NOS 292-295 and 114, respectively, in order of appearance). FIG. 73 is referred to as FIG. 73 or FIG. 1-Ex. 2 throughout the specification and Examples.

Figure 74:
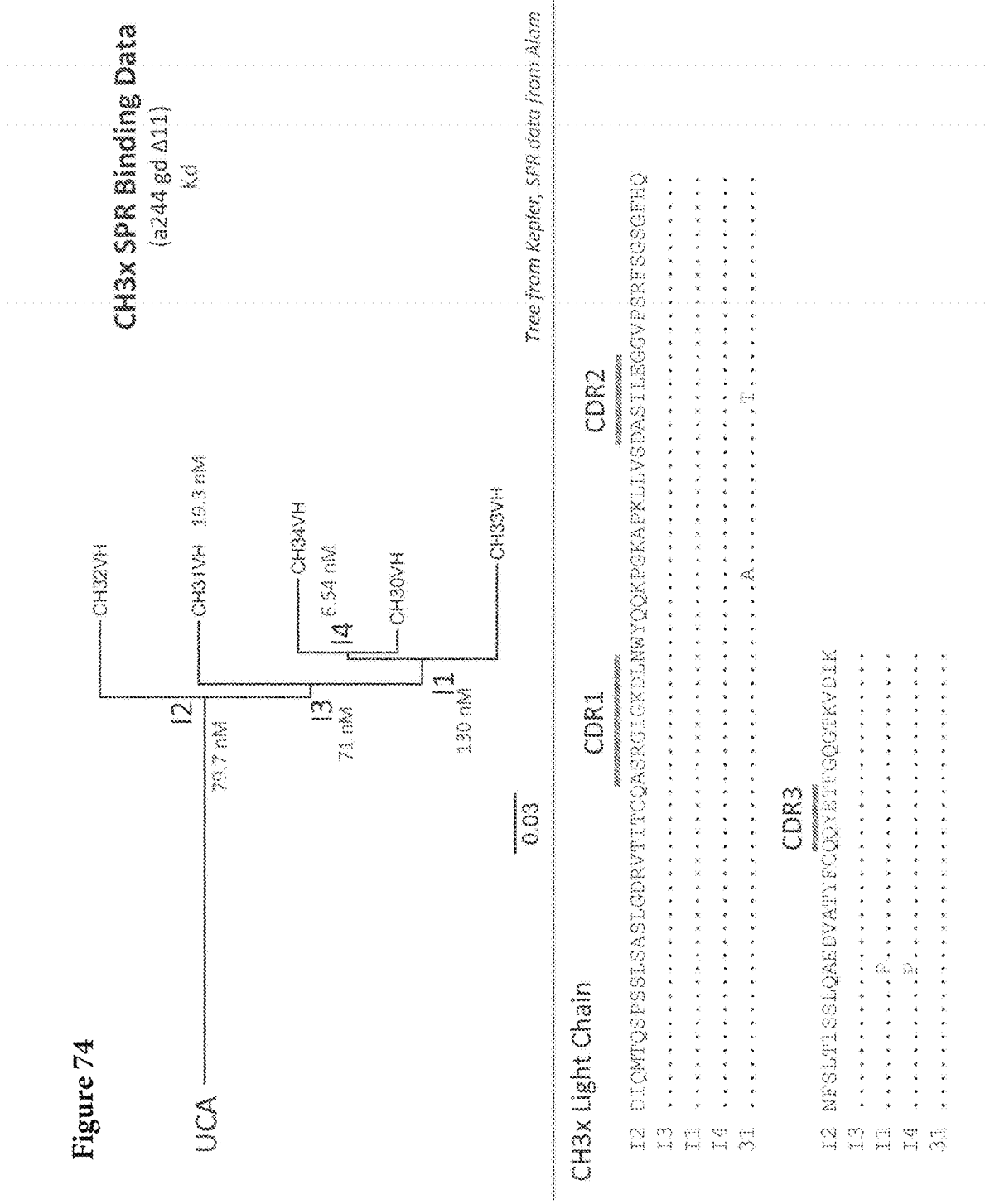

FIG. 74 shows the same binding data as in FIG. 73 but with sequences of the clonal lineage light chains (SEQ ID NOS 296-297, 124, and 124-125, respectively, in order of appearance). FIG. 74 is referred to as FIG. 74 or FIG. 2-Ex. 2 throughout the specification and Examples.

Figure 3A:
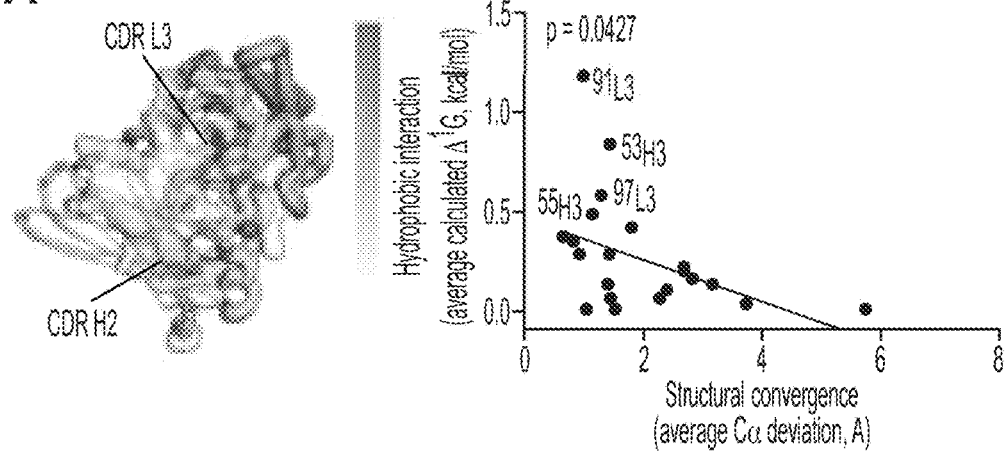
Figure 75:
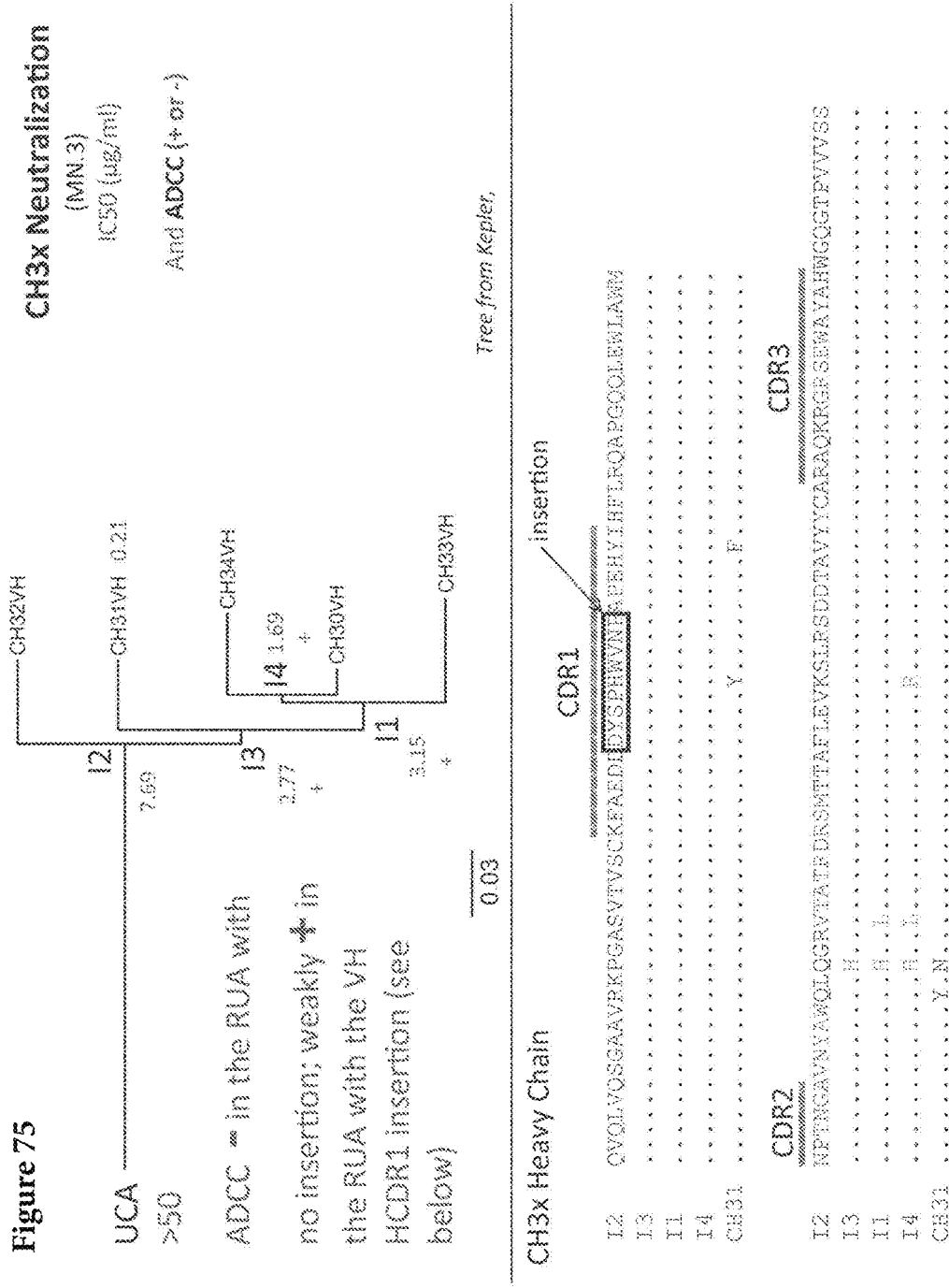

FIG. 75 shows the progressive increase in potency of neutralizing antibodies against HIV-1 isolate MN with progressive decrease in inhibitory concentration 50s as affinity maturation progresses. Sequence data provided are a repeat of the VH sequences (SEQ ID NOS 292-295 and 114, respectively, in order of appearance). Also shown are indications of what antibodies mediate ADCC as + or − (see FIG. 76). FIG. 75 is referred to as FIG. 75 or FIG. 3-Ex. 2 throughout the specification and Examples.

FIG. 76 shows antibody dependent cellular cytotoxicity assay curves of RUAs, IAs and CH31 antibody against CM235 HIV infected CD4 T cells. These data, along with FIGS. 77-79, imply that what is needed to induce these broad neutralizing antibodies are immunogens designed using the RUAs as templates. FIG. 76 is referred to as FIG. 76 or FIG. 4-Ex. 2 throughout the specification and Examples.

Figure 77:
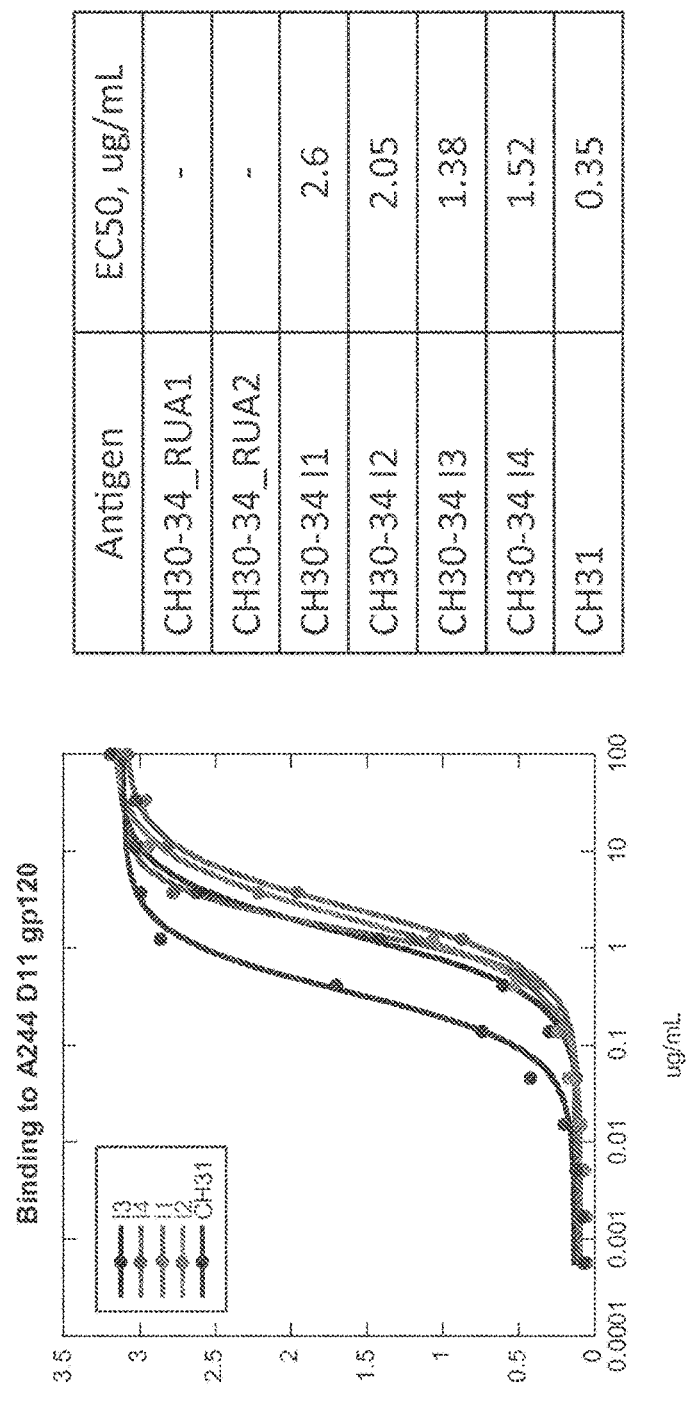

FIG. 77 shows binding curves of the members of the clonal lineage to the E.A244 gp120 recombinant Env protein. This figure also shows that the RUAs do not react with these envs while the IAs and CH31 do react. These data, along with FIGS. 76 and 78-79, imply that what is needed to induce these broad neutralizing antibodies are immunogens designed using the RUAs as templates. FIG. 77 is referred to as FIG. 77 or FIG. 5-Ex. 2.

Figure 78:
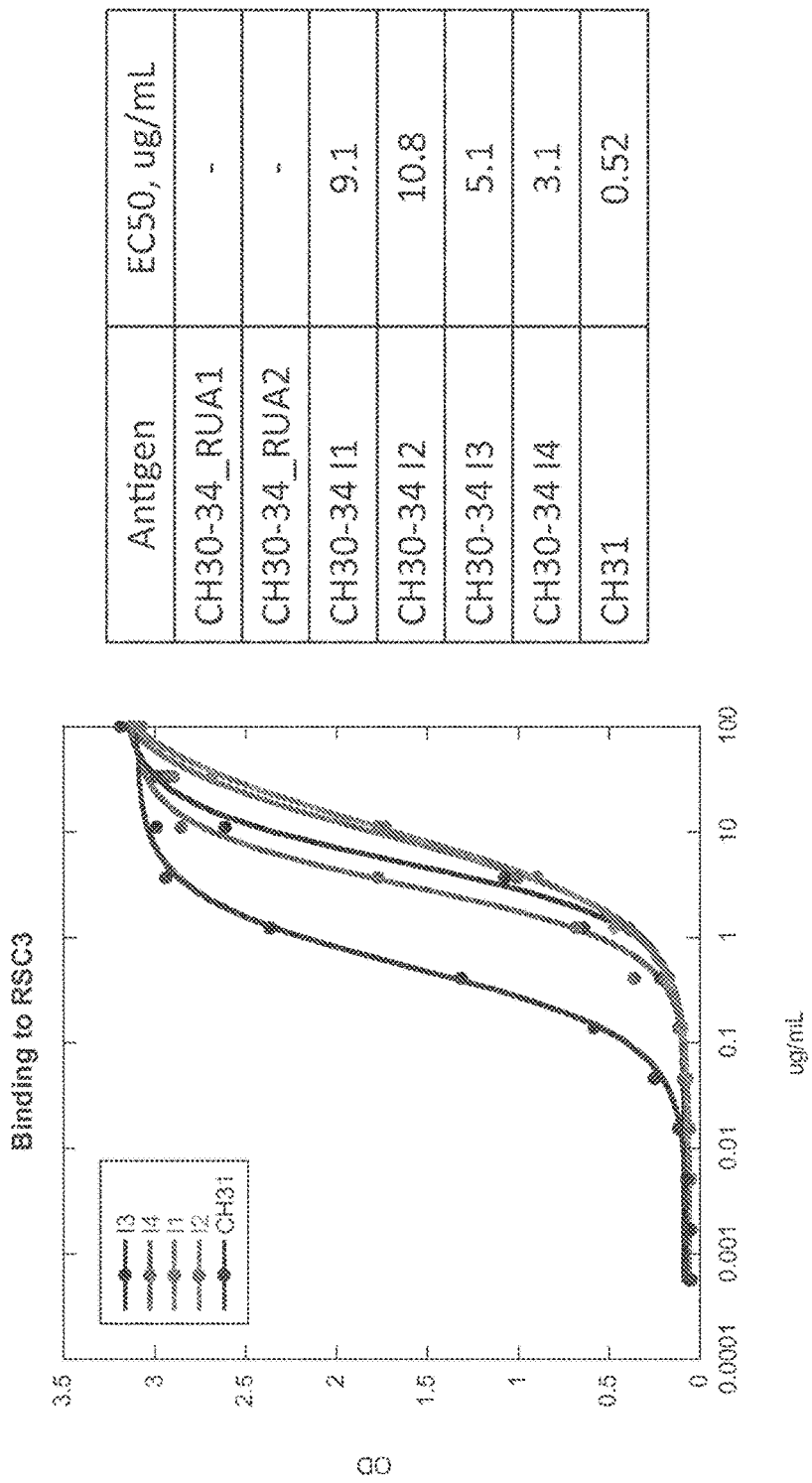

FIG. 78 shows binding curves to the resurfaced core protein (RSC). This figure also shows that the RUAs do not react with these envs while the IAs and CH31 do react. These data, along with FIGS. 76-77 and 79, imply that what is needed to induce these broad neutralizing antibodies are immunogens designed using the RUAs as templates. FIG. 78 is referred to as FIG. 78 or FIG. 6-Ex. 2.

Figure 79:
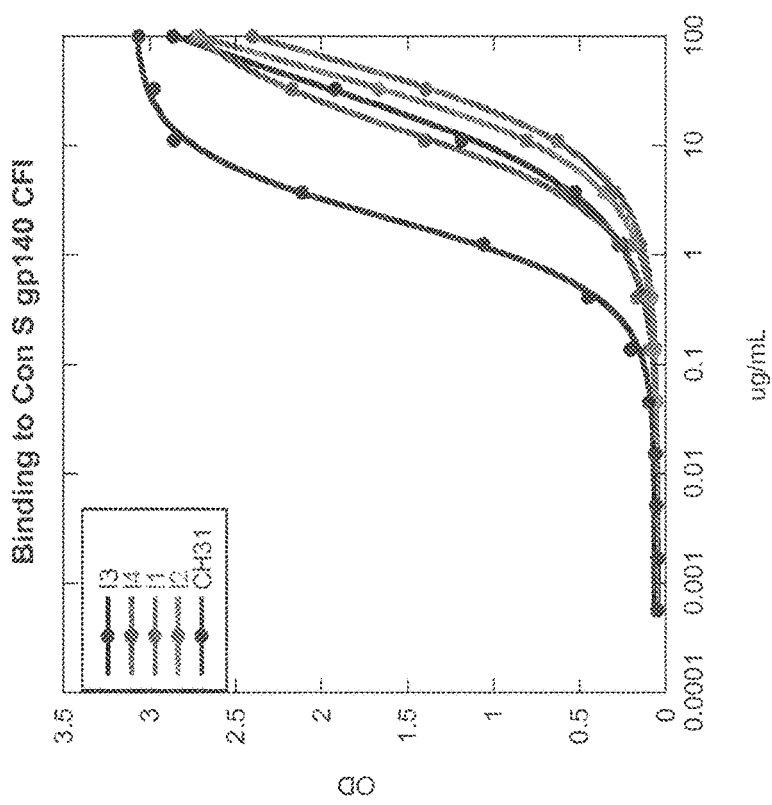

FIG. 79 shows binding curves to the group M consensus Env CONS gp120 protein. This figure also shows that the RUAs do not react with these envs while the IAs and CH31 do react. These data, along with FIGS. 76-78, imply that what is needed to induce these broad neutralizing antibodies are immunogens designed using the RUAs as templates. FIG. 79 is referred to as FIG. 79 or FIG. 7-Ex. 2.

Figure 80:
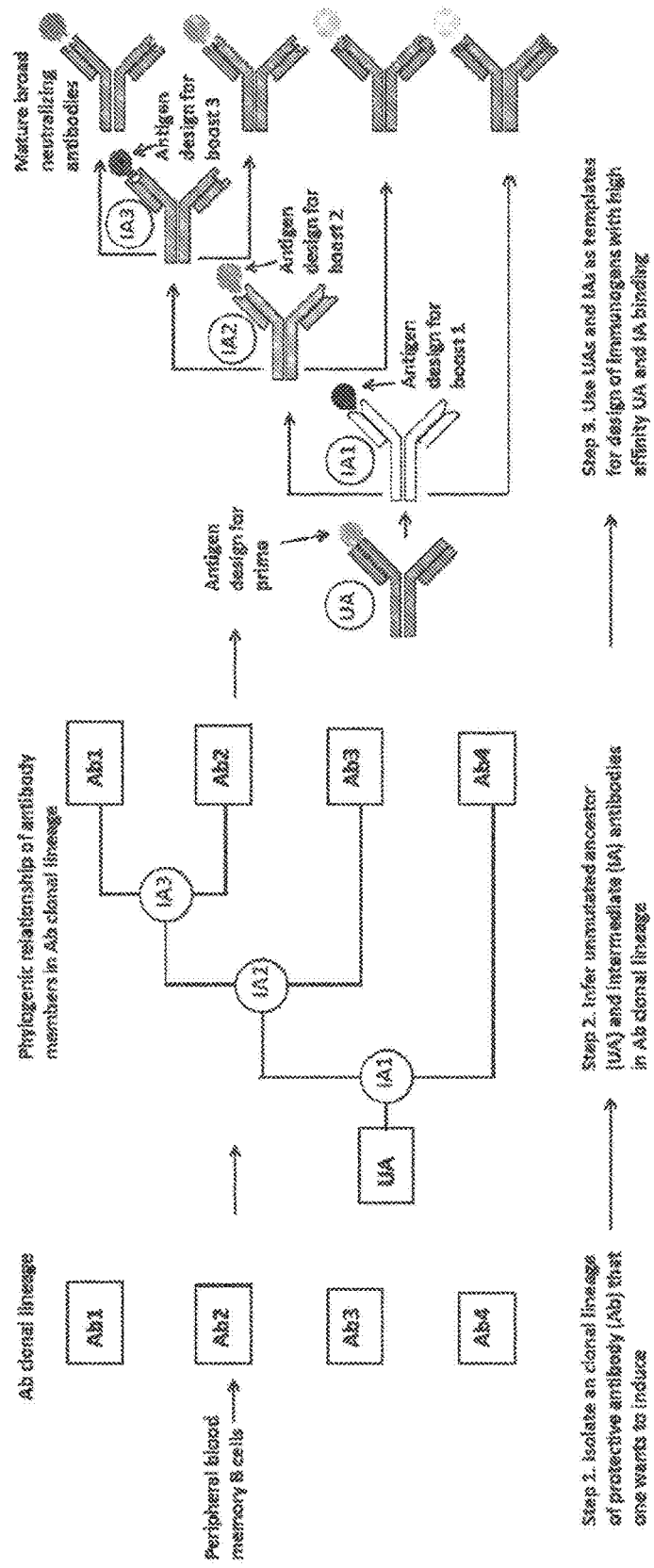

FIG. 80 shows the steps of a B cell lineage-based approach (see also U.S. Prov. 61/542,469). FIG. 80 is referred to as FIG. 8-Ex. 2 throughout the specification and Examples. FIG. 80 is referred to as FIG. 80 or FIG. 8-Ex. 2 throughout the specification and Examples.

FIG. 81 shows Tables S1, the ELISA binding profiles of VRC-PG04, VRC-PG04b, VRC-CH30, VRC-CH31 and VRC-CH32 compared to a panel of known CD4bs mAbs. FIG. 81 is referred to as Table S1 throughout the specification and Examples.

FIG. 82 shows Table S2, the gene family analysis of mAbs VRC-PG04, VRC-PG04b, VRC-CH30, VRC-CH31 and VRC-CH32. FIG. 82 is referred to as Table S2 throughout the specification and Examples.

FIG. 83 shows Table S3a, a summary of the breadth and potency of antibody neutralization against 180 HIV-1 Env-pseudoviruses. FIG. 83 is referred to as Table S3a throughout the specification and Examples.

Figure 84:
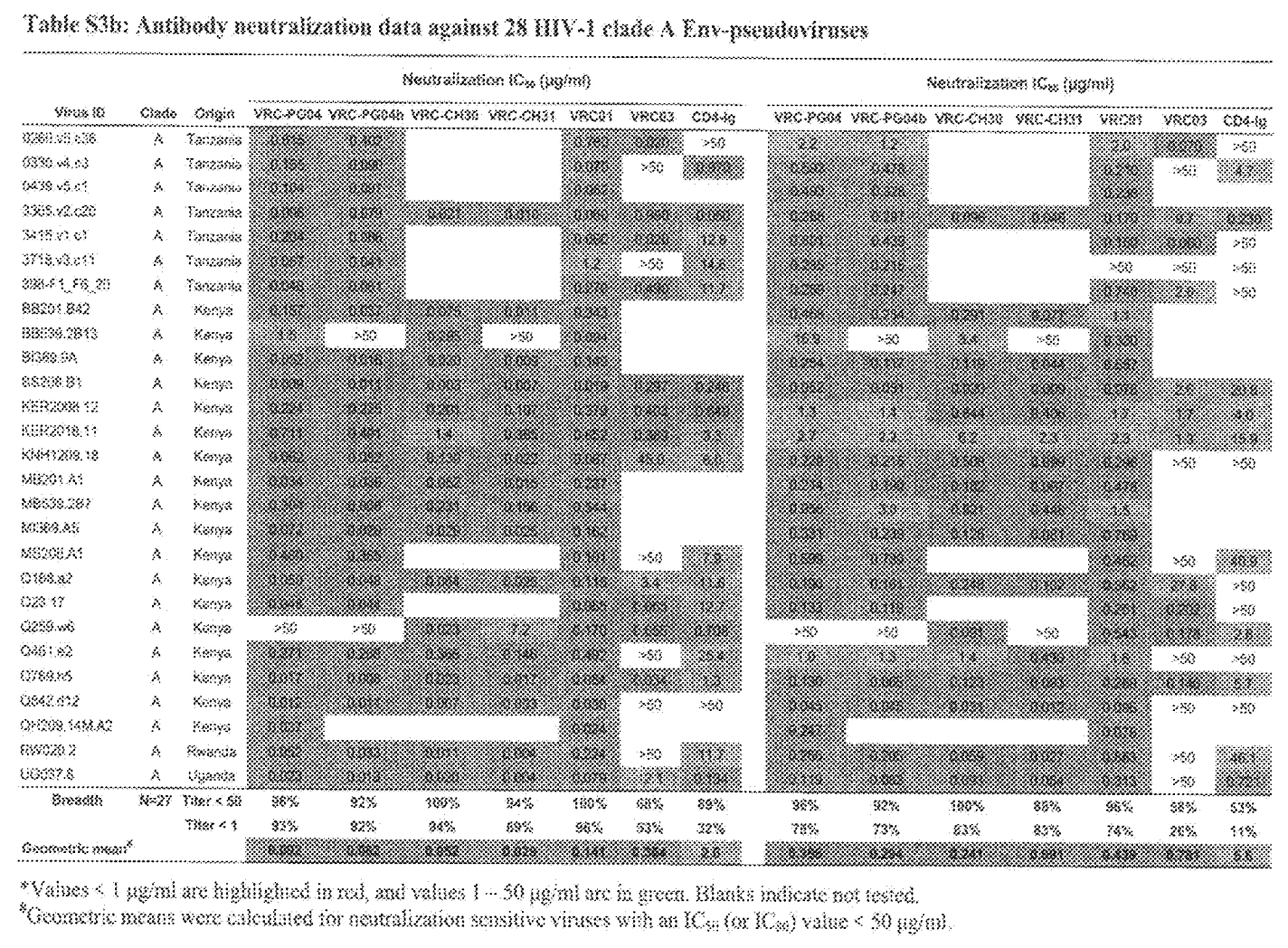

FIG. 84 shows Table S3b, the antibody neutralization data against 28 HIV-1 clade A Env-pseudoviruses. FIG. 84 is referred to as Table S3b throughout the specification and Examples.

Figure 85:
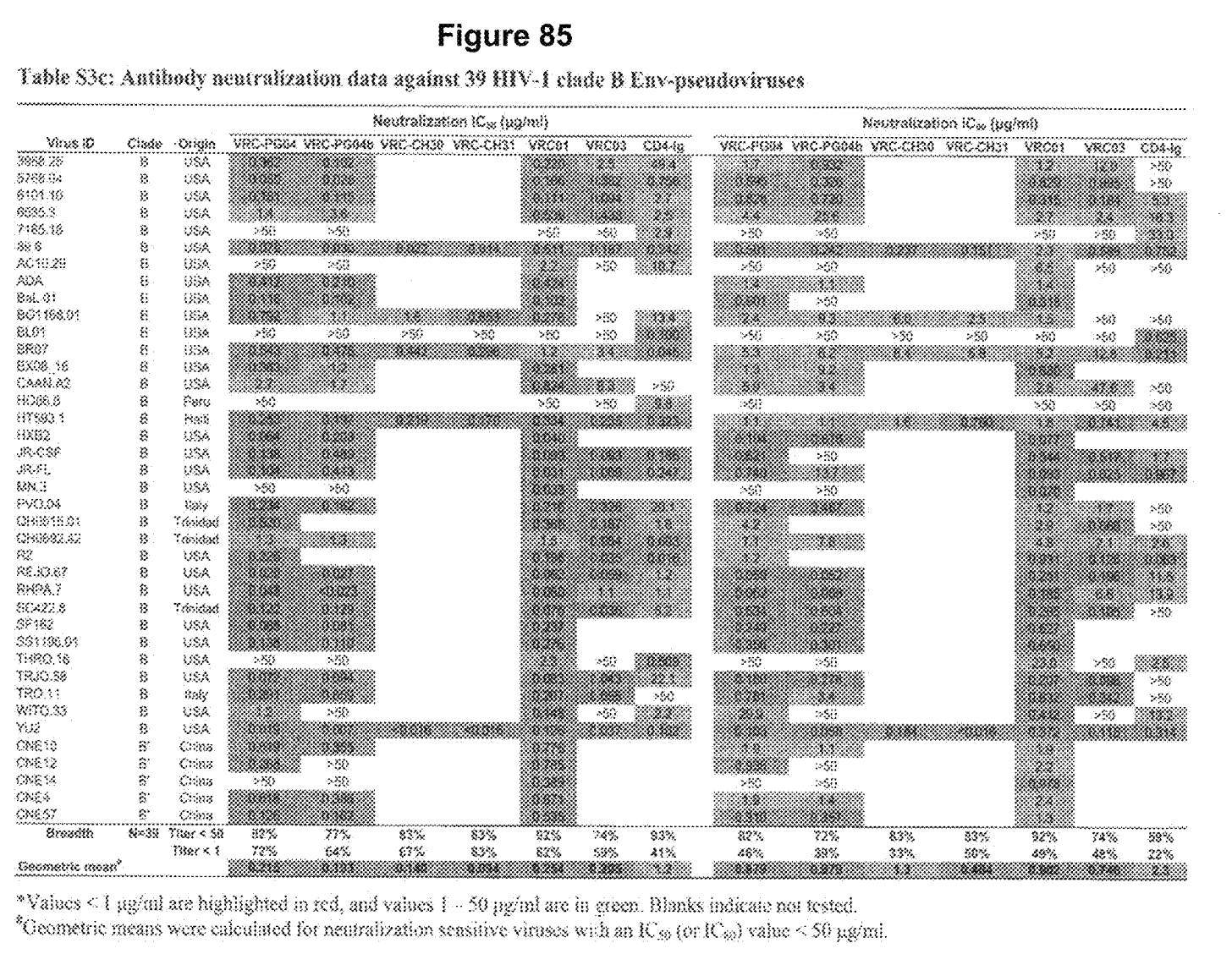

FIG. 85 shows Table S3c, the antibody neutralization data against HIV-1 clade B Env-pseudoviruses. FIG. 85 is referred to as Table S3c throughout the specification and Examples.

Figure 86:
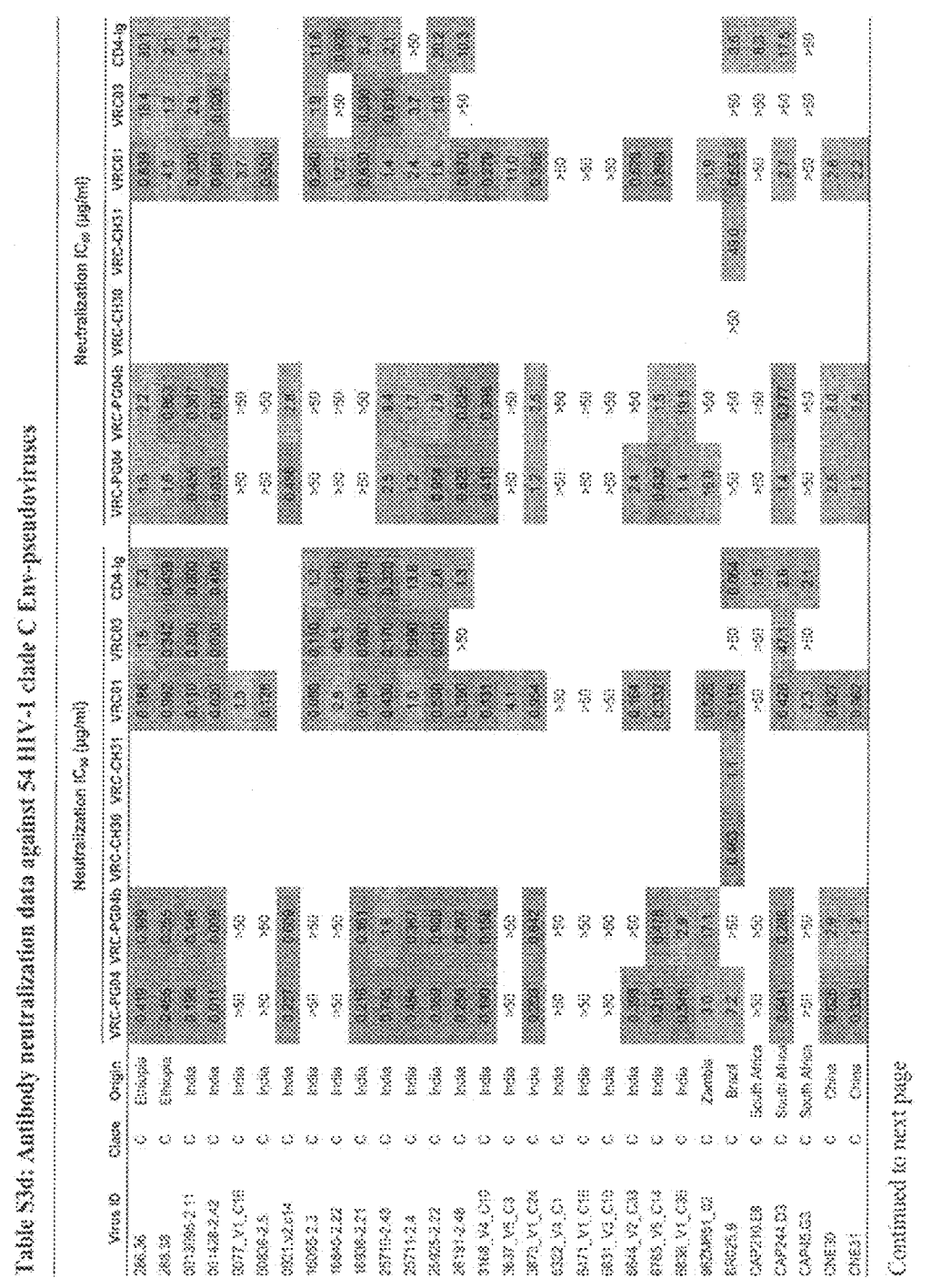
Figure 86:
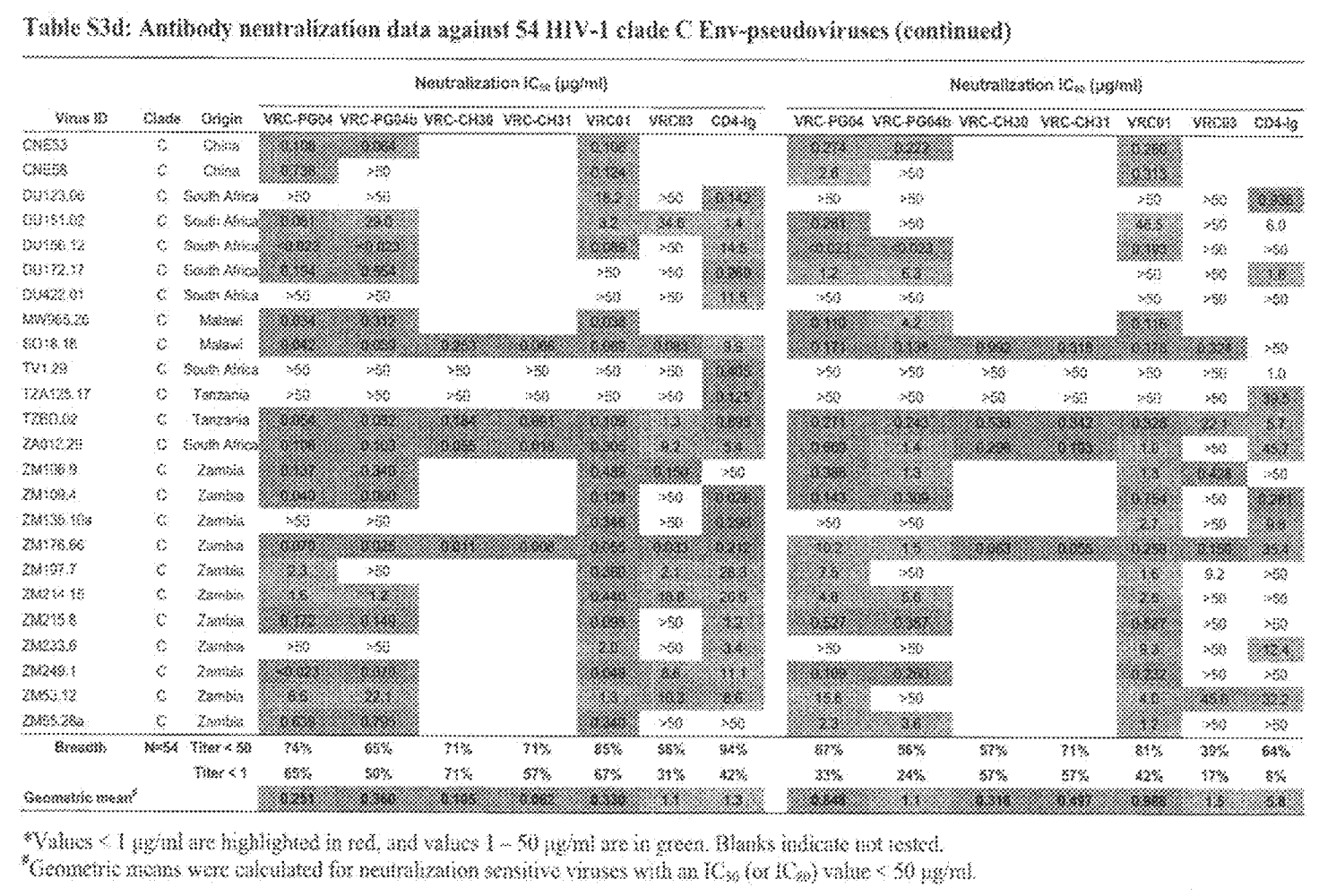

FIG. 86 shows Table S3d, the antibody neutralization data against 54 HIV-1 clade C Env-pseudoviruses. FIG. 86 is referred to as Table S3d throughout the specification and Examples.

Figure 87:
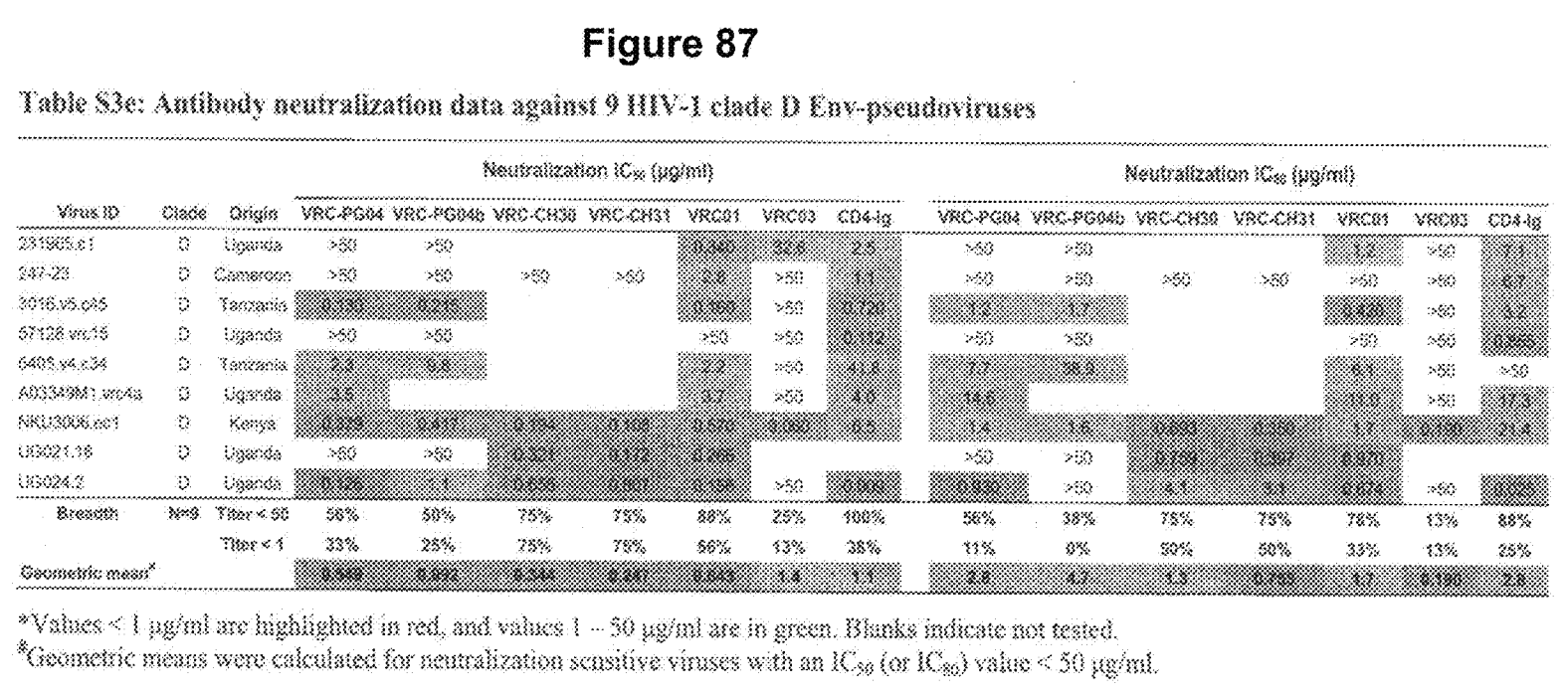

FIG. 87 shows Table S3e, the antibody neutralization data against 9 HIV-1 clade D Env-pseudoviruses. FIG. 87 is referred to as Table S3e throughout the specification and Examples.

FIG. 88 shows Table S3f, the antibody neutralization data against 16 HIV-1 CRF01_AE Env-pseudoviruses. FIG. 88 is referred to as Table S3f throughout the specification and Examples.

Figure 89:
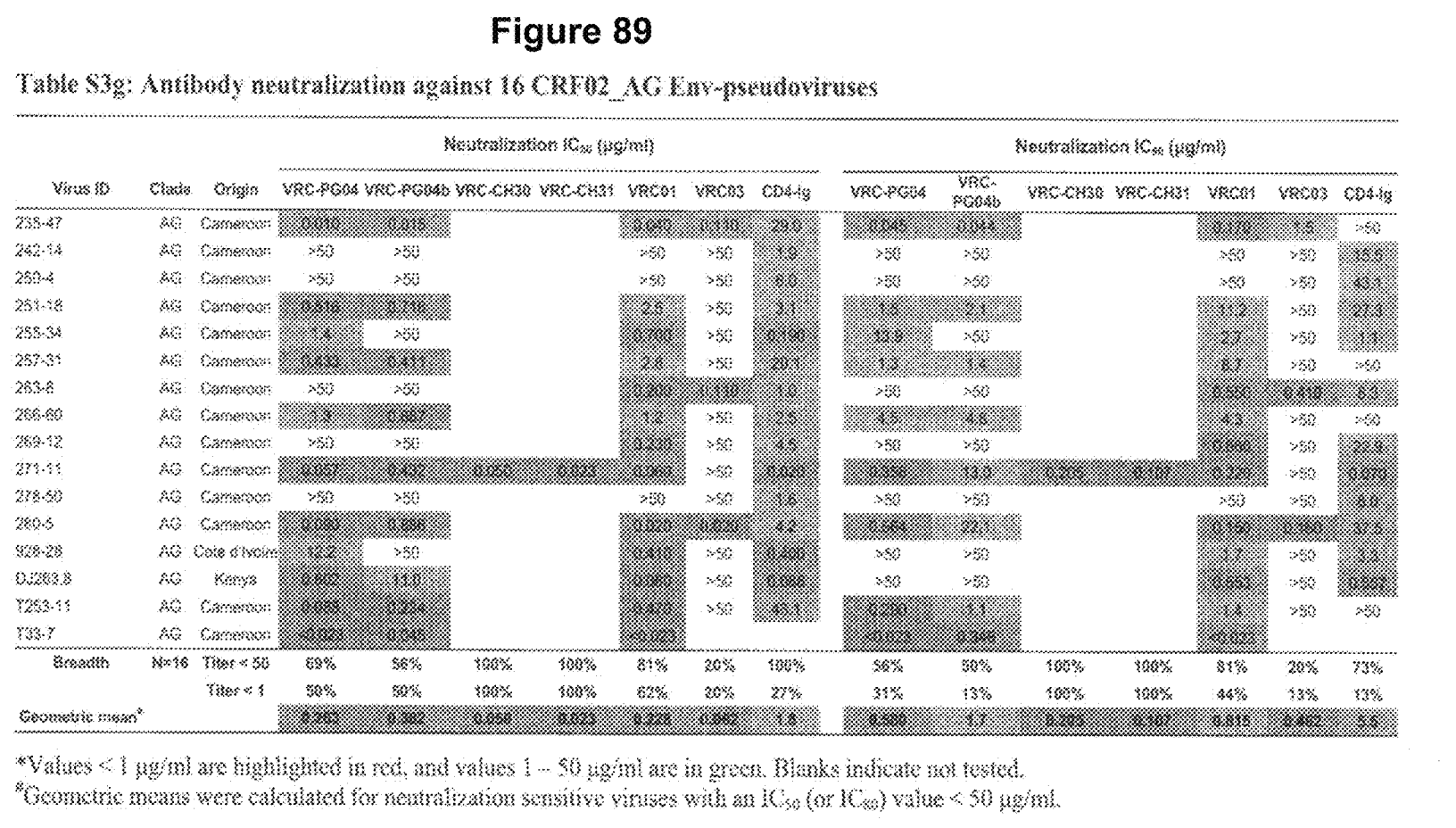

FIG. 89 shows Table S3g, the antibody neutralization data against 16 CRF02_ AG Env-pseudoviruses. FIG. 89 is referred to as Table S3g throughout the specification and Examples.

Figure 90:
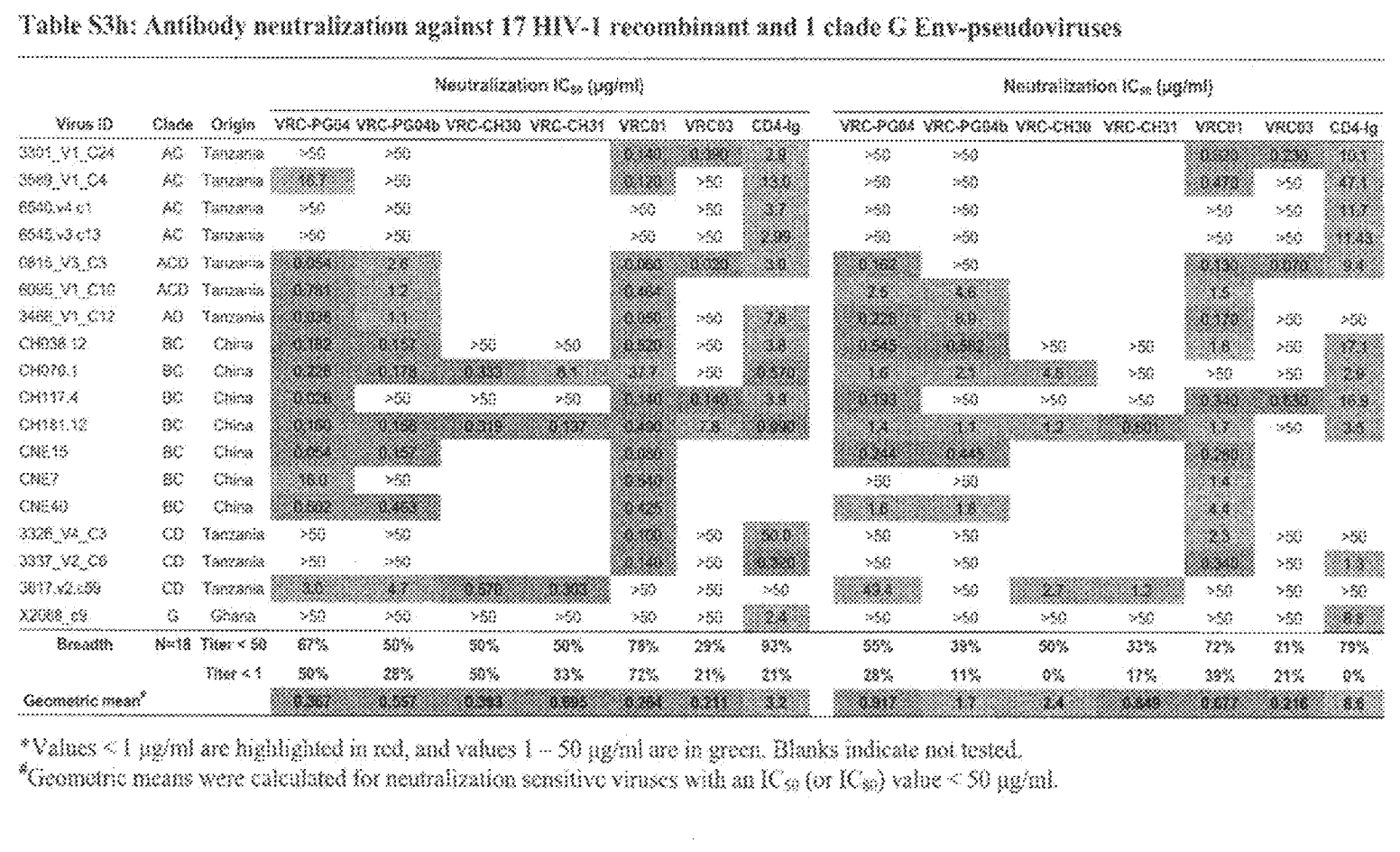

FIG. 90 shows Table S3h, the antibody neutralization data against 17 HIV-1 recombinant and 1 clade G Env-pseudoviruses. FIG. 90 is referred to as Table S3h throughout the specification and Examples.

FIG. 91 shows Table S4, X-ray crystallographic data and refinement statistics for VRC-PG04:gp120 and VRC03:gp120 complexes. FIG. 91 is referred to as Table S4 throughout the specification and Examples.

FIG. 92 shows Table S5a, a list of VRC-PG04 heavy chain residues that interact with HIV-1 gp120 (table discloses the residues at positions 528-561 and 98-100A as SEQ ID NOS 10-11, respectively). FIG. 92 is referred to as Table S5a throughout the specification and Examples.

FIG. 93 shows Table 5b, a list of VRC-PG04 light chain residues that interact with HIV-1 gp120. FIG. 93 is referred to as Table S5b throughout the specification and Examples.

FIG. 94 shows Table S5c, a list of HIV-1 gp120 residues that interact with VRC-PG04 heavy chain (table discloses the residues at positions 279-283, 365-368, and 455-459, as SEQ ID NOS 12-14, respectively). FIG. 94 is referred to as Table S5c throughout the specification and Examples.

FIG. 95 shows Table S5d, a list of HIV-1 gp120 residues that interact with VRC-PG04 light chain. FIG. 95 is referred to as Table S5d throughout the specification and Examples.

FIG. 96 shows Table S6a, a list of VRC03 heavy chain residues that interact with HIV-1gp120 (table discloses the residues at positions 52-62 and 73-76A as SEQ ID NOS 15-16, respectively). FIG. 96 is referred to as Table S6a throughout the specification and Examples.

FIG. 97 shows Table S6b, a list of VRC03 light chain residues that interact with HIV-1 gp120. FIG. 97 is referred to as Table S6b throughout the specification and Examples.

FIG. 98 shows Table S6c, a list of HIV-1 gp120 residues that interact with VRC03 heavy chain (table discloses the residues at positions 279-283, 365-368, 455-461, and 472-475, as SEQ ID NOS. FIG. 98 is referred to as Table S6c throughout the specification and Examples.

FIG. 99 shows Table S6d, a list of HIV-1 gp120 residues that interact with VRC03 light chain (table discloses the residues at positions 458-462 as SEQ ID NO: 19). FIG. 99 is referred to as Table S6d throughout the specification and Examples.

FIG. 100 shows Table S7, a comparison of gp120 recognition by CD4-induced antibodies derived from a common IGVH1-69 allele. Pair-wise RMSDs and angles for both heavy and light chains of all antibodies were calculated after gp120s in the complexes were superposed. Corresponding fragments in the frameworks 1, 2, 3 and 4 of the heavy and light chains were used in the computation. Though sharing a common VH1-69 gene in their heavy chains, CD4-induced antibodies 17b, 412d and X5 had substantial variation in gp120 recognition. FIG. 100 is referred to as Table S7 throughout the specification and Examples.

FIG. 101 shows Table S8, the orientations of RSC3-reactive CD4-binding site antibodies in gp120: antibody complexes. To compare how different CD4-binding site antibodies approach HIV-1 gp120, pairwise RMSDs and angles for both heavy and light chains of all antibodies were calculated after gp120s in the complexes were superposed. Only corresponding fragments in the frameworks 1, 2, 3 and 4 of the heavy and light chains were used in the computation. Pairs with RMSD<10 Å were colored red and those with RMSD>10 Å were colored green. The results clearly showed that VRC01, VRC03 and VRC-PG04 had very similar modes of approach towards HIV-1 gp120, while other RSC-reactive CD4-binding site antibodies such as b12, b13 had different orientations in recognition. FIG. 101 is referred to as Table S8 throughout the specification and Examples.

FIG. 102 shows Table S9, the Heavy/Light-chain complementation of VRC01-like antibody. FIG. 102 is referred to as Table S9 throughout the specification and Examples.

FIG. 103 shows Table S10, the neutralization $IC_{50}$ titers* (μg/ml) of chimeric antibodies derived from known VRC01-like antibodies against 20 HIV-1 clade A, B and C Env-pseudoviruses FIG. 103 is referred to as Table S10 throughout the specification and Examples.

FIG. 104 shows Table S11, the sequences selected from the IGHV1-2*02 family of donor 45 heavy-chain 2008 antibodyome with high predicted structural compatibility with known VRC01-like antibody-gp120 complexes[a]. [a]The germline divergence of sequences in the IGHV1-2*02 family was divided into 12 bins ranging from 0 to 36%. In each divergence bin, the sequence that has the lowest threading score to any of the VRC01-, VRC03- and VRC-PG04-gp120 complex structures was selected as candidate for synthesis and listed in this table. Note that only 9 sequences remained because the divergence bin 24-27% was empty, the sequence selected from the 27-30% bin was identical to VRC03, and the sequence from the 33-36% bin was discarded due to severe sequencing errors. For each sequence, the listed columns include index number, germline divergence, normalized DFIRE threading across score (S39, 43) to VRC01, VRC03 and VRC-PG04 complex structures, and nucleotide sequence identities to VRC01, VRC03 and VRC-PG04 heavy chains. FIG. 104 is referred to as Table S11 throughout the specification and Examples.

FIG. 105 shows Table S12, the sequences selected from the non-IGHV1-2*02 families of donor 45 heavy-chain 2008 antibodyome with high germline divergence and large family size[a]. [a]For each of the 9 non-IGHV1-2*02 germline families of donor 45 heavy-chain 2008 antibodyome, the most divergent 10 sequences were subjected to a clustering procedure using a sequence identity cutoff of 75%. The center of the cluster that has at least two members was selected as candidate for synthesis and listed in the table. For each sequence, the listed columns include index number, V-gene family name, germline divergence, and nucleotide sequence identifies to VRC01, VRC03 and VRC-PG04 heavy chains. FIG. 105 is referred to as Table S12 throughout the specification and Examples.

FIG. 106 shows Table S13, the expression of antibodies with selected heavy chains derived from donor 45, 2008 (SEQ ID NOS 20-36, respectively, in order of appearance). FIG. 106 is referred to as Table S13 throughout the specification and Examples.

FIG. 107 shows Table S14, the expression of antibodies with selected heavy chains from donor V74, 2008, paired with VRC-PG04 light chain (SEQ ID NOS 37-106, respectively, in order of appearance). FIG. 107 is referred to as Table S14 throughout the specification and Examples.

Figure 108:
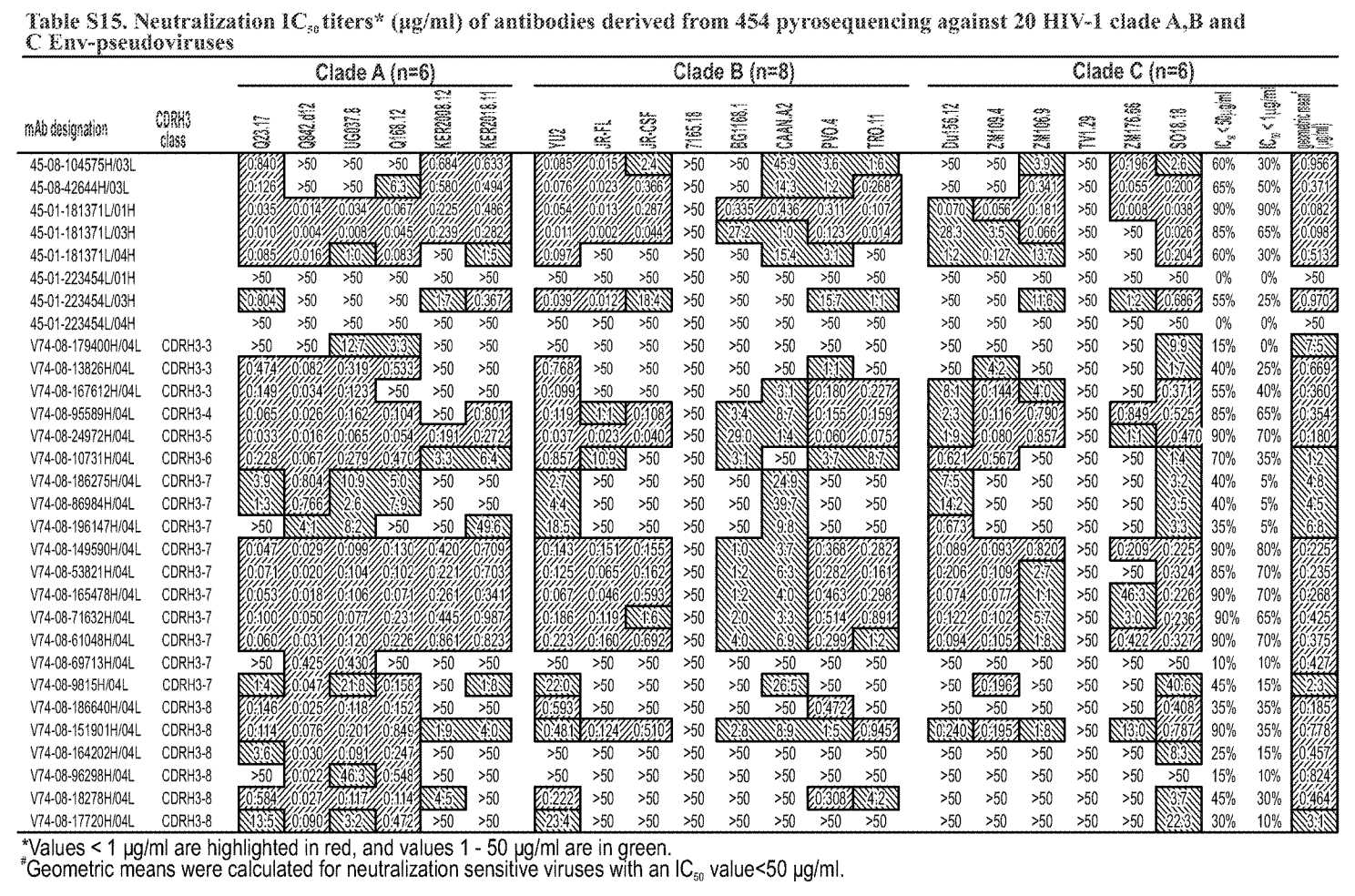

FIG. 108 shows Table S15, the neutralization IC50 titers* (μg/ml) of antibodies derived from 454 pyrosequencing against 20 HIV-1 clade A,B and C Env-pseudoviruses. FIG. 108 is referred to as Table S15 throughout the specification and Examples.

FIG. 109 shows Table S16, the expression of antibodies with phylogenetic-segregation selected light chains. FIG. 109 is referred to as Table S16 throughout the specification and Examples.

DETAILED DESCRIPTION

The present invention relates to HIV-1 neutralizing antibodies and to methods of using same therapeutically or prophylactically in a subject (e.g., a human subject). The invention results, at least in part, from the identification of broadly neutralizing antibodies against the CD4 binding site of HIV-1 (see Example that follows). FIG. 1C includes heavy and light chain amino acid sequences of VRC-CH30, VRC-CH31 and VRC-CH-31. FIG. 1G includes heavy and light chain gene sequences that include sequences encoding the amino acid sequences shown in FIG. 1C. These antibodies have the characteristics of being heavily somatically mutated, short HCDR3 regions, and are derived from VH1-2 heavy chain family. They all broadly neutralize HIV-1. (See also Wu X et al, Science 329:856-61 (2010)).

The invention relates to antibodies that comprise a heavy and/or light chain as set forth in FIG. 1C, or at least one or more CDR's of such chains. The invention also includes antibodies having the binding specificity of VRC-CH30, VRC-CH31 and VRC-CH-32. The invention further includes nucleic acid sequences encoding such amino acid sequences/antibodies. The invention also relates to prophylactic and therapeutic uses of such antibodies.

Antibodies that are suitable for use in the prophylactic/therapeutic methods of the invention include dimeric, trimeric and multimeric antibodies, bispecific antibodies, chimeric antibodies, human and humanized antibodies, recombinant and engineered antibodies, and antigen-binding fragments thereof (e.g., Fab', F(ab')2 fragments). Also suitable are single domain antibodies, Fv, single chain Fv, linear antibodies, diabodies, etc. The techniques for preparing and using various antibody-based constructs and fragments are well known in the art (see, for example, Kohler and Milstein, Nature 256:495 (1975), Kosbor et al, Immunol. Today 4:72

(1983), Cote et al, PNAS 80:2026 (1983), Morrison et al, PNAS 81:6851 (1984), Neuberger et al, Nature 312:604 (1984), Takeda et al, Nature 314:452 (1985), U.S. Pat. No. 4,946,778, EP 404,097, WO93/11161, Zapata et al, Prot. Eng. 8:1057 (1995) and Liao et al, J. Virol. Methods 158(1-2):171-179 (2009)).

Antibodies of the invention can be expressed in a system that produces them as IgG1 antibodies, the dominant type present in human plasma (Liao et al, J. Virol. Methods 158(1-2):171-179 (2009) and Smith et al, Nature Protocols 4(3)(January 1):372-384 (2009)). IgG1 antibodies can be passed through the placenta to infants prior to birth and can also become available at mucosal surfaces active or passive transport. In addition to the IgG1 expression system, antibodies of the invention can be expressed as other isotypes, in particular, as an IgA1 or IgA2 antibody (Carayannopoulos et al, Proc. Natl. Sci. USA 91(8) (August 30):8348-8352 (1994)), Such antibodies can provide additional protection at mucosal surfaces.

The antibodies of the invention can be used, for example, in humans, in a variety of prophylactic/therapeutic regimens. For example, the antibodies can be used for pre exposure prophylaxis, post exposure prophylaxis (i.e., exposure following sex or, in babies, following nursing), and for the treatment of HIV-1 infected individuals. The antibodies can be used in passive immunotherapy strategies to prevent or treat HIV-1 during pregnancy. The antibodies can also be used to prevent or treat perinatally acquired/congenital HIV-1 in infants.

Antibodies of the invention also find use as adjunctive therapeutics in combination with other anti-HIV-1 therapies.

The antibodies, or antibody fragments, of the invention can be formulated using standard techniques. Advantageously, the antibody/fragment is present in a composition, for example, a sterile composition suitable for injection (e.g., subcutaneously or intramuscularly) or intravenous infusion, or by other parenteral means. The composition can also take the form of a cream or ointment suitable for administration to skin or a mucosal surface (e.g., in the context of a microbicide for the prevention of HIV-1 infection in a susceptible population). The optimum amount and route of administration can vary with the antibody/fragment, the patient and the effect sought. Optimum dosing strategies can be readily established by one skilled in the art.

The invention includes nucleic acid sequences encoding the antibodies and antibody fragments disclosed herein and vectors (for example, viral vectors such as adeno associated viral vectors) comprising same. Such nucleic acid constructs can be used to express the antibodies against the CD4 binding site (e.g., VRC-CH30, VRC-CH31 and VRC-CH-32), e.g., in a subject. (See Johnson et al, Nature Medicine 15:901-6 (2009)).

All references and other information sources cited herein are incorporated in their entirety by reference.

Example 1

HIV-1 exhibits extraordinary genetic diversity and has evolved multiple mechanisms of resistance to evade the humoral immune response (1-3). Despite these obstacles, 10-25% of HIV-1-infected individuals develop cross-reactive neutralizing antibodies after several years of infection (4-9). Elicitation of such antibodies could form the basis for an effective HIV-1 vaccine, and intense effort has focused on identifying responsible antibodies and delineating their characteristics. A variety of monoclonal antibodies (mAbs) have been isolated that recognize a range of epitopes on the functional HIV-1 viral spike, which is composed of three highly glycosylated gp120 exterior envelope glycoproteins and three transmembrane gp41 molecules. Some broadly neutralizing antibodies are directed against the membrane-proximal external region of gp41 (10, 11), but the majority recognize gp120. These include the quaternary structure-preferring antibodies PG9, PG 16, and CH01-04 (12, 13), the glycan-reactive antibodies 2G12 and PGT121-144 (14, 15), and antibodies b12, HJ16 and VRC01-03, which are directed against the region of HIV-1 gp120 involved in initial contact with the CD4 receptor (16-19).

One unusual characteristic of all these gp120-reactive broadly neutralizing antibodies is a high level of somatic mutation. Antibodies typically accumulate 5-10% changes in variable domain-amino acid sequence during the affinity maturation process (20), but for these gp120-reactive antibodies, the degree of somatic mutation is markedly increased, ranging from .about.15-20% for the quaternary structure-preferring antibodies (12) and antibody HG16 (17), to .about.25% for antibody 2012 (21, 22) and to .about.30% for the CD4-binding-site antibodies, VRC01, VRC02, and VRC03 (18).

In the case of VRC01, the mature antibody accumulates almost 70 total changes in amino acid sequence during the maturation process. The mature VRC01 can neutralize .about.90% of HIV-1 isolates at a geometric mean IC50 of 0.3 µg/ml (18), and structural studies show that it achieves this neutralization by precisely recognizing the initial site of CD4 attachment on HIV-1 gp120 (19). By contrast, the predicted unmutated germline ancestor of VRC01 has weak affinity for typical strains of gp120 (.about.mM) (19). Moreover, with only two unique VRC01-like antibodies identified in a single individual (donor 45), it has been unclear whether the VRC01 mode of recognition, genetic origin, and pathway of affinity maturation represent general features of the B-cell response to HIV-1. Here we isolate VRC01-like antibodies from two additional HIV-1-infected donors, determine their liganded-crystal structures with gp120, examine cross-donor complementation of heavy and light chain function, and use deep sequencing to analyze the repertoire, lineage, and maturation pathways of related antibody sequences in each of two donors. The analysis presented here focuses primarily on the heavy chain, although some analysis of the light chain is also undertaken. Definition of the structural convergence and maturation pathways by which VRC01-like antibodies achieve broad neutralization of HIV-1 provides a framework for understanding the development of these antibodies and for efforts to guide their induction.

Isolation of Neutralizing Antibodies from Donors 74 and 0219 with a CD4-Binding-Site Probe.

Figure 1A:
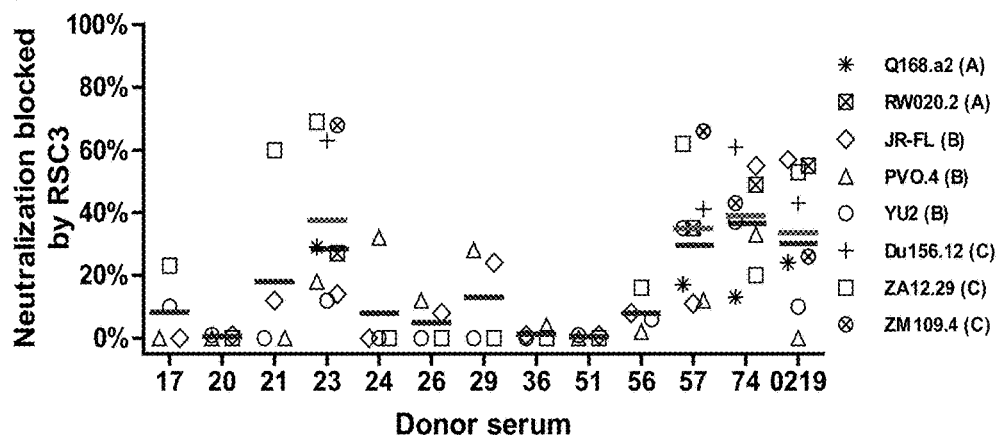

We previously used structure-guided resurfacing to alter the antigenic surfaces on HIV-1 gp120 while preserving the initial site of attachment to the CD4 receptor (18). With the resurfaced stabilized core 3 probe (RSC3), over 30% of the surface residues of core gp120 were altered and the conformation stabilized by the addition of interdomain-disulfide bonds and cavity-filling point mutations (18). We used RSC3 and a mutant version containing a single amino acid deletion in the CD4-binding loop (ΔRSC3) to interrogate a panel of 12 broadly neutralizing sera derived from the IAVI protocol G cohort of HIV-1 infected individuals (6, 23) (FIG. 1A). A substantial fraction of neutralization of three sera was specifically blocked by RSC3 compared with ΔRSC3, indicating the presence of CD4-binding-site-directed neutralizing antibodies. RSC3-neutralization competition assays also confirmed the presence of CD4-bindingsite antibodies in the previously characterized sera 0219, identified in the CHAVI 001 cohort (8) (FIG. 1A).

Figure 1B:
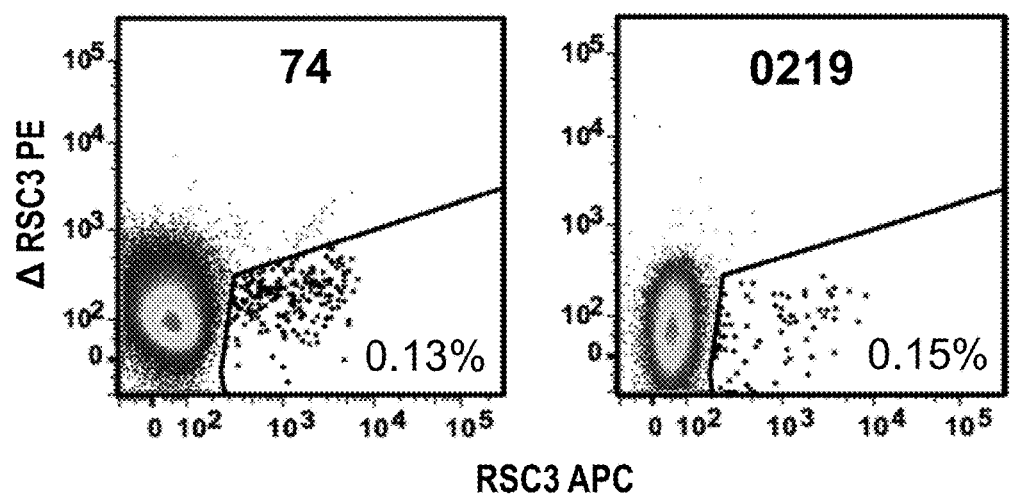
Figure 1C:
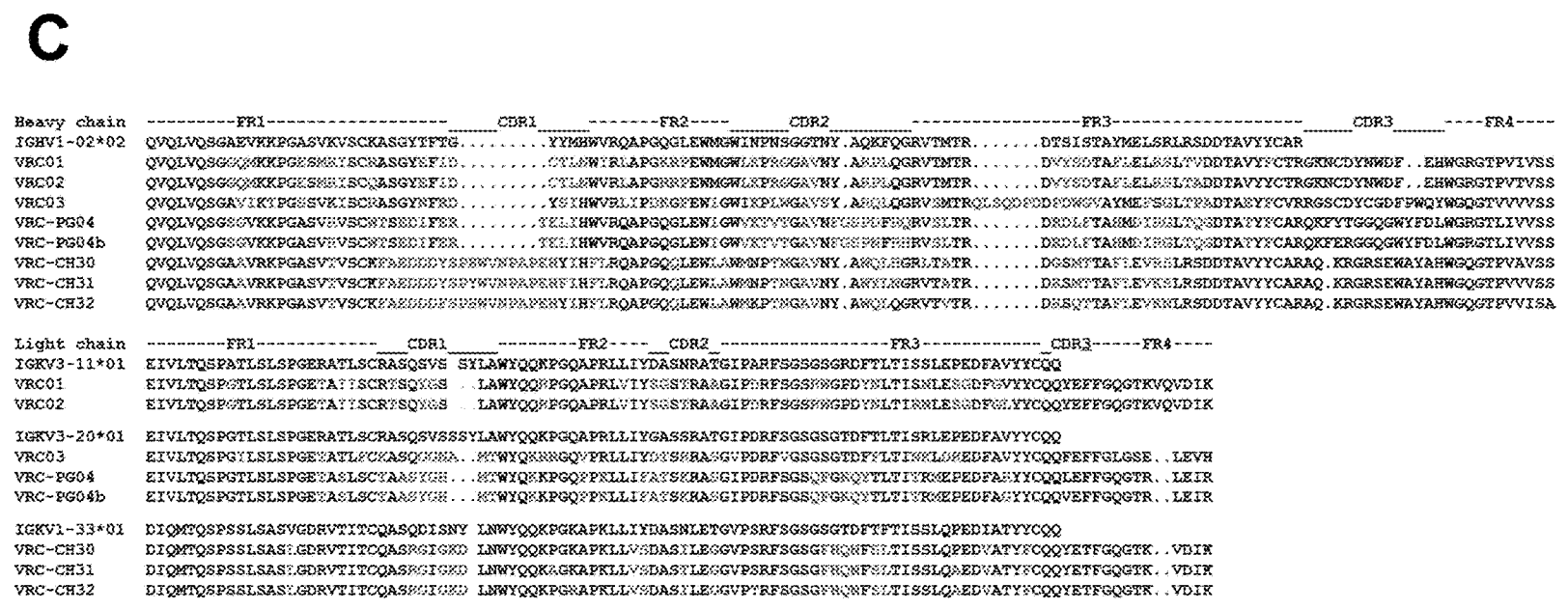

Peripheral blood mononuclear cells (PBMCs) from protocol G donor 74 (infected with A/D recombinant) and from CHAVI donor 0219 (infected with clade A) were used for antigen-specific B-cell sorting and antibody isolation. PBMCs were incubated with both RSC3 and ΔRSC3, each conjugated to a different fluorochrome, and flow cytometric analysis was used to identify and to sort individual IgG+ B cells reactive with RSC3 and not ΔRSC3. For donor 74 and 0219, respectively, a total of 0.13% and 0.15% of IgG+ B cells were identified (FIGS. 1B and S1). The heavy and light chain immunoglobulin genes from individual B-cells were amplified and cloned into IgG1 expression vectors that reconstituted the full IgG (18, 24). From donor 74, two somatically related antibodies named VRC-PG04 and VRC-PG04b demonstrated strong binding to several versions of gp120 and to RSC3 but .about.100-fold less binding to ΔRSC3 (Fig. S2 and Table S1). From donor 0219, three somatically related antibodies named VRC-CH30, 31, and 32 displayed a similar pattern of RSC3/ΔRSC3 reactivity (Fig. S2 and Table S1). Sequence analysis of these two sets of unique antibodies (FIG. 1C and Table S2) revealed that they originated from the same inferred immunoglobulin heavy chain variable (IGHV) precursor gene allele IGHV1-2*02. Despite this similarity in heavy chain V-gene origin, the two unique antibody clones originated from different heavy chain J segment genes and contained different light chains. The light chains of the VRC-PG04 and 04b somatic variants originated from an IGκV3 allele while the VRC-CH30, 31 and 32 somatic variants derived from an IGκV1 allele. Of note, all five antibodies contained unusually high mutation frequencies: VRC-PG04 and 04b displayed a VH gene mutation frequency of 30% relative to the germline IGHV1-2*02 allele, a level of affinity maturation similar to that previously observed with VRC01-03; the VRC-CH30, 31 and 32 antibodies were also highly affinity matured, with VH mutation frequency of 23-24%.

Figures 1D, 1E:
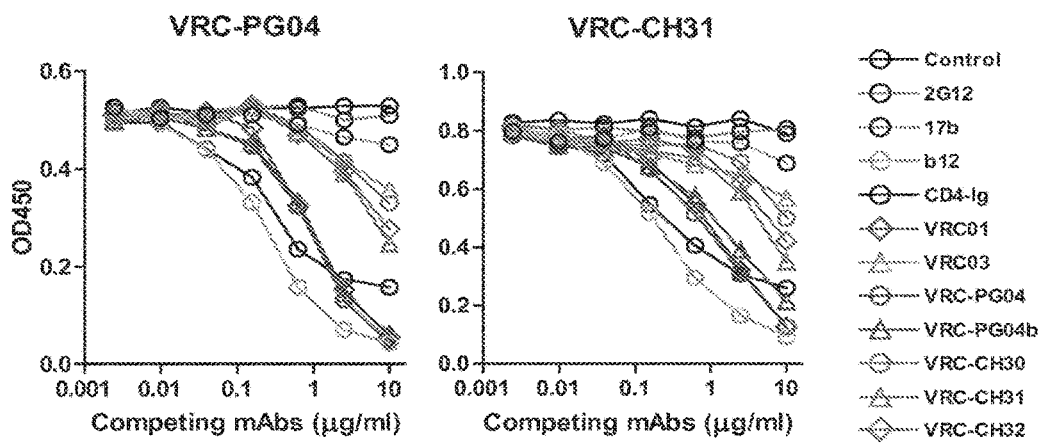
Figure 1F:
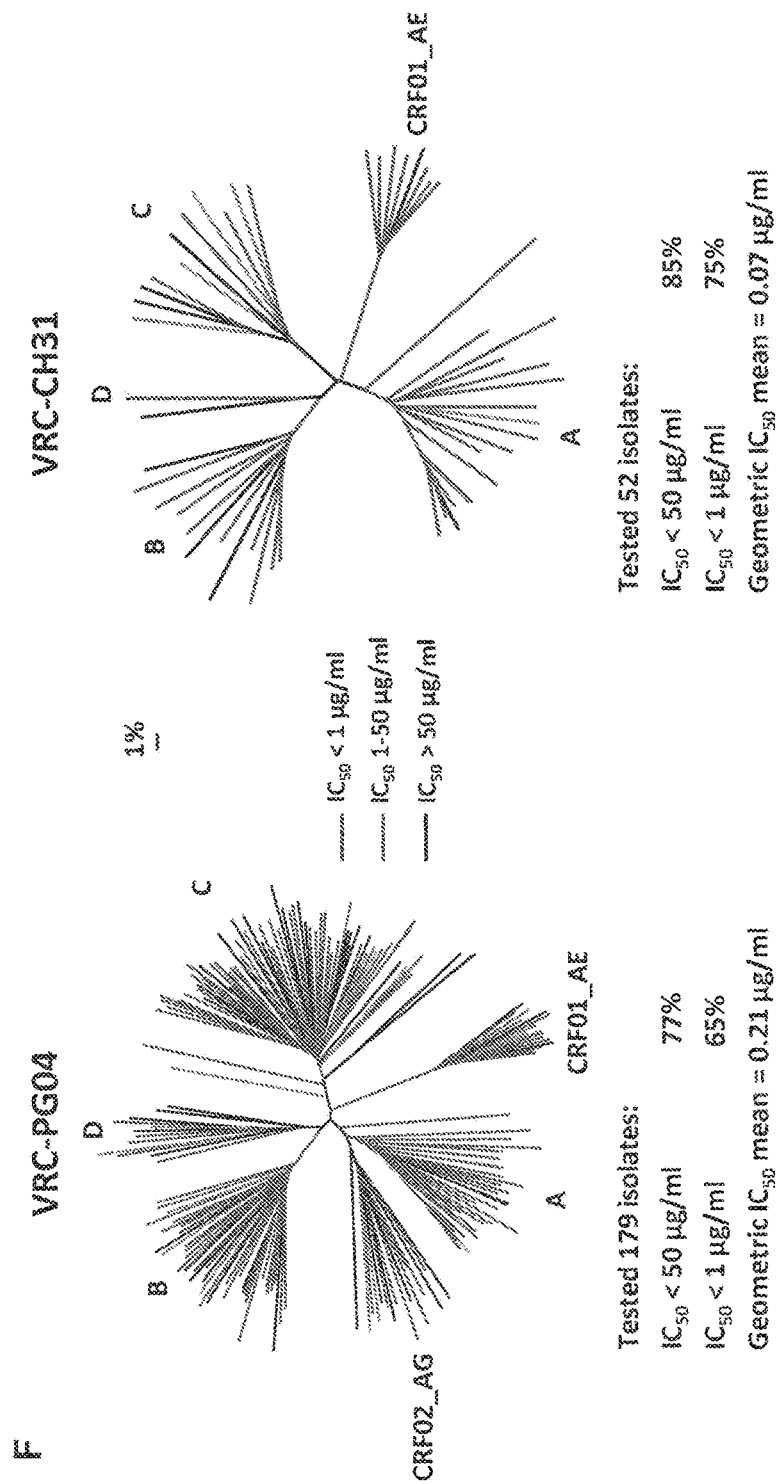

To define the reactivities of these new antibodies on gp120, we performed competition ELISAs with a panel of well-characterized mAbs. Binding by each of the new antibodies was competed by VRC01-03, by other CD4-binding-site antibodies and by CD4-Ig, but not by antibodies known to bind gp120 at other sites (FIGS. 1D and S3). Despite similarities in gp120 reactivity and VH-genomic origin, sequence similarities of heavy and light chain gene regions did not readily account for their common mode of gp120 recognition (FIG. 1E). Finally, assessment of VRC-PG04 and VRC-CH31 neutralization on a panel of Env-pseudoviruses revealed their ability to potently neutralize a majority of diverse HIV-1 isolates (FIG. 1F and Table S3).

Figures 2A, 2B, 2C:
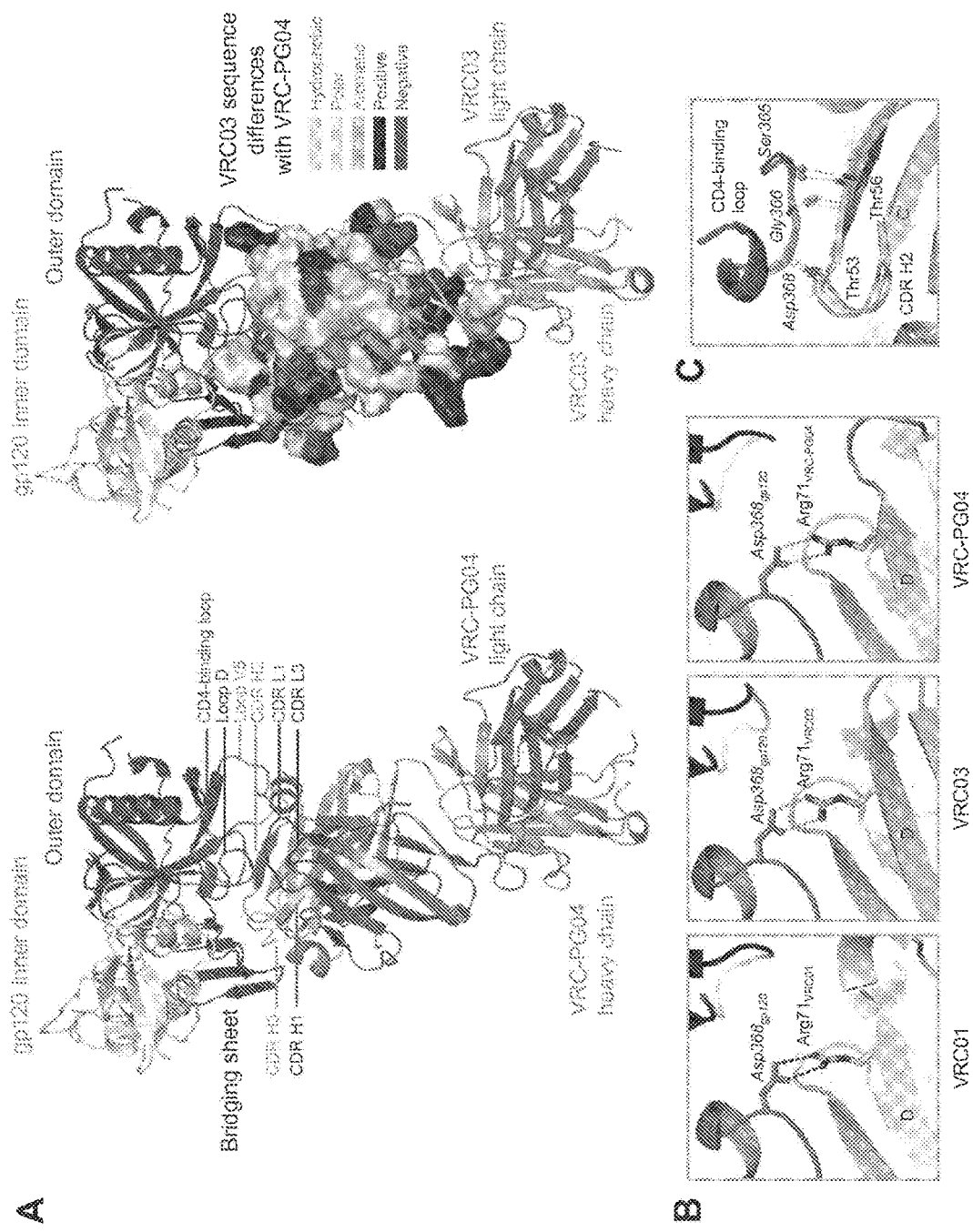
FIGS. 2A-C. Structure of antibodies VRC-PG04 and VRC03 in complex with HIV-1 gp120. Despite being elicited and maturing in different individuals, broadly neutralizing antibodies VRC-PG04 and VRC03 display remarkable similarities in recognition of HIV-1. (A) Overall structures. The liganded complex for the Fab of antibody VRC-PG04 from donor 74 and the HIV-1 gp120 envelope glycoprotein from isolate 93TH057 is depicted with polypeptide backbones in ribbon representation in the left image. The complex of Fab VRC03 from donor 45 is depicted in the right image, with surfaces of all variable domain residues that differ between VRC03 and VRC-PG04 colored according to their chemical characteristics. Although VRC-PG04 and VRC03 derive from the same inferred heavy chain V-gene, roughly 40% of their variable domain residues have been altered relative to each other during the maturation process. (B and C) Interaction close-ups. Critical interactions are shown between the CD4-binding loop of gp120 (purple) and the CDR H2 region of the broadly neutralizing mAbs, VRC03 and VRC-PG04 (reported here) and VRC01 (reported previously (19)), with hydrogen bonds depicted as dotted lines. The 1.9 and 2.1 .ANG. resolution structures of VRC03 and VRC-PG04, respectively, were sufficient to define interfacial waters shown in (C), which were unclear in the 2.9 .ANG. structure of VRC01. The orientation shown in (C) is .about.180° rotated about the vertical axis from the orientation shown in (B).

Structural Definition of Gp120 Recognition by RSC3-Identified Antibodies from Different Donors:

A remarkable convergence. To define the mode of gp120 recognition employed by donor 74-derived VRC-PG04, we crystallized its antigen-binding fragment (Fab) in complex with a gp120 core from the clade A/E recombinant 93TH057 that was previously crystallized with VRC01 (19). Diffraction data to 2.1 .ANG. resolution were collected from orthorhombic crystals, and the structure solved by molecular replacement and refined to a crystallographic R-value of 19.8% (FIG. 2A and Tables S4 and S5). The structure of VRC-PG04 in complex with HIV-1 gp120 showed striking similarity with the previously determined complex with VRC01, despite different donor origins and only 50% amino acid identity in the heavy chain-variable region (FIG. 2). When gp120s were superimposed, the resultant heavy chain positions of VRC-PG04 and VRC01 differed by a root-mean-square deviation (rmsd) of 2.1 .ANG. in Cα-atoms, with even more precise alignment of the heavy chain second complementary determining (CDR H2) region (1.5 .ANG. rmsd). Critical interactions such as the $Asp368_{gp\ 120}$ salt bridge to $Arg71_{VRC01}$ were maintained in VRC-PG04 (FIG. 2B).

We also crystallized the gp120-Fab complex of donor 45-derived VRC03. VRC03 and VRC-PG04 share only 51% heavy chain-variable protein sequence identity, and the heavy chain of VRC03 contains an unusual insertion in the framework 3 region (18). Diffraction data to 1.9 .ANG. resolution were collected from orthorhombic crystals, and the structure solved by molecular replacement and refined to a crystallographic R-value of 18.8% (FIG. 2 and Tables S4 and S6). VRC03 also showed recognition of gp120 that was strikingly similar to that of VRC-PG04 and VRC01, with pairwise rmsds in Cα-atoms of 2.4 .ANG. and 1.9 .ANG. In particular, CDR H2 and CDR L3 regions showed similar recognition (pairwise Cα-rmds ranged from 0.7-1.6 .ANG.) (Fig. S4).

In general, the repertoire of possible immunoglobulin products is very large and highly similar modes of antibody recognition are expected to occur infrequently (25). We analyzed other families of HIV-1 specific antibodies that share a common IGVH-gene origin (26-29), including the CD4-induced antibodies, which often derive from a common VH1-69 allele. Analysis of the recognition of gp120 by these antibodies indicated substantial variation in their recognition, with angular difference in heavy chain recognition of over 90° (Table S7). We also analyzed other CD4-binding site antibodies that are also recognized well by the RSC3 probe, such as antibodies b12 and b13 (16, 30); these other RSC3-reactive antibodies also showed dramatic differences in heavy chain orientation (Table S8).

Figure 3B:
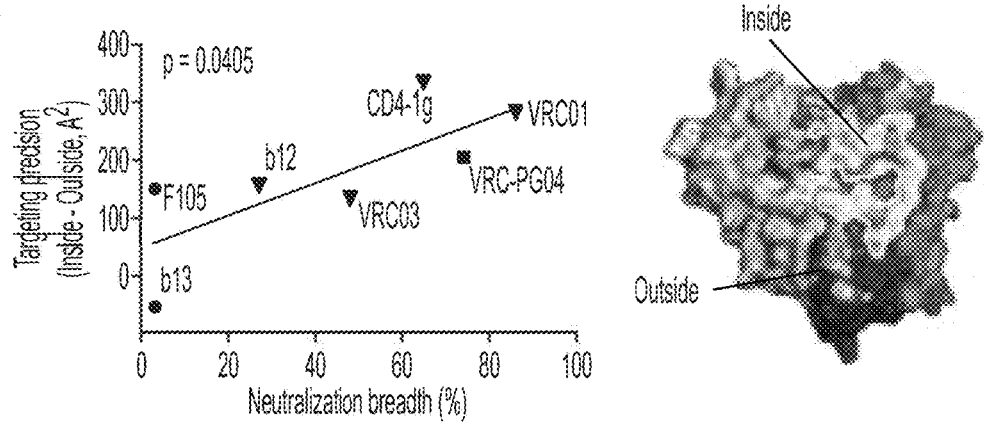

The remarkable convergence in recognition observed with VRC01, VRC03, and VRC-PG04 suggested a common mode of HIV-1 gp120 recognition, conserved between donors infected with a Glade B (donor 45) and Glade A/D (donor 74) strain of HIV-1. The precision required for this mode of recognition likely arises as a consequence of the multiple mechanisms of immune evasion that protect the site of CD4 attachment on HIV-1 gp120 (30). We analyzed paratope surface properties and found that the average energy of antibody hydrophobic interactions ($\Delta^{iG}$) correlated with the convergence in antibody recognition (P=0.0427) (FIG. 3A) (31). Thus while precise H-bonding is required for this mode of recognition (FIG. 2C), the convergence in structure appears to optimize regions with hydrophobic interactions. Another important feature of this mode of recognition is its ability to focus precisely on the initial site of CD4 receptor attachment (19, 32). Indeed, the breadth of HIV-1 neutralization among CD4-binding-site ligands correlated with targeting onto this site (P=0.0405) (FIG. 3B).

Figure 3C:
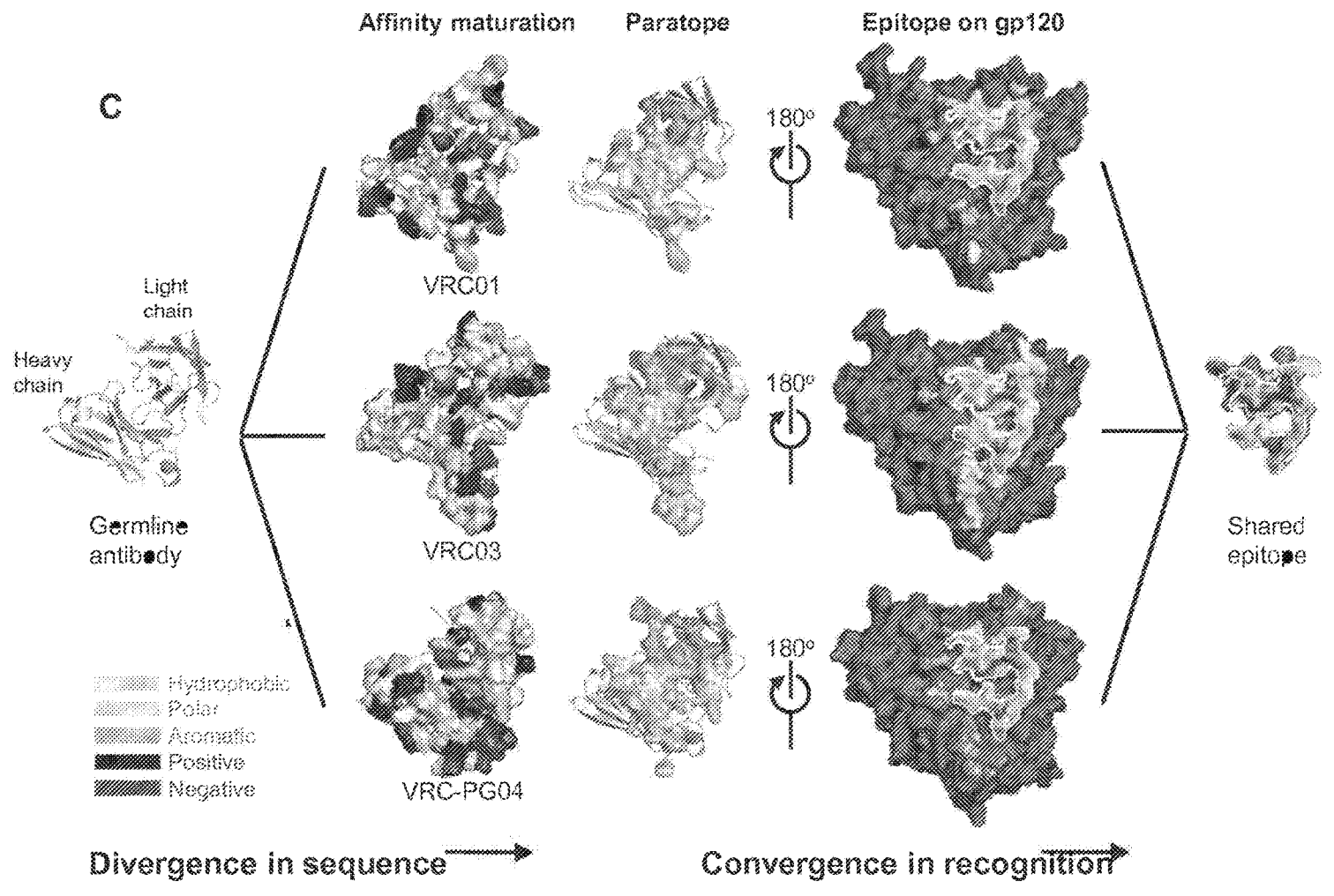

This convergence in epitope recognition is accompanied by a divergence in antibody sequence identity (FIGS. 1C, 1E and 3C). All eight antibodies isolated by RSC3 binding utilize the germline IGHV1-2*02 and accrue 70-90 nucleotide changes. Despite the similarity in mature antibody recognition, only 2 residues from the germline IGHV1-2*02 allele change to the same amino acids (FIG. 1C). Both of these changes occur at a hydrophobic contact in the critical CDR H2 region ($Gly_{56}$Thr.fwdarw.$Ala_{56}$Val). The light chains for donors 45 and 74 antibodies arise from either IGVκ3-11*01 or IGVκ3-20*01, while the light chains of donor 0219 antibodies are derived from from IGVκ1-33*01.

For these light chains, no maturational changes are identical. Despite this diversity in maturation, comparison of the VRC01, VRC03, and VRC-PG04 paratopes shows that many of these changes are of conserved chemical character (FIG. 3C); a hydrophobic patch in the CDR L3, for example, is preserved. These observations suggest that divergent amino acid changes among VRC01-like antibodies nevertheless afford convergent recognition when guided by affinity maturation.

Functional Complementation of Heavy and Light Chains Among VRC01-Like Antibodies.

While the identification and sorting of antigen-specific B cells with resurfaced probes has resulted in the isolation of several broadly neutralizing antibodies, genomic analysis of B-cell cDNA libraries provide substantially greater sequence complexity. These sequences specify the functional antibodyome, the repertoire of expressed antibody heavy and light chain sequences in each individual. High-throughput sequencing methods provide heavy chain and light chain sequences, but do not retain information about their pairings. For VRC01-like antibodies, the structural convergence revealed by the crystallographic analysis indicated a potential solution: different heavy and light chains might achieve functional complementation within this antibody family.

Figure 4A:
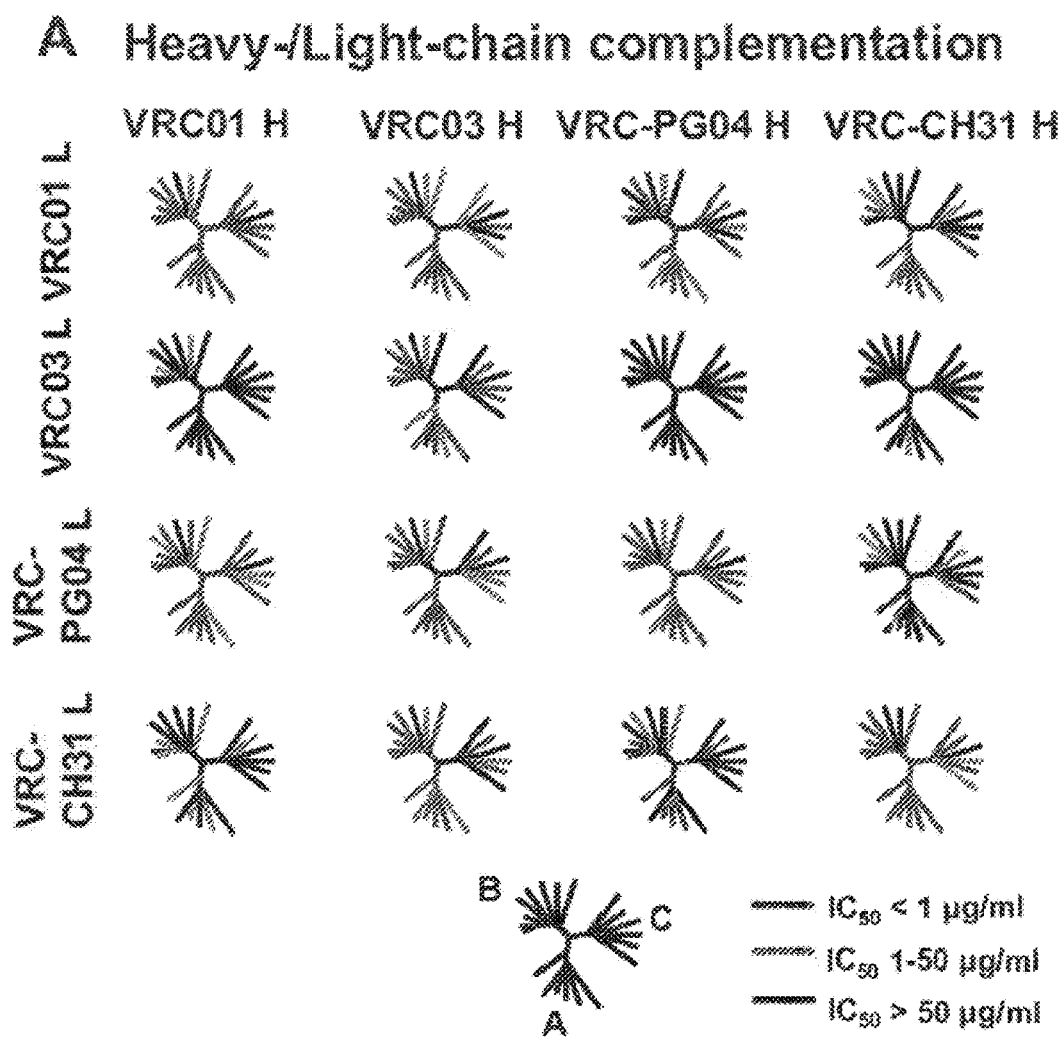

Heavy and light chain chimeras of VRC01, VRC03, VRC-PG04 and VRC-CH31 were produced by transient transfection (Table S9) and tested for HIV-1 neutralization (Table S10). VRC01 (donor 45) and VRC-PG04 (donor 74) light chains were functionally compatible with VRC01, VRC03 and VRC-PG04 heavy chains, though the VRC03 light chain was compatible only with the VRC03 heavy chain (FIG. 4A and Table S10). Similarly, despite .about.50% differences in sequence identity (FIG. 1E), the VRC-CH31 (donor 0219) heavy and light chains were able to functionally complement most of the other antibodies (FIG. 4A and Table S10).

Identification of VRC01-Like Antibodies by Deep Sequencing of Donors 45 and 74.

To study the antibody repertoire in these individuals, we performed deep sequencing of cDNA from donor 45 PBMC (33). Because the variable regions of heavy and light chains are roughly 400 nucleotides in length, 454 pyrosequencing methods, which allow read lengths of 500 nucleotides, were used for deep sequencing. We first assessed heavy chain sequences from a 2008 PBMC sample from donor 45, the same time point from which antibodies VRC01, VRC02, and VRC03 were isolated by RSC3-probing of the memory B-cell population (18). mRNA from 5 million PBMC was used as the template for PCR to preferentially amplify the IgG and IgM genes from the IGHV1 family. 454 pyrosequencing provided 221,104 sequences of which 33,386 encoded heavy chain variable domains that encompassed the entire V(D)J region (Appendix 1).

To categorize the donor 45-heavy chain sequence information, we chose characteristics particular to the heavy chains of VRC01 and VRC03 as filters: (i) sequence identity, (ii) IGHV gene allele origin, and (iii) sequence divergence from the germline IGHV-gene as a result of affinity maturation (FIG. 4B). Specifically, we divided sequences into IGHV1-2*02 allelic origin (4597 sequences) and non-IGHV1-2*02 origin (28,789 sequences), and analyzed divergence from inferred germline genes, and sequence identity to the template antibodies VRC01 and VRC03 (FIG. 4B). Interestingly, no sequence of higher than 75% identity to the VRC01 or VRC02 heavy chain was found, although 109 sequences of greater than 90% sequence identity to VRC03 were found and all were of IGHV1-2*02 origin (FIGS. 4B and S6). These sequences formed a well segregated cluster on a contour plot. To assess biological function, chimeric antibodies were made by pairing each of the two heavy chain sequences from the 454 sequence set with the VRC03 light chain. In both cases, potent neutralization was observed, with neutralization similar to the original VRC03 antibody (FIG. 4E and Table S15) (34).

A similar heavy chain-deep sequencing analysis was performed with donor 74 PBMC from the same 2008 time point from which VRC-PG04 and VRC-PG04b were isolated. In the initial analysis, despite obtaining 263,764 sequences of which 85,851 encompassed the full V(D)J regions of the heavy chain, no sequences of greater than 75% identity to VRC-PG04 were found (Fig. S8 and Appendix 4). Because the number of unique heavy chain mRNAs present in the PBMC sample was likely much larger than the number of unique sequences obtained in the initial analysis, we repeated the deep sequencing of this sample with an increased number of 454 pyrosequencing reads and with protocols that optimized read length. In this analysis, 110,386 sequences of IGHV1-2*02 origin and 606,047 sequences of non-IGHV1-2*02-origin were found to encompassed the V(D)J region of the heavy chain, a 10-fold increase in sequencing depth. Among these sequences, 4920 displayed greater than 75% identity to VRC-PG04 (FIG. 4B and Appendix 2). Heavy chain sequences of the IGHV1-2*02 allelic origin segregated into several clusters, one at .about.25% divergence and .about.85% identity to the VRC-PG04 heavy chain, and several at 25-35% divergence and 65%, 85%, and 95% identity to VRC-PG04 (FIG. 4B).

Figure 4C:
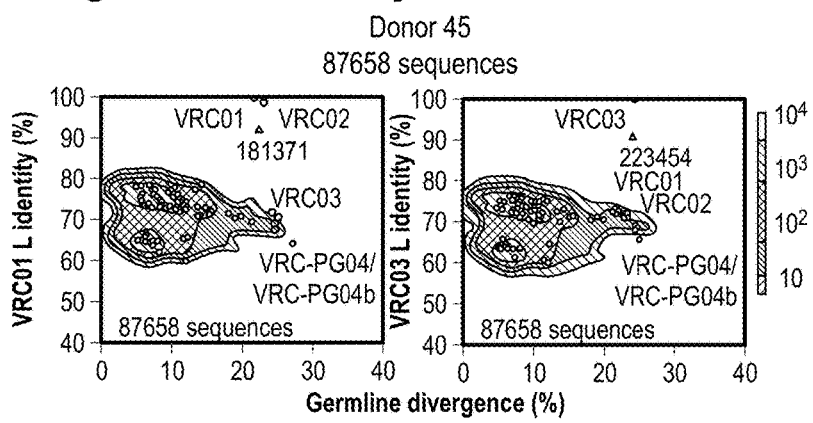
Figure 4D:
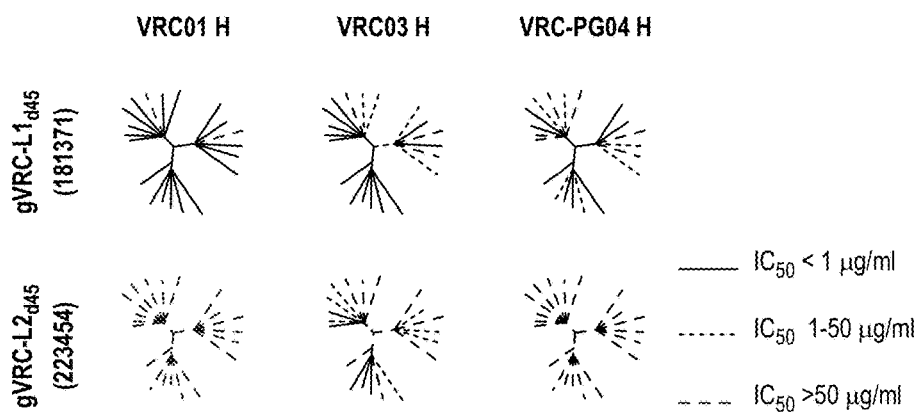
Figure 4E:
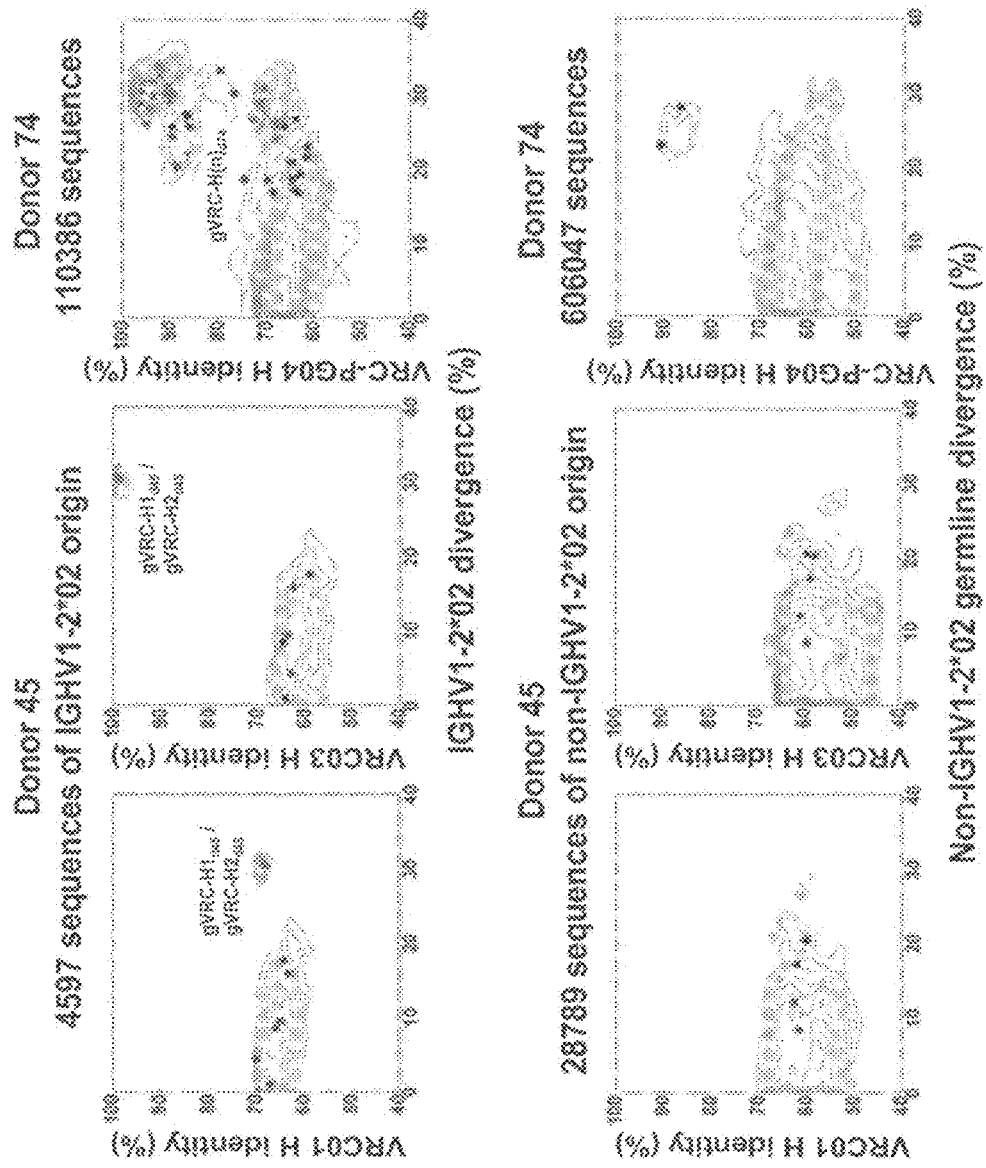

To assess the biological function of these numerous 454-identified heavy chain sequences, we selected representative sequences from the quadrant defined by high divergence (16-38%) and high sequence similarity (60-100%) to VRC-PG04 (Fig. S9). A total of 63 sequences were synthesized and expressed with the VRC-PG04 light chain (Table S14). Remarkably, many of these antibodies displayed potent HIV-1 neutralization (35), confirming that these were functional VRC-PG04-like heavy chains (FIG. 4E and Table S15).

We next performed a similar analysis of the antibody light chain. Because VRC01-03 and VRC-PG04 derive from IGκV3 alleles, we used primers designed to amplify the IGκV3 gene family. We chose a donor 45 2001 time point to maximize the likelihood of obtaining light chain sequences capable of functional complementation (36). A total of 305,475 sequences were determined of which 87,658 sequences encompassed the V-J region of the light chain (Appendix 3). To classify the donor 45-light chain sequences into useful subsets, we again chose biologically specific characteristics: A distinctive 2-amino acid deletion in the first complementary-determining region and high affinity maturation (17% and 19% for VRC01 and VRC-PG04, respectively). Two such sequences with .about.90% sequence identity to their VRC01 and VRC03 light chains, respectively, were identified (FIG. 4C). We assessed their biological function after synthesis in combination with the VRC01, VRC03, and VRC-PG04 heavy chains (Table S16). When paired with their respective matching wild type heavy chain to produce a full IgG, both chimeric antibodies displayed neutralization similar to the wild type antibody (FIG. 4D and Table S15).

Maturation Similarities of VRC01-Like Antibodies in Different Donors Revealed by Phylogenetic Analysis.

Figure 5A:
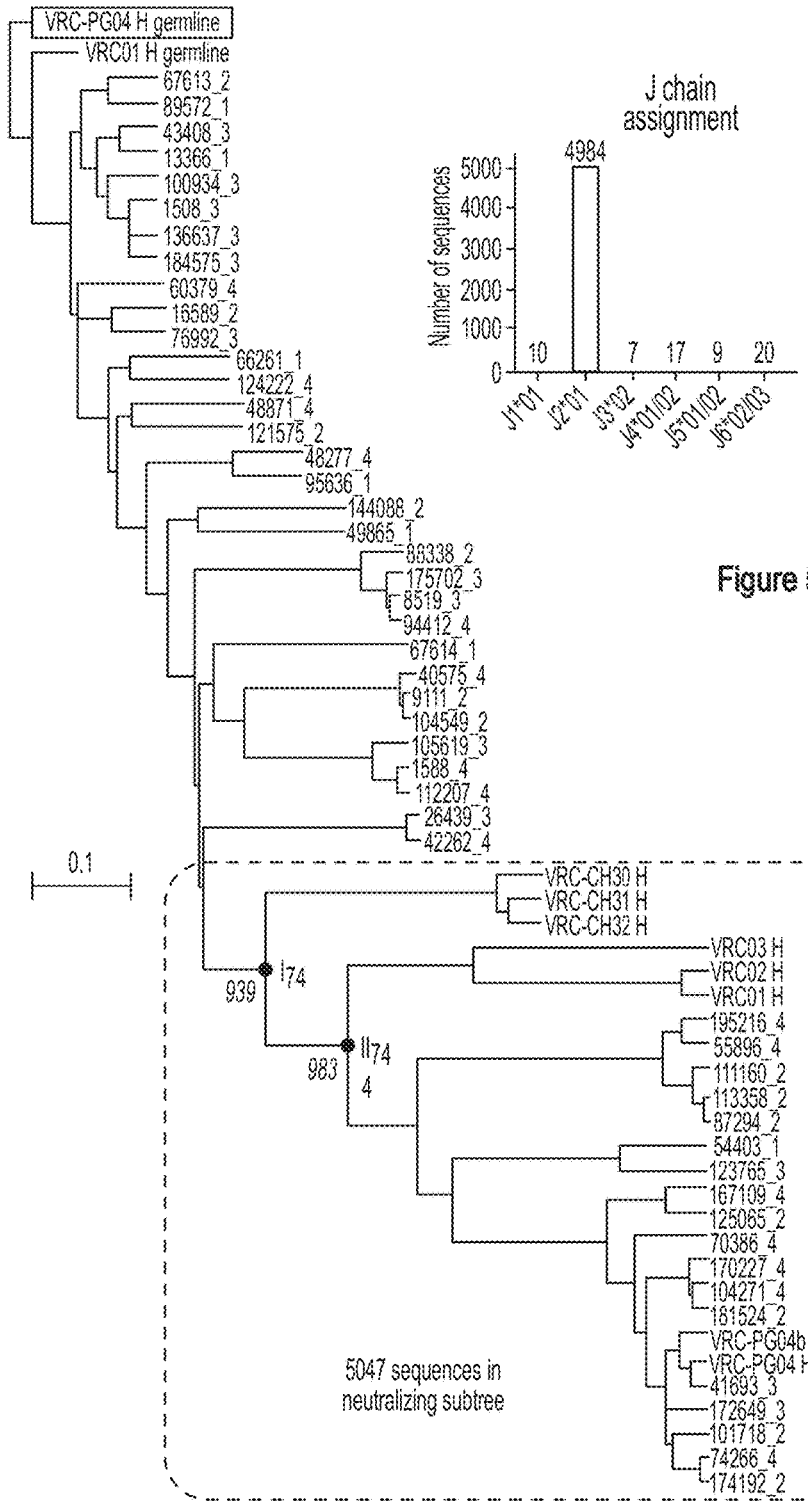
FIGS. 5A-B. Maturational similarities of VRC01-like antibodies in different donors revealed by phylogenetic analysis. The structural convergence in maturation of VRC01-like antibodies suggested similarities of their maturation processes; phylogenetic analysis revealed such similarities and allowed maturation intermediates to be inferred. (A) Neighbor-joining phylogenetic trees of heavy chain sequences from donor 45 (left) and donor 74 (right). The donor 45 tree is rooted by the putative reverted unmutated ancestor of the heavy chain of VRC01, and also includes specific neutralizing sequences from donor 74 and 0219 (shown in red). Similarly the donor 74 tree is rooted in the putative reverted unmutated ancestor of the heavy chain of VRC-PG04, and sequences donor 45 and 0219 are included in the phylogenetic analysis. Bars representing 0.1 changes per nucleotide sequence are shown. Insets show J chain assignments for all sequences within the neutralizing subtree identified by the exogenous donor sequences. (B) Phylogenetically inferred maturation intermediates. Backbone ribbon representations are shown for HIV-1 gp120 (red) and the heavy chain variable domains (green). Critical intermediates defined from the phylogenetic tree in (A) are labeled $I_{45}$, $II_{45}$, $III_{45}$, $I_{74}$ and $II_{74}$. The number of VH-gene mutations is provided (e.g. $I_{45}$: 23), and the location of these is highlighted in the surface representation and colored according to their chemistry.

The structural convergence in gp120 recognition and the functional complementation between VRC01-like antibodies from different donors suggested similarities in their maturation processes. We therefore performed phylogenetic analysis to assess the evolutionary relationship among sequences derived from the same precursor germline gene. We hypothesized that if known VRC01-like sequences from one donor were added to the analysis of sequences of another donor, a genomic-rooted phylogenetic tree might reveal similarities in antibody maturation pathways. Specifically, with such an analysis, the exogenous sequences would be expected to interpose between branches in the dendrogram containing VRC01-like antibodies and branches containing non-VRC01-like antibodies from the original donor's antibodyome. We performed this analysis with heavy chains, as all of the probe-identified VRC01-like antibodies derived from the same heavy chain IGHV1-2*02 allele. We added the donor 74-derived VRC-PG04 and 4b and donor 0219-derived VRC-CH30, 31 and 32 heavy chain sequences to the donor 45 antibodyome sequences of IGHV1-2*02 genomic origin and constructed a phylogenetic tree rooted by the predicted VRC01 unmutated germline ancestor (18). This analysis revealed that sequences of high identity to VRC03 clustered as a subtree of a common node that was also the parent to donor 74 and 0219 VRC01-like heavy chain sequences (FIG. 5A, left). When donor 45 neutralization was assessed according to this phylogenetic segregation, a P-value less than 0.0001 was observed indicating significant correlation between the phylogenetic segregation and predicted neutralization (Fig. S7).

Figure 6A:
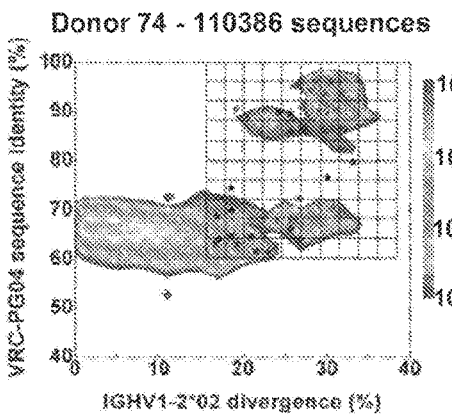
Figure 6C:
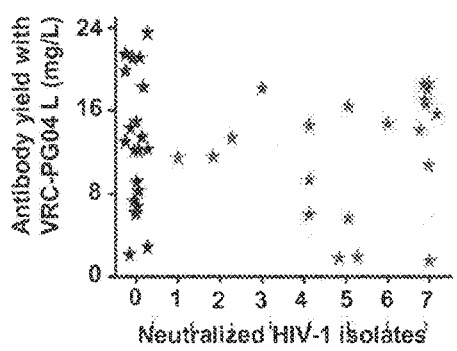
Figure 6D:
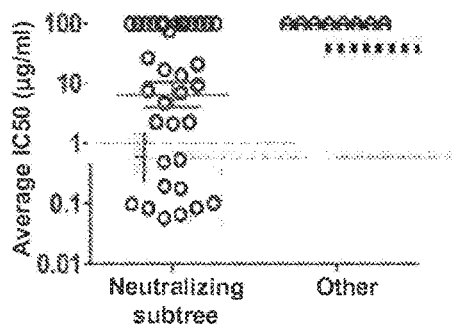
Figure 6B:
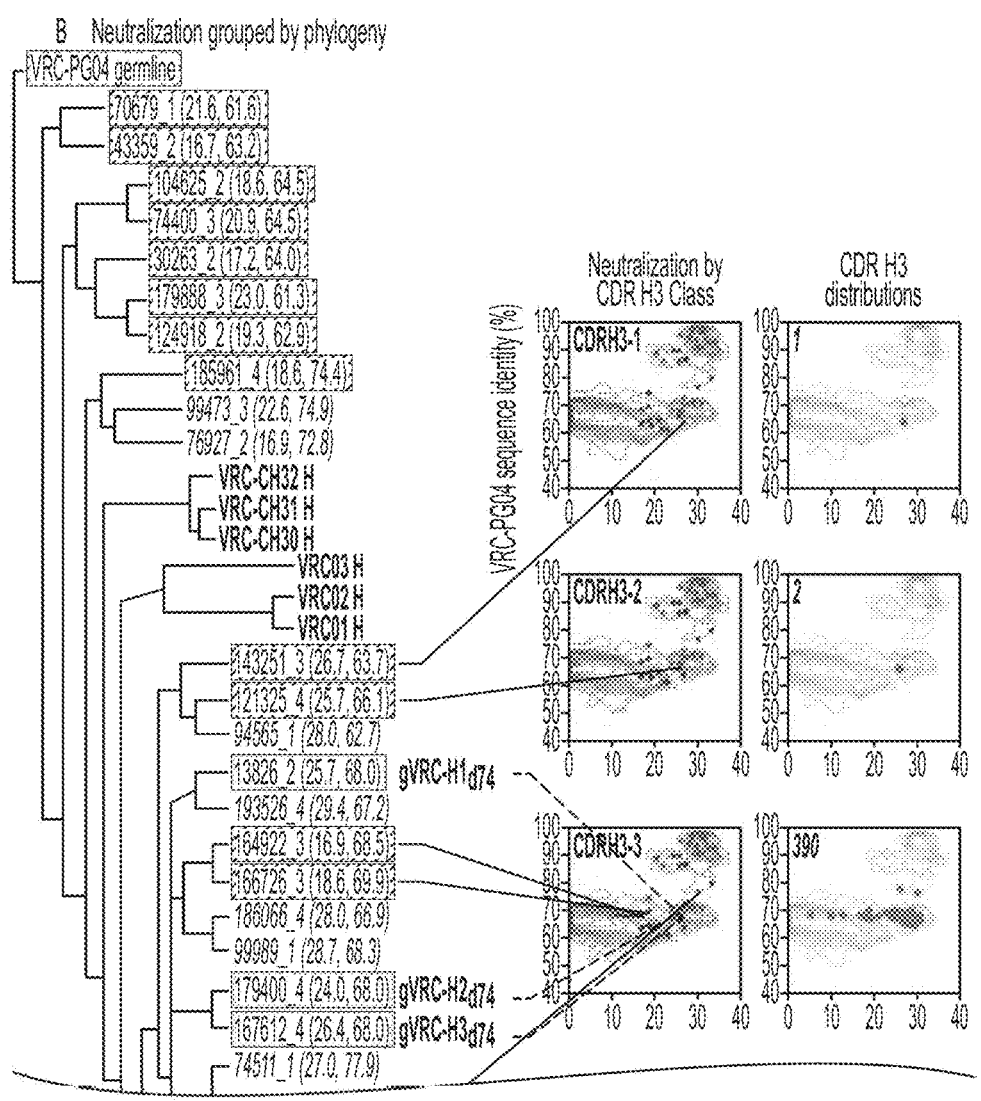
Figure 6B:
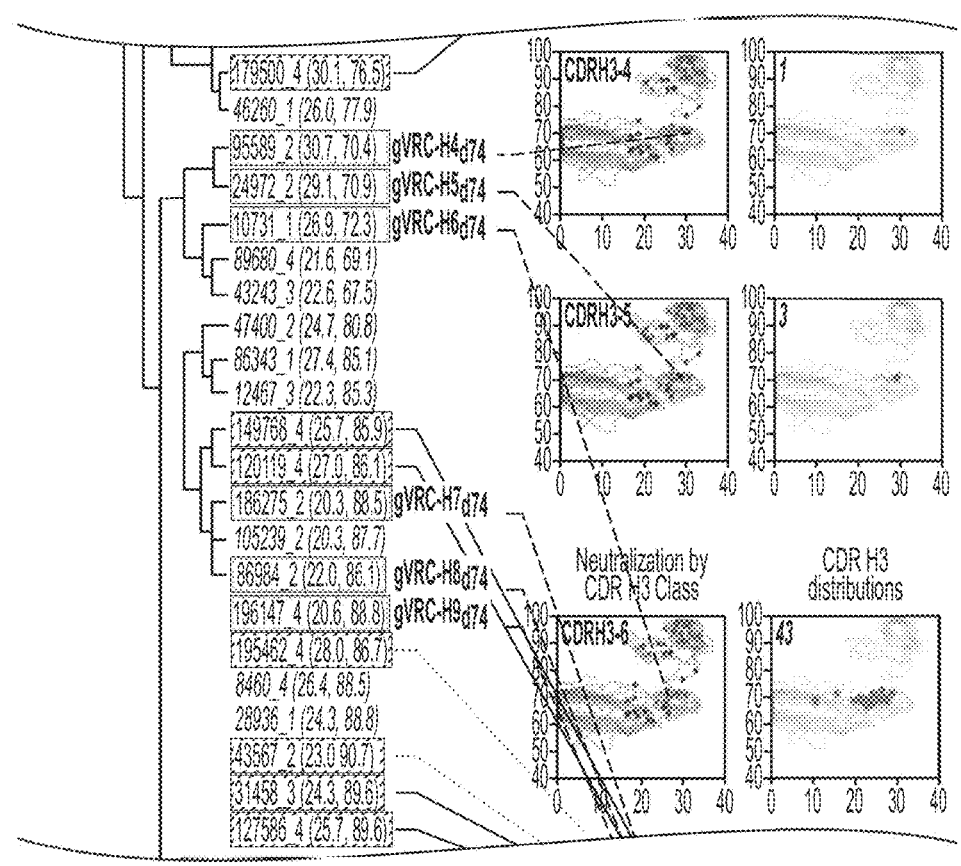
Figure 6B:
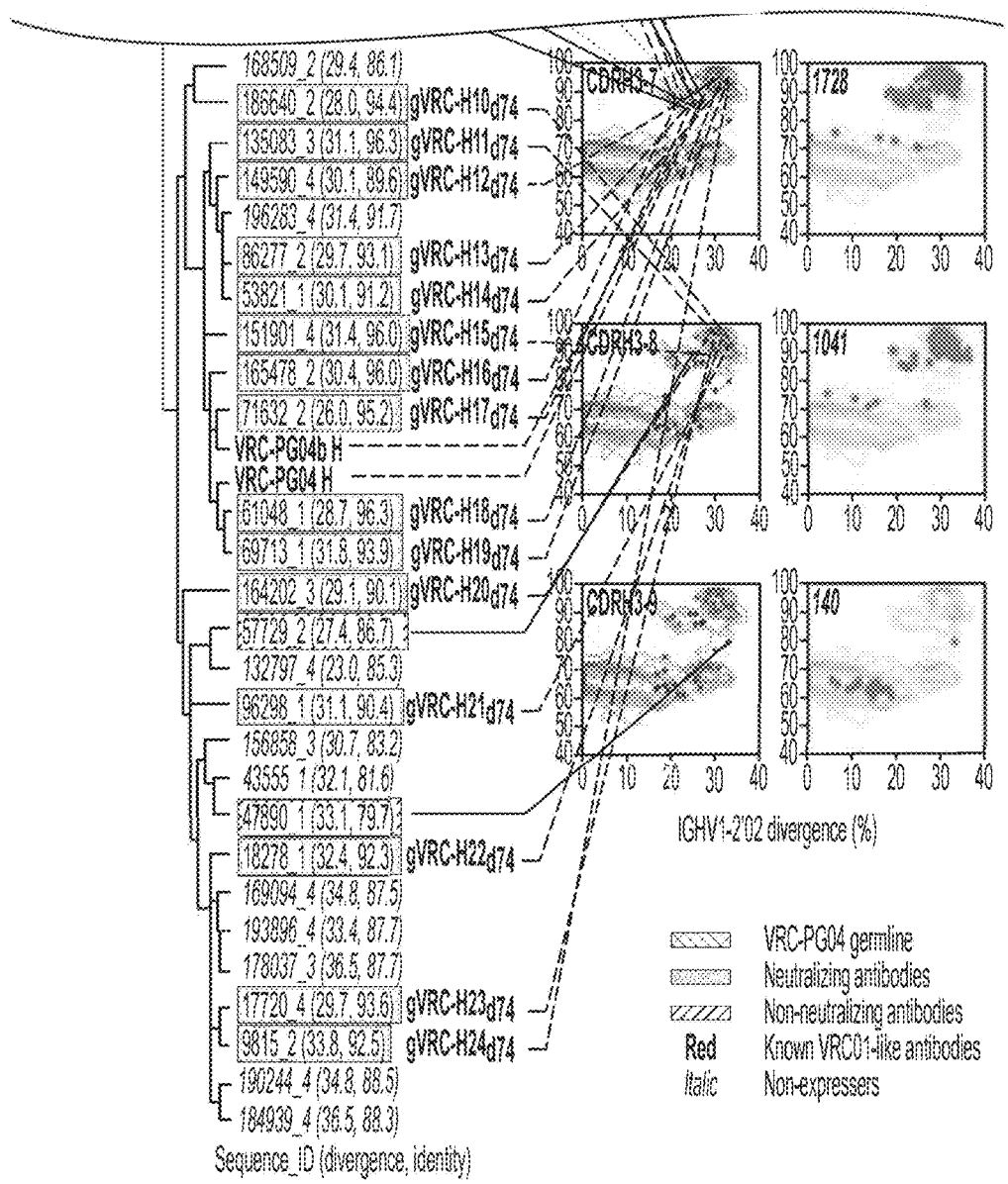

We also assessed the donor 74-derived IGHV1-2*02 heavy chain sequences by including probe-identified VRC01-like antibodies from donor 45 and donor 0219 in the phylogenetic analysis. In the tree rooted by the predicted VRC-PG04 unmutated germline ancestor, 5047 sequences segregated within the donor 45 and 0219-identified subtree (FIG. 5A, right). This subtree included the actual VRC-PG04 and 04b heavy chain sequences, 4693 sequences of >85% identity to VRC-PG04, and several hundred sequences with identities as low as 68% to VRC-PG04. To test the functional activity of heavy chain sequences identified by this phylogenetic analysis, we first assessed the phylogenetic location of the 63 heavy chain sequences that were identified and expressed from the previously described identity/divergence grid (Fig. S9). To these 63 sequences, we added 7 additional sequences from the donor 74 phylogenetic tree to enhance coverage of the phylogenetically segregated sequences (Fig. S10). These sequences were also synthesized and expressed with the VRC-PG04 light chain (Table S14). Among these 70 synthesized heavy chain sequences, 27 did not express. Of the remaining 43 reconstituted antibodies, 22 were able to neutralize HIV-1 (Table S15). Remarkably, all of the neutralizing sequences segregated into the subtree identified by the exogenously added donor 45 and 0219 VRC01-like antibodies (P-value=0.0085) (FIG. 6D).

We also applied this phylogenetic-segregation method to the light chains antibodyome of donor 45. The light chains from donor 74 and 0219 did not segregate with known VRC01-like light chains from donor 45 (Fig. S11), likely because these three light chains do not arise from the same inferred germline sequences. This difference may also reflect the dissimilarities in focused maturation of the two chains (see FIG. 3A): in the heavy chain, focused maturation occurs in the CDR H2 region (encompassed solely within the *02 VH gene from which all VRC01-like heavy chains derive) and, in the light chain, selection pressures occur in the CDR L3 region (which is a product of different types of V-J recombination).

CDR H3-Lineage Analysis.

The 35 heavy chain sequences that both segregated into the VRC01-neutralizing subtree and expressed when reconstituted with the VRC-PG04 light chain could be clustered into 9 CDR H3 classes (FIG. 6B), with sequences in each class containing no more than 5 nucleotide differences in CDR H3 from other sequences in the same class (Fig. S12). A detailed junction analysis of the V(D)J recombination origins of these classes suggested that 8 of the 9 classes arose by separate recombination events (Figs. S13a-b); two of the classes (7 and 8) differed primarily by a single three residues insert/deletion, Arg-Tyr-Ser, and may have arisen from a single V(D)J recombination event (FIG. S13b). Three of these classes (CDR H3-1, 2, and 9) were represented only by non-neutralizing antibodies, three by a single neutralizing antibody (CDR H3-4, 5 and 6), and three by a mixtures of neutralizing and non-neutralizing antibodies (CDR H3-3, 7 and 8). While it was not clear if the non-neutralizing heavy chain sequences truly lacked neutralization function or if this phenotype was due to incompatibilities in light chain pairing, we chose to analyze CDR H3 classes only for those in which neutralization had been confirmed.

Figures 7A, 7B:
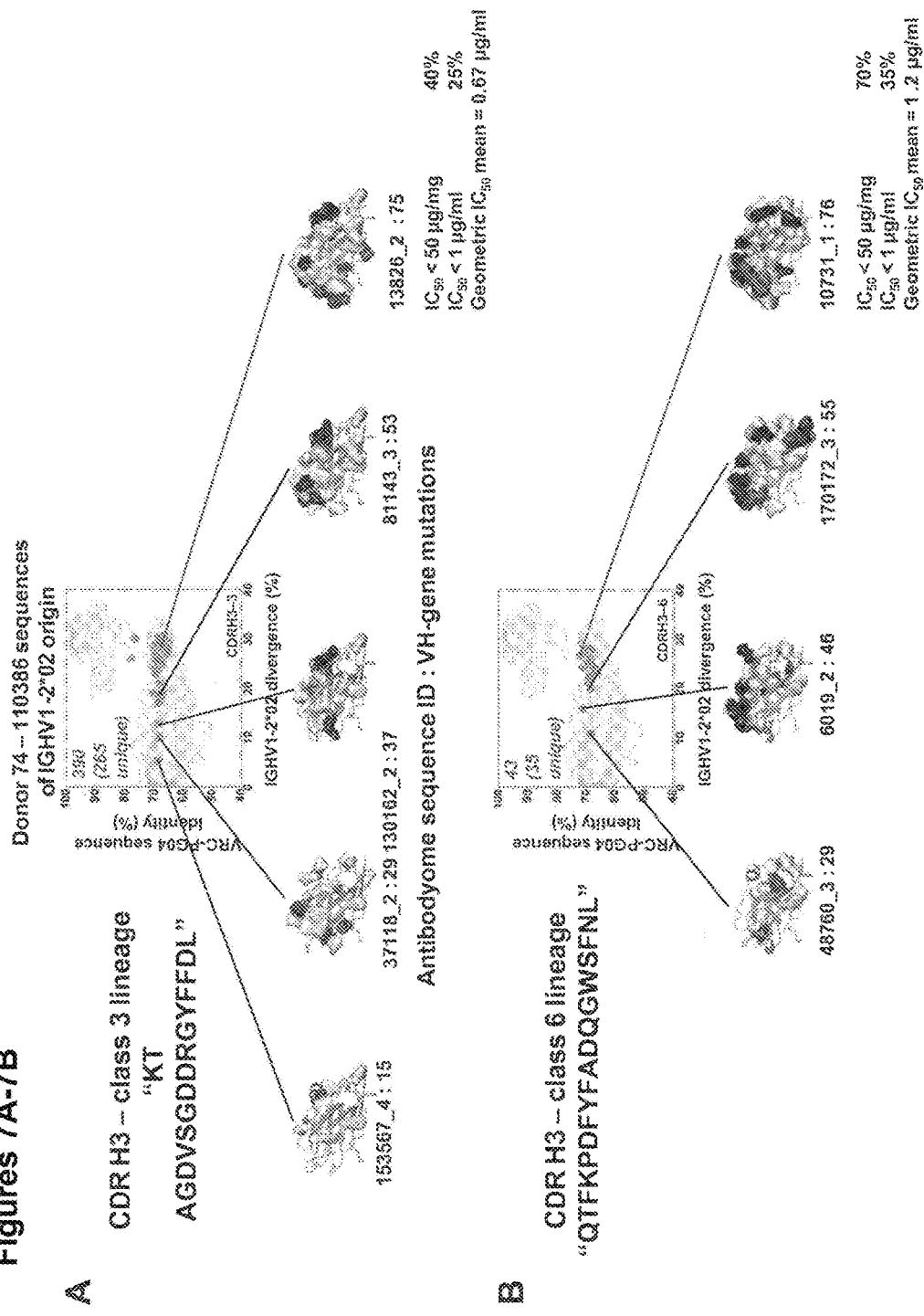
FIGS. 7A-C. Maturation lineages of four unique VRC01-like heavy chains in donor 74. The CDR H3 sequence, a product of V(D)J gene recombination and N nucleotide addition and removal, provides a signature to trace the lineage of a particular B cell. (A) Lineage analysis of CDR H3 class 3 (SEQ ID NO: 133). Grid positions are displayed for the 390 heavy chain sequences with a CDR H3 sequence identical to the identified CDR H3 class 3. These sequences cluster into an elongated family of sequences with moderate identity to VRC-PG04. Representative sequences ranging from low to high IGVH1-2*02 sequence divergence (representing low to high levels of affinity maturation) are shown as structural models of the heavy chain variable domain, with maturation changes highlighted in surface mode colored by chemistry as in FIG. 5B. Sequences of displayed structures are shown in FIG. 22. Overall neutralization breadth and potency for sequence ID 13826_2 was assessed on a 20-isolate HIV-1 panel, with individual neutralization results tabulated in Table S15. (B) Lineage analysis of CDR H3 class 6 (SEQ ID NO: 134) was performed as described above. The sequence ID 10731_1 that was selected in the grid analysis and found to be neutralizing is shown as a member of this family. (C) CDR H3 classes 7 and 8. Analysis of the CDR H3 of classes 7 and 8 (SEQ ID NOS 135-136, respectively) suggest that these might be clonally related (FIG. 21). Sequences from these related classes segregate in similar ways, suggestive of related maturational pathways.
Figure 7C:
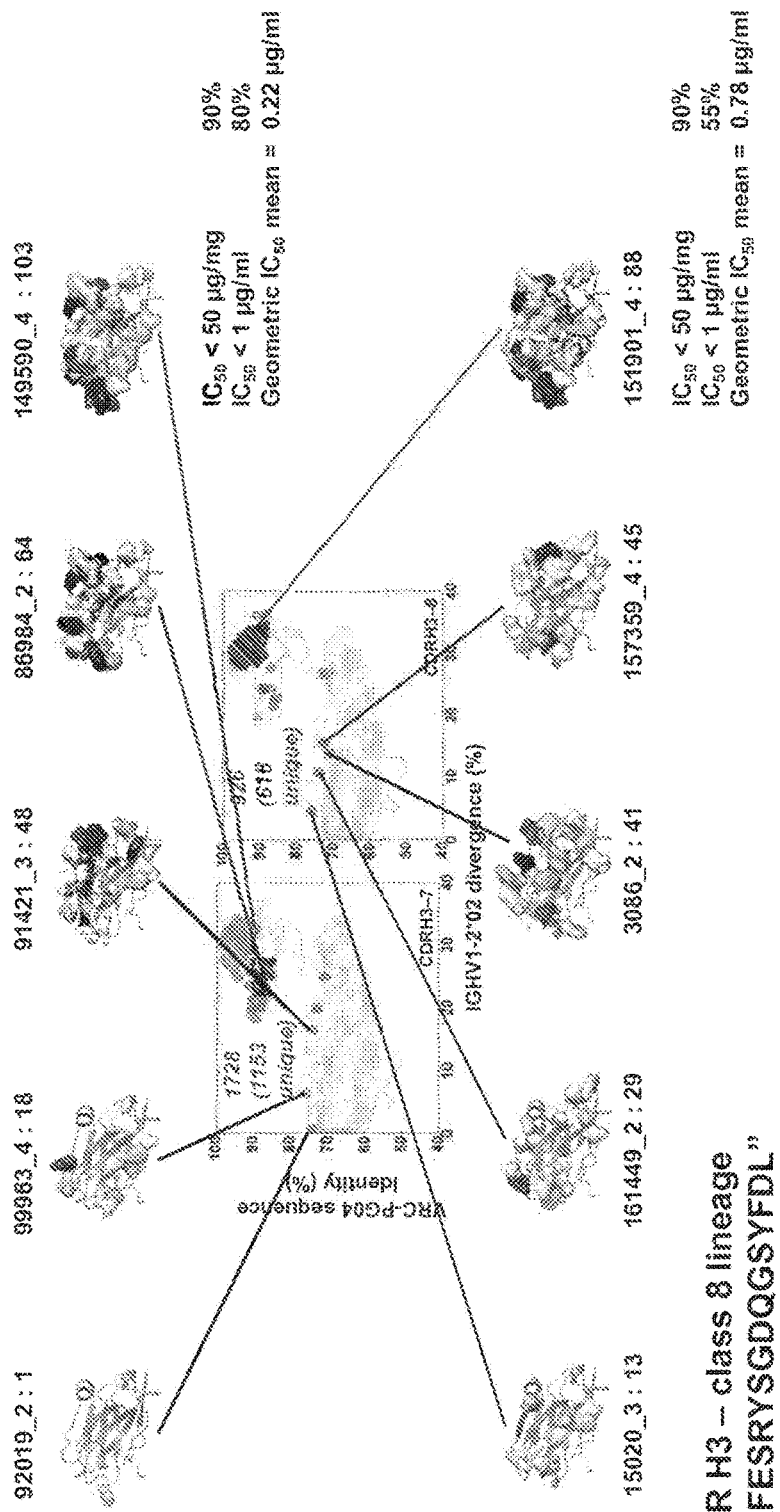
Figure 9:
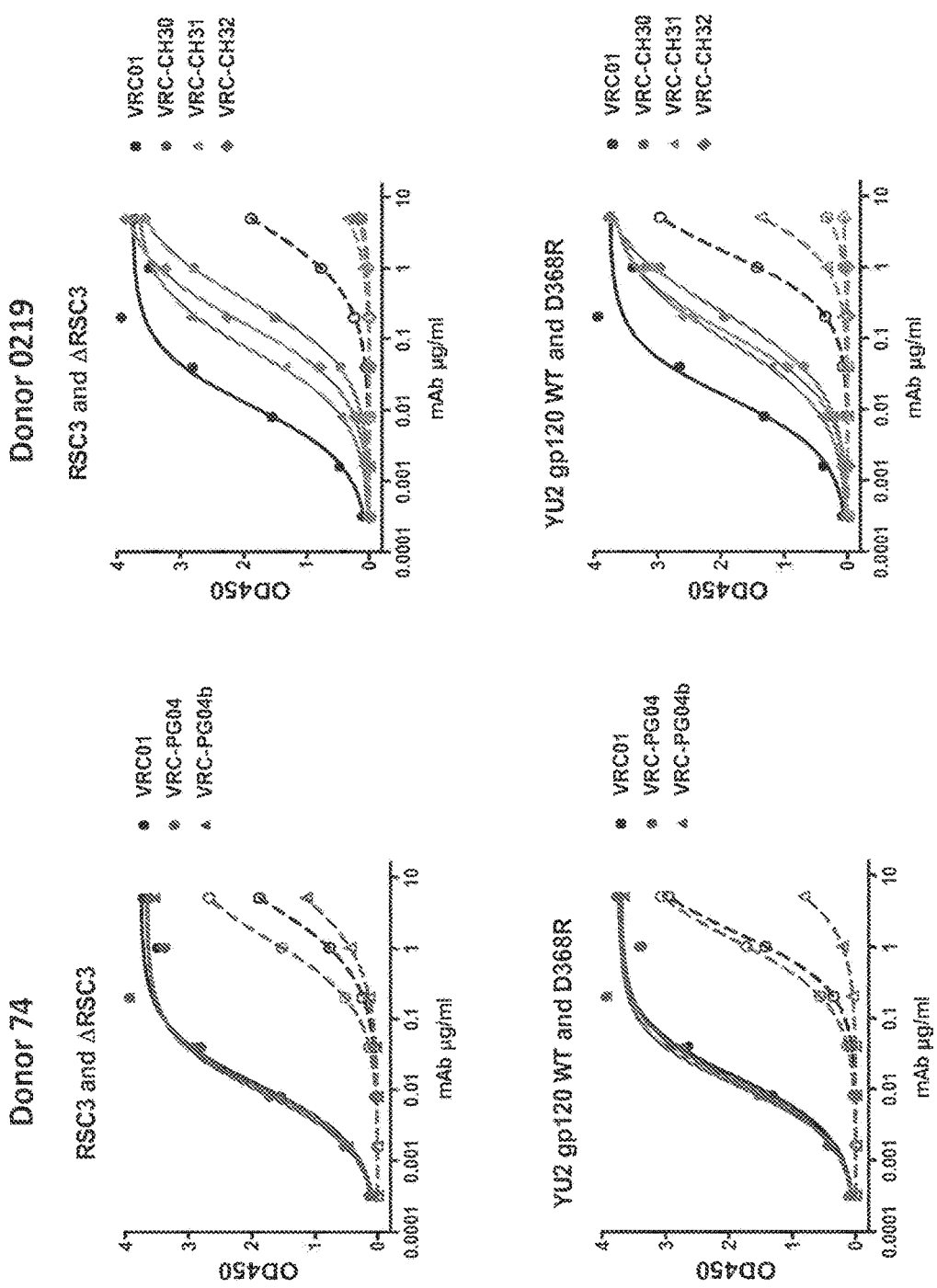
FIG. 9. Antigen binding profiles of five newly isolated mAbs, VRC-PG04, VRC-PG04b, VRC-CH30, VRC-CH31 and VRC-CH32, measured by ELISA. Solid symbols show mAb binding to RSC3 (top) and YU2 gp120 (bottom). Open symbols indicate mAb binding to ΔRSC3 or to the CD4bs knockout mutant of gp120, D368R.
Figure 10:
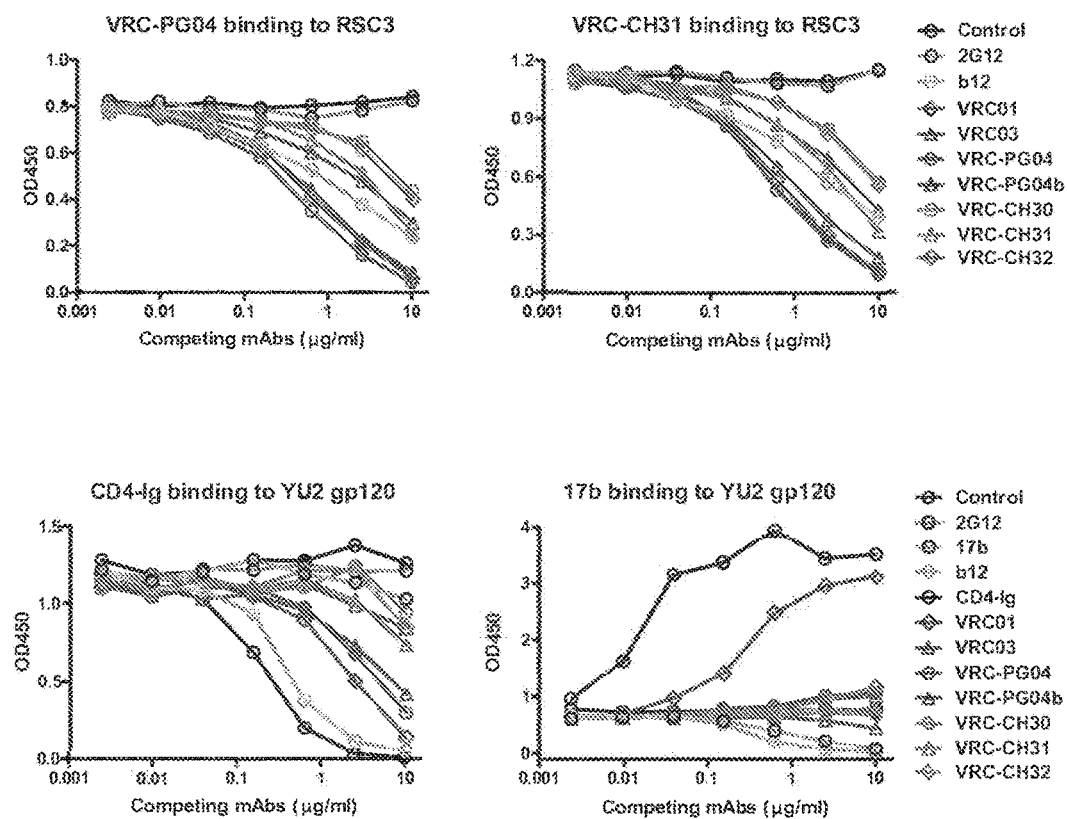
FIG. 10. Competition ELISAs show that mAbs VRC-PG04 and VRC-CH31 are directed to the CD4bs of HIV-1 gp120. The competition ELISAs were performed with a single concentration of biotin-labeled VRC-PG04 or VRC-CH31. Unlabeled mAbs were titrated into the ELISA at increasing concentrations to evaluate the effect on VRC-PG04 or VRC-CH31 binding to RSC3 (top). The competition ELISAs were also performed with a single concentration of biotin-labeled CD4-Ig or the co-receptor binding site mAb 17b. Unlabeled mAbs were titrated into the ELISA at increasing concentrations to evaluate the effect on CD4-Ig or 17b binding to YU2 gp120 (bottom). CD4-Ig is a fusion protein of the N-terminal two domains of CD4 fused with IgG1 Fc to serve as a CD4 surrogate.
Figures 11A, 11B, 11C:
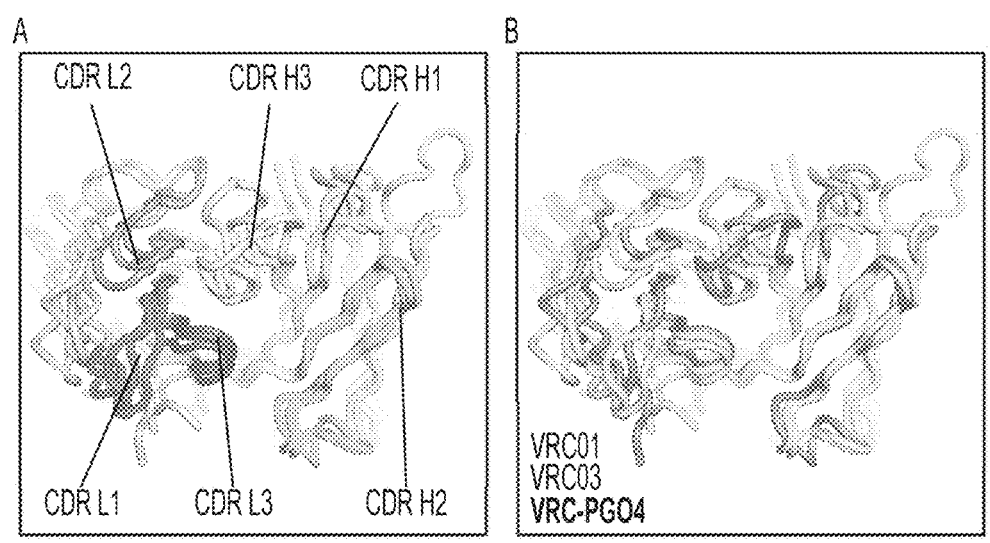
FIGS. 11A-C. CDR H2 and CDR L3 regions of VRC01-like antibodies showed high degree of similarity in recognition. (A) When gp120 were superimposed, orientations of the antibodies in the gp120:antibody complexes were compared. CDR H2 and CDR L3 regions of VRC01-like antibodies showed high precision alignment. (B) Ribbon representation of VRC01, VRC03 and VRC-PG04 in the same orientation as panel A. (C) Pairwise root-mean-square deviation (RMSD) of CDR loops between VRC01, VRC03 and VRC-PG04.
Figure 12:
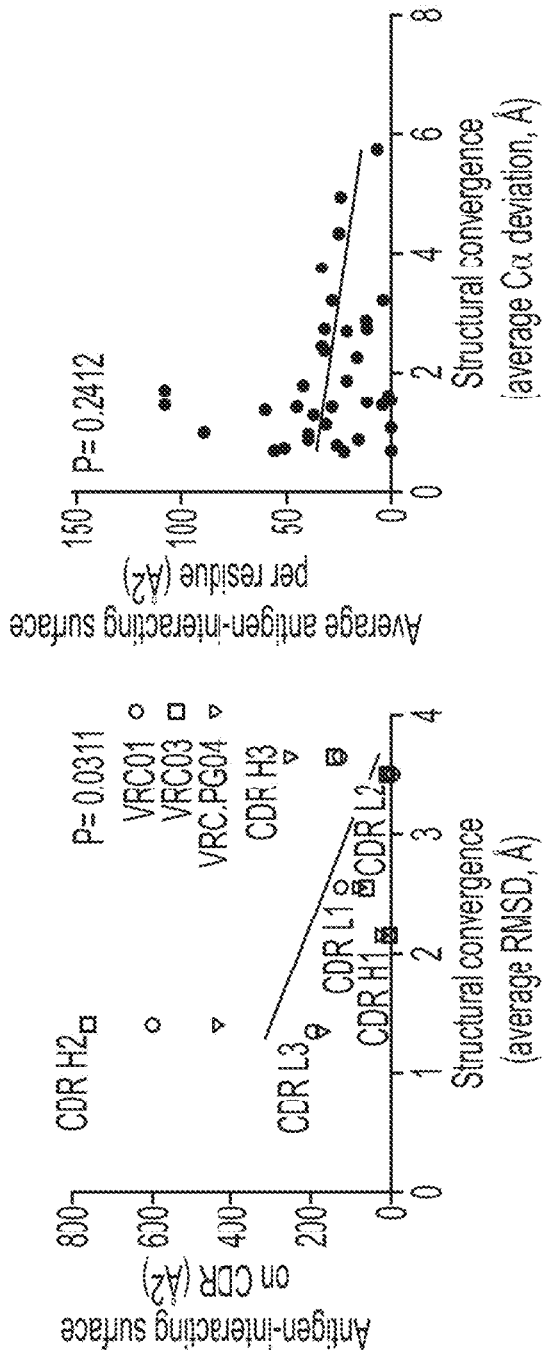
FIG. 12. Correlations between structural convergence and antigen-interacting surface areas of antibody. (left) A significant correlation was found between antigen-interfacing surface on CDR and average RMSD for the six CDR regions in the three available structures (VRC01, VRC03, and VRC-PG04). The point for CDR L3 of VRC03 overlaps almost perfectly with the point for CDR L3 of VRC01 and is not visible. (right) While no correlation was found between average antigen-interfacing surface and Cα deviation for each interface residue, residues with large interface surface were observed to have low Cα deviations.
Figure 13:
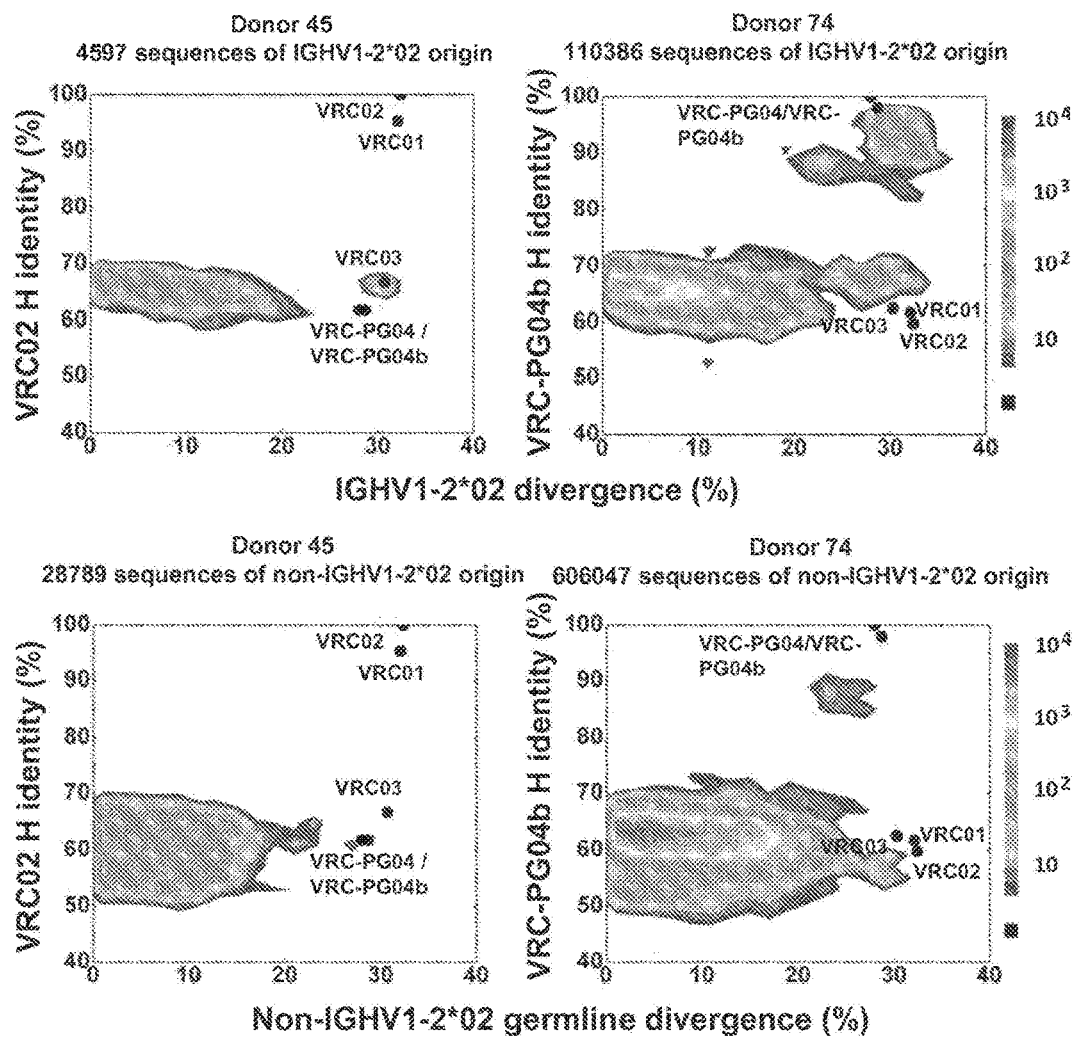
FIG. 13. The 454 sequence distribution of donor 45 and donor 74 heavy-chain antibodyomes plotted as a function of sequence identity to VRC02 and VRC-PG04b and sequence divergence from respective germlines. Row one plots sequences of IGHV1-2*02 and row two plots sequences of other origins.
Figure 14:
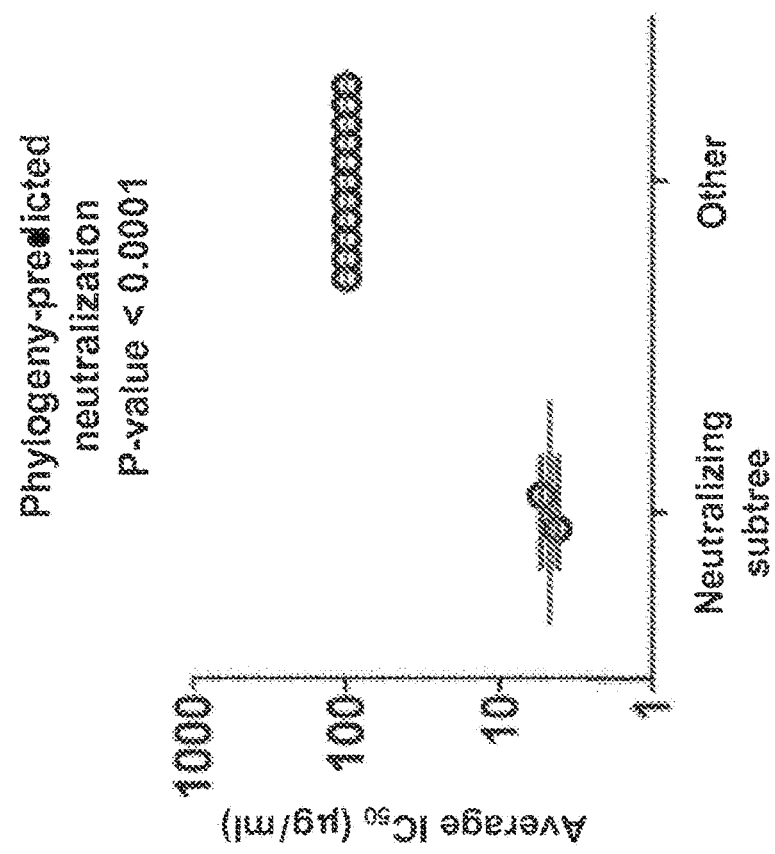
FIG. 14. Neutralization of expressed phylogeny-segregated sequences and sequences selected by other criteria from donor 45 2008 heavy-chain antibodyome. Specifically, the two neutralizing sequences were selected from the phylogenetic subtree of IGHV1-2*02 sequences (see FIG. 5) where they segregate with VRC01, VRC02, VRC03, VRC-PG04 and VRC-PG04b, whereas the 11 non-neutralizing sequences were selected either from different divergence bins of IGHV1-2*02 family with high predicted structural compatibility with known VRC01-like antibody-gp120 structure complexes or from other germline families with high divergence and large family size (see Tables S11 and S12).
Figure 16:
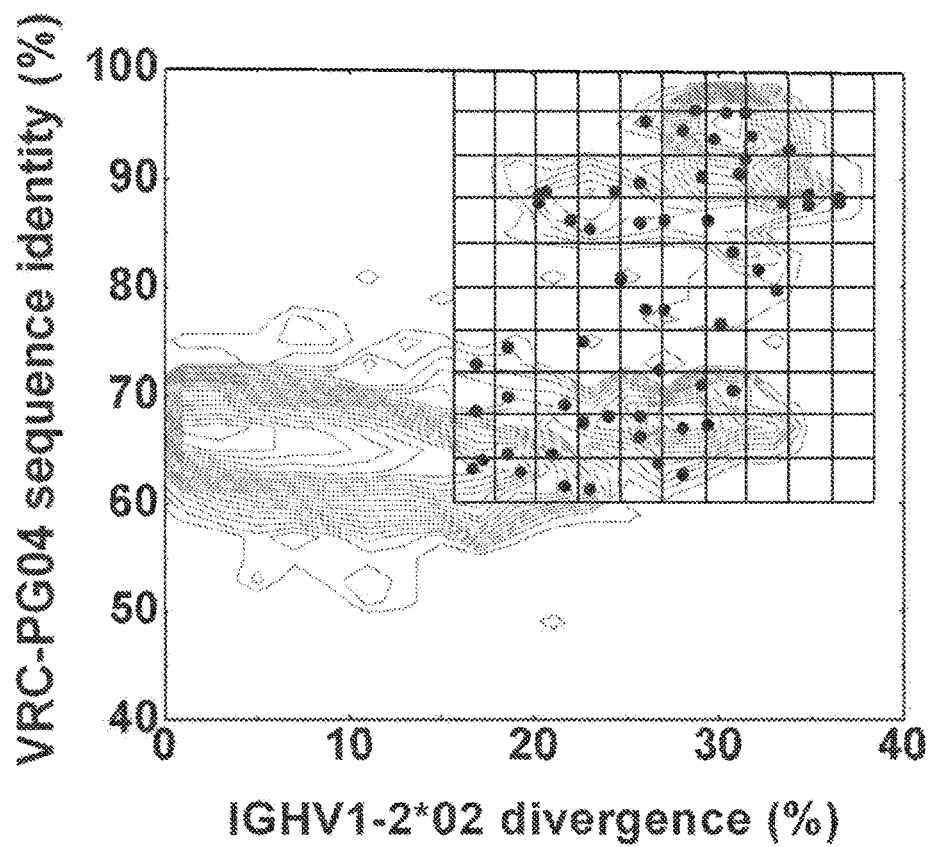
FIG. 16. Identity/divergence-grid assessment of donor 74 heavy-chain 2008 antibodyome. A 10×10 grid was placed over the quadrant defined by high divergence and high sequence identity to VRC-PG04. The sequences within each square of the grid were subjected to a clustering procedure with a sequence identity cutoff of 90%. A sequence was then randomly selected from the largest cluster as candidate. An initial set of 57 sequences was obtained using this approach. Sequences with a identity of 95% or greater to others or containing uncorrected sequencing errors were replaced by new ones selected from the grid. Note that every time a new sequence was selected, the possibility of overlapping with sequences of neighboring squares was examined using sequence clustering. A total of 56 grid-selected sequences were synthesized to assess the function of 454-pyrosequencing-determined heavy-chain sequences.
Figure 17:
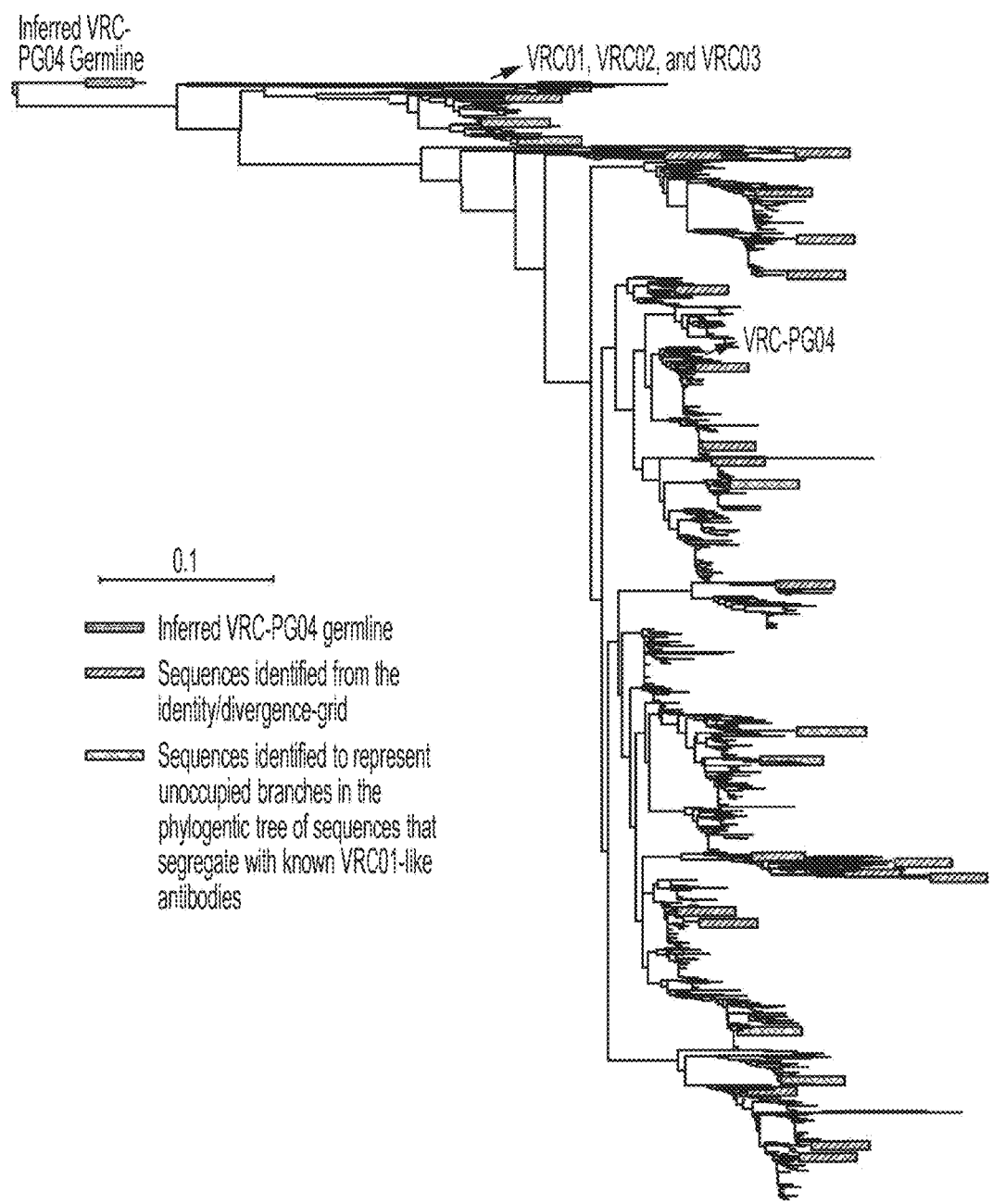
FIG. 17. Additional sequences selected to enhance the coverage of phylogeny-segregated sequences. In the iterative phylogenetic analysis of IGHV1-2*02 family of donor 74 2008 heavy-chain antibodyorne, 5047 sequences were found to segregate with VRC01, VRC02, VRC03 and VRC-PG04 on a district branch. A neighbor-joining (NJ) tree of these 5047 sequences, rooted at the inferred VRC-PG04 germline, is shown in this figure. 38 out of the 57 identity/divergence-grid-derived sequences were found within these sequences and are labeled by blue rectangles. 7 additional sequences were selected to represent unoccupied branches and are labeled by yellow rectangles.
Figure 18:
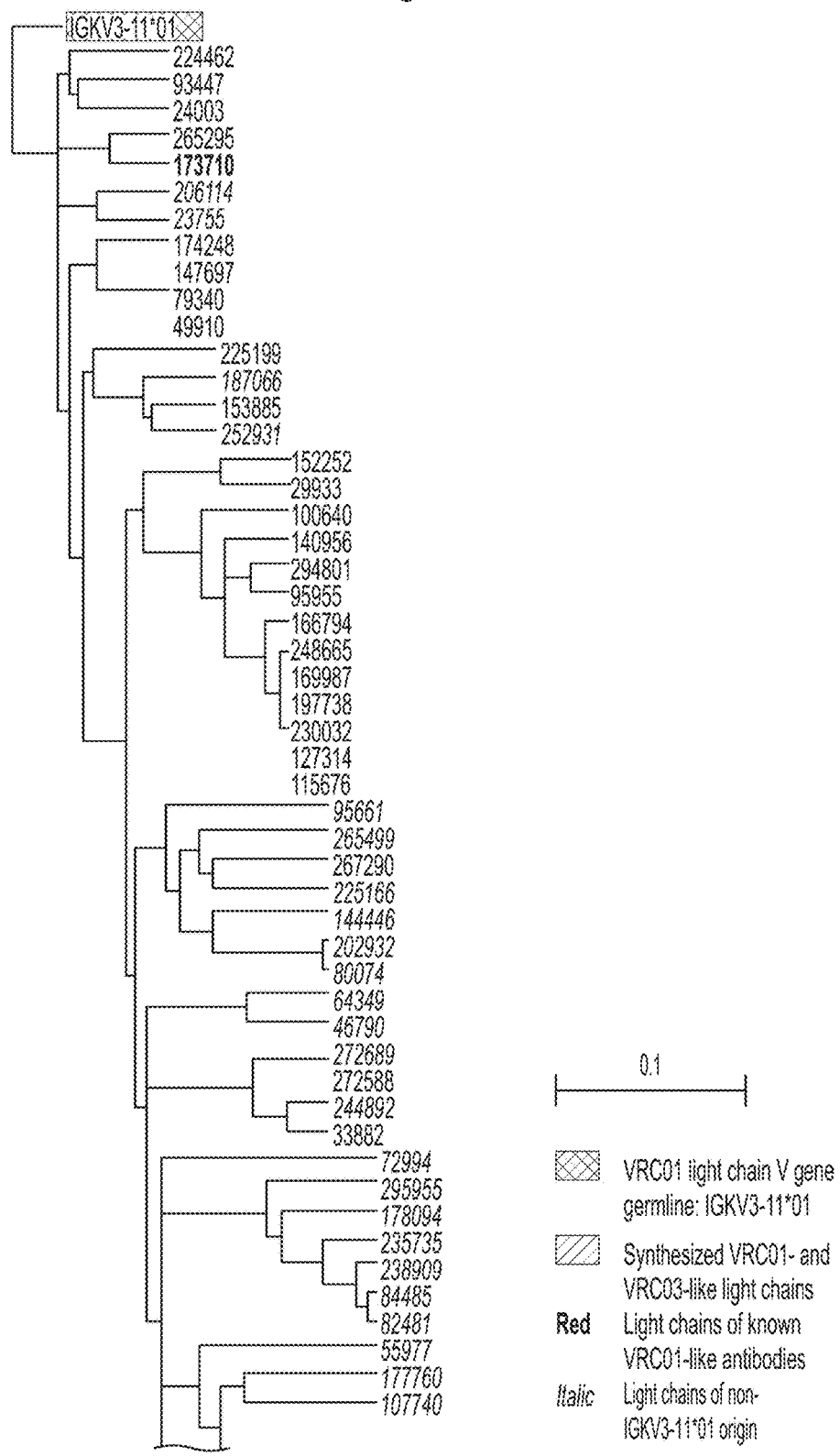
FIG. 18. Phylogenetic tree of 98 sequences from donor 45 light-chain 2001 antibodyome that have the same VRC01-like and VRC03-like deletions. The maximum likelihood (ML) tree is rooted at the IGKV3-11*01, VRC01 light-chain V-gene germline, which is highlighted in green. The known VRC01-like antibody light-chain sequences are colored in red and the two synthesized sequences that show functional complementation with VRC01-like heavy chains are highlighted in red.
Figure 18:
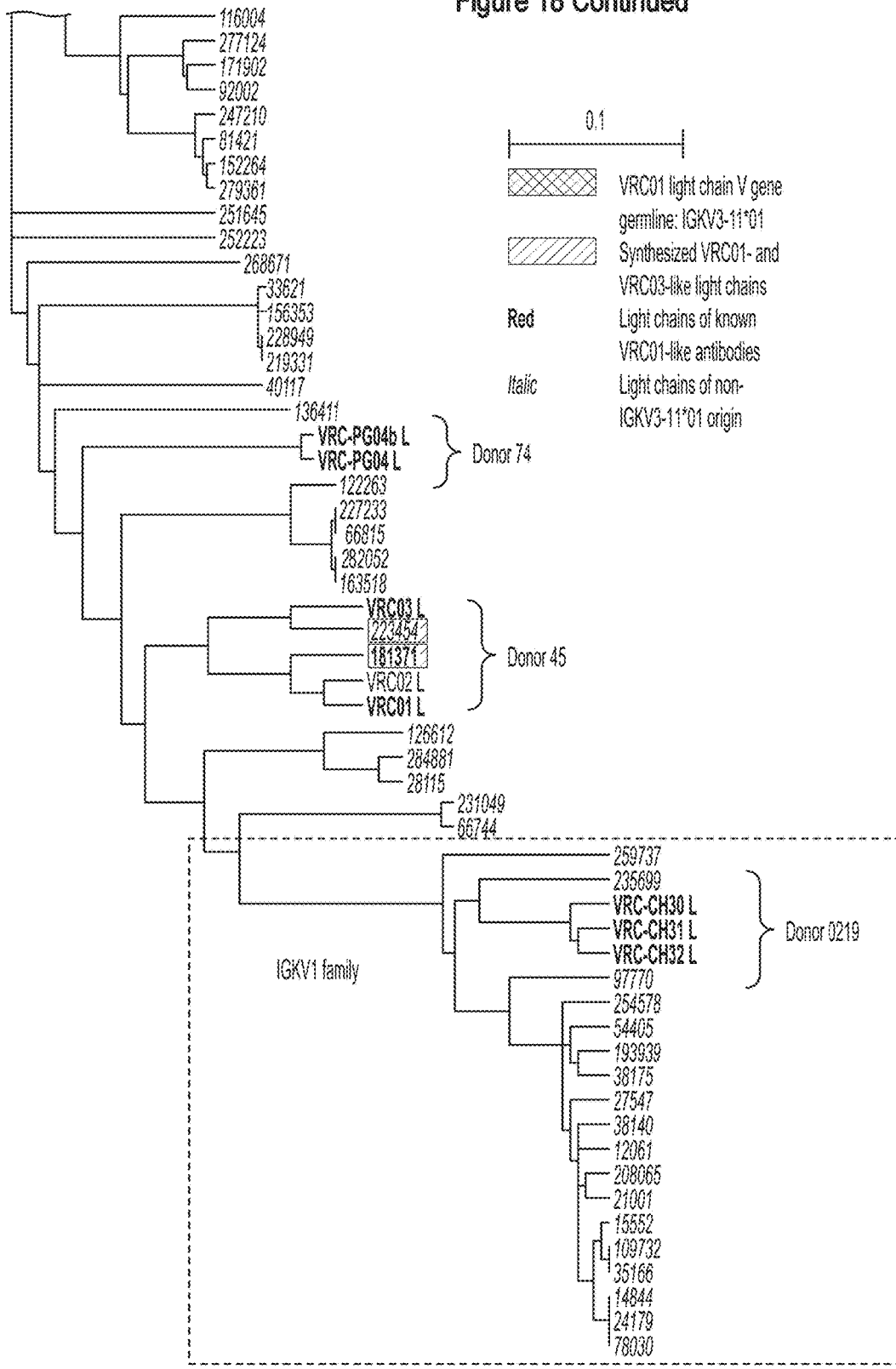
Figure 23:
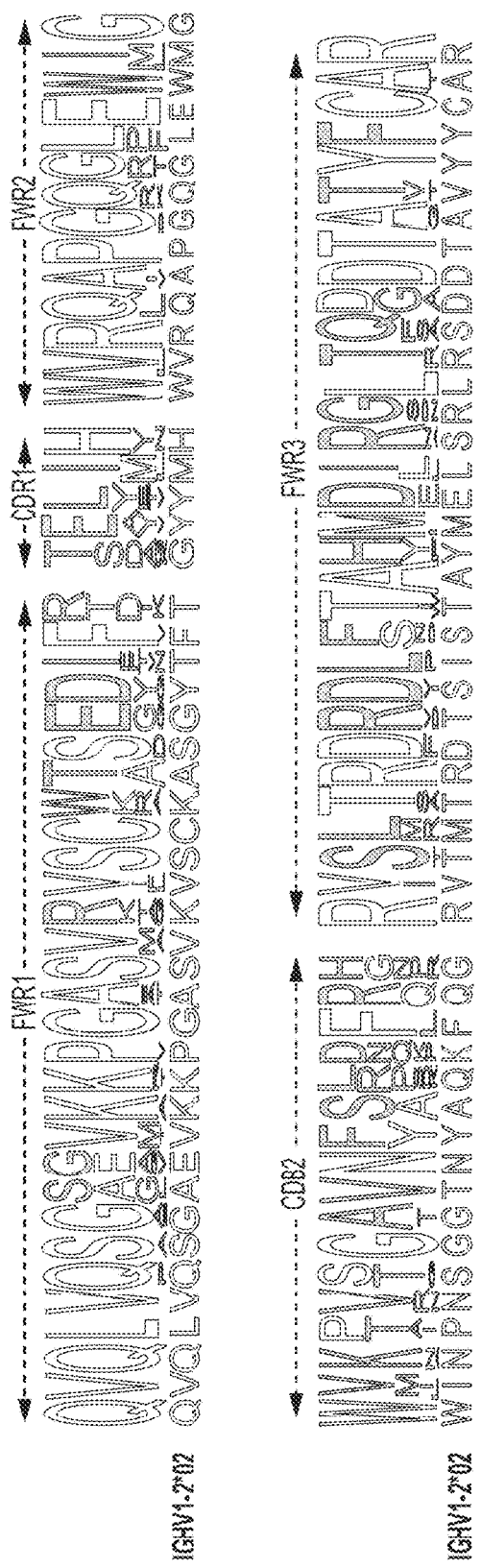
FIG. 23. Amino acid frequencies in the VH domains of VRC01-like neutralizing antibodies. Sequence alignment was generated for the VH domains of the twenty-two identified neutralizing sequences from donor 74, along with VRC01, VRC02, VRC03, VRC-PG04, and VRC-PG04b. The amino acid frequencies for each of the VH residue positions were plotted using Weblogo (S42). The height of each letter is proportional to the frequency with which the respective amino acid type is observed for the given residue position. The IGHV1-2*02 germ line sequence (SEQ ID NO: 107) is shown for comparison; insertions with respect to IGHV1-2*02 were not included in this analysis. For each residue position, the amino acid identity of IGHV1-2*02 is shown in maroon, while all other amino acid types are shown in black. Residue positions for which the IGHV1-2*02 identity is of low or zero frequency could indicate affinity maturation changes of functional significance.
Figure 24:
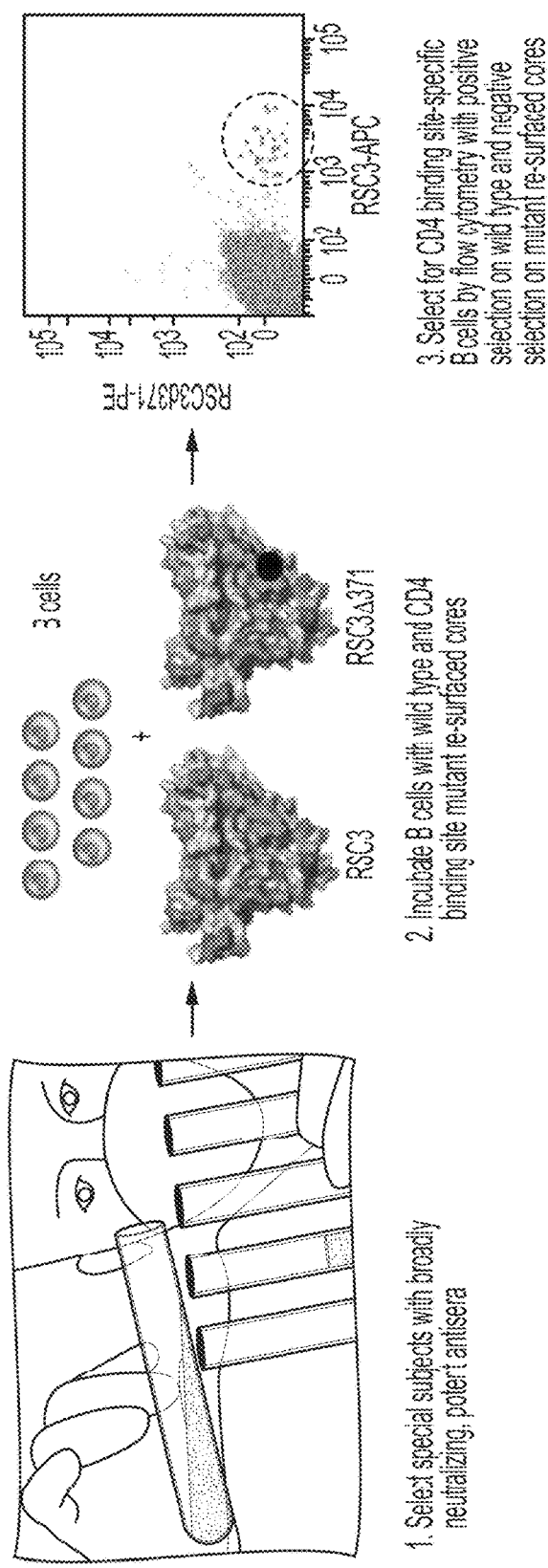
FIG. 24. Deep sequencing and structural bioinformatics methodologies facilitate direct analysis of the human antibodyome from PBMCs. The initial process of antibody identification (steps 1-7) involved sorting, single cell sequencing, characterization of neutralization, crystallographic analyses, and 454 pyrosequencing. The computational bioinformatic methods described here allow for identification of neutralizing antibodies directly from deep sequencing data (shortcut shown by red arrow). Step 7 discloses residues 1-120 of SEQ ID NO: 109, residues 1-13, 39-75, and 101-130 of SEQ ID NO: 110, residues 1-12, 37-73, and 93-121 of SEQ ID NO: 291, residues 1-13, 39-73, and 94-120 of SEQ ID NO: 108, residues 1-13, 39-73, and 94-120 of SEQ ID NO: 109, and SEQ ID NOS 110 and 291, respectively, in order of appearance.
Figure 24:
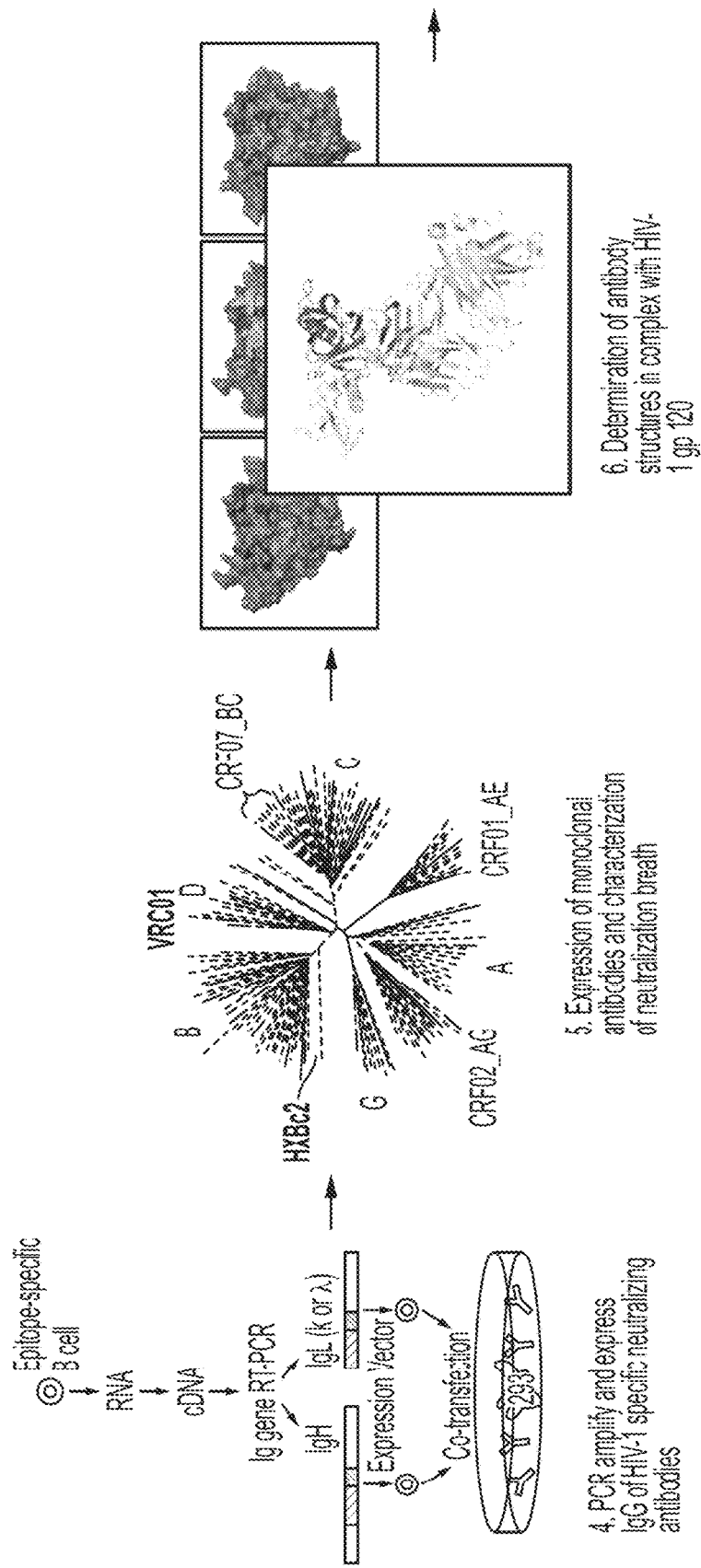
Figure 24:
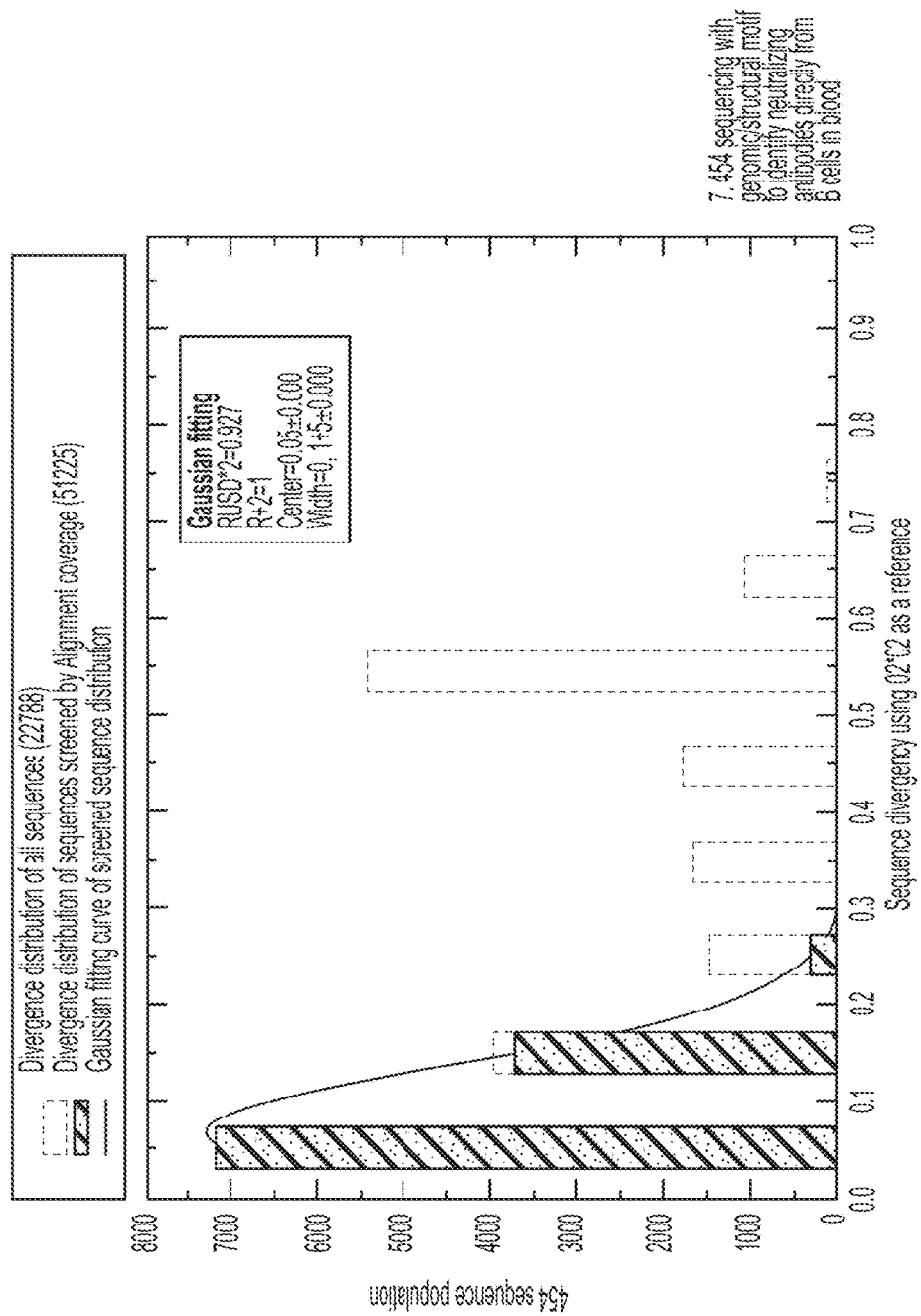
Figure 24:
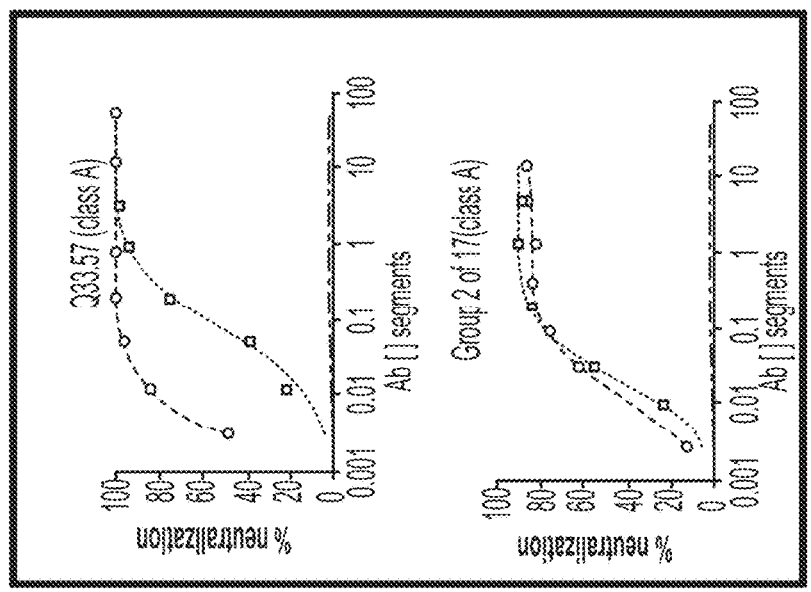
Figure 25:
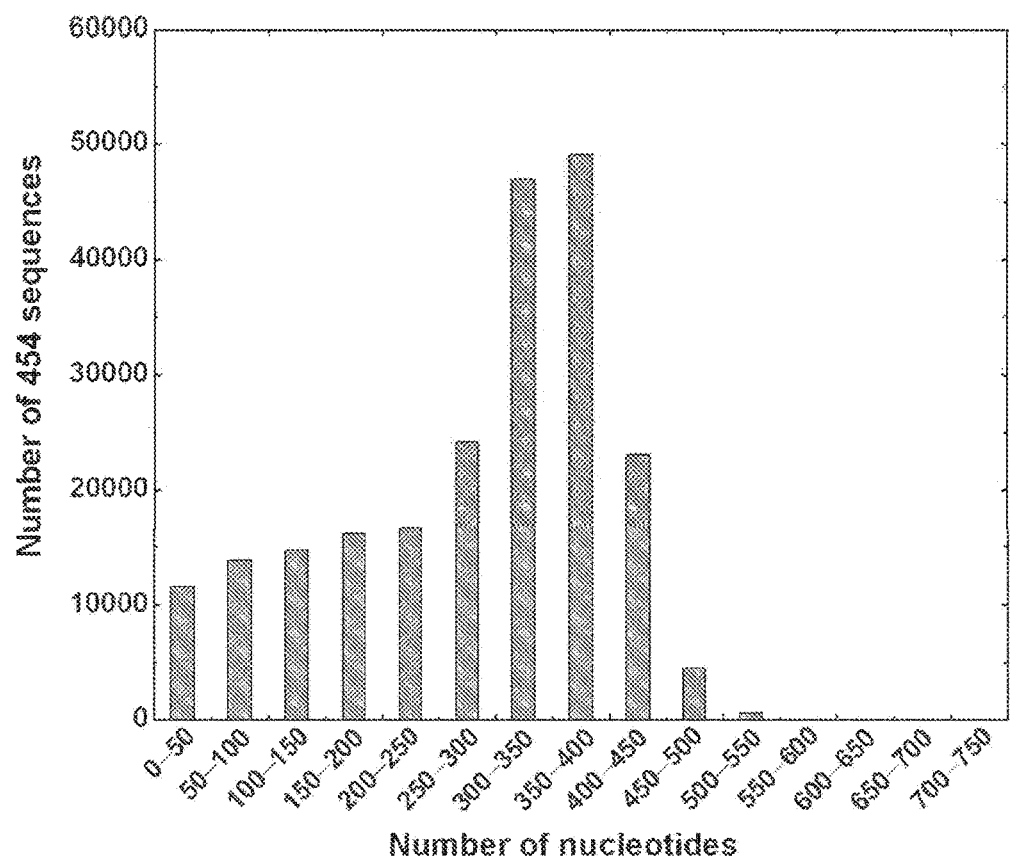
FIG. 25. There are 221104 reads in the data set. 78045 (or 35.3%) reads are longer than 350 nucleotides. The average read length is 283.4.
Figure 26:
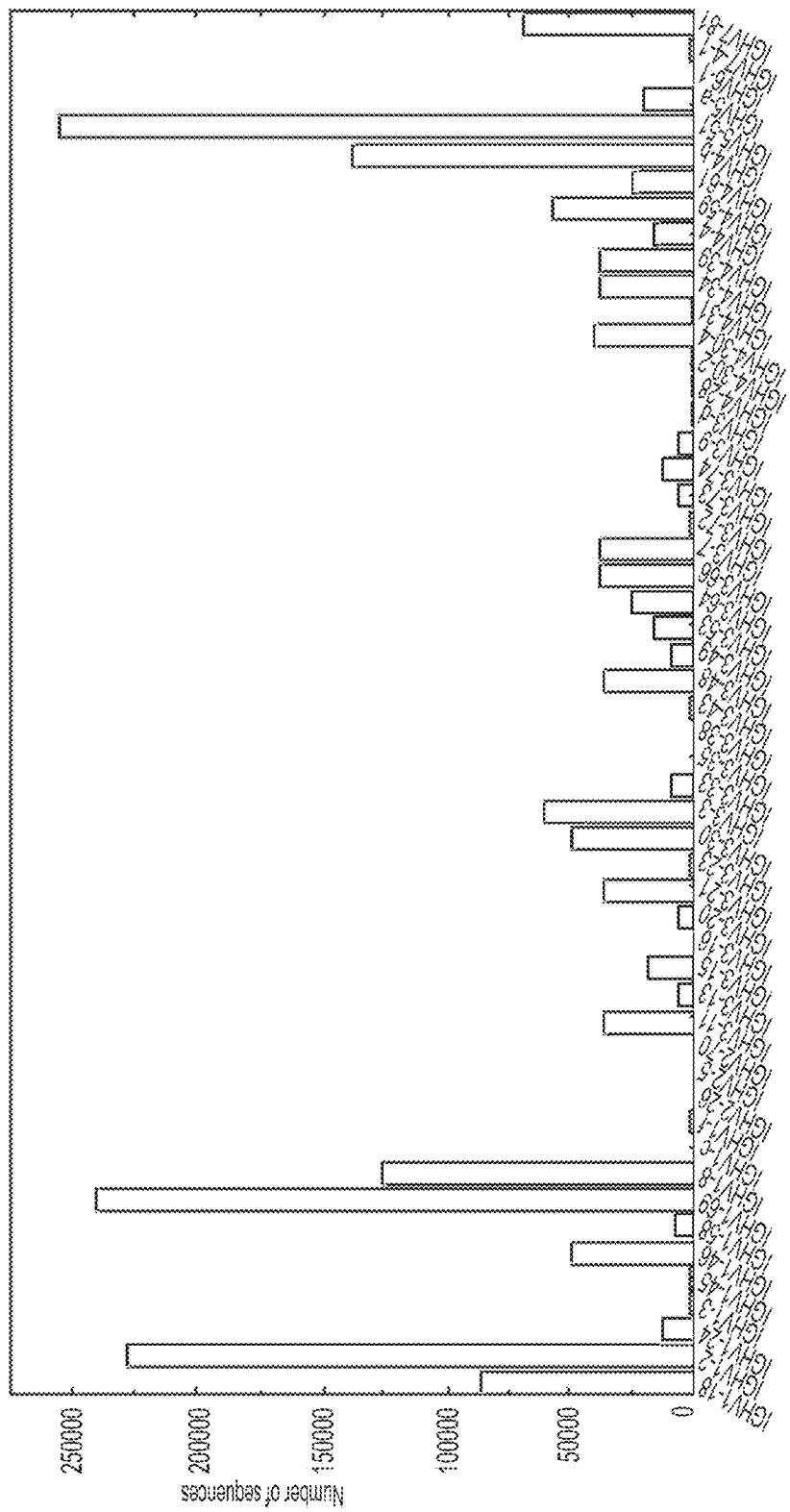
FIG. 26. E-value from IGBlast was used to determine whether the assignment is reliable. A cutoff of 1.0E-3 was used in current analysis. 158309 reads remained after removing the sequences with an E-value lower than 1.0E-3 22790 sequences were assigned to IGHV1-2 family with four possible alleles, IGHV1-2*01, IGHV1-2*02, IGHV1-2*03 and IGHV1-2*04.

We further analyzed donor 74 IGHV1-2*02 heavy chain sequences to identify those with CDR H3 sequences identical to the CDR H3s in each of the neutralizing classes (FIG. 7). This analysis identified four clonal lineages (CDR H3-classes 3, 6, 7 and 8), with sequences that extended to 15% or less affinity maturation. CDR H3 class 7 included the probe-identified antibodies, VRC-PG04 and 04b. In each case, a steady accumulation of changes lead to increased neutralization activity, and changes at positions 48, 52, 58, 69, 74, 82 and 94 in the V gene, among others, appeared to be selected in several lineages (FIG. 7). Overall, more than 2000 unique sequences could be classified into these four CDR H3 lineages (FIG. 7). Although these CDR H3 lineages were inferred from a single timepoint they likely provide insight into the specific maturation pathway by which the heavy chain of a VRC01-like antibody evolves from an initial recombinant to a broadly neutralizing antibody.

J Chain Analysis and Maturation Complexities.

In the heavy chains of VRC01-like sequences identified by phylogenetic analysis, a significant skewing of J chain usage was observed (FIG. 5A): in donor 45, over 87% of the phylogenetic-segregated sequences utilize the IGHJ1*01 allele, and in donor 74, 99% of the segregated sequences utilize the IGHJ2*01 allele. This preferential J chain usage does not appear to be a requirement for binding specificity; indeed, the use of the J1 allele in VRC01, the J2 allele in VRC-PG04, and the J4 allele in VRC-CH31 provide examples for the functional compatibility of at least three different IGHJ alleles in VRC01-like antibodies. In addition to preferential J chain usage, other complexities in the maturation process could be inferred from similarities in mature heavy chain genes and differences in CDR H3 sequence. In the absence of information on the natural pairing of heavy and light chains, the antibody maturation processes underlying these complexities is difficult to infer. Nevertheless, the deep sequencing data, with thousands of CDR H3-defined maturation intermediates (FIG. 7), provide sufficient information to suggest that the maturation may involve heavy chain revision or other mechanisms of B cell diversification (37, 38).

Antibody Genomics, HIV-1 Immunity, and Vaccine Implications.

Affinity maturation that focuses a developing antibody onto a conserved site of HIV-1 vulnerability provides a mechanism to achieve broad recognition of HIV-1 gp120.

Such focused evolution may be common to broadly neutralizing antibodies that succeed in overcoming the immune evasion that protect HIV-1 gp120 from humoral recognition; the multiple layers of evasion may constrain or focus the development of nascent antibodies to particular pathways during maturation.

The structure-based genomics approach described here provides tools for understanding antibody maturation. We show how deep sequencing can be utilized to determine the repertoire of sequences that compose the light chain and heavy chain antibodyomes in HIV-1 infected individuals. These antibodyomes can then be interrogated for unusual properties in sequence, or in maturation, to identify antibodies for functional characterization. We demonstrate three means of sieving a large database of antibody sequences: 1) by identity to a known mAb sequence and by divergence from putative germline (identity/divergence-grid analysis), 2) by cross-donor phylogenetic analysis of maturation pathway relationships, and 3) by CDR H3-lineage analysis. An important aspect of our analyses was the functional characterization of selected sequences achieved through expression of and reconstitution with known VRC01-like heavy or light chains, although other means of pairing such as by frequency analysis (39) are possible. While neutralization has been assessed on less than 100 of the antibodyomics-derived heavy-light reconstituted antibodies, the thousands of identified sequences provide a large dataset for analysis, which should enhance our understanding of the critical features of VRC01-like antibodies. For example, the correlation of sequence variation at particular positions with neutralization should provide insight into the allowed diversity and required elements of neutralization by this family of antibodies (Fig. S15).

Figure 5B:
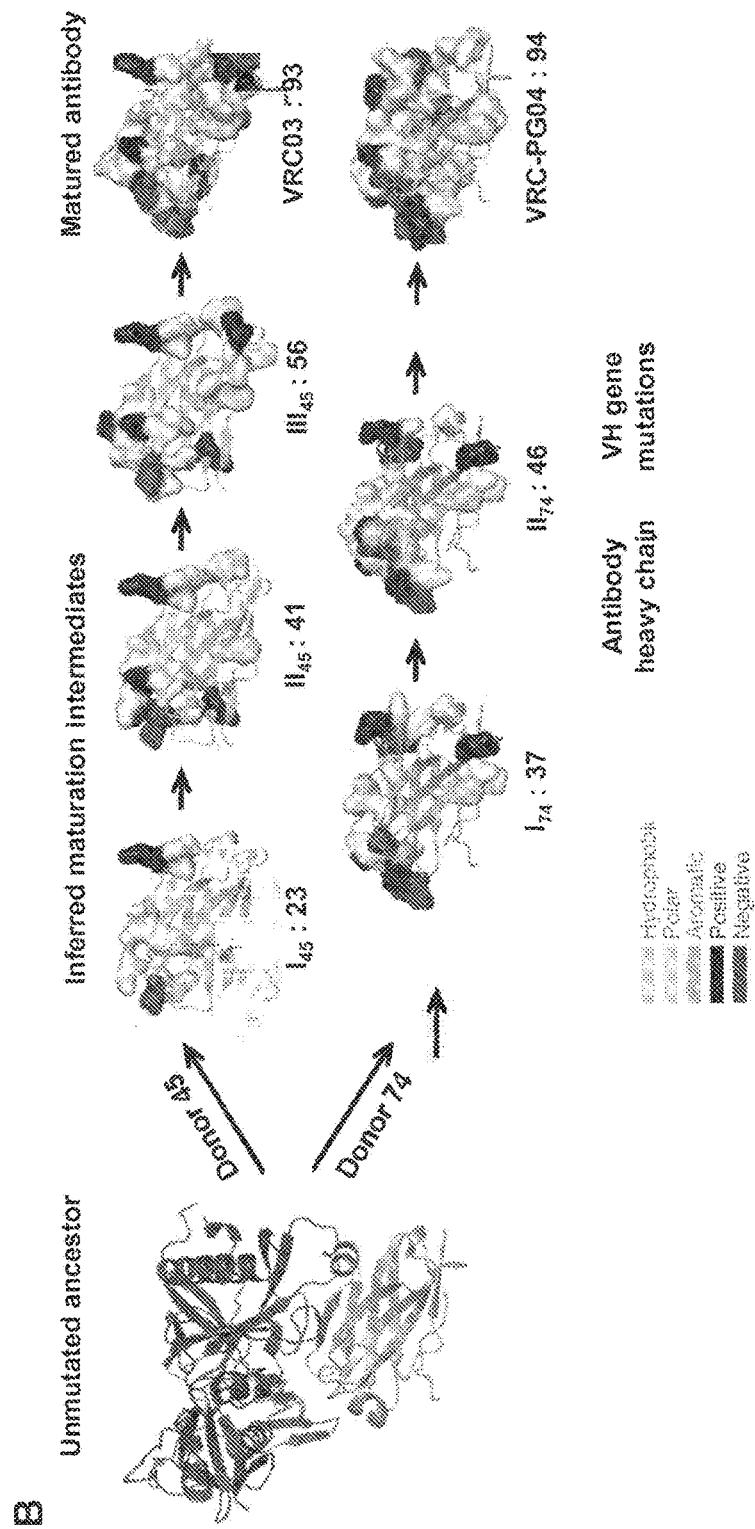

The deep sequencing and structural bioinformatics methodologies presented here facilitate analysis of the human antibodyome (Fig. S16). This genomics technology allows interrogation of the antibody responses from infected donors, uninfected individuals or even vaccine recipients and has several implications. For example, a genomic rooted phylogenetic analysis of the VRC01 antibodyome may reveal a general maturation pathway for the production of VRC01-like antibodies. Indeed, cross-donor phylogenetic analysis (FIG. 5B) suggests that common maturation intermediates with 20-30 affinity maturation changes from the IGHV1-2*02 genomic precursor are found in different individuals. These intermediates give rise to mature, broadly neutralizing VRC01-like antibodies, which have about 70-90 changes from the IGHV1-2*02 precursor (FIG. 5). If modified gp120s with affinity to the maturation intermediates represented by the nodes of the phylogenetic tree were to stimulate the elicitation of these intermediates, then the analysis presented here can help guide the vaccine-induced elicitation of VRC01-like antibodies. Deep sequencing not only provides a means to identify such intermediates, but also a means to facilitate their detection. Overall, the application of genomic technologies to analysis of antibodies facilitates both highly sensitive feedback and an unprecedented opportunity to understand the response of the antibodyome to infection and vaccination.

REFERENCES AND NOTES

1. D. R. Burton et al., HIV vaccine design and the neutralizing antibody problem. Nat Immunol 5, 233 (2004).
2. R. Pantophlet, D. R. Burton, GP120: target for neutralizing HIV-1 antibodies. Annu Rev Immunol 24, 739 (2006).
3. P. D. Kwong et al., HIV-1 evades antibody-mediated neutralization through conformational masking of receptor-binding sites. Nature 420, 678 (2002).
4. L. Stamatatos, L. Morris, D. R. Burton, J. R. Mascola, Neutralizing antibodies generated during natural HIV-1 infection: good news for an HIV-1 vaccine? Nat Med 15, 866 (2009).
5. D. N. Sather et al., Factors associated with the development of cross-reactive neutralizing antibodies during human immunodeficiency virus type 1 infection. J Virol 83, 757 (2009).
6. it D. Simek et al., Human immunodeficiency virus type 1 elite neutralizers: individuals with broad and potent neutralizing activity identified by using a high-throughput neutralization assay together with an analytical selection algorithm. J Virol 83, 7337 (2009).
7. N. A. Doria-Rose et al., Breadth of human immunodeficiency virus-specific neutralizing activity in sera: clustering analysis and association with clinical variables. J Virol 84, 1631 (2010).
8. S. Gnanakaran et al., Genetic signatures in the envelope glycoproteins of HIV-1 that associate with broadly neutralizing antibodies. PLoS Comput Biol 6, e1000955 (2010).
9. E. S. Gray et al., Antibody specificities associated with neutralization breadth in plasma from human immunodeficiency virus type 1 subtype C-infected blood donors. J Virol 83, 8925 (2009).
10. T. Muster et al., A conserved neutralizing epitope on gp41 of human immunodeficiency virus type 1. J. Virol 67, 6642 (1993).
11. M. B. Zwick et al., Broadly neutralizing antibodies targeted to the membrane-proximal external region of human immunodeficiency virus type 1 glycoprotein gp41. J Virol 75, 10892 (2001).
12. L. M. Walker et al., Broad and potent neutralizing antibodies from an African donor reveal a new HIV-1 vaccine target. Science 326, 285 (2009).
13. M. Bonsignori et al., Immunoregulation of HIV-1 broadly neutralizing antibody responses: deciphering maturation paths for antibody induction. Aids Res Hum Retrov 26, A153 (2010).
14. A. Trkola et al., Human monoclonal antibody 2G12 defines a distinctive neutralization epitope on the gp120 glycoprotein of human immunodeficiency virus type 1. J Virol 70, 1100 (1996).
15. L. Walker et al., High through-put functional screening of activated B cells from 4 African elite neutralizers yields a panel of novel broadly neutralizing antibodies. Aids Research and Human Retroviruses 26, A32 (2010).
16. D. R, Burton et al., Efficient neutralization of primary isolates of HIV-1 by a recombinant human monoclonal antibody. Science 266, 1024 (1994).
17. D. Corti et al., Analysis of memory B cell responses and isolation of novel monoclonal antibodies with neutralizing breadth from HIV-1-infected individuals. PLoS One 5, e8805 (2010).
18. X. Wu et al., Rational design of envelope identifies broadly neutralizing human monoclonal antibodies to HIV-1. Science 329, 856 (2010).
19. T. Zhou et al., Structural basis for broad and potent neutralization of HIV-1 by antibody VRC01. Science 329, 811 (2010).
20. J. Wrammert et al., Broadly cross-reactive antibodies dominate the human B cell response against 2009 pandemic H1N1 influenza virus infection. J Exp Med 208, 181 (2011).

21, M. Huber et al., Very few substitutions in a germ line antibody are required to initiate significant domain exchange. J Virol 84, 10700 (2010).
22. X. Xiao et al., Germline-like predecessors of broadly neutralizing antibodies lack measurable binding to HIV-1 envelope glycoproteins: implications for evasion of immune responses and design of vaccine immunogens. Biochem Biophys Res Commun 390, 404 (2009).
23. Materials and methods are available as supporting material on Science Online. [0063] 24. J. F. Scheid et al., Broad diversity of neutralizing antibodies isolated from memory B cells in HIV-infected individuals. Nature 458, 636 (2009).
25. R. A. Lerner, Rare antibodies from combinatorial libraries suggests an S.O.S. component of the human immunological repertoire. Mol Biosyst 7, 1004 (2011).
26. C. C. Huang et al., Structural basis of tyrosine sulfation and VH-gene usage in antibodies that recognize the HIV type 1 coreceptor-binding site on gp120. Proc Natl Acad Sci USA 101, 2706 (7004).
27. C. Sabin et al., Crystal structure and size-dependent neutralization properties of HK20, a human monoclonal antibody binding to the highly conserved heptad repeat 1 of gp41. PLoS Pathog 6, e1001195 (2010).
28. F. Breden et al., Comparison of Antibody Repertoires Produced by HIV-1 Infection, Other Chronic and Acute Infections, and Systemic Autoimmune Disease. PLoS One 6, e16857 (2011).
29. M. K. Gorny et al., Preferential use of the VH5-51 gene segment by the human immune response to code for antibodies against the V3 domain of HIV-1. Mol Immunol 46, 917 (2009).
30. L. Chen et al., Structural basis of immune evasion at the site of CD4 attachment on HIV-1 gp120. Science 326, 1123 (2009).
31. Significant correlations were not observed between rmsd of VRC01-like antibody interaction with gp120 and size of CDR interaction or surface area in general (Fig. S5).
32. T. Zhou et al., Structural definition of a conserved neutralization epitope on HIV-1 gp120. Nature 445, 732 (2007).
33. The mRNA was extracted from 20 million PBMC, reverse transcribed with oligo (dT)12-18 (SEQ ID NO: 1), and a quarter of the resultant cDNA (equivalent to the transcripts of 5 million PBMC) was used as the template for PCR to preferentially amplify the IGHV1 gene family from both the IgG and IgM expressing cells. PCR products were gel purified and analyzed by 454 pyrosequencing.
34. We also assessed 454-derived sequences for structural compatibility with the VRC01, VRC03, and VRC-PG04 gp120-complex crystal structures using a threading algorithm which assessed structural compatibility using the DFIRE statistical potential (40). None of the ten sequences with optimal DFIRE scores (Table S11), nor those with high germline divergence of non-IGHV1-2*02 genomic origin (Table S12) gave neutralization when reconstituted with the VRC01 light chain (FIGS. 4E and S7 and Table S13). Thus, sequence similarity, IGHV1-2*02 origin, and divergence all correlate with neutralization potential, but other factors such as predicted structural compatibility failed to identify VRC01-like antibodies.
35. Six of the reconstituted antibodies displayed a mean $IC_{50}$ of .about.0.1 µg/ml, a level of potency similar to that observed with the original probe-identified VRC-PG04 antibodies.
36. 1. VRC03L does not complement well; 2. VRC01 and VRC02 H no longer present in 2008 plasmablasts; 3. VRC03 H is present in 2008; 4. VRC01-3 are in memory B-cell population; Results 1-4 suggests that VRC03 came after VRC01; we therefore choose a pre-2008 timepoint to maximize chances of obtaining light chains that allowed for functional complementation with known VRC01 heavy chains.
37. D. Nemazee, M. Weigert, Revising B cell receptors. J Exp Med 191, 1813 (2000).
38. E. Edry, D. Melamed, Receptor editing in positive and negative selection of B lymphopoiesis. J Immunol 173, 4265 (2004).
39. J. Glanville et al., Precise determination of the diversity of a combinatorial antibody library gives insight into the human immunoglobulin repertoire. Proceedings of the National Academy of Sciences of the United States of America 106, 20216 (2009).
40. H. Zhou, Y. Zhou, Distance-scaled, finite ideal-gas reference state improves structure-derived potentials of mean force for structure selection and stability prediction. Protein Sci 11, 2714 (2002).
41. E. A. Kabat, T. T. Wu, Sequences of Proteins of Immunological Interest. (ed. 5th, 1991).
42. E. Krissinel, K. Henrick, Inference of macromolecular assemblies from crystalline state. Journal of molecular biology 372, 774 (2007).
43. The peak at .about.25% IGHV1-2*02 divergence and 88% identity also showed a peak in the sequence plot for sequences of non-IGHV1-2*02 origin. Phylogenetic analysis and CDR H3 analysis shows that these putative non-IGHV1-2*02 derived sequences segregate with VRC01-like antibodies in dendrograms and have CDR H3s which are identical to confirmed VRC01-like antibodies (FIG. 7), indicating that sequences in the non-IGHV1-2*02 cluster are likely miss-assigned and actually of IGHV1-2*02 origin.
44. X. W., T. Z., J. Z., G. J. N., M. R., L. S., P. D. K. and J. R. M. designed research; B. Z., C. W., X. C., M. L., K. M., S. O. D., S. P., S. D. S., W. S., L. W., Y. Y., Z. Y. Y., Z. Y., NISC and J. M. performed experiments, X. W. isolated and characterized VRC01-like antibodies by RSC3 probe, devised and prepared samples for 454 pyrosequencing and assisted with functional characterization, T. Z. determined and analyzed structures of VRC-PG04 and VRC03 with gp120 and assisted with functional characterization, J. Z. devised and carried out computational bioinformatics on the antibodyome, M. B., J. A. C, S. H. K, S. E. N., B. F. H. contributed donor 0219 materials, M. S., D. R. B., and W. C. K contributed PG materials including donor 74, and N. D. R. and M. C. contributed donor 45 materials; X. W., T. Z., J. Z, I. G., N. S. L., Z. Z., L. S., P. D. K., and J. R. M. analyzed the data, L. S., P. D. K. and J. R. M. wrote the first draft of the paper, on which all authors commented. We thank J. Almeida and D. Douek for protocols of PBMC cDNA preparation and for helpful discussions, H. Coleman, M. Park, B. Schmidt, and A. Young for 454 pyrosequencing at the NIH Intramural Sequencing Center (NISC), J. Stuckey for assistance with figures, T. Wrin for sequence information on the donor 74 virus, J. Binley, D. Montefiori, L. Morris and G. Tomaras for donor 0219 serum characterization, all of the IAVI Protocol G team members and the Protocol G clinical investigators, specifically, G. Miiro, A. Pozniak, D. McPhee, O. Manigart, E. Karita, A. Inwoley, W. Jaoko, J. DeHovitz, L.-G. Bekker, P. Pitisuttithum, R. Paris, J. Serwanga, and S. Allen. We also thank I. Wilson and members of the Structural Biology Section and Structural Bioinformatics Core, Vaccine Research Center, for discussions and comments on the manuscript. Support for this work was provided by the Intramural Research Program of the Vaccine Research Center, National Institute of Allergy and Infectious Diseases and the National Human Genome Research Institute, National Institutes of Health, and by grants from the International AIDS Vaccine Initiative's Neutralizing Antibody Consortium and by the Center for HIV AIDS Vaccine Immunology Grant AI 5U19 AI 067854-06 from the National Institutes from Health. Use of sector 22 (Southeast Region Collaborative Access team) at the Advanced Photon Source was supported by the US Department of Energy, Basic Energy Sciences, Office of Science, under contract number W-31-109-Eng-38. We are in the process of depositing structure factors and coordinates for antibodies VRC03 and VRC-PG04 in complex with HIV-1 gp120. We are also in the process of depositing deep sequencing data for donors 45 and 74 used in this study as well as the more than 2000 unique sequences associated with specific CDR H3 lineages shown in FIG. 7.

Supporting Material

Supplementary Materials and Methods
Human Specimens.

The sera and peripheral blood mononuclear cells (PBMCs) of donor 45 (S1-2) and donors from the international AIDS-vaccine initiative (IAVI) protocol G (S3-4), and donor 0219 from the center for HIV/AIDS vaccine immunology (CHAVI) 001 cohort (S5-6) have been described previously. Donor 45, from whom monoclonal antibodies (mAbs) VRC01, VRC02 and VRC03 were isolated (S1), was infected with an HIV-1 clade B virus. The IAVI protocol G donor 74, from whom mAbs VRC-PG04 and VRC-PG04b were isolated, was infected with a A/D recombinant virus. Donor 0219, from whom mAbs VRC-CH30, VRC-CH31 and VRC-CH32 were isolated, was infected with a clade A virus. These three donors were chronically infected and had not initiated antiretroviral treatment at the time of PBMC sampling. All human samples were collected with informed consent under clinical protocols approved by the appropriate institutional review board (IRB).

Protein Expression and Purification.

Monomeric gp120s, gp120 with the CD4-binding site knockout mutation D368R (S2, 7), gp120 cores, RSC3 and ΔRSC3 (S1) were expressed by transient transfection of 293F cells as previously described (S1). Briefly, genes encoding the proteins of interest were each synthesized with a C-terminal His tag (GeneArt, Regensburg, Germany), and cloned into a mammalian CMV/R expression vector (S8). Proteins were produced by transient tranfection using 293fectin (Invitrogen, Carlsbad, Calif.) in 293F cells (Invitrogen) maintained in serum-free free-style medium (Invitrogen). Culture supernatants were harvested 5-6 days after transfection, filtered through a 0.45 μm filter, and concentrated with buffer-exchange into 500 mM NaCl, 50 mM Tris (pH 8.0). Proteins were purified by Co-NTA (cobalt-nitrilotriacetic acid) chromatography method using a HiTrap IMAC HP column (GE Healthcare, Piscataway, N.J.). The peak fractions were collected, and further purified by gel-filtration using a HiLoad 16/60 Superdex 200 pg column (GE Healthcare). The fractions containing monomers of each protein were combined, concentrated and flash frozen at −80° C.

Antibodies, Plasmids, Antibody and Protein Expression and Purification.

Anti-gp120 mAb 2012 was purchased from Polymun Scientific Inc. (Vienna, Austria). Anti-CD4bs mAbs b12, VRC01 and VRC03 were described (S1, 9). The mAb 17b, directed to the co-receptor region of gp120, was provided by James Robinson (Tulane University). Other antibody sequences were synthesized and cloned into the CMV/R expression vector containing the constant regions of IgG 1. Full-length IgGs were expressed from transient transfection of 293F cells, and purified by affinity chromatography using HiTrap Protein A HP Columns (GE Healthcare). The CD4-Ig plasmid construct was provided by Joseph Sodroski (Dana Farber Cancer Institute) and the fusion protein was expressed by transient transfection as described above.

Isolation of Antigen-Specific Memory B Cells by Fluorescence Activated Cell Sorting (FACS).

As described previously (S1), the Avi-tagged RSC3 and RSC3 were expressed, purified, and biotinylated using the biotin ligase Bir A (Avidity, Denver, Colo.). Biotinylation of the RSC proteins was confirmed by ELISA. The proteins were then conjugated with the streptavidin-fluorochrome reagents, streptavidin-allophycocyanin (SA-APC) (Invitrogen) for RSC3 and streptavidin-phycoerythrin (SA-PE) (Sigma) for ΔRSC3. About 20 million donor PBMC were stained with RSC3-APC, ΔRSC3-PE, and an antibody cocktail consisting of anti-CD3-APC-Cy7 (BD Pharmingen), CD8-Qdot705 (VRC), CD19-Qdot585 (VRC), CD20-Pacific Blue (VRC), CD27-APC-AlexaFluor700 (Beckman Coulter), CD14-Qdot800 (VRC), IgG-FITC (BD Pharmingen), and IgM-PE-Cy5 (BD Pharmingen). In addition, aqua blue (Invitrogen) was used to exclude dead cells. The stained PBMC were washed with PBS, then analyzed and sorted using a modified 3-laser FACSAria cell sorter (configuration in fig. S1) using the FACSDiva software (BD Biosciences). Single cells with the phenotype of CD3−, CD8−, aqua blue−, CD14−, CD19+, CD20+, IgG+, IgM−, RSC3+ and ΔRSC3− were sorted into 96-well PCR plates containing 20 μl of lysis buffer per well. The lysis buffer contained 0.5 μl of RNasc Out (Invitrogen), 5 μl of 5.times. first strand buffer (Invitrogen), 1.25 μl of 0.1M DTT (Invitrogen) and 0.0625 μl of Igepal (Sigma). The PCR plates with sorted cells were stored at −80° C. The total content of the donor PBMC sample passing through the sorter was saved in FCS files for further analysis with FlowJo software (TreeStar, Cupertino, Calif.).

Single B-Cell Immunoglobulin Gene Amplification and Cloning.

As described previously (S1), the frozen plates with single B-cell RNA were thawed at room temperature, and the reverse-transcription was carried out by adding 3 d of random hexamers (Gene Link, Hawthorne, N.Y.) at 150 ng/μl, 2 μl of dNTP mix, each at 10 mM, and 1 μl of SuperScript III (Invitrogen) into each well. The thermocycle for reverse-transcription was 42° C. for 10 min, 25° C. for 10 mM, 50° C. for 60 min and 94° C. for 5 min. The cDNA plates were stored at −20° C., and the IgH, Igκ and Igλ, variable region genes were amplified independently by nested PCR starting from 5 μl of cDNA as template. All PCRs were performed in 96-well PCR plates in a total volume of 50 μl containing water, 5 μl of 10.times. buffer, 1 μl of dNTP mix, each at 10 mM, 1 μl of MgCl$_2$ at 25 mM (Qiagen, Valencia, Calif.) for 1st round PCR or 10 μl 5.times. Q-Solution (Qiagen) for 2nd round PCR, 1 μl of primer or primer mix (S10) for each direction at 25 μM, and 0.4 μl of HotStar Taq DNA polymerase (Qiagen). Each round of PCR was initiated at 94° C. for 5 min, followed by 50 cycles of 94° C. for 30 sec, 58° C. for IgH and Igκ or 60°

C. for Igλ for 30 sec, and 72° C. for 1 min, followed by 72° C. for 10 min. The positive 2nd round PCR products were cherry-picked for direct sequencing with both forward and reverse PCR primers. PCR products that gave a productive IgH, Igκ or Igλ rearranged sequence were re-amplified from the 1st round PCR using custom primers containing unique restriction digest sites and subsequently cloned into the corresponding Igγ1, Igκ and Igλ. expression vectors as previously described (S10). The full-length IgG1 was expressed by co-transfection of 293F cells with equal amount of the paired heavy and light chain plasmids, and purified using a recombinant protein-A column (GE Healthcare).

IgG Gene Family Analysis.

IgG Gene Family Analysis.

The IgG heavy and light chain nucleotide sequences of the variable region were analyzed with JoinSolver.® (S11) and IMGT/V-Quest (S12). The VRC mAb Vκ gene use was determined by homology to germline genes in the major 2p11.2 IGK locus (S13). The VRC mAb D gene use was determined by homology to genes in the major 14q32.33 IGH locus, A combination of consecutive matching length with a +1/−2.02 scoring algorithm in the context of the V to J distance was applied for determining IGHD alignments and VD and DJ junctions in mutated sequences. Immunoglobulin rearrangements were grouped into classes based upon the VDJ gene use, similarity of replacement and silent mutations and the CDR3 identity.

ELISA Analyses.

As previously described (S1), each antigen in PBS at 2 μg/ml was used to coat plates overnight at 4° C. Coated plates were blocked with B3T buffer (150 mM NaCl, 50 mM Tris-HCl, 1 mM EDTA, 3.3% fetal bovine serum, 2% bovine albumin, 0.07% Tween 20) for 1 hour at 37° C., followed by incubation with antibody serially diluted in B3T buffer for 1 hour at 37° C. Horseradish peroxidase (HRP)-conjugated goat anti-human IgG Fc antibody (Jackson ImmunoResearch Laboratories Inc., West Grove, Pa.) at 1:10,000 was added for 1 hour at 37° C. All volumes were 100 μl/well except that 200 μl/well was used for blocking. Plates were washed between each step with 0.1% Tween 20 in PBS. Plates were developed using either 3,3',5,5'-tetramethylbenzidine (TMB) (Kirkegaard & Perry Laboratories) and read at 450 nm. For competitive ELISA analyses, plates were coated with 1 μg/ml of a sheep anti-gp120 C5 antibody, D7324 (Cliniqa Corp., Fallbrook, Calif.) or 10 μg/ml of *Galanthus nivalis* lectin (Sigma) to capture 2 μg/ml of purified YU2 gp120 or RSC3 respectively. After blocking, serial dilutions of the competitor antibodies or CD4-Ig were added to the captured gp120 or RSC3 in 50 μl of B3T buffer, followed by adding 50 μl of biotin-labeled antibody or CD4-Ig at fixed concentrations: 200 ng/ml of VRC-PG04 and 500 ng/ml of VRC-CH31 to bind to YU2 gp120 or RSC3, 150 ng/ml of CD4-Ig and 80 ng/ml of 17b to bind to YU2 gp120. The plates were incubated at 37° C. for 1 hour, followed by incubation with 250 ng/ml of streptavidin-HRP (Sigma) at room temperature for 30 min, and developed with TMB as described above.

HIV-1 Neutralization and Protein Competition Assays.

Neutralization was measured using single-round-of-infection HIV-1 Env-pseudoviruses and TZM-b1 target cells, as described previously (S14-16). Neutralization curves were fit by nonlinear regression using a 5-parameter hill slope equation as previously described (S15). The 50% and 80% inhibitory concentrations ($IC_{50}$ and $IC_{80}$) were reported as the antibody concentrations required to inhibit infection by 50% and 80% respectively. Competition of serum or mAb neutralization (S1) was assessed by adding a fixed concentration (25 μg/ml) of the RSC3 or ΔRSC3 glycoprotein to serial dilutions of antibody for 15 min prior to the addition of virus. The resulting $IC_{50}$ values were compared to the control with mock PBS added. The neutralization blocking effect of the proteins was calculated as the percent reduction in the $ID_{50}$ (50% inhibitory dilution) value of the serum in the presence of protein compared to PBS, Construction of the HIV-1 Envelope Sequence Phylogenetic Trees.

HIV-1 gp160 protein sequences of the 180 isolates used in the neutralization assays were aligned using MUSCLE, for multiple sequence comparison by log-expectation (S17-18). The protein distance matrix was calculated by "protdist" and the dendrogram was constructed using the neighbor-joining method (S19) by "Neighbor". All analysis and the programs used were performed at the NIAID Biocluster. The tree was displayed with Dendroscope (S20).

Crystallization of the gp120:VRC-PG04 and gp120:VRC03 Complexes.

The same HIV-1 clade A/E 93TH057 ΔV123 gp120 that crystallized with VRC01 (S21) was used to form complexes with antibodies VRC03 and VRC-PG04 for crystallization trials. The gp120 was expressed, purified and deglycosylated as previously described (S21). The antigen-binding fragments (Fabs) of VRC-PG04 and VRC03 were generated by LyS-C(Roche) digestion of IgG1 (S21). The gp120: VRC-PG04 or gp120:VRC03 complexes were formed by mixing deglycosylated 93TH057 gp120 and antibody Fabs (1:1.2 molar ratio) at room temperature and purified by size exclusion chromatography (Hiload 26/60 Superdex S200 prep grade, GE Healthcare) with buffer containing 0.35 M NaCl, 2.5 mM Tris pH 7.0, 0.02% $NaN_3$. Fractions with gp120:antibody complexes were concentrated to ~10 mg/ml, flash frozen with liquid nitrogen before storing at −80° C. and used for crystallization screening experiments.

Three commercially available screens, Hampton Crystal Screen (Hampton Research), Precipitant Synergy Screen (Emerald BioSystems), and Wizard Screen (Emerald BioSystems), were used for initial crystallization trials of the gp120:antibody complexes. Vapor-diffusion sitting drops were set up robotically by mixing 0.1 μl of protein with an equal volume of precipitant solutions (Honeybee, DigiLab). Droplets were allowed to equilibrate at 20° C. and imaged at scheduled times with RockImager (Formulatrix.). Robotic crystal hits were optimized manually using the hanging drop vapor-diffusion method. Crystals of diffraction-quality for the gp120:VRC03 complex were obtained at 9% PEG 4000, 200 mM $Li_2SO_4$, 100 mM Tris/Cl⁻, pH 8.5. For the gp120:VRC-PG04 complex, best crystals were grown in 9.9% PEG 4000, 9.0% isopropanol, 100 mM $Li_2SO_4$, 100 mM HEPES, pH 7.5.

X-Ray Data Collection, Structure Determination and Refinement for the gp120:VRC-PG04 and gp120:VRC03 Complexes.

Diffraction data of the gp120:VRC03 and gp120:VRC-PG04 crystals were collected under cryogenic conditions. Best cryo-protectant conditions were obtained by screening several commonly used cryo-protectants as described previously (S21). X-ray diffraction data were collected at beam-line ID-22 (SER-CAT) at the Advanced Photon Source, Argonne National Laboratory, with 1.0000 .ANG. radiation, processed and reduced with HKL2000 (S22). For the gp120:VRC-PG04 crystals, a 2.0 .ANG. data set was collected using a cryoprotectant solution containing 18.0% PEG 4000, 10.0% isopropanol, 100 mM $Li_2SO_4$, 100 mM HEPES, pH 7.5, 12.5% glycerol and 7.5% 2R,3R-butanediol. For the gp120:VRC03 crystals, a 1.9 .ANG. data set was collected using a cryoprotectant solution containing 15% PEG4000, 200 mM $Li_2SO_4$, 100 mM Tris/Cl⁻, pH 8.5 and 30% ethylene glycol.

The crystal structures of gp120:VRC-PG04 and gp120:VRC03 complexes were solved by molecular replacement using Phaser (S23) in the CCP4 Program Suite (S24). The gp120:VRC-PG04 crystal was in a P212121 space group with dimensions a=61.8, b=66.5, c=237.3, $\alpha=\beta=\gamma=90.0$. The gp120:VRC03 crystal also belonged to a space group P212121 with cell dimensions a=61.0, b=70.3, c=217.9, $\alpha=\beta=\gamma=90.0$. Both crystals contained only one molecule per asymmetric unit (table S4). The structure of 93TH057 gp120 in the previously solved VRC01 complex (PDB ID 3NGB) was used as an initial model to place gp120 in the complexes. With gp120 fixed in the search model, a variable domain of antibody Fab was then used to locate antibody VRC03 or VRC-PG04 in the complexes.

Further refinements were carried out with PHENIX (S25). Starting with torsion-angle simulated annealing with slow cooling, iterative manual model building was carried out on Xtalview (S26) and COOT (S27) with maps generated from combinations of standard positional, individual B-factor, TLS refinement algorithms and non-crystallographic symmetry (NCS) restraints. Ordered solvents were added during each macro cycle. Throughout the refinement processes, a cross validation ($R_{free}$) test set consisting of 5% of the data was used and hydrogens were included as riding model. Structure validations were performed periodically during the model building/refinement process with MolProbity (S28) and pdb-care (S29). X-ray crystallographic data and refinement statistics are summarized in table S4.

Numbering of Amino Acid Residues in Antibody.

We follow the Kabat (S30) nomenclature for amino acid sequences in antibodies.

Protein Structure Analysis and Graphical Representations.

GRASP (S31) and APBS (S32) were used in calculations of molecular surfaces, volumes, and electrostatic potentials. PISA (S33) was used to perform protein-protein interfaces analysis. CCP4 (S27) was used for structural alignments. All graphical representation with protein crystal structures were made with Pymol (S34).

Analysis of Structural Convergence Vs. Binding Interactions.

To evaluate antibody structural convergence, the gp120 molecules from the three complex structures (with VRC01, VRC03, and VRC-PG04) were aligned. Residue correspondence in the three antibodies was determined based on the resulting structural alignment (rather than a sequence alignment). Residues in a given antibody that were not structurally aligned to residues in the other two antibodies were discarded from further analysis. For each of the three pairs of structures, Cα RMSD was computed for the six CDR regions, while Cα deviation was computed for each residue. Structural convergence for each CDR was then evaluated based on the average of the three pairwise Cα RMSDs for the given CDR. Structural convergence for the per-residue comparisons was evaluated based on the average of the three pairwise Cα deviation values for each residue. Residue numbering was based on the VRC-PG04 structure.

Interface surface areas and hydrophobic interactions were computed using the PISA server. CDR interface surface areas for each antibody were computed as the sum of the interface surface areas of the corresponding residues. The average of the interface surface areas for each paratope residue was computed over the three structures. The average of the solvation energy values $\Delta^{iG}$ for each paratope residue i (as obtained from the PISA Interface Residues Table) was also computed over the three structures. Residues with positive average PISA $\Delta^{iG}$ were deemed to participate in hydrophobic interactions and were included in the correlation analysis against the respective per-residue Cα deviations.

Analysis of Neutralization Breadth Vs. Targeting Precision.

The CD4-defined initial site of vulnerability included the following gp120 residues (S21): 257, 279, 280, 281, 282, 283, 365, 366, 367, 368, 370, 371, 455, 456, 457, 458, 459, 460, 469, 472, 473, 474, 475, 476, 477. For each antibody, the interface surface areas on gp120 were determined using the PISA server. In each case, the interface surface area corresponding to the residues from the initial site of vulnerability was termed 'Inside', while the remaining interface surface area was termed 'Outside'. Targeting precision was defined as the function 'Inside-Outside'. The neutralization breadth of CD4-Ig and the different antibodies was determined using $IC_{50}$ values for Tier 2 viruses, as obtained from: (S1) (VRC01, VRC03, b12, and CD4-Ig), (S35) (b13 and F105), and the present study (VRC-PG04).

Sample Preparation for 454 Pyrosequencing.

Briefly, mRNA was extracted from 20 million PBMC into 200 μl of elution buffer (Oligotex kit, Qiagen), then concentrated to 10-30 μl by centrifuging the buffer through a 30 kD micron filter (Millipore). The reverse-transcription was performed in one or multiple 35 μl-reactions, each composed of 13 μl of mRNA, 3 μl of oligo(dT)12-18 (SEQ ID NO: 1) at 0.5 μg/μl (invitrogen), 7 μl of 5.times. first strand buffer (Invitrogen), 3 μl of RNase Out (Invitrogen), 3 μl of 0.1M DTT (Invitrogen), 3 μl of dNTP mix, each at 10 mM, and 3 μl of SuperScript II (Invitrogen). The reactions were incubated at 42° C. for 2 hours. The cDNAs from each sample were combined, cleaned up and eluted in 20 μl of elution buffer (NucleoSpin Extract II kit, Clontech). Therefore, 1 μl of the cDNA was equivalent of transcripts from 1 million PBMC. The immunoglobulin gene-specific PCRs were set up using 5 μl of the cDNA as template (equivalent of transcripts from 5 million PBMC), using the Platinum Taq DNA Polymerase High Fidelity system (Invitrogen) in a total volume of 50 The reaction mix was composed of water, 5 μl of 10.times. buffer, 2 μl of dNTP mix, each at 10 mM, 2 μl of MgSO4, 1 μl of each primer at 25 μM, and 1 μl of platinum Taq DNA polymerase high fidelity. The forward primers for VH1 gene amplification were 5'L-VH1, 5'ACAGGTGCCCACTCCCAGGTGCAG 3' (SEQ ID NO: 2); 5'L-VH1#2, 5'GCAGCCACAGGTGCCCACTCC3' (SEQ ID NO: 3); 5'L-VH1-24, 5TAGCAGCTACAGG CACCCACGC3' (SEQ ID NO: 4); 5'L-VH1-69, 5'GGCAGCAGCTACAGGTGTCCAGTCC3' (SEQ ID NO: 5); the reverse primers were 3'Cγ-CH1, 5'GGGGGAAGACCGATGGGCCCTTGGTGG3' (SEQ ID NO: 6), and 3' Cμ-CH1, 5'GGGAATTCTCACAGGAGACGA3' (SEQ ID NO: 7), The forward primer for VK3 amplification was 5'L-VK3, 5'CTCTTCCTCCTGCTACTCTGGCTCCCAG3' (SEQ ID NO: 8); the reverse primer was 3'CK494, 5'GTGCTGTCCTTGCTGTCCTGCT3' (SEQ ID NO: 9). The PCRs were initiated at 95° C. for 2 min, followed by 25 cycles of 95° C. for 30 sec, 58° C. for 30 sec, and 72° C. for 1 min, followed by 72° C. for 10 min. The PCR products at the expected size (450-500 bp) were gel purified (Qiagen), followed by phenol/chloroform extraction.

454 Library Preparation.

PCR products were quantified using Qubit (Life Technologies, Carlsbad, Calif.). Following end repair 454 adapters were added by ligation. Library concentrations were determined using the KAPA Biosystems qPCR system (Woburn, Mass.) with 454 standards provided in the KAPA system.

454 Pyrosequencing.

454 pyrosequencing of the PCR products was performed on a GS FLX sequencing instrument (Roche-454 Life Sciences, Bradford, Conn.) using the manufacturer's suggested methods and reagents. Initial image collection was performed on the GS FLX instrument and subsequent signal processing, quality filtering, and generation of nucleotide sequence and quality scores were performed on an off-instrument linux cluster using 454 application software (version 2.5.3). The amplicon quality filtering parameters were adjusted based on the manufacturer's recommendations (Roche-454 Life Sciences Application Brief No. 001-2010). Quality scores were assigned to each nucleotide using methodologies incorporated into the 454 application software to convert flowgram intensity values to Phred-based quality scores and as described (S36). The quality of each run was assessed by analysis of internal control sequences included in the 454 sequencing reagents. Reports were generated for each region of the PicoTiterPlate (PTP) for both the internal controls and the samples.

Bioinformatics Analysis of 454-Pyrosequencing-Determined Antibodyomes.

A general bioinformatics pipeline has been developed to process and analyze 454 pyrosequencing-determined antibodyomes. The information generated in each step of the process was used to characterize the basic features of antibodyomes as well as to identify potential neutralizing antibody sequences for functional validation. Specifically, each sequence read was (1) reformatted and labeled with a unique index number; (2) assigned to variable (V) gene family and allele using an in-house implementation of IgBLAST; (3) compared with the germline V-gene and known VRC01-like antibodies using nucleotide sequences and a global alignment module implemented in CLUSTALW2 (S37); (4) subjected to a template-based error correction scheme where 454 homopolymer errors in V gene were detected and corrected based on the alignment to germline sequence; (5) translated to amino acid sequence, which was further compared with known VRC01-like antibodies; (6) filtered using characteristic sequence motifs in variable domain sequence such as QVQ (or other possible triplets) at the N-terminus, CAR (or other possible triplets) at the end of V region, WGXG at the end of CDR H3, and VSS (or other possible triplets) at the C-terminus of variable domain. As an optional step, the structural compatibility of a 454-pyrosequencing-derived heavy- or light-chain sequence with known VRC01-like antibody/gp120 complex structures can be evaluated by threading (S38-39).

Phylogenetic Analysis of Donor Antibodyomes.

Three phylogenetic analyses were performed for donor 45 and donor 74 2008 heavy-chain antibodyomes. The first analysis was performed on a small set of "representative" sequences selected from the IGHV1-2*02 family. The sequence selection was done by first dividing the full-length sequences into 50 bins with an increment of 0.7% germline divergence and then randomly selecting a sequence from each bin, resulting in 38 sequences for donor 45 and 50 for donor 74. After incorporating the inferred germline sequence of VRC03 or VRC-PG04 and matured VRC01-like mAb sequences into the data set, phylogenetic analysis was performed using maximum-likelihood (ML) method assuming a constant rate of mutation, as implemented in the dnamlk program of PHYLIP package. 1,000 bootstrapped sets were then generated using the seqboot program and the majority-rule consensus tree was calculated using the consense program. Bootstrap values of the key intermediate states shown in FIG. 5 were extracted from the consense output. In the second analysis, "VRC01-like" antibody heavy-chain sequences in an antibodyome were obtained using an iterative screening procedure. Briefly, in each round the full-length sequences of IGHV1-2*02 origin were divided into subsets with each having no more than 5,000 sequences; a neighbor-joining (NJ) tree was constructed for each subset using the "Phylogenetic trees" option in CLUSTALW2 (S37); after rooted at the inferred germline of VRC01 (for donor 45) or VRC-PG04 (for donor 74) the sequences residing on the smallest branch that contains VRC01, VRC02, VRC03 and VRC-PG04 were extracted from the NJ tree and deposited into a new data set for the next round of analysis. Using this approach, we obtained 109 VRC03-like sequences and 5,047 VRC-PG04-like sequences from donor 45 and 74 antibodyomes, respectively. From these two data sets, 45 and 1,889 non-redundant sequences were identified using the blastclust module in NCBI BLAST package (S40). Third, after error correction using VRC03 or VRC-PG04 as a template, the ancestral sequences of V region were inferred for the key intermediate states shown in FIG. 5 from the maximum-likelihood (ML) trees of non-redundant VRC03-like or VRC-PG04 like sequences. The calculation was done using the dnamlk program of PHYLIP package.

Analysis of CDR H3 Lineage.

Due to the sequence variation, we adopted a template-based approach to CDR H3 identification for 454-pyrosequencing-determined heavy chain sequences. Specifically, a 454-derived heavy chain sequence was aligned to the VRC01 heavy chain sequence using CLUSTALW2 (S37); then the nucleotide sequences of two motifs that define the CDR H3 in VRC01-CTR and WGXG—were used as "anchors" to locate the CDR H3 region in the 454-derived heavy chain sequence. For sequences with long CDR H3s, gap insertion may occur in the two motif regions and cause ambiguities in the CDR H3 identification, which were dealt with by allowing a maximum of 10 gaps between two adjacent nucleotides in the motif recognition. Using this template-based approach, the CDR H3 sequence and length were calculated for all full-length sequences in the IGHV1-2*02 family. In the CDR H3 lineage analysis, the 35 expressed and experimentally tested heavy-chain sequences shown in FIG. 6 were divided into 9 CDR H3 groups, allowing no more than 5-nucleotide difference between members within the group. For each lineage, the characteristic CDR H3 sequences were used to search for other sequences with the same CDR H3s from the IGHV1-2*02 family. The number of sequences in each CDR H3 lineage was listed in FIG. 6.

Analysis of J Chain.

109 VRC03-like and 5,047 VRC-PG04-like heavy-chain sequences identified using iterative phylogenetic analysis were submitted to the SoDA2 (S41) server for assignment of variable (V), diverse (D), and joining (J) germline genes and junction analysis. For 14 VRC03-like sequences with non-IGHJ1*01 assignment and 66 VRC-PG04-like sequences with non-IGHJ2*01 assignment, the J segment was manually alignment to IGHJ1*01 or IGHJ2*01 for comparison.

Statistical Analysis.

Statistical analyses were performed using GraphPad Prism version 5.0 (GraphPad Software Inc.).

SUPPORTING REFERENCES

S1. X. Wu, Z. Y. Yang, Rational design of envelope identifies broadly neutralizing human monoclonal antibodies to HIV-1. Science 329, 856-861 (2010).

S2. Y. Li, S. A. Migueles, Broad HIV-1 neutralization mediated by CD4-binding site antibodies. Nat Med 13, 1032-1034 (2007).

S3. L. M. Walker, M. D. Simek, A limited number of antibody specificities mediate broad and potent serum neutralization in selected HIV-1 infected individuals. PLoS Pathog 6 (2010).

S4. M. D. Simek, W. Rida, Human immunodeficiency virus type 1 elite neutralizers: individuals with broad and potent neutralizing activity identified by using a high-throughput neutralization assay together with an analytical selection algorithm. J Virol 83, 7337-7348 (2009).

S5. S. Gnanakaran, M. G. Daniels, Genetic signatures in the envelope glycoproteins of HIV-1 that associate with broadly neutralizing antibodies. PLoS Comput Biol 6, e1000955 (2010).

S6. M. Bonsignori, K. Hwang, Immunoregulation of HIV-1 broadly neutralizing antibody responses: deciphering maturation paths for antibody induction. AIDS Res Hum Retroviruses 26, A153 (2010).

S7. Y. Li, K. Svehla, Analysis of neutralization specificities in polyclonal sera derived from human immunodeficiency virus type 1-infected individuals. J Virol 83, 1045-1059 (2009).

S8. D. H. Barouch, G. J. Nabel, Adenovirus vector-based vaccines for human immunodeficiency virus type 1. Hum Gene Ther 16, 149-156 (2005).

S9. D. R. Burton, J. Pyati, Efficient neutralization of primary isolates of HIV-1 by a recombinant human monoclonal antibody. Science 266, 1024-1027 (1994).

S10. T. Tiller, E. Meffre, Efficient generation of monoclonal antibodies from single human B cells by single cell RT-PCR and expression vector cloning. J Immunol Methods 329, 112-124 (2008).

S11. M. M. Souto-Carneiro, N. S. Longo, Characterization of the human Ig heavy chain antigen binding complementarity determining region 3 using a newly developed software algorithm, JOINSOLVER. J Immunol 172, 6790-6802 (2004).

S12. X. Brochet, M. P. Lefranc, IMGT/V-QUEST: the highly customized and integrated system for IG and TR standardized V-J and V-D-J sequence analysis. Nucleic Acids Res 36, W503-508 (2008).

S13. S. Malcolm, P. Barton, Localization of Human Immunoglobulin K Light Chain Variable Region Genes to the Short Arm of Chromosome 2 by in situ hybridization. Proc Natl Acad Sci USA 79, 4957-4961 (1982).

S14. M. Li, F. Gao, Human Immunodeficiency Virus Type 1 env Clones from Acute and Early Subtype B Infections for Standardized Assessments of Vaccine-Elicited Neutralizing Antibodies. J Virol 79, 10108-10125 (2005).

S15. M. S. Seaman, H. Janes, Tiered categorization of a diverse panel of HIV-1 Env pseudoviruses for neutralizing antibody assessment. J Virol 84, 1439-1452 (2010).

S16. X. Wu, T. Zhou, Mechanism of human immunodeficiency virus type 1 resistance to monoclonal antibody B12 that effectively targets the site of CD4 attachment. J Virol 83, 10892-10907 (2009).

S17. R. C. Edgar, MUSCLE: a multiple sequence alignment method with reduced time and space complexity. BMC Bioinformatics 5, 113 (2004).

S18. R. C. Edgar, MUSCLE: multiple sequence alignment with high accuracy and high throughput. Nucleic Acids Res 32, 1792-1797 (2004).

S19. M. K. Kuhner, J. Felsenstein, A simulation comparison of phylogeny algorithms under equal and unequal evolutionary rates. Mol Biol Evol 11, 459-468 (1994).

S20. D. 11. Huson, D. C. Richter, Dendroscope: An interactive viewer for large phylogenetic trees. BMC Bioinformatics 8, 460 (2007).

S21. T. Zhou, I. Georgiev, Structural basis for broad and potent neutralization of HIV-1 by antibody VRC01. Science 329, 811-817 (2010).

S22. Z. Otwinowski, W. Minor, Processing of X-ray diffraction data collected in oscillation mode. Methods in Enzymology 276, 307-326 (1997).

S23. A. J. McCoy, R. W. Grosse-Kunstleve, Phaser crystallographic software. J Appl Crystallogr 40, 658-674 (2007).

S24. N. Collaborative Computational Project, The CCP4 suite: programs for protein crystallography. Acta Crystallographica Section D 50, 760-763 (1994).

S25. P. D. Adams, R. W. Grosse-Kunstleve, PHENIX: building new software for automated crystallographic structure determination. Acta Crystallographica Section D 58, 1948-1954 (2002).

S26. D. E. McRee, XtalView/Xfit—A versatile program for manipulating atomic coordinates and electron density. J Struct Biol 125, 156-165 (1999).

S27. P. Emsley, K. Cowtan, Coot: model-building tools for molecular graphics. Acta Crystallographica Section D 60, 2126-2132 (2004).

S28. I. W. Davis, A. Leaver-Fay, MolProbity: all-atom contacts and structure validation for proteins and nucleic acids. Nucleic Acids Res 35, W375-383 (2007).

S29. T. Lutteke, C. W. von der Lieth, pdb-care (PDB carbohydrate residue check): a program to support annotation of complex carbohydrate structures in PDB files. BMC Bioinformatics 5, 69 (2004).

S30. E. A. Kabat, T. T. Wu, Sequences of Proteins of Immunological Interest. 5th Edition (1991).

S31. A. Nicholls, K. A. Sharp, Protein folding and association: insights from the interfacial and thermodynamic properties of hydrocarbons. Proteins 11, 281-296 (1991).

S32. N. A. Baker, D. Sept, Electrostatics of nanosystems: application to microtubules and the ribosome. Proc Natl Acad Sci USA 98, 10037-10041 (2001).

S33. E. Krissinel, K. Henrick, Inference of macromolecular assemblies from crystalline state. J Mol Biol 372, 774-797 (2007).

S34. W. L. DeLano, The PyMOL Molecular Graphics System. DeLano Scientific, San Carlos, Calif., USA (2002).

S35. L. Chen, Y. D. Kwon, Structural basis of immune evasion at the site of CD4 attachment on HIV-1 gp120. Science 326, 1123-1127 (2009).

S36. W. Brockman, P. Alvarez, Quality scores and SNP detection in sequencing-by-synthesis systems. Genome Res 18, 763-770 (2008).

S37. M. A. Larkin, G. Blackshields, Clustal W and Clustal X version 2.0. Bioinformatics 23, 2947-2948 (2007).

S38. D. Petrey, Z. Xiang, Using multiple structure alignments, fast model building, and energetic analysis in fold recognition and homology modeling. Proteins 53 Suppl 6, 430-435 (2003).

S39. H. Zhou, Y. Zhou, Distance-scaled, finite ideal-gas reference state improves structure-derived potentials of mean force for structure selection and stability prediction. Protein Sci 11, 2714-2726 (2002).

S40. S. F. Altschul, T. L. Madden, Gapped BLAST and PSI-BLAST: a new generation of protein database search programs. Nucleic Acids Res 25, 3389-3402 (1997).

S41. S. Munshaw, T. B. Kepler, SoDA2: a Hidden Markov Model approach for identification of immunoglobulin rearrangements. Bioinformatics 26, 867-872 (2010).

S42. G. E. Crooks, G. Hon, WebLogo: a sequence logo generator. Genome Res 14, 1188-1190 (2004).

S43. J. Zhu, H. Fan, Refining homology models by combining replica-exchange molecular dynamics and statistical potentials. Proteins 72, 1171-1188 (2008).

APPENDIX

The bioinformatics analysis of four antibodyomes obtained from 454 pyroseqeuncing of PBMCs of two HIV-1 infected individuals, donor 45 and donor 74, is summarized in this Appendix. As described in the Methods section, a computational pipeline has been developed to process and analyze the 454-pyrosequencing-determined antibodyomes. The results obtained from each step of the pipeline can be used to characterize the basic features of antibodyome and to identify potentially neutralizing antibodies for experimental validation. For each antibodyome, the following analyses are shown in this appendix: read length distribution, germline family distribution, query/germline alignment coverage, germline divergence distribution, sequence identity distribution, gap opening distribution, error-correction/improvement correlation, sequence-quality improvement distribution, and sequence identity/protein length distribution.

1. Analysis of donor 45 heavy-chain 2008 antibodyome (BC) (Figures A-1 to A-13) 2. Analysis of donor 74 heavy-chain 2008 antibodyome (NISC) (Figures A-14 to A-24) 3. Analysis of donor 45 light-chain 2001 antibodyome (BC) (Figures A-25 to A-37) 4. Analysis of donor 74 heavy-chain 2008 antibodyome (BC) (Figures A-38 to A-48)

Example 2

Development and Ontogeny of CD4 Binding Site Broad Neutralizing Antibodies

Described below is the natural clone of CH30-34 clonal lineage with the reverted unmutated common ancestors (RUAs) and the clonal lineage intermediates (lAs). These RUAs and IAs are needed for B cell lineage design for design of immunogens that bind well to these RUAs and IAs. (See, e.g., U.S. Prov. 61/542,469 filed Oct. 3, 2011.) The RUAs do not bind well gp120 Envs that the IAs and mature antibodies do. Thus, the RUAs can be used as templates for vaccine design to start of a B cell clone, like the CH30-34 clonal lineage.

FIG. 1--Ex.2 shows the clonal lineage of the broadly neutralizing antibodies CH30-34 with unmutated common ancestors and intermediate antibodies (I1, I2, I3, I4), as well as mature antibodies (CH30, CH31, CH32, CH33, CH34). The RUAs and IAs are inferred models of the B cell receptors of precursors of mature CH30-CH34 antibodies. The figure shows the Kds of binding of the antibodies in the clonal lineage to the E.A244 gp120 Delta 11 recombinant Env as measured in surface plasmon reasonance. The sequences shown are the sequences of the clonal lineage heavy chains.

FIG. 2--Ex.2 shows the same binding data as in FIG. 1--Ex.2 but with sequences of the clonal lineage light chains.

FIG. 3--Ex.2 shows the progressive increase in potency of neutralizing antibodies against HIV-1 isolate MN with progressive decrease in inhibitory concentration 50s as affinity maturation progresses. Sequence data provided are a repeat of the VH sequences. Also shown are indications of what antibodies mediate ADCC as + or − (see FIG. 4--Ex.2).

FIG. 4--Ex.2 shows antibody dependent cellular cytotoxicity assay curves of RUAs, IAs and CH31 antibody against CM235 HIV infected CD4 T cells.

FIGS. 5--Ex.2, 6--Ex.2 and 7-Ex-2 show binding curves of the members of the clonal lineage to the E.A244 gp120 recombinant Env protein (Fig. Ex.2), to the resurfaced core protein (RSC) (FIG. 6--Ex.2) and to the group M consensus Env CONS gp120 protein (FIG. 7--Ex.2). All three figures show that the RUAs do not react with these envs while the IAs and CH31 do react. These data imply that what is needed to induce these broad neutralizing antibodies are immunogens designed using the RUAs as templates.

FIG. 8--Ex.2 shows the steps of a B cell lineage-based approach (see also U.S. Prov. 61/542,469).

What is claimed is:

1. An isolated recombinant antibody or antigen binding fragment thereof against the CD4 binding site of HIV-1 envelope comprising:
   a variable heavy (VH) chain amino acid sequence of antibody CH30 (SEQ ID NO:113), antibody CH31 (SEQ ID NO:114), antibody CH32 (SEQ ID NO:115), antibody I1 (SEQ ID NO: 294), antibody I2 (SEQ ID NO: 292), antibody I3 (SEQ ID NO: 293), or antibody I4 (SEQ ID NO: 295); and
   a variable light (VL) chain amino acid sequence of antibody CH30 (SEQ ID NO:124), antibody CH31 (SEQ ID NO:125), antibody CH32 (SEQ ID NO:126), or antibody I2 (SEQ ID NO: 296);
wherein the recombinant antibody or antigen binding fragment thereof binds to the CD4 binding site of HIV-1 envelope.

2. The isolated recombinant antibody or antigen binding fragment thereof of claim 1 wherein the VH chain amino acid sequence is of antibody CH31 (SEQ ID NO: 114) and the VL chain amino acid sequence is of antibody CH31 (SEQ ID NO: 125).

3. The isolated recombinant antibody or antigen binding fragment thereof of any one of claim 1 or 2 wherein the antibody is an IgG type.

4. The isolated recombinant antibody or antigen binding fragment thereof of any one of claim 1 or 2 wherein the antibody is an IgA type.

5. A composition comprising the recombinant antibody or antigen binding fragment thereof according to claim 3 and a carrier.

6. A composition comprising the recombinant antibody or antigen binding fragment thereof according to claim 4 and a carrier.

7. A method of inhibiting HIV-1 infection in a patient comprising administering to said patient a composition according to claim 5 in an amount sufficient to inhibit or prevent said infection.

8. A method of inhibiting HIV-1 infection in a patient comprising administering to said patient a composition according to claim 6 in an amount sufficient to inhibit or prevent said infection.

9. A composition comprising the recombinant antibody or antigen binding fragment thereof according to any one of claim 1 or 2 and a carrier.

10. The isolated recombinant antibody or antigen binding fragment thereof of according to any one of claim 1 or 2 comprising an engineered constant domain.

11. A method of inhibiting HIV-1 infection in a patient comprising administering to said patient a composition according to claim 9 in an amount sufficient to inhibit or prevent said infection.

12. The method according to claim 11 wherein said antibody or antigen binding fragment thereof is administered parenterally or at a mucosal surface.

13. An isolated recombinant antibody or antigen binding fragment thereof against the CD4 binding site of HIV-1 envelope comprising a variable heavy (VH) chain amino acid sequence and a variable light (VL) chain amino acid sequence, wherein the VH chain amino acid sequence is of antibody CH30 (SEQ ID NO: 113), antibody I1 (SEQ ID NO: 294), or antibody I4 (SEQ ID NO: 295) and the VL chain amino acid sequence is of antibody CH30 (SEQ ID NO: 124);

or wherein the VH chain amino acid sequence is of antibody CH31 (SEQ ID NO: 114) and the VL chain amino acid sequence is of antibody CH31 (SEQ ID NO: 125);

or wherein the VH chain amino acid sequence is of antibody CH32 (SEQ ID NO: 115) and the VL chain amino acid sequence is of antibody CH32 (SEQ ID NO: 126);

or wherein the VH chain amino acid sequence is of antibody I2 (SEQ ID NO: 292) or antibody I3 (SEQ ID NO: 293) and the VL chain amino acid sequence is of antibody 12 (SEQ ID NO: 296).

14. The isolated recombinant antibody or antigen binding fragment thereof of claim 13 wherein the VH chain amino acid sequence is of antibody CH30 (SEQ ID NO: 113) and the VL chain amino acid sequence is of antibody CH30 (SEQ ID NO: 124).

15. The isolated recombinant antibody or antigen binding fragment thereof of claim 13 wherein the VH chain amino acid sequence is of antibody CH32 (SEQ ID NO: 115) and the VL chain amino acid sequence is of antibody CH32 (SEQ ID NO: 126).

16. An isolated recombinant antibody or antigen binding fragment thereof against the CD4 binding site of HIV-1 envelope comprising:

a variable heavy (VH) chain amino acid sequence and a variable light (VL) chain amino acid sequence, wherein the VH chain amino acid sequence comprises CH31 VH chain (SEQ ID NO: 114), except that the amino acid residue at position 42 is tyrosine, the amino acid residue at position 72 is glutamine, the amino acid residue at position 74 is histidine or glutamine, the amino acid residue at position 77 is valine or leucine, the amino acid at position 83 is arginine or glycine, the amino acid at position 93 is lysine or arginine, and the amino acid residue at position 128 is valine or alanine; and wherein the VL chain amino acid sequence comprises CH31 VL chain (SEQ ID NO: 125), except that the amino acid residue at position 40 is alanine or proline, the amino acid residue at position 42 is lysine or arginine, the amino acid residue at position 60 is serine or threonine, and the amino acid residue at position 80 is alanine or proline, and wherein the recombinant antibody or antigen binding fragment thereof binds to the CD4 binding site of HIV-1 envelope.

17. The isolated recombinant antibody or antigen binding fragment thereof of claim 13 wherein the antibody is an IgG type or an IgA type.

18. A composition comprising the recombinant antibody or antigen binding fragment thereof according to claim 16 and a carrier.

19. The isolated recombinant antibody or antigen binding fragment thereof according to claim 13 comprising an engineered constant domain.

20. A method of inhibiting HIV-1 infection in a patient comprising administering to said patient a composition according to claim 18 in an amount sufficient to inhibit or prevent said infection.

21. The isolated recombinant antibody or antigen binding fragment of claim 16, except that the amino acid residue at position 74 of the VH chain is histidine.

22. The isolated recombinant antibody or antigen binding fragment of claim 16, except that the amino acid residue at position 83 of the VH chain is arginine, the amino acid residue at position 93 is lysine, and the amino acid residue at position 128 is valine.

23. The isolated recombinant antibody or antigen binding fragment of claim 22, except that the amino acid residue at position 77 of the VH chain is valine.

24. A composition comprising the recombinant antibody or antigen binding fragment thereof according to claim 2.

25. A method of inhibiting HIV-1 infection in a patient comprising administering to said patient a composition according to claim 24 in an amount sufficient to inhibit or prevent said infection.

26. A composition comprising the recombinant antibody or antigen binding fragment thereof according to claim 16.

27. A method of inhibiting HIV-1 infection in a patient comprising administering to said patient a composition according to claim 26 in an amount sufficient to inhibit or prevent said infection.

28. A composition comprising the recombinant antibody or antigen binding fragment thereof according to claim 21.

29. A method of inhibiting HIV-1 infection in a patient comprising administering to said patient a composition according to claim 28 in an amount sufficient to inhibit or prevent said infection.

30. A composition comprising the recombinant antibody or antigen binding fragment thereof according to claim 22.

31. A method of inhibiting HIV-1 infection in a patient comprising administering to said patient a composition according to claim 30 in an amount sufficient to inhibit or prevent said infection.

32. A composition comprising the recombinant antibody or antigen binding fragment thereof according to claim 23.

33. A method of inhibiting HIV-1 infection in a patient comprising administering to said patient a composition according to claim 32 in an amount sufficient to inhibit or prevent said infection.

34. A method of inhibiting HIV-1 infection in a patient comprising administering to said patient a composition comprising the recombinant antibody or antigen binding fragment thereof according to claim 10 in an amount sufficient to inhibit or prevent said infection.

35. A method of inhibiting HIV-1 infection in a patient comprising administering to said patient a composition comprising the recombinant antibody or antigen binding fragment thereof according to claim 13 in an amount sufficient to inhibit or prevent said infection.

36. A method of inhibiting HIV-1 infection in a patient comprising administering to said patient a composition comprising the recombinant antibody or antigen binding fragment thereof according to claim 19 in an amount sufficient to inhibit or prevent said infection.

37. The isolated recombinant antibody or antigen binding fragment thereof of claim 16 wherein the antibody is an IgG type.

38. The isolated recombinant antibody or antigen binding fragment thereof of claim 16 wherein the antibody is an IgA type.

39. The isolated recombinant antibody or antigen binding fragment thereof according to claim 16 comprising an engineered constant domain.

40. A method of inhibiting HIV-1 infection in a patient comprising administering to said patient a composition comprising the recombinant antibody or antigen binding fragment thereof according to claim 39 in an amount sufficient to inhibit or prevent said infection.

* * * * *

UNITED STATES PATENT AND TRADEMARK OFFICE
CERTIFICATE OF CORRECTION

PATENT NO. : 10,273,291 B2
APPLICATION NO. : 14/116710
DATED : April 30, 2019
INVENTOR(S) : John R. Mascola et al.

Page 1 of 1

It is certified that error appears in the above-identified patent and that said Letters Patent is hereby corrected as shown below:

On the Title Page

(73) Assignees should read:
Duke University, Durham, NC (US);
THE UNITED STATES OF AMERICA, AS REPRESENTED BY THE SECRETARY, DEPARTMENT OF HEALTH AND HUMAN SERVICES OFFICE OF TECHNOLOGY TRANSFER, NATIONAL INSTITUTES OF HEALTH, Bethesda, MD (US);

Signed and Sealed this
Eighteenth Day of June, 2019

Andrei Iancu
*Director of the United States Patent and Trademark Office*